United States Patent
Kato et al.

(10) Patent No.: US 7,115,750 B1
(45) Date of Patent: Oct. 3, 2006

(54) MELANIN CONCENTRATING HORMONE ANTAGONIST

(75) Inventors: Kaneyoshi Kato, Kawanishi (JP); Jun Terauchi, Ikeda (JP); Masaaki Mori, Tsukuba (JP); Nobuhiro Suzuki, Nishinomiya (JP); Yukio Shimomura, Tsukuba (JP); Shiro Takekawa, Nishinomiya (JP); Yuji Ishihara, Itami (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 2 days.

(21) Appl. No.: 10/088,771

(22) PCT Filed: Sep. 19, 2000

(86) PCT No.: PCT/JP00/06375

§ 371 (c)(1),
(2), (4) Date: Mar. 19, 2002

(87) PCT Pub. No.: WO01/21577

PCT Pub. Date: Mar. 29, 2001

(30) Foreign Application Priority Data

| Sep. 20, 1999 | (JP) | ................. | 11/266298 |
| Dec. 16, 1999 | (JP) | ................. | 11/357889 |
| Apr. 20, 2000 | (JP) | ................. | 2000/126272 |

(51) Int. Cl.
C09B 5/00 (2006.01)
A61K 3/41 (2006.01)
C07D 209/56 (2006.01)
C07D 487/00 (2006.01)
C07D 491/00 (2006.01)

(52) U.S. Cl. .................. 548/416; 548/418; 548/452; 514/359

(58) Field of Classification Search ............... 546/337, 546/205, 276.4, 90; 514/357, 374, 319, 428, 514/326, 316, 238.2, 255.03, 359; 548/237, 548/567, 416, 418, 452; 544/165, 393
See application file for complete search history.

(56) References Cited

U.S. PATENT DOCUMENTS 6,197,798 B1 * 3/2001 Fink et al. ................... 514/354

FOREIGN PATENT DOCUMENTS

| EP | DE 2108185 | 9/1972 |
| EP | DE 2448257 | 4/1976 |
| EP | DE 2502588 | 7/1976 |
| EP | 0533266 | 3/1993 |
| EP | 0920864 | 6/1999 |
| WO | WO 95/32967 | 12/1995 |
| WO | WO 96/35671 | 11/1996 |
| WO | WO 98/15274 | 4/1998 |
| WO | WO 98/38156 | 9/1998 |
| WO | WO 99/01127 | 1/1999 |
| WO | WP 99/52857 | 10/1999 |

OTHER PUBLICATIONS

CAS printout of Perregaard et al. Chem. Abs. 124:232261, 1995.*
CAS printout of Werbel et al. Chem. Abs. 73:109549, 1995.*
Mewshaw, et al. "New Generation Dopaminergic Agents. 1. Discovery of a Novel Scaffold Which Embraces the $D_7$ Agonist Pharmacophore. Structure—Activity Relationships of a Series of 2-(Aminomethyl)chromans" Journal of Medicinal Chemistry 40:4235-56 (1997).
Birch, et al. "N-Substituted (2,3-Dihydro-1,4-benzodioxin-2-yl)methylamine Derivatives as $D_1$ Antagonists/5-$HT_{1A}$ Partial Agonists with Potential as Atypical Antitipsychotic Agents" Journal of Medicinal Chemistry 42-3342-55(1999).
Qu, et al. "A role for melanin-concentrating hormone in the central regulation of feeding behaviour". Nature 380:243-247(Mar. 21, 1996).
Beilstein Registry No. 5345411, XP-002155831, (May 4, 1993).

* cited by examiner

Primary Examiner—James O. Wilson
Assistant Examiner—Matthew L. Fedowitz
(74) Attorney, Agent, or Firm—Elaine M. Ramesh; Mark Chao

(57) ABSTRACT

A melanin-concentrating hormone antagonist which comprises a compound of the formula:

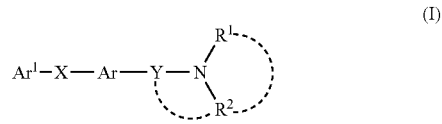

wherein $Ar^1$ is a cyclic group which may have substituents;
X is a spacer having a main chain of 1 to 6 atoms;
Y is a bond or a spacer having a main chain of 1 to 6 atoms;
Ar is a monocyclic aromatic ring which may be condensed with a 4 to 8 membered non-aromatic ring, and may have further substituents;
$R^1$ and $R^2$ are independently hydrogen atom or a hydrocarbon group which may have substituents; $R^1$ and $R^2$, together with the adjacent nitrogen atom, may form a nitrogen-containing hetero ring which may have substituents; $R^2$ may form a spiro ring together with Ar; or $R^2$, together with the adjacent nitrogen atom and Y, may form a nitrogen-containing hetero ring which may have substituents; or a salt thereof;
which is useful as an agent for preventing or treating obesity, etc.

14 Claims, No Drawings

MELANIN CONCENTRATING HORMONE ANTAGONIST

This application is the National Phase filing of International Patent Application No. PCT/JP00/06375, filed Sep. 19, 2000.

TECHNICAL FIELD

The present invention relates to a melanin-concentrating hormone antagonist which is useful as an agent for preventing or treating obesity, etc.

BACKGROUND ART

Feeding behavior is an essential action for many living beings including humans. Therefore, if irregularities in feeding behavior occur, disorders, often connected to diseases, will occur in normal life-maintaining activities. Accompanying recent changes of our dietary environment, obesity is now becoming a social problem. In addition, not only is obesity a serious risk factor for life-style diseases such as diabetes, hypertension, and arteriosclerosis; it is also widely known that increased body weight places excessive burdens on joints such as knee joints, causing arthritis and pain.

The "diet boom," etc. show that there is a potentially great percentage of the population hoping to reduce body weight; on the other hand, many cases of feeding problems such as overeating, occurring due to causes such as hereditary neurosis or neurosis due to stress, have been reported.

Therefore, research on and development of agents for preventing or treating obesity, or agents for inhibiting eating, have been vigorously done for a long time.

The centrally acting anorectic drug, Mazindol, is now being marketed.

Many appetite control factors such as leptin, have recently been discovered, and the development of anti-obesity agents or anorectic agents which will regulate the functions of these appetite control factors is progressing.

In particular, it is known that melanin-concentrating hormone (hereinafter also abbreviated as "MCH") originates in the hypothalamus and has orexigenic action. In addition, it has been reported that even though the daily behavior of MCH knock-out mice was normal, the amount of feeding by MCH knock-out mice was significantly reduced and their body weights were lighter than those of normal mice [Nature, Vol. 396, p. 670, 1998]. This indicates that, if a MCH antagonist was produced, it can be expected to be an excellent anorectic agent or anti-obesity agent; but at present there are no known compound, especially non-peptide type compounds, which possess MCH antagonistic actions.

On the other hand, the following compounds are known as amine derivatives.

1) WO98/38156 describes a compound of the formula:

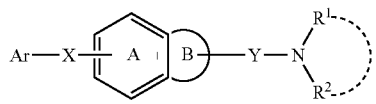

wherein Ar is an optionally substituted ring assembly aromatic group or an optionally substituted condensed aromatic group; X is a bond, etc.; Y is an optionally substituted bivalent $C_{1-6}$ aliphatic hydrocarbon group which may have an intervening oxygen atom or sulfur atom; $R^1$ and $R^2$ are independently hydrogen atom or a lower alkyl, or $R^1$ and $R^2$, together with the adjacent nitrogen atom, form an optionally substituted nitrogen-containing hetero ring; Ring A is a benzene ring which may have further substituents in addition to the groups of the formula: —X—Ar where each symbol has the same meaning as defined above; Ring B is a 4 to 8 membered ring which may have further substituents in addition to the group of the formula: —Y—NR$^1$R$^2$ where each symbol has the same meaning as defined above; with the proviso that the condensed ring formed by ring A and ring B is an indole ring, the group of the formula: —X—Ar where each symbol has the same meaning as defined above is substituted at the 4-, 6-, or 7-position on the indole ring; or its salt, which has an action of inhibiting the production and secretion of β-amyloid protein.

2) WO95/32967 describes compound of the formula:

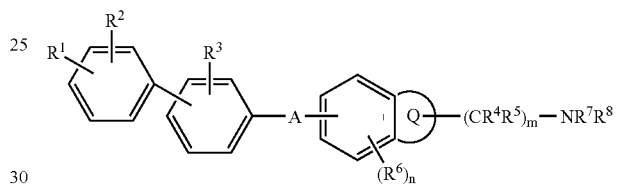

wherein A is CONR, in which R is hydrogen or $C_{1-6}$ alkyl; Q is an optionally substituted 5 to 7 membered hetero ring containing 1 to 3 hetero atoms selected from nitrogen or sulfur; $R^1$ is hydrogen, halogen, etc.; $R^2$ and $R^3$ are independently hydrogen, halogen, etc.; $R_4$ and $R_5$ are independently hydrogen or $C_{1-6}$ alkyl; $R^6$ is halogen, hydroxy, etc.; $R_7$ and $R_8$ are independently hydrogen, $C_{1-6}$ alkyls, etc.; m is 0 to 4; n is 0, 1 or 2; or its salt, which has 5HT1D antagonist activity and can be expected to ameliorate anorexia.

3) WO98/15274 describes a compound of the formula:

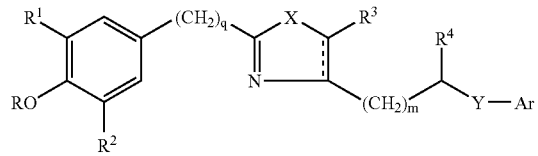

wherein Ar is phenyl, etc.; X is —O— or —S—; Y is CR$^5$R$^5$— where R$^5$ is H and R$^5$ is —H, etc.; Z is —CH$_2$— or —N—; R is H or —(C1–C6) alkyl; R$^1$ and R$^2$ are independently —(C1–C6) alkyl, etc.; R$^3$ is H etc.; R$^4$ is hydrogen, etc.; m is an integer of 0 to 2; q is 0 or 1; n is an integer of 0 to 4; p is an integer of 1 to 6; t is an integer of 1 to 4; which has an anti-oxidant activity and can be expected to ameliorate Alzheimer's disease.

4) EP533266

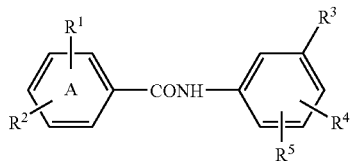

wherein $R^1$ is halogen, etc.; $R^2$ is phenyl optionally substituted by 1 or 2 substituents selected from halogen, etc.; $R^3$ is

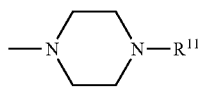

; $R^4$ and $R^5$ are independently hydrogen, halogen, etc.; $R^{11}$ is hydrogen or $C_{1-6}$ alkyl; which has 5HT1D antagonist activity, and can be expected to ameliorate anorexia.

There has been great desire for the development of a melanin-concentrating hormone antagonist which is useful as an agent for preventing or treating obesity, excellent in oral absorbency, and safe.

DISCLOSURE OF INVENTION

As a result of intensive studies of compounds with a MCH antagonistic action, the present inventors found that a derivative which is obtained by introducing a group of the formula: $Ar^1$—X— where each symbol has the same meaning as defined hereafter, into a compound of the formula

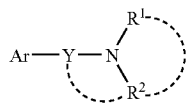

wherein each symbol has the same meaning as defined hereinafter, had an excellent MCH antagonistic actions, to complete this invention.

Namely, the present invention relates to
(1) a melanin-concentrating hormone antagonist which comprises a compound of the formula:

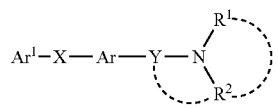

(I)

wherein $Ar^1$ is a cyclic group which may have substituents;
X is a spacer having a main chain of 1 to 6 atoms;
Y is a bond or a spacer having a main chain of 1 to 6 atoms;
Ar is a monocyclic aromatic ring which may be condensed with a 4 to 8 membered non-aromatic ring, and may have further substituents;
$R^1$ and $R^2$ are independently hydrogen atom or a hydrocarbon group which may have substituents; $R_1$ and $R^2$, together with the adjacent nitrogen atom, may form a nitrogen-containing hetero ring which may have substituents; $R^2$ may form a spiro ring together with Ar; or $R^2$, together with the adjacent nitrogen atom and Y, may form a nitrogen-containing hetero ring which may have substituents; or a salt thereof;

(2) an antagonist according to the above (1), wherein Y is a spacer having a main chain of 1 to 6 atoms; $R^1$ and $R^2$ are independently hydrogen atom or a hydrocarbon group which may have substituents; $R^1$ and $R^2$, together with the adjacent nitrogen atom, may form a nitrogen-containing hetero ring which may have substituents; or $R^2$ may form a spiro ring together with Ar;

(3) an antagonist according to the above (2), wherein $Ar^1$ is an aromatic group which may have substituents; and "a hydrocarbon group which may have substituents" for $R^1$ and $R^2$ is "$C_{1-6}$ alkyl which may have substituents";

(4) an antagonist according to the above (1), wherein the cyclic group for $Ar^1$ is $C_{6-14}$ monocyclic or condensed polycyclic aromatic hydrocarbon group;

(5) an antagonist according to the above (1), wherein the cyclic group for $Ar^1$ is a group formed by removing an optional one hydrogen atom from an aromatic ring assemble in which 2 or 3 $C_{6-14}$ monocyclic or condensed polycyclic aromatic hydrocarbon groups are directly bonded by single bonds;

(6) an antagonist according to the above (1), wherein the cyclic group for $Ar^1$ is a group formed by removing an optional one hydrogen atom from an aromatic ring assemble in which $C_{6-14}$ monocyclic or condensed polycyclic aromatic hydrocarbon and 5 to 10 membered aromatic hetero ring are directly bonded by a single bond;

(7) an antagonist according to the above (1), wherein $Ar^1$ is phenyl, biphenylyl, phenyl-pyridyl, phenyl-furyl, phenyl-isoxazolyl, diphenyl-oxazolyl, pyridyl-phenyl, phenyl-pyrimidinyl, benzofuranyl-phenyl, furyl-phenyl, terphenyl, thienyl-phenyl, indolyl, naphthyl-oxadiazolyl, benzofuranyl-oxadiazolyl benzothienyl, benzofuranyl, fluorenyl, pyridyl-pyrrolyl or thioxanthenyl;

each of which may have 1 to 3 substituents selected from the group consisting of halogen atom; nitro; $C_{1-3}$ alkylene-dioxy; optionally halogenated $C_{1-6}$ alkyl; hydroxy-$C_{1-6}$ alkyl; optionally halogenated $C_{3-6}$ cycloalkyl; optionally halogenated $C_{1-6}$ alkoxy; optionally halogenated $C_{1-6}$ alkylthio; hydroxy; $C_{7-19}$ aralkyloxy which may have substituents; $C_{6-14}$ aryloxy which may have substituents; amino; mono-$C_{1-6}$ alkylamino; di-$C_{1-6}$ alkylamino; 5 to 7 membered saturated cyclic amino which may have substituents and may be condensed with a benzene ring; 5 to 7 membered non-aromatic heterocyclic groups which may have substituents; formyl; carboxy; $C_{6-14}$ aryl-carbonyl which may have substituents; $C_{6-14}$ aryl-carbamoyl which may have substituents; aromatic hetero ring-carbamoyl which may have substituents; $C_{1-6}$ alkoxy-carbonyl; optionally halogenated $C_{1-6}$ alkyl-carboxamide; $C_{6-14}$ aryl-carboxamide which may have substituents; $C_{7-19}$ aralkyl-carboxamide which may have substituents; aromatic hetero ring-carboxamide which may have substituents; N-($C_{6-14}$ aryl-carbonyl which may have substituents)-N—$C_{1-6}$ alkylamino; $C_{6-14}$ aryl-aminocarbonylamino which may have substituents; $C_{6-14}$ arylsulfonylamino which may have substituents; $C_{6-14}$ aryl-carbonyloxy which may have substituents; oxo; carboxy-$C_{1-6}$ alkyl; $C_{1-6}$ alkoxy-carbonyl-$C_{1-6}$ alkyl; $C_{7-19}$ aralkyl which may have substituents; aromatic hetero ring-$C_{1-6}$ alkoxy; and cyano;

(8) an antagonist according to the above (1), wherein $Ar^1$ is piperidinyl, piperazinyl, pyrrolidinyl, dihydropyridyl or tetrahydropyridyl; each of which may have 1 or 2 substituents selected from the group consisting of oxo, $C_{6-14}$ aryl which may have substituents, hydroxy, $C_{7-19}$ aralkyloxy-carbonyl, and $C_{7-19}$ aralkyl;

(9) an antagonist according to the above (1), wherein the "spacer having a main chain of 1 to 6 atoms" for X and Y is a bivalent group consisting of 1 to 3 species selected from —O—, —S—, —CO—, —SO—, —SO$_2$—, —NR$^8$— (R$^8$ is hydrogen atom, optionally halogenated $C_{1-6}$ alkyl, optionally halogenated $C_{1-6}$ alkyl-carbonyl, optionally halogenated $C_{1-6}$ alkylsulfonyl), and a bivalent $C_{1-6}$ non-cyclic hydrocarbon group which may have substituents;

(10) an antagonist according to the above (1), wherein X is —CONR$^{8c}$—, —NR$^{8c}$CO—, —CH=CH—CONR$^{8c}$— or —SO$_2$NR$^{8c}$— wherein R$^{8c}$ is hydrogen atom or $C_{1-6}$ alkyl;

(11) an antagonist according to the above (1), wherein Y is an optionally halogenated bivalent $C_{1-6}$ non-cyclic hydrocarbon group;

(12) an antagonist according to the above (1), wherein Ar is a ring of the formula:

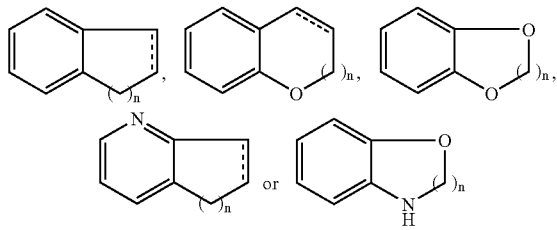

wherein ==== is a single bond or double bond, n is an integer of 1 to 4;

(13) an antagonist according to the above (1), wherein $R^1$ and $R^2$ are hydrogen atom or $C_{1-6}$ alkyl which may have substituents; or $R^1$ and $R^2$, together with the adjacent nitrogen atom, form a 3 to 8 membered nitrogen-containing hetero ring;

(14) an antagonist according to the above (1), which is an agent for preventing or treating diseases caused by a melanin-concentrating hormone;

(15) an antagonist according to the above (1), which is an agent for preventing or treating obesity;

(16) an antagonist according to the above (1), which is an anorectic agent;

(17) a pharmaceutical, which comprises a melanin-concentrating hormone antagonist in combination with at least one species selected from the group consisting of an agent for treating diabetes, an agent for treating hypertension and an agent for treating arteriosclerosis;

(18) a compound of the formula:

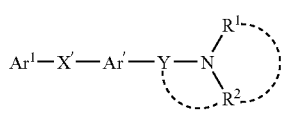

(I')

wherein $Ar^1$ is a cyclic group which may have substituents;

Ar' is a ring of the formula:

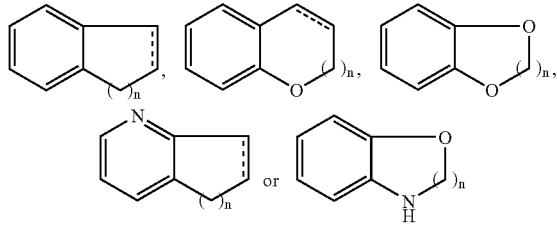

wherein ==== is a single bond or double bond, n is an integer of 1 to 4, and each ring may have substituents;

X' is —CONR$^{8c}$—, —NR$^{8c}$CO—, —CH=CH—CONR$^{8c}$— or —SO$_2$NR$^{8c}$— where R$^{8c}$ is hydrogen atom or $C_{1-6}$ alkyl;

Y is a spacer having a main chain of 1 to 6 atoms;

$R^1$ and $R^2$ are independently hydrogen atom or a hydrocarbon group which may have substituents; $R^1$ and $R^2$, together with the adjacent nitrogen atom, may form a nitrogen-containing hetero ring which may have substituents; or $R^2$, together with the adjacent nitrogen atom and Y, may form a nitrogen-containing hetero ring which may have substituents;

provided that Ar' is a ring of the formula:

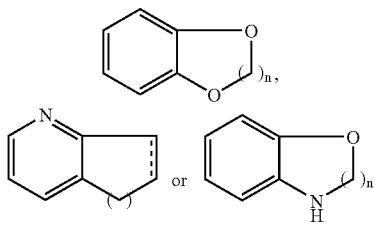

wherein symbols have the same meanings as defined above, and each ring may have substituents, when X' is —SO$_2$NH—;

and provided that Ar$^1$ is not biphenylyl which may be substituted, when X' is —CONH— and Ar' is any one of benzopyran, dihydrobenzopyran, dihyrobenzoxazine, dihydrobenzoxazole or tetrahydrobenzoxazepine;

(excluding N-[2-(N,N-dimethylamino)methyl-6-tetralinyl]-4-biphenylylcarboxamide); or a salt thereof;

(19) a compound of the formula:

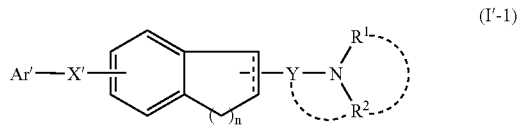

(I'-1)

wherein $Ar^1$ is a cyclic group which may have substituents;

==== is a single bond or double bond;

n is an integer of 1 to 4;

X' is —CONR$^{8c}$—, —NR$^{8c}$CO— or —CH=CH—CONR$^{8c}$— where R$^{8c}$ is hydrogen atom or $C_{1-6}$ alkyl;

Y is a spacer having a main chain of 1 to 6 atoms;

$R^1$ and $R^2$ are independently hydrogen atom or a hydrocarbon group which may have substituents; $R^1$ and $R^2$, together with the adjacent nitrogen atom, may form a nitrogen-containing hetero ring which may have substituents; or R², together with the adjacent nitrogen atom and Y, may form a nitrogen-containing hetero ring which may have substituents;

a ring of the formula:

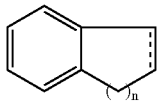

wherein symbols have the same meanings as defined above, may have further substituents;

provided that N-[2-(N,N-dimethylamino)methyl-6-tetralinyl]-4-biphenylylcarboxamide is excluded; or a salt thereof;

(20) a compound according to the above (19), which is of the formula:

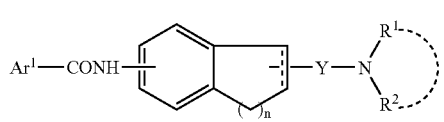

(I'-2)

wherein R¹ and R² are independently hydrogen atom or a hydrocarbon group which may have substituents; R¹ and R², together with the adjacent nitrogen atom, may form a nitrogen-containing hetero ring which may have substituents; the other symbols have the same meanings as defined in the above (19);

(21) a compound according to the above (20), wherein Ar¹ is an aromatic group which may have substituents; and "a hydrocarbon group which may have substituents" for R¹ and R² is "$C_{1-6}$ alkyl which may have substituents.";

(22) a compound of the formula:

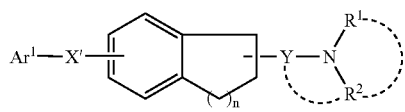

(I'-3)

wherein Ar¹ is a cyclic group which may have substituents;
n is an integer of 1 to 4;
X' is —$CONR^{8c}$—, —$NR^{8c}CO$— or —CH=CH—$CONR^{8c}$— where $R^{8c}$ is hydrogen atom or $C_{1-6}$ alkyl;
Y is a spacer having a main chain of 1 to 6 atoms;
R¹ and R² are independently hydrogen atom or a hydrocarbon group which may have substituents; R¹ and R², together with the adjacent nitrogen atom, may form a nitrogen-containing hetero ring which may have substituents; or R², together with the adjacent nitrogen atom and Y, may form a nitrogen-containing hetero ring which may have substituents;

a ring of the formula:

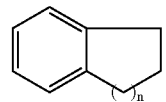

wherein n has the same meaning as defined above, may have further substituents;

provided that N-[2-(N,N-dimethylamino)methyl-6-tetralinyl]-4-biphenylylcarboxamide is excluded; or a salt thereof;

(23) a compound according to the above (22), which is of the formula:

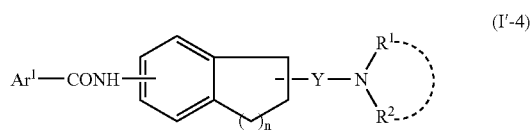

(I'-4)

wherein R¹ and R² are independently hydrogen atom or a hydrocarbon group which may have substituents; R¹ and R², together with the adjacent nitrogen atom, may form a nitrogen-containing hetero ring which may have substituents; the other symbols have the same meanings as defined in the above (22);

(24) a compound according to the above (23), wherein Ar¹ is an aromatic group which may have substituents; and "a hydrocarbon group which may have substituents" for R¹ and R² is "$C_{1-6}$ alkyl which may have substituents";

(25) a compound of the formula:

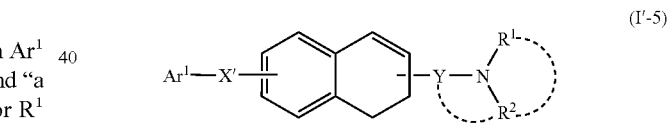

(I'-5)

wherein Ar¹ is a cyclic group which may have substituents;
X' is —$CONR^{8c}$—, —$NR^{8c}CO$— or —CH=CH—$CONR^{8c}$— where $R^{8c}$ is hydrogen atom or $C_{1-6}$ alkyl;
Y is a spacer having a main chain of 1 to 6 atoms;
R¹ and R² are independently hydrogen atom or a hydrocarbon group which may have substituents; R¹ and R², together with the adjacent nitrogen atom, may form a nitrogen-containing hetero ring which may have substituents; or R², together with the adjacent nitrogen atom and Y, may form a nitrogen-containing hetero ring which may have substituents;

a ring of the formula:

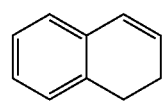

may have further substituents; or a salt thereof;

(26) a compound according to the above (25), which is of the formula:

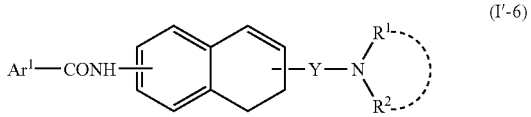

wherein $R^1$ and $R^2$ are independently hydrogen atom or a hydrocarbon group which may have substituents; $R^1$ and $R^2$, together with the adjacent nitrogen atom, may form a nitrogen-containing hetero ring which may have substituents; the other symbols have the same meanings as defined in the above (25);

(27) a compound according to the above (26), wherein $Ar^1$ is an aromatic group which may have substituents; and "a hydrocarbon group which may have substituents for $R^1$ and $R^2$ is "$C_{1-6}$ alkyl which may have substituents";

(28) a compound of the formula:

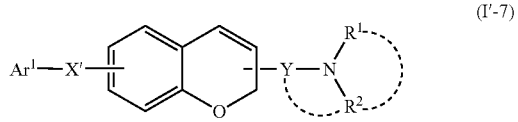

wherein $Ar^1$ is a cyclic group which may have substituents; X' is —$CONR^{8c}$—, —$NR^{8c}CO$—, —CH=CH—$CONR^{8c}$— or —$SO_2NR^{8c}$— where $R^{8c}$ is hydrogen atom or $C_{1-6}$ alkyl;

Y is a spacer having a main chain of 1 to 6 atoms;

$R^1$ and $R^2$ are independently hydrogen atom or a hydrocarbon group which may have substituents; $R^1$ and $R^2$, together with the adjacent nitrogen atom, may form a nitrogen-containing hetero ring which may have substituents; or $R^2$, together with the adjacent nitrogen atom and Y, may form a nitrogen-containing hetero ring which may have substituents;

a ring of the formula:

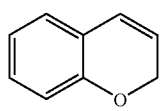

may have further substituents;

provided that $Ar^1$ is not biphenylyl which may be substituted, when X' is —CONH—; or a salt thereof;

(29) a compound of the formula:

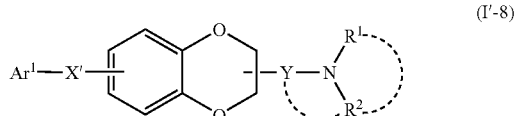

wherein $Ar^1$ is a cyclic group which may have substituents; X' is —$CONR^{8c}$—, —$NR^{8c}CO$—, —CH=CH—$CONR^{8c}$— or —$SO_2NR^{8c}$— where $R^{8c}$ is hydrogen atom or $C_{1-6}$ alkyl;

Y is a spacer having a main chain of 1 to 6 atoms;

$R^1$ and $R^2$ are independently hydrogen atom or a hydrocarbon group which may have substituents; $R^1$ and $R^2$, together with the adjacent nitrogen atom, may form a nitrogen-containing hetero ring which may have substituents; or $R^2$, together with the adjacent nitrogen atom and Y, may form a nitrogen-containing hetero ring which may have substituents;

a ring of the formula:

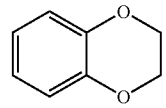

may have further substituents; or a salt thereof;

(30) a compound of the formula:

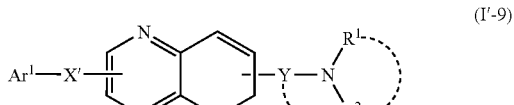

wherein $Ar^1$ is a cyclic group which may have substituents; X' is —$CONR^{8c}$—, —$NR^{8c}CO$—, —CH=CH—$CONR^{8c}$— or —$SO_2NR^{8c}$— where $R^{8c}$ is hydrogen atom or $C_{1-6}$ alkyl;

Y is a spacer having a main chain of 1 to 6 atoms;

$R^1$ and $R^2$ are independently hydrogen atom or a hydrocarbon group which may have substituents; $R^1$ and $R^2$, together with the adjacent nitrogen atom, may form a nitrogen-containing hetero ring which may have substituents; or $R^2$, together with the adjacent nitrogen atom and Y, may form a nitrogen-containing hetero ring which may have substituents;

a ring of the formula:

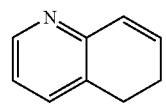

may have further substituents; or a salt thereof;

(31) a compound of the formula:

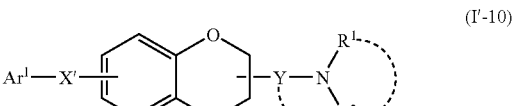

wherein $Ar^1$ is a cyclic group which may have substituents; X' is —$CONR^{8c}$—, —$NR^{8c}CO$—, —CH=CH—$CONR^{8c}$— or —$SO_2NR^{8c}$— where $R^{8c}$ is hydrogen atom or $C_{1-6}$ alkyl;

Y is a spacer having a main chain of 1 to 6 atoms;

$R^1$ and $R^2$ are independently hydrogen atom or a hydrocarbon group which may have substituents; $R^1$ and $R^2$, together with the adjacent nitrogen atom, may form a nitrogen containing hetero ring which may have substituents; or R², together with the adjacent nitrogen atom and Y, may form a nitrogen-containing hetero ring which may have substituents;

a ring of the formula:

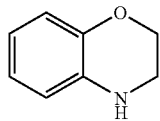

may have further substituents;

provided that Ar¹ is not biphenylyl which may be substituted, when X' is —CONH—; or a salt thereof;

(32) a pharmaceutical composition which comprises a compound as defined in anyone of the above (18), (19), (22), (25), (26), (28), (29), (30) and (31);

(33) a prodrug of a compound as defined in any one of the above (18), (19), (22), (25), (26), (28), (29), (30) and (31);

(34) a compound according to the above (18), which is
N-[2-(N,N-dimethylamino)methyl-6-tetralinyl]-(4'-methoxybiphenyl-4-yl)carboxamide;
4'-fluoro-N-[6-[(N,N-dimethylamino)methyl]-7,8-dihydro-2-naphthalenyl][1,1'-biphenyl]-4-carboxamide;
4'-fluoro-N-[6-(1-piperidinylmethyl)-7,8-dihydro-2-naphthalenyl][1,1'-biphenyl]4-carboxamide;
4'-fluoro-N-[6-[(N,N-dimethylamino)methyl]-5,6,7,8-tetrahydro-2-naphthalenyl][1,1'-biphenyl]-4-carboxamide;
(+)-4'-fluoro-N-[6-[(N,N-dimethylamino)methyl]-5,6,7,8-tetrahydro-2-naphthalenyl][1,1'-biphenyl]-4-carboxamide;
(−)-4'-fluoro-N-[6-[(N,N-dimethylamino)methyl]-5,6,7,8-tetrahydro-2-naphthalenyl][1,1'-biphenyl]-4-carboxamide;
4'-chloro-N-[3-[(N,N-dimethylamino)methyl]-2H-chromen-7-yl][1,1'-biphenyl]-4-carboxamide;
4'-fluoro-N-[6-(1-pyrrolidinylmethyl)-7,8-dihydro-2-naphthalenyl][1,1'-biphenyl]-4-carboxamide;
N-[3-[(dimethylamino)methyl]-2H-chromen-7-yl]-4'-fluoro-[1,1'-biphenyl]-4-carboxamide;
4'-chloro-N-[6-[(dimethylamino)methyl]-5-methyl-7,8-dihydro-2-naphthalenyl][1,1'-biphenyl]-4-carboxamide;
6-(4-methoxyphenyl)-N-[5-methyl-6-(1-pyrrolidinylmethyl)-7,8-dihydro-2-naphthalenyl]nicotinamide;
4'-chloro-N-[7-[(dimethylamino)methyl]-5,6-dihydro-3-quinolinyl][1,1'-biphenyl]-4-carboxamide;
4-(4-chlorophenyl)-N-[6-(1-pyrrolidinylmethyl)-7,8-dihydro-2-naphthalenyl]-3,6-dihydro-[(2H)-pyridinecarboxamide;
N-[6-[(dimethylamino)methyl]-7,8-dihydro-2-naphthalenyl]-4-(4-fluorophenyl)-1-piperidinecarboxamide;
4-(4-methoxyphenyl)-N-[6-(1-pyrrolidinylmethyl)-5-methyl-7,8-dihydro-2-naphthalenyl-1-piperidinecarboxamide;
4'-fluoro-N-[6-[2-(1-pyrrolidinyl)ethyl]-7,8-dihydro-2-naphthalenyl][1,1'-biphenyl]-4-carboxamide;
4'-chloro-N-[6-[2-(1-pyrrolidinyl)ethyl]-7,8-dihydro-2-naphthalenyl][1,1'-biphenyl]-4-carboxamide;
4'-chloro-N-[2-[(dimethylamino)methyl]-3,4-dihydro-2H-1,4-benzoxazin-6-yl][1,1'-biphenyl]-4-carboxamide;
4-(4-methoxyphenyl)-N-[5-methyl-6-(1-pyrrolidinylmethyl)-7,8-dihydro-2-naphthalenyl]-1-piperidinecarboxamide;
4-(4-chlorophenyl)-N-[6-[(4-methyl-1-piperazinyl)methyl]-7,8-dihydro-2-naphthalenyl]-1-piperidinecarboxamide;
4'-chloro-N-[2-[(dimethylamino)methyl]-1H-inden-6-yl][1,1'-biphenyl]-4-carboxamide;
4'-fluoro-N-[2-(1-pyrrolidinylmethyl)-3,4-dihydro-2H-1,4-benzoxazin-6-yl][1,1'-biphenyl]-4-carboxamide;
4'-fluoro-N-[5-methyl-6-[(4-methyl-1-piperazinyl)methyl]-7,8-dihydro-2-naphthalenyl][1,1'-biphenyl]-4-carboxamide;
4'-chloro-N-[5-methyl-6-[(4-methyl-1-piperazinyl)methyl]-7,8-dihydro-2-naphthalenyl][1,1'-biphenyl]-4-carboxamide; or
4-(4-chlorophenyl)-N-[5-methyl-6-[(4-methyl-1-piperazinyl)methyl]-7,8-dihydro-2-naphthalenyl]-1-piperidinecarboxamide;

(35) a method for preventing or treating diseases caused by a melanin-concentrating hormone in a mammal in need thereof, which comprises administering to said mammal an effective amount of a compound or a salt thereof as defined in the above (1);

(36) a method for preventing or treating obesity in a mammal in need thereof, which comprises administering to said mammal an effective amount of a compound or a salt thereof as defined in the above (1);

(37) use of a compound or a salt thereof as defined in the above (1), for the manufacture of a pharmaceutical preparation for preventing or treating diseases caused by a melanin-concentrating hormone; and

(38) use of a compound or a salt thereof as defined in the above (1), for the manufacture of a pharmaceutical preparation for preventing or treating obesity.

Examples of "cyclic group" in the "cyclic group which may have substituents" for Ar¹ include aromatic groups, non-aromatic cyclic hydrocarbon groups, non-aromatic heterocyclic groups.

Here, examples of "aromatic groups" include monocyclic aromatic groups, condensed aromatic groups, and ring assembly aromatic groups.

Examples of the concerned monocyclic aromatic groups include univalent groups which can be formed by removing an optional one hydrogen atom from a monocyclic aromatic ring. Example of the "monocyclic aromatic ring" include a benzene ring and a 5 or 6 membered aromatic hetero ring.

Examples of the "5 or 6 membered aromatic hetero ring" include a 5 or 6 membered aromatic hetero ring containing one or more (for example, 1 to 3) hetero atom selected from nitrogen, sulfur and oxygen atom in addition to a carbon atom. Concretely, thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, furazan, etc., can be mentioned.

Concrete examples of the "monocyclic aromatic groups" include phenyl, 2- or 3-thienyl, 2-, 3-, or 4-pyridyl, 2- or 3-furyl, 2-, 4- or 5-thiazonyl, 2-, 4- or 5-oxazolyl, 1-, 3- or 4-pyrazolyl, 2-pyrazinyl, 2-, 4- or 5-pyrimidinyl, 1-, 2- or 3-pyrrolyl, 1-, 2- or 4-imidazolyl, 3- or 4-pyridazinyl, 3-isothiazolyl, 3-isooxazolyl. 1,2,4-oxadiazol-5-yl, 1,2,4-oxadiazol-3-yl.

The "condensed aromatic groups" mean a univalent group that can be formed by removing an optional one hydrogen atom from condensed polycyclic (preferably bicyclic to tetracyclic, more preferably bicyclic or tricyclic) aromatic rings. Examples of the "condensed aromatic groups" include condensed polycyclic aromatic hydrocarbons, condensed polycyclic aromatic hetero rings.

Examples of the "condensed polycyclic aromatic hydrocarbons" include $C_{9-14}$ condensed polycyclic (bicyclic or tricyclic) aromatic hydrocarbons (e.g. naphthalene, indene, fluorene, anthracene, etc.).

Examples of the "condensed polycyclic aromatic hetero rings" include 9 to 14 membered, preferably, 9 or 10 membered, condensed polycyclic aromatic hetero rings containing one or more (for instance, 1 to 4 atoms) hetero atoms selected from nitrogen, sulfur and oxygen atom in addition to carbon atoms. Concrete examples of the "condensed polycyclic aromatic hetero rings" include benzofuran, benzimidazole, benzoxazole, benzothiazole, benzisothiazole, naphtho[2,3-b]thiophene, isoquinoline, quinoline, indole, quinoxaline, phenanthridine, phenothiadine, phenoxazine, phthalazine, naphthylidine, quinazoline, cinnoline, carbazole, β-carboline, acridine, phenazine, phthalimide, thioxanthene.

Concrete examples of "condensed aromatic groups" include 1-naphthyl; 2-naphthyl; 2-, 3-, 4-, 5- or 8-quinolyl; 1-, 3-, 4-, 5-, 6-, 7- or 8-isoquinolyl; 1-, 2-, 3-, 4-, 5-, 6- or 7-indolyl; 1-, 2-, 4- or 5-isoindolyl; 1-, 5- or 6-phthalazinyl; 2-, 3- or 5-quinoxalinyl; 2-, 3-, 4-, 5- or 6-benzofuranyl; 2-, 4-, 5- or 6-benzothiazolyl; 1-, 2-, 4-, 5- or 6-benzimidazolyl; 1-, 2-, 3- or 4-fluorenyl; thioxanthenyl.

"Ring assembly aromatic group" means a group formed by removing an optional one hydrogen atom from an aromatic ring assembles in which 2 or more (preferably 2 or 3) aromatic rings are directly bonded by single bonds, and in which the number of bonds which directly bond the rings, is less by one than the number of ring systems.

Examples of the aromatic ring assembles include an aromatic ring assembles formed by 2 or 3 (preferably 2) species selected from $C_{6-14}$ monocyclic or condensed polycyclic aromatic hydrocarbons (e.g. benzene and naphthalene) and 5 to 10 membered (preferably 5 or 6 membered) aromatic hetero rings.

Preferable example of the aromatic ring assembles include aromatic ring assembles comprising 2 or 3 aromatic rings selected from benzene, naphthalene, pyridine, pyrimidine, thiophene, furan, thiazole, isothiazole, oxazole, isoxazole, 1,2,4-oxadiazole, 1,3,4-oxadiazole, 1,2,4-thiadiazole, 1,3,4-thiadiazole, quinoline, isoquinoline, indole, benzothiophene, benzoxazole, benzothiazole, benzofuran and pyrrole.

Concrete examples of the "ring assembly aromatic groups" include 2-, 3- or 4-biphenyl; 3-(1-naphthyl)-1,2,4-oxadiazol-5-yl; 3-(2-naphthyl)-1, 2, 4-oxadiazol-5-yl; 3-(2-benzofuranyl)-1,2,4-oxadiazol-5-yl; 3-phenyl-1,2,4-oxadiazol-5-yl; 3-(2-benzoxazolyl)-1,2,4-oxadiazol-5-yl; 3-(3-indolyl)-1,2,4-oxadiazol-5-yl; 3-(2-indolyl)-1,2,4-oxadiazol-5-yl; 4-phenylthiazol-2-yl; 4-(2-benzofuranyl) thiazol-2-yl; 4-phenyl-1,3-oxazol-5-yl; 5-phenyl-isothiazol-4-yl; 5-phenyloxazol-2-yl; 4-(2-thienyl)phenyl; 4-(3-thienyl)phenyl; 3-(3-pyridyl)phenyl; 4-(3-pyridyl)phenyl; 6-phenyl-3-pyridyl; 5-phenyl-1,13,4-oxadiazol-2-yl; 4-(2-naphthyl)phenyl; 4-(2-benzofuranyl)phenyl; 4,4'-terphenyl; 5-phenyl-2-pyridyl; 2-phenyl-5-pyrimidinyl; 4-(4-pyridyl) phenyl; 2-phenyl-1,3-oxazol-5-yl; 2,4-diphenyl-1,3-oxazol-5-yl; 3-phenyl-isoxazol-5-yl; 5-phenyl-2-furyl; 4-(2-furyl) phenyl; 3-(4-pyridyl)pyrrolyl.

Preferable groups among the above "aromatic groups" are "$C_{6-14}$ monocyclic or condensed polycyclic aromatic hydrocarbon groups (preferably, phenyl, etc.)", "a group formed by removing an optional one hydrogen atom from an aromatic ring assembles in which 2 or 3 $C_{6-14}$ monocyclic or condensed polycyclic aromatic hydrocarbon groups are directly bonded by single bonds (preferably, 2-, 3- or 4-biphenylyl; 4,4-terphenyl, etc.)" and "a group formed by removing an optional one hydrogen atom from an aromatic ring assembles in which a $C_{6-14}$ monocyclic or condensed polycyclic aromatic hydrocarbon and 5 to 10 membered aromatic hetero ring are directly bonded by a single bond (preferably, 6-phenyl-3-pyridyl, 5-phenyl-2-pyridyl, etc.)".

Examples of "non-aromatic cyclic hydrocarbon groups" include $C_{3-8}$ Cycloalkyl, $C_{3-8}$ cycloalkenyl.

Here, concrete examples of $C_{3-8}$ cycloalkyl include cyclopropyl, cyclobutyl, cyclopentyl, cyclohexyl, cycloheptyl, cyclooctyl.

Concrete examples of $C_{3-8}$ cycloalkenyl include cyclopropenyl, cyclobutenyl, cyclopentenyl, cyclohexenyl, cycloheptenyl, cyclooctenyl.

Among the above "non-aromatic cyclic hydrocarbon groups", $C_{3-8}$ cycloalkyl is preferable, and cyclohexyl is particularly preferable.

Examples of "non-aromatic heterocyclic groups" include monocyclic non-aromatic heterocyclic groups, condensed polycyclic non-aromatic heterocyclic groups.

Examples of the "monocyclic non-aromatic heterocyclic groups" include univalent groups formed by removing an optional one hydrogen atom from monocyclic non-aromatic hetero ring. Examples of the "monocyclic non-aromatic heterocyclic groups" include 5 to 8 membered monocyclic non-aromatic heterocyclic groups containing one or more (e.g. 1 to 3) hetero atoms selected from nitrogen, sulfur and oxygen atom in addition to carbon atoms. Concretely, tetrahydrothiophene, tetrahydrofuran, pyrrolidine, imidazoline, imidazolidine, pyrazoline, pyrazolidine, tetrahydrothiazole, tetrahydroisothiazole, tetrohydrooxazole, tetrahydroisoxazole, piperidine, tetrahydropyridine, dihydropyridine, piperazine, morpholine, thiomorpholine, tetrahydropyrimidine, tetrahydropyridazine, hexamethyleneimine, etc. can be mentioned.

"Condensed polycyclic non-aromatic heterocyclic group" means a univalent group formed by removing an optional one hydrogen atom from a condensed polycyclic (preferably bicyclic to tetracyclic, more preferably bicyclic or tricyclic) non-aromatic hetero ring. Examples of the "condensed polycyclic non-aromatic hetero ring" include 9 to 14 membered, preferably 9 or 10 membered condensed polycyclic non-aromatic hetero rings which contain one or more (e.g. 1 to 4) hetero atoms selected from nitrogen, sulfur and oxygen atom in addition to carbon atoms.

Concretely, dihydrobenzofuran, dihydrobenzimidazole, dihydrobenzoxazole, dihydrobenzothiazole, dihydrobenzisothiazole, dihydronaphtho[2,3-b]thiophene, tetrahydroquinoline, indoline, isoindoline, tetrahydroquinoxaline, tetrahydrophenanthridine, hexahydrophenothiadine, hexahydrophenoxazine, tetrahydrophthalazine, tetrahydronaphthylidine, tetrahydroquinazoline, tetrahydrocinnoline, tetrahydrocarbazole, tetrahydro-β-carboline, tetrahydroacridine, tetrahydrophenazine, tetrahydrothioxantene, etc., can be mentioned.

Among the above "non-aromatic heterocyclic groups", "5 to 8 membered monocyclic non-aromatic heterocyclic groups (preferably piperidinyl; piperazinyl; pyrrolidinyl; dihydropyridyl; tetrahydropyridyl, etc.)" are preferable.

Examples of "substituents" in the "cyclic group which may have substituents" for $Ar^1$ include oxo, halogen atoms (e.g. fluorine, chlorine, bromine, iodine, etc.), $C_{1-3}$ alkylenedioxy (e.g. methylenedioxy, ethylenedioxy, etc.), nitro, cyano, optionally halogenated $C_{1-6}$ alkyl, hydroxy-$C_{1-6}$ alkyl, carboxy-$C_{1-6}$ alkyl, $C_{1-6}$ alkoxy-carbonyl-$C_{1-6}$ alkyl, $C_{6-14}$ aryloxy-$C_{1-6}$ alkyl (e.g. phenoxymethyl, etc.), $C_{1-6}$ alkyl-$C_{6-14}$ aryl-$C_{1-6}$ alkenyl (e.g. methylphenylethenyl, etc.), optionally halogenated $C_{3-6}$ cycloalkyl, optionally halogenated $C_{1-6}$ alkoxy, optionally halogenated $C_{1-6}$ alkylthio, $C_{7-19}$ aralkyl which may have substituents, hydroxy, $C_{6-14}$ aryloxy which may have substituents, $C_{7-19}$ aralkyloxy which may have substituents, $C_{6-14}$ aryl-carbamoyl which may have substituents, amino, amino-$C_{1-6}$ alkyl (e.g. aminomethyl, aminoethyl, aminopropyl, aminobutyl, etc.), mono-$C_{1-6}$ alkylamino (e.g. methylamino, ethylamino, propylamino, isopropylamino, butylamino, etc.), di-$C_{1-6}$ alkylamino (e.g. dimethylamino, diethylamino, dipropylamino, dibutylamino, ethylmethylamino, etc.), mono-$C_{1-6}$ alkylamino-$C_{1-6}$ alkyl (e.g. methylaminomethyl, ethylaminomethyl, propylaminomethyl, isopropylaminoethyl, butylaminoethyl, etc.), di-$C_{1-6}$ alkylamino-$C_{1-6}$ alkyl (e.g. dimethylaminomethyl, diethylaminomethyl, dipropylaminomethyl, diisopropylaminoethyl, dibutylaminoethyl, etc.), 5 to 7 membered saturated cyclic amino which may have substituents, 5 to 7 membered non-aromatic heterocyclic groups which may have substituents, acyl, acylamino, acyloxy, aromatic hetero ring-$C_{1-6}$ alkoxy.

The "cyclic group" for $Ar^1$ may have 1 to 5, preferably 1 to 3, of the above-mentioned substituents at a substitutable position on the cyclic group. When the number of substituents is 2 or more, each substituents can be the same or different.

Also, when the "cyclic group" for $Ar^1$ is a non-aromatic cyclic hydrocarbon group or a non-aromatic heterocyclic group, the "cyclic group" may have as its substituents, $C_{6-14}$ aryl which may have substituents, and 5 to 10 membered aromatic heterocyclic groups which may have substituents.

Here, the groups exemplified as "substituents" in the "5 to 7 membered saturated cyclic amino which may have substituents" mentioned hereinafter, can be mentioned as "$C_{6-14}$ aryl which may have substituents, and "5 to 10 membered aromatic heterocyclic groups which may have substituents". The number of substituents is, for instance, 1 to 3. When the number of substituents is 2 or more, each substituents can be the same or different.

Concrete examples of the above optionally halogenated $C_{1-6}$ alkyl include $C_{1-6}$ alkyl (e.g. methyl, ethyl, propyl, isopropyl, butyl, isobutyl, sec-butyl, tert-butyl, pentyl, hexyl, etc.) which may have 1 to 5, preferably 1 to 3, halogen atoms (e.g. fluorine, chlorine, bromine, iodine, etc.). Concrete examples include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl.

The $C_{1-6}$ alkyl in the above "optionally halogenated $C_{1-6}$ alkyl" can be mentioned as the $C_{1-6}$ alkyl in the above "hydroxy-$C_{1-6}$ alkyl", "carboxy-$C_{1-6}$ alkyl" and "$C_{1-6}$ alkoxy-carbonyl-$C_{1-6}$ alkyl". Examples of $C_{1-6}$ alkoxy in the "$C_{1-6}$ alkoxy-carbonyl-$C_{1-6}$ alkyl" include methoxy, ethoxy, propoxy, butoxy, pentyloxy.

Examples of the above "optionally halogenated $C_{3-6}$ cycloalkyl" include $C_{3-6}$ cycloalkyl (e.g. cyclopropyl, cyclobutyl, cyclopentyl, cyclohexyl, etc.) which may have 1 to 5, preferably 1 to 3, halogen atoms (e.g. fluorine, chlorine, bromine, iodine, etc.). Concrete examples include cyclopropyl, cyclobutyl, cyclopentyl, cyclohexyl, 4,4-dichlorocyclohexyl, 2,2,3,3-tetrafluorocyclopentyl, 4-chlorocyclohexyl.

Examples of the above "optionally halogenated $C_{1-6}$ alkoxy" include $C_{1-6}$ alkoxy (e.g. methoxy, ethoxy, propoxy, butoxy, pentyloxy, etc.) which may have 1 to 5, preferably 1 to 3, halogen atoms (e.g. fluorine, chlorine, bromine, iodine, etc.). Concrete examples include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy.

Examples of the above "optionally halogenated $C_{1-6}$ alkylthio" include $C_{1-6}$ alkylthio (e.g. methylthio, ethylthio, propylthio, isopropylthio, butylthio, sec-butylthio, tert-butylthio, etc.) which may have 1 to 5, preferably 1 to 3, halogen atoms (e.g. fluorine, chlorine, bromine, iodine, etc.). Concrete examples include methylthio, difluoromethylthio, trifluoromethylthio, ethylthio, propylthio, isopropylthio, butylthio, 4,4,4-trifluorobutylthio, pentylthio, hexylthio.

Examples of the "$C_{7-19}$ aralkyl" in the above "$C_{7-19}$ aralkyl which may have substituents" include benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl. Benzyl is particularly preferable.

Examples of the "substituents" in the above "$C_{7-19}$ aralkyl which may have substituents" include halogen atom (e.g. fluorine, chlorine, bromine, iodine, etc.), $C_{1-3}$ alkylene dioxy (e.g. methylenedioxy, ethylenedioxy, etc.), nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino (e.g. methylamino, ethylamino, propylamino, isopropylamino, butylamino, etc.), di-$C_{1-6}$ alkylamino (e.g. dimethylamino, diethylamino, dipropylamino, dibutylamino, ethylmethylamino, etc.), amino-$C_{1-6}$ alkyl (e.g. aminomethyl, aminoethyl, aminopropyl, aminobutyl, etc.), mono-$C_{1-6}$ alkylamino-$C_{1-6}$ alkyl (e.g. methylaminomethyl, ethylaminomethyl, propylaminomethyl, isopropylaminoethyl, butylaminoethyl, etc.), di-$C_{1-6}$ alkylamino-$C_{1-6}$ alkyl (e.g. dimethylaminomethyl, diethylaminomethyl, dipropylaminomethyl, diisopropylaminoethyl, dibutylaminoethyl, etc.), formyl, carboxy, carbamoyl, thiocarbamoyl, optionally halogenated $C_{1-6}$ alkyl-carbonyl, $C_{1-6}$ alkoxy-carbonyl (e.g., methoxycarbonyl, ethoxycarbonyl, propoxycarbonyl, tert-butoxycarbonyl, etc.), mono-$C_{1-6}$ alkyl-carbamoyl (e.g., methylcarbamoyl, ethylcarbamoyl, etc.), di-$C_{1-6}$ alkyl-carbamoyl (e.g. dimethylcarbamoyl, diethylcarbamoyl, ethylmethylcarbamoyl, etc.), optionally halogenated $C_{1-6}$ alkylsulfonyl, formylamino, optionally halogenated $C_{1-6}$ alkylcarboxamide, $C_{1-6}$ alkoxy-carboxamide (e.g. methoxycarboxamide, ethoxycarboxamide, prpoxycarboxamide, butoxycarboxamide, etc.), $C_{1-6}$ alkylsulfonylamino (e.g. methylsulfonylamino, ethylsulfonylamino, etc.), $C_{1-6}$ alkyl-carbonyloxy(e.g. acetoxy, propanoyloxy, etc.), $C_{1-6}$ alkoxy-carbonyloxy (e.g. methoxycarbonyloxy, ethoxycarbonyloxy, propoxycarbonyloxy, butoxycarbonyloxy, etc.) mono-$C_{1-6}$ alkyl-carbamoyloxy (e.g. methylcarbamoyloxy, ethylcarbamoyloxy, etc.), di-$C_{1-6}$ alkyl-carbamoyloxy (e.g. dimethylcarbamoyloxy, diethylcarbamoyloxy, etc.). The number of substituents is, for instance, 1 to 5, preferably 1 to 3. When the number of substituents is 2 or more, each substituents can be the same or different.

As "optionally halogenated $C_{1-6}$ alkyl", "optionally halogenated $C_{3-6}$ cycloalkyl", "optionally halogenated $C_{1-6}$ alkoxy" and "optionally halogenated $C_{1-6}$ alkylthio", those exemplified as "substituents" in the above "cyclic group which may have substituents" can be used respectively.

Examples of the above "optionally halogenated $C_{1-6}$ alkylcarbonyl" include $C_{1-6}$ alkyl-carbonyl (e.g. acetyl, propanoyl, butanoyl, pentanoyl, hexanoyl, etc.) which may have 1 to 5, preferably 1 to 3, halogen atoms (e.g., fluorine, chlorine, bromine, iodine, etc.). Concrete examples include acetyl, monochloroacetyl, trifluoroacetyl, trichloroacetyl, propanoyl, butanoyl, pentanoyl, hexanoyl.

Examples of the above "optionally halogenated $C_{1-6}$ alkylsulfonyl" include $C_{1-6}$ alkylsulfonyl (e.g. methylsulfonyl, ethylsulfonyl, propylsulfonyl, isopropylsulfonyl, butylsulfonyl, sec-butylsulfonyl, tert-butylsulfonyl, etc.) which may have 1 to 5, preferably 1 to 3, halogen atoms (e.g., fluorine, chlorine, bromine, iodine, etc.). Concrete examples include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl, hexylsulfonyl.

Examples of the above "optionally halogenated $C_{1-6}$ alkyl-carboxamide" include $C_{1-6}$ alkyl-carboxamide (e.g. acetamide, propanamide, butanamide, etc.) which may have 1 to 5, preferably 1 to 3, halogen atoms (e.g. fluorine, chlorine, bromine, iodine, etc.). Concrete examples include acetamide, trifluoroacetamide, propanamide, butanamide.

Examples of "$C_{6-14}$ aryloxy" in the above "$C_{6-14}$ aryloxy which may have substituents" include phenyloxy, 1-naphthyloxy, 2-naphthyloxy.

Examples of "$C_{7-19}$ aralkyloxy" in the above "$C_{7-19}$ aralkyloxy which may have substituents" include benzyloxy, phenethyloxy, diphenylmethyloxy, triphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy.

Examples of "$C_{6-14}$ arylcarbamoyl" in the above "$C_{6-14}$ arylcarbamoyl which may have substituents" include phenylcarbamoyl, 1-naphthylcarbamoyl, 2-naphthylcarbamoyl.

As the substituents" in the "$C_{6-14}$ aryloxy which may have substituents", "$C_{7-19}$ aralkyloxy which may have substituents" and "$C_{6-14}$ aryl-carbamoyl which may have substituents", those exemplified for "substituents" in the above "$C_{7-19}$ aralkyl which may have substituents" can be used. The number of substituents is, for instance, 1 to 5, preferably 1 to 3. When the number of substituents is 2 or more, each substituents can be the same or different.

Examples of the "5 to 7 membered saturated cyclic amino" in the above "5 to 7 membered saturated cyclic amino which may have substituents" include morpholino, thiomorpholino, piperazin-1-yl, piperidino, pyrrolidin-1-yl. The "5 to 7 membered saturated cyclic amino" can be condensed with a benzene ring.

Examples of "substituents" in the "5 to 7 membered saturated cyclic amino which may have substituents" include oxo, optionally halogenated $C_{1-6}$ alkyl, optionally halogenated $C_{1-6}$ alkyl-carbonyl, optionally halogenated $C_{1-6}$ alkylsulfonyl, $C_{6-14}$ aryl which may have substituents, $C_{7-19}$ aralkyl which may have substituents, $C_{6-14}$ aryl-carbonyl which may have substituents, 5 to 10 membered aromatic heterocyclic group which may have substituents, 5 to 8 membered monocyclic non-aromatic heterocyclic group (e.g., piperidino, piperazinyl, pyrrolidinyl, dihydropyridyl, etc.). The number of substituents is, for instance, 1 to 5, preferably 1 to 3. When the number of substituents is 2 or more, each substituents can be the same or different.

Here, as "optionally halogenated $C_{1-6}$ alkyl" and "$C_{7-19}$ aralkyl which may have substituents", those exemplified as "substituents" in the above "cyclic group which may have substituents" can be used.

As "optionally halogenated $C_{1-6}$ alkyl-carbonyl" and "optionally halogenated $C_{1-6}$ alkylsulfonyl", those exemplified as "substituents" in the above "$C_{7-19}$ aralkyl which may have substituents" can be used.

Examples of the "$C_{6-14}$ aryl" in the $C_{6-14}$ aryl which may have substituents" include phenyl, 1-naphthyl, 2-naphthyl, 2-indenyl, 2-anthryl. Phenyl is especially preferable.

As the substituents in the "$C_{6-14}$ aryl which may have substituents", those exemplified as "substituents" in the above "$C_{7-19}$ aralkyl which may have substituents" can be used. The number of substituents is, for instance, 1 to 5, preferably 1 to 3. When the number of substituents is 2 or more, each substituents can be the same or different.

Examples of the "$C_{6-14}$ aryl-carbonyl" in the "$C_{6-14}$ arylcarbonyl which may have substituents" include benzoyl, 1-naphthoyl, 2-naphthoyl.

As the "substituents" in the "$C_{6-14}$ aryl-carbonyl which may have substituents", those exemplified as "substituents" in the above "$C_{7-19}$ aralkyl which may have substituents" can be used. The number of substituents is, for instance, 1 to 5, preferably 1 to 3. When the number of substituents is 2 or more, each substituents can be the same or different.

Examples of "5 to 10 membered aromatic heterocyclic groups" in "5 to 10 membered aromatic heterocyclic groups which may have substituents" include 5 to 10 membered (monocyclic or bicyclic) aromatic heterocyclic groups containing 1 or 2 kinds of, preferably 1 to 4 hetero atoms selected from nitrogen, sulfur and oxygen atom in addition to carbon atoms. Concrete examples include 2- or 3-thienyl; 2-, 3- or 4-pyridyl; 2- or 3-furyl; 2-, 4- or 5-thiazolyl; 2-, 4- or 5-oxazolyl; 1-, 3- or 4-pyrazolyl; 2-pyrazinyl; 2-, 4- or 5-pyrimidinyl; 1-, 2- or 3-pyrrolyl; 1-, 2- or 4-imidazolyl; 3- or 4-pyridazinyl; 3-isothiazolyl; 3-isoxazolyl; 1,2,4-oxadiazol-5-yl; 1,2,4-oxadiazol-3-yl; 2-, 3-, 4-, 5- or 8-quinolyl; 1-, 3-, 4-, 5-, 6-, 7- or 8-isoquinolyl; 1-, 2-, 3-, 4-, 5-, 6- or 7-indolyl; 1-, 2-, 4- or 5-isoindolyl; 1-, 5- or 6-phthalazinyl; 2-, 3- or 5-quinoxalinyl; 2-, 3-, 4-, 5- or 6-benzofuranyl; 2-, 4-, 5- or 6-benzothiazolyl; 1-, 2-, 4-, 5- or 6-benzimidazolyl.

Examples of the "substituents" in the "5 to 10 membered aromatic heterocyclic groups which may have substituents" include halogen atom (e.g. fluorine, chlorine, bromine and iodine, etc.), $C_{1-3}$ alkylenedioxy (e.g. methylenedioxy, ethylenedioxy, etc.), nitro, cyano, optionally halogenated $C_{1-6}$ alkyl, $C_{6-14}$ aryloxy-$C_{1-6}$ alkyl (e.g. phenoxymethyl, etc.), $C_{1-6}$ alkyl-$C_{6-14}$ aryl-$C_{2-6}$ alkenyl (e.g. methylphenylethenyl, etc.), optionally halogenated $C_{3-6}$ cycloalkyl, optionally halogenated $C_{1-6}$ alkoxy, optionally halogenated $C_{1-6}$ alkylthio, $C_{7-19}$ aralkyl which may have substituents, hydroxy, $C_{6-14}$ aryloxy which may have substituents, $C_{7-19}$ aralkyloxy which may have substituents, amino, amino-$C_{1-6}$ alkyl (e.g. aminomethyl, aminoethyl, aminopropyl, aminobutyl, etc.), mono-$C_{1-6}$ alkylamino (e.g. methylamino, ethylamino, propylamino, isopropylamino, butylamino, etc.), di-$C_{1-6}$ alkylamino (e.g. dimethylamino, diethylamino, dipropylamino, dibutylamino, ethylmethylamino, etc.), mono-$C_{1-6}$ alkylamino-$C_{1-6}$ alkyl (e.g. methylaminomethyl, ethylaminomethyl, propylaminomethyl, isopropylaminoethyl, butylaminoethyl, etc.), di-$C_{1-6}$ alkylamino-$C_{1-6}$ alkyl (e.g. dimethylaminomethyl, diethylaminomethyl, dipropylaminomethyl, diisopropylaminoethyl, dibutylaminoethyl, etc.), 5 to 7 membered saturated cyclic amino, acyl, acylamino, acyloxy. The number of substituents is, for instance, 1 to 5, preferably 1 to 3. When the number of substituents is 2 or more, each substituents can be the same or different.

Here, as "optionally halogenated $C_{1-6}$ alkyl", "optionally halogenated $C_{3-6}$ cycloalkyl", "optionally halogenated $C_{1-6}$ alkoxy", "optionally halogenated $C_{1-6}$ alkylthio", "$C_{7-19}$ aralkyl which may have substituents", "$C_{6-14}$ aryloxy which may have substituents", "$C_{7-19}$ aralkyloxy which may have substituents", those exemplified as the "substituent" in the above "cyclic group which may have substituents" can be used respectively.

As a "5 to 7 membered saturated cyclic amino", those exemplified as "5 to 7 membered saturated cyclic amino"

regarding "5 to 7 membered saturated cyclic amino which may have substituents" which is a "substituent" in the above "5 to 7 membered saturated cyclic amino which may have substituents" can be used.

Examples of the above "acyl" include acyl of the formulae: —CO—R$^3$, —CO—OR$^3$, —CO—NR$^3$R$^4$, —CS—NR$^3$R$^4$, SO$_2$—R$^{3a}$, —SO—R$^{3a}$, —PO(—OR$^3$)—OR$^4$ or —PO$^2$—R$^{3a}$ wherein R$^3$ is (i) hydrogen atom, (ii) a hydrocarbon group which may have substituents, or (iii) a heterocyclic group which may have substituents; R$^{3a}$ is (i) a hydrocarbon group which may have substituents, or (ii) a heterocyclic group which may have substituents; R$^4$ is hydrogen atom or C$_{1-6}$ alkyl; R$^3$ and R$^{3a}$, together with the adjacent nitrogen atom, can form a nitrogen-containing hetero ring which may have substituents.

Examples of the "hydrocarbon group" in "hydrocarbon group which may have substituents" for R$^3$ or R$^4$ include straight-chain or cyclic hydrocarbon groups (e.g. alkyl, alkenyl, alkynyl, cycloalkyl, aryl, aralkyl, etc.). Among these, C$_{1-19}$ straight chain or cyclic hydrocarbon groups as shown below are preferable.

a) C$_{1-6}$ alkyl (e.g. methyl, ethyl, propyl, isopropyl, butyl, isobutyl, sec-butyl, tert-butyl, pentyl, hexyl, etc.);
b) C$_{2-6}$ alkenyl (e.g., vinyl, allyl, isopropenyl, 2-butenyl, etc.);
c) C$_{2-6}$ alkynyl (e.g. ethynyl, propargyl, 2-butynyl, etc.);
d) C$_{3-6}$ cycloalkyl (e.g. cyclopropyl, cyclobutyl, cyclopentyl, cyclohexyl, etc.); the C$_{3-6}$ cycloalkyl can be condensed with one benzene ring;
e) C$_{6-14}$ aryl (e.g. phenyl, 1-naphthyl, 2-naphthyl, 2-indenyl, 2-anthryl, etc.), preferably phenyl;
f) C$_{7-19}$ aralkyl (e.g. benzyl, phenethyl, diphenylmethyl, triphenylmethyl, 1-naphthylmethyl, 2-naphthylmethyl, 2,3-diphenylethyl, 3-phenylpropyl, 4-phenylbutyl, 5-phenylpentyl, etc.), preferably benzyl.

The "hydrocarbon groups" are preferably C$_{1-6}$ alkyl, C$_{6-14}$ aryl, C$_{7-19}$ aralkyl, etc.

Examples of the "substituent" in "hydrocarbon groups which may have substituents" include halogen atom (e.g. fluorine, chlorine, bromine, iodine, etc.), C$_{1-3}$ alkylenedioxy (e.g. methylenedioxy, ethylenedioxy, etc.), nitro, cyano, optionally halogenated C$_{1-6}$ alkoxy, optionally halogenated C$_{1-6}$ alkylthio, hydroxy, amino, mono-C$_{1-6}$ alkylamino (e.g. methylamino, ethylamino, propylamino, isopropylamino, butylamino, etc.), di-C$_{1-6}$ alkylamino (e.g. dimethylamino, diethylamino, dipropylamino, dibutylamino, ethylmethylamino, etc.), formyl, carboxy, carbamoyl, thiocarbamoyl, optionally halogenated C$_{1-6}$ alkyl-carbonyl, C$_{1-6}$ alkoxy-carbonyl (e.g., methoxycarbonyl, ethoxycarbonyl, propoxycarbonyl, tertbutoxycarbonyl, etc.), 5 to 10 membered aromatic heterocyclic groups which may have substituents, C$_{6-14}$ aryl-carbonyl which may have substituents, C$_{6-14}$ aryloxy-carbonyl which may have substituents, C$_{7-19}$ aralkyloxy-carbonyl which may have substituents, 5 to 6 membered hetero ring-carbonyl which may have substituents, mono-C$_{1-6}$ alkyl-carbamoyl (e.g. methylcarbamoyl, ethylcarbamoyl, etc.), di-C$_{1-6}$ alkyl-carbamoyl (e.g. dimethylcarbamoyl, diethylcarbamoyl, ethylmethylcarbamoyl, etc.), C$_{6-14}$ aryl-carbamoyl which may have substituents, 5 to 6 membered hetero ring-carbamoyl which may have substituents, optionally halogenated C$_{1-6}$ alkylsulfonyl, C$_{6-14}$ arylsulfonyl which may have substituents, formylamino, C$_{1-6}$ alkyl-carbonyloxy (e.g. acetoxy, propanoyloxy, etc.), C$_{6-14}$ aryl-carbonyloxy which may have substituents, C$_{1-6}$ alkoxycarbonyloxy (e.g. methoxycarbonyloxy, ethoxycarbonyloxy, propoxycarbonyloxy, butoxycarbonyloxy, etc.), mono-C$_{1-6}$ alkyl-carbamoyloxy (e.g. methylcarbamoyloxy, ethylcarbamoyloxy, etc.), di-C$_{1-6}$ alkyl-carbamoyloxy (e.g. dimethylcarbamoyloxy, diethylcarbamoyloxy, etc.), C$_{6-14}$ aryl-carbamoyloxy which may have substituents, nicotinoyloxy. The number of substituents is, for instance, 1 to 5, preferably 1 to 3. When the number of substituents is 2 or more, each substituents can be the same or different.

Here, as "optionally halogenated C$_{1-6}$ alkoxy", "optionally halogenated C$_{1-6}$ alkylthio" and "C$_{6-14}$ aryl-carbamoyl which may have substituents", those exemplified as a "substituent" in the above "cyclic group which may have substituents" can be used.

As "optionally halogenated C$_{1-6}$ alkyl-carbonyl" and "optionally halogenated C$_{1-6}$ alkylsulfonyl", those exemplified as a "substituent" in the above "C$_{7-19}$ aralkyl which may have substituents" can be used.

As the above "5 to 10 membered aromatic heterocyclic groups which may have substituents" and "C$_{6-14}$ aryl-carbonyl which may have substituents", those exemplified as "substituent" in the above "5 to 7 membered saturated cyclic amino which may have substituents" can be used.

Examples of "C$_{6-14}$ aryloxy-carbonyl" in "C$_{6-14}$ aryloxy-carbonyl which may have substituents" include phenyloxycarbonyl, 1-naphthyloxycarbonyl, 2-naphthyloxycarbonyl.

Examples of "C$_{7-19}$ aralkyloxy-carbonyl" in "C$_{7-19}$ aralkyloxy-carbonyl which may have substituents" include benzyloxycarbonyl, phenethyloxycarbonyl, diphenylmethyloxycarbonyl, triphenylmethyloxycarbonyl, 1-naphthylmethyloxycarbonyl, 2-naphthylmethyloxycarbonyl, 2,2-diphenylethyloxycarbonyl, 3-phenylpropyloxycarbonyl, 4-phenylbutyloxycarbonyl, 5-phenylpentyloxycarbonyl.

Examples of "5 to 6 membered hetero ring-carbonyl" in the above "5 to 6 membered hetero ring-carbonyl which may have substituents" include nicotinoyl, isonicotinoyl, 2-thenoyl, 3-thenoyl, 2-furoyl, 3-furoyl, morpholinocarbonyl, piperidinocarbonyl, pyrrolidin-1-ylcarbonyl.

Examples of the "5 to 6 membered hetero ring-carbamoyl" in the above "5 to 6 membered hetero ring-carbamoyl which may have substituents" include morpholinocarbamoyl, piperidinocarbamoyl, 2-pyridylcarbamoyl, 3-pyridylcarbamoyl, 4-pyridylcarbamoyl, 2-thienylcarbamoyl, 3-thienylcarbamoyl.

Examples of "C$_{6-14}$ arylsulfonyl" in the above "C$_{6-14}$ arylsulfonyl which may have substituents" include phenylsulfonyl, 1-naphthylsulfonyl, 2-naphthylsulfonyl.

Examples of "C$_{6-14}$ aryl-carbonyloxy" in the above "C$_{6-14}$ aryl-carbonyloxy which may have substituents" include benzoyloxy, 1-naphthoyloxy, 2-naphthoyloxy.

Examples of "C$_{6-14}$ aryl-carbamoyloxy" in the above "C$_{6-14}$ aryl-carbamoyloxy which may have substituents" include phenylcarbamoyloxy, naphthylcarbamoyloxy.

As the "substituents" in the above "C$_{6-14}$ aryloxy-carbonyl which may have substituents", "C$_{7-19}$ aralkyloxy-carbonyl which may have substituents", "5 to 6 membered hetero ring-carbonyl which may have substituents", "5 to 6 membered hetero ring-carbamoyl which may have substituents", "C$_{6-14}$ arylsulfonyl which may have substituents", "C$_{6-14}$ aryl-carbonyloxy which may have substituents" and "C$_{6-14}$ aryl-carbamoyloxy which may have substituents", those exemplified as "substituents" in the above "C$_{7-19}$ aralkyl which may have substituents" can be mentioned. The number of the substituents is, for instance, 1 to 5, preferably 1 to 3. When the number of substituents is 2 or more, each substituents can be the same or different.

Examples of "heterocyclic groups" in the "heterocyclic groups which may have substituents for R$^3$ or R$^{3a}$ include a 5 to 14 membered (monocyclic, bicyclic or tricyclic) hetero ring containing 1 or 2 kinds of, 1 to 4 hetero atoms selected from nitrogen, sulfur and oxygen atom in addition to carbon atoms. Preferably, univalent groups formed by removing an optional one hydrogen atom from (i) an aromatic hetero ring, (ii) a 5 to 10 membered nonaromatic hetero ring, or (iii) a 7 to 10 membered hetero-bridge ring, can be mentioned.

Here, examples of the "aromatic hetero ring" include a 5 to 14 membered, preferably 5 to 10 membered, aromatic hetero ring containing one or more hetero atom (e.g. 1 to 4) selected from nitrogen, sulfur and oxygen atom in addition to carbon atoms.

Concrete examples include aromatic hetero rings such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, furazan, benzothiophene, benzofuran, benzimidazole, benzoxazole, benzothiazole, benzisothiazole, naphtho[2,3-b]thiophene, phenoxathiin, indole, isoindole, 1H-indazole, purine, 4H-quinolidine, isoquinoline, quinoline, phthalazine, naphthylidine, quinoxaline, quinazoline, cinnoline, carbazole, β-carboline, phenanthridine, acridine, phenazinephenothiadine, phenoxazine, phthalimide, etc.; or a ring formed by condensing these rings (preferably monocyclic rings) with one to multiple (preferably 1 or 2) aromatic rings (e.g. benzene ring, etc.).

Examples of 5 to 10 membered non-aromatic hetero rings" include 2- or 3-pyrroline, pyrrolidine, 2- or 3-imidazoline, 2-oxazoline, oxazolidine, 2- or 3-pyrazoline, pyrazolidine, 2-thiazoline, piperidine, piperazine, hexamethylenimine, morpholine, thiomorpholine.

Examples of "7 to 10 membered hetero-bridge rings" include quinuclidine, 7-azabicyclo[2.2.1]heptane.

The "hetero cyclic groups" are preferably 5 to 10 membered (monocyclic or bicyclic) heterocyclic groups, containing 1 or 2 kinds of, preferably 1 to 4, hetero atoms selected from nitrogen, sulfur and oxygen atom in addition to carbon atoms. Concretely examples include aromatic heterocyclic groups such as 2- or 3-thienyl; 2-, 3- or 4-pyridyl; 2- or 3-furyl; 2-, 4- or 5-thiazolyl; 2-, 4- or 5-oxazolyl; 1-, 3- or 4-pyrazolyl; 2-pyrazinyl; 2-, 4- or 5-pyrimidinyl; 1-, 2- or 3-pyrrolyl; 1-, 2- or 4-imidazolyl; 3- or 4-pyridazinyl; 3-isothiazolyl; 3-isoxazolyl; 1,2,4-oxadiazol-5-yl; 1,2,4-oxadiazol-3-yl; 2-, 3-, 4-, 5- or 8-quinolyl; 1-, 3-, 4-, 5-, 6-, 7- or 8-isoquinolyl; 1-, 2-, 3-, 4-, 5-, 6- or 7-indolyl; 1-, 2-, 4- or 5-isoindolyl; 1-, 5- or 6-phthalazinyl; 2-, 3- or 5-quinoxalinyl; 2-, 3-, 4-, 5- or 6-benzofuranyl; 2-, 3-, 4-, 5- or 6-benzothienyl; 2-, 4-, 5- or 6-benzothiazolyl; 1-, 2-, 4-, 5- or 6-benzimidazolyl; and non-aromatic heterocyclic groups such as 1-, 2- or 3-pyrrolidinyl; 1-, 2-, 4- or 5-imidazolidinyl; 2- or 4-imidazolinyl; 2-, 3- or 4-pyrazolidinyl; piperidino; 2-, 3- or 4-piperidyl; 1- or or 2-piperazinyl; morpholino.

As the "substituents" in the "heterocyclic groups which may have substituents", those exemplified as substituents" in the above "5 to 10 membered aromatic heterocyclic groups which may have substituents can be used. The number of substituents is, for instance, 1 to 5, preferably 1 to 3. When the number of substituents is 2 or more, each substituents can be the same or different.

Examples of "$C_{1-6}$ alkyl" for $R^4$ include methyl, ethyl, propyl, isopropyl, butyl, isobutyl, sec-butyl, tert-butyl, pentyl, hexyl.

Examples of "nitrogen-containing hetero ring" in the "nitrogen-containing hetero ring which may have substituents" formed by $R^3$ and $R^4$ together with the adjacent nitrogen atoms, include a 5 to 7 membered nitrogen-containing hetero ring which contains at least one nitrogen atom in addition to carbon atoms and may contain 1 to 3 hetero atoms selected from nitrogen, sulfur and oxygen atom. The "nitrogen-containing hetero rings" are preferably piperidine, morpholine, thiomorpholine, piperazine, pyrrolidine, etc.

As the "substituents" in the "nitrogen-containing hetero ring which may have substituents", those exemplified as "substituents" in the above "5 to 10 membered aromatic heterocyclic groups which may have substituents" can be used. The number of substituents is, for instance, 1 to 5, preferably 1 to 3. When the number of substituents is 2 or more, each substituents can be the same or different.

The "acyl" is preferably formyl, carboxy, carbamoyl, optionally halogenated $C_{1-6}$ alkyl-carbonyl (e.g. acetyl, etc.), $C_{1-6}$ alkoxy-carbonyl (e.g. methoxycarbonyl, ethoxycarbonyl, propoxycarbonyl, tert-butoxycarbonyl, etc.), $C_{6-14}$ arylcarbonyl which may have substituents (e.g. benzoyl, 1-naphthoyl, 2-naphthoyl, etc.), $C_{6-14}$ aryloxycarbonyl which may have substituents (e.g. phenyloxycarbonyl, 1-naphthyloxycarbonyl, 2-naphthyloxycarbonyl, etc.), $C_{7-19}$ aralkyloxycarbonyl which may have substituents (e.g. benzyloxycarbonyl, phenethyloxycarbonyl, etc.), a 5 to 6 membered hetero ring-carbonyl which may have substituents (e.g. nicotinoyl, etc.), mono-$C_{1-6}$ alkyl-carbamoyl (e.g. methylcarbamoyl, ethylcarbamoyl, etc.), di-$C_{1-6}$ alkylcarbamoyl (e.g. dimethylcarbamoyl, diethylcarbamoyl, ethylmethylcarbamoyl, etc.), $C_{6-14}$ aryl-carbamoyl which may have substituents (e.g. phenylcarbamoyl, 4-methoxyphenylcarbamoyl, 3,4-dimethoxyphenylcarbamoyl, etc.), aromatic hetero ring-carbamoyl which may have substituents (e.g. 2-pyridinylcarbamoyl, 2-quinolinylcarbamoyl etc.), optionally halogenated $C_{1-6}$ alkylsulfonyl (e.g. methylsulfonyl, etc.), $C_{6-14}$ arylsulfonyl which may have substituents (e.g. phenylsulfonyl etc.), etc.

Here, as "optionally halogenated $C_{1-6}$ alkyl-carbonyl" and "optionally halogenated $C_{7-19}$ aralkylsulfonyl", those exemplified as "substituents" in the above "$C_{7-19}$ aralkyl which may have substituents" can be used.

As "$C_{6-14}$ aryl-carbonyl which may have substituents", "substituents" in the above "5 to 7 membered saturated cyclic amino which may have substituents" can be used.

As "$C_{6-14}$ aryloxy-carbonyl which may have substituents", "$C_{7-19}$ aralkyloxy-carbonyl which may have substituents", 5 to 6 membered hetero ring-carbonyl which may have substituents", "aromatic hetero ring-carbamoyl which may have substituents" and "$C_{6-14}$ arylsulfonyl which may have substituents", those exemplified as "substituents" in the above "hydrocarbon groups which may have substituents" can be used.

As "$C_{6-14}$ aryl-carbamoyl which may have substituents", those exemplified as "substituents" in the above "cyclic group which may have substituents" can be used.

Examples of the above "acylamino" include amino which is substituted by 1 or 2 of the above "acyl". Preferably, acylamino of the formulae: —NR$^5$—COR$^6$, —NR$^5$—COOR$^{6a}$, —NR$^5$— SO$_2$R$^{6a}$, —NR$^5$—CONR$^{6a}$R$^{6b}$, —PO (—OR$^5$)—OR$^6$, or —PO$_2$—R$^6$ wherein R$^5$ is hydrogen atom or $C_{1-6}$ alkyl; R$^6$ has the same meaning as the above R$^3$; R$^{6a}$ has the same meaning as the above R$^{3a}$; and R$^{6b}$ has the same meaning as R$^4$], can be mentioned.

As "$C_{1-6}$ alkyl" for R$^5$, the same one as in "$C_{1-6}$ alkyl" for the above R$^4$ can be mentioned.

The "acylamino" is preferably formylamino, optionally halogenated $C_{1-6}$ alkyl-carboxamide (e.g. methylcarboxamide, trifluoromethylcarboxamide, isopropylcarboxamide, etc.), $C_{6-14}$ aryl-carboxamide which may have substituents (e.g. phenylcarboxamide, 2-methoxyphenylcarboxamide, 4-methoxyphenylcarboxamide, etc.), N—($C_{6-14}$ aryl-carbonyl which may have substituents)-N-$C_{1-6}$ alkylamino (e.g.

N-4-methoxybenzoyl-N-methylamino, etc.), $C_{7-19}$ aralkyl-carboxamide which may have substituents (e.g. benzylcarboxamide, etc.), aromatic hetero ring-carboxamide which may have substituents (e.g. benzothiophen-2-ylcarboxamide, etc.), optionally halogenated $C_{1-6}$ alkoxy-carboxamide (e.g. methoxycarboxamide, ethoxycarboxamide, propoxycarboxamide, butoxycarboxamide, etc.), $C_{6-14}$ arylaminocarbonylamino which may have substituents (e.g. phenylaminocarbonylamino, etc.), optionally halogenated $C_{1-6}$ alkylsulfonylamino (e.g. methylsulfonylamino, trifluoromethylsulfonylamino, ethylsulfonylamino, etc.), $C_{6-14}$ arylsulfonylamino which may have substituents (e.g. 4-methoxyphenylsulfonylamino, etc.).

Here, as "substituents" in "$C_{6-14}$ aryl-carboxamide which may have substituents", "N—($C_{6-14}$ aryl-carbonyl which may have substituents)-N—$C_{1-6}$ arylkylamino", "$C_{7-19}$ aralkyl-carboxamide which may have substituents", "aromatic hetero ring-carboxamide which may have substituents", "$C_{6-14}$ arylamino-carbonylamino which may have substituents" and "$C_{6-14}$ arylsulfonylamino which may have substituents", those exemplified as "substituents" in the above "$C_{7-19}$ aralkyl which may have substituents" can be mentioned. The number of substituents is, for instance, 1 to 5, preferably 1 to 3. When the number of substituents is 2 or more, each substituents can be the same or different.

Examples of the above "acyloxy" include oxy substituted by one of the above "acyl". Preferably, acyloxy of the formulae: —O—$COR^7$, —O—$COOR^7$, —O—$CONHR^7$, —PO(OH)—$OR^7$ or —$PO_2$—$R^7$ wherein $R^7$ has the same meaning as the above $R^3$, can be mentioned.

The "acyloxy" is preferably optionally halogenated $C_{1-6}$ alkyl-carbonyloxy (e.g. acetoxy, propanoyloxy, etc.), $C_{6-14}$ aryl-carbonyloxy which may have substituents (e.g. benzoyloxy, 4-methoxybenzoyloxy, etc.), optionally halogenated $C_{1-6}$ alkoxy-carbonyloxy (e.g. methoxycarbonyloxy, trifluoromethoxycarbonyloxy, ethoxycarbonyloxy, propoxycarbonyloxy, butoxycarbonyloxy, etc.), mono-$C_{1-6}$ alkyl-carbamoyloxy (e.g. methylcarbamoyloxy, ethylcarbamoyloxy, etc.), di-$C_{1-6}$ alkyl-carbamoyloxy (e.g. dimethylcarbamoyloxy, diethylcarbamoyloxy, etc.), $C_{6-14}$ aryl-carbamoyloxy which may have substituents (e.g. phenylcarbamoyloxy, naphthylcarbamoyloxy, etc.), nicotinyloxy, etc.

As "substituents" in "$C_{6-14}$ aryl-carbonyloxy which may have substituents" and "$C_{6-14}$ aryl-carbamoyloxy which may have substituents", those exemplified as "substituents" in the above "$C_{7-19}$ aralkyl which may have substituents" can be mentioned. The number of substituents is, for instance, 1 to 5, preferably 1 to 3. When the number of substituents is 2 or more, each substituents can be the same or different.

Examples of the "5 to 7 membered non-aromatic heterocyclic groups which may have substituents", which is "substituents" in "cyclic group which may have substituents" for $Ar^1$, include 4,5-dihydro-1,3-oxazol-2-yl, 4,5-dihydro-1,3-thiazol-2-yl, 4,5-dihydro-1H-2-imidazolyl. As "substituents" in the "5 to 7 membered non-aromatic heterocyclic groups which may have substituents", those exemplified as "substituents" in the above "5 to 7 membered saturated cyclic amino which may have substituents" can be used.

As "acyl", "acyloxy" and "acylamino", which are "substituents" in the "cyclic group which may have substituents" for $Ar^1$, those exemplified as "substituents" in the above "5 to 10 membered aromatic heterocyclic groups which may have "substituents" can be used.

Regarding "aromatic hetero ring-$C_{1-6}$ alkoxy" which is "substituents" in the "cyclic group which may have substituents" for $Ar^1$, as "aromatic hetero ring", those exemplified as the above $R_3$ can be used. Examples of $C_{1-6}$ alkoxy" include methoxy, ethoxy, propoxy, butoxy, pentyloxy.

"Substituents" in the "cyclic group which may have substituents" for $Ar^1$ are preferably halogen atom (preferably fluorine, chlorine and bromine, etc.); nitro; $C_{3-6}$ alkylenedioxy (preferably methylenedioxy, etc.); optionally halogenated $C_{1-6}$ alkyl (preferably, methyl, ethyl, propyl, trifluoromethyl, etc.); hydroxy-$C_{1-6}$ alkyl (preferably hydroxymethyl, etc.); optionally halogenated $C_{3-6}$ cycloalkyl (preferably cyclohexyl, etc.); optionally halogenated $C_{1-6}$ alkoxy (preferably methoxy, ethoxy, etc.); optionally halogenated $C_{1-6}$ alkylthio (preferably methylthio, etc.); hydroxy; $C_{7-19}$ aralkyloxy which may have substituents (preferably, 1 to 3 substituents selected from halogen atom, optionally halogenated $C_{1-6}$ alkyl, optionally halogenated $C_{1-6}$ alkoxy, optionally halogenated $C_{1-6}$ alkylthio, etc.) (preferably benzyloxy, 4-methoxybenzyloxy, 3-methoxybenzyloxy, 4-fluorobenzyloxy, 4-methylthiobenzyloxy, 4-ethylbenzyloxy, etc.); $C_{6-14}$ aryloxy which may have substituents (preferably, 1 to 3 optionally halogenated $C_{1-6}$ alkoxy, etc.) (preferably phenyloxy, 4-methoxyphenyloxy, etc.); amino; mono-$C_{1-6}$ alkylamino (preferably methylamino, etc.); di-$C_{1-6}$ alkylamino (preferably dimethylamino, etc.); 5 to 7 membered saturated cyclic amino which may have substituents (preferably 1 to 3 oxo) and may be condensed with a benzene ring (preferably 1,3-dioxo-1,3-dihydro-2H-isoindol-2-yl, etc.); 5 to 7 membered non-aromatic heterocyclic groups which may have substituents (preferably 4,5-dihydro-1,3-oxazol-2-yl, etc.); formyl; carboxy; $C_{6-14}$ arylcarbonyl which may have substituents (preferably benzoyl, etc.); $C_{6-14}$ aryl-carbamoyl which may have substituents (preferably, 1 to 3 optionally halogenated $C_{1-6}$ alkoxy, etc.) (preferably, phenylcarbamoyl, 4-methoxyphenylcarbamoyl, 3,4-dimethoxyphenylcarbamoyl, etc.); aromatic hetero ring-carbamoyl which may have substituents (preferably 2-pyridinylcarbamoyl, 2-quinolinylcarbamoyl, etc.); $C_{1-6}$ alkoxy-carbonyl (preferably methoxycarbonyl, ethoxycarbonyl, etc.); optionally halogenated $C_{1-6}$ alkyl-carboxamide (preferably methylcarboxamide, trifluoromethylcarboxamide, isopropylcarboxamide, etc.); $C_{6-14}$ aryl-carboxamide which may have substituents (preferably, 1 to 3 optionally halogenated $C_{1-6}$ alkoxy, etc.) (preferably phenylcarboxamide, 2-methoxyphenylcarboxamide, 4-methoxyphenylcarboxamide, etc.); $C_{7-19}$ aralkyl-carboxamide which may have substituents (preferably benzylcarboxamide, etc.); aromatic hetero ring-carboxamide which may have substituents (preferably benzothiophen-2-yl-carboxamide, etc.); N—($C_{6-14}$ arylcarbonyl which may have substituents (preferably, 1 to 3 optionally halogenated $C_{1-6}$ alkoxy, etc.))—N—$C_{1-6}$ alkylamino (preferably N-4-methoxybenzoyl-N-methylamino, etc.); $C_{6-14}$ arylamino-carbonylamino which may have substituents (preferably phenylaminocarbonylamino, etc.); $C_{6-14}$ arylsulfonylamino which may have substituents (preferably, 1 to 3 optionally halogenated $C_{1-6}$ alkoxy, etc.) (preferably 4-methoxyphenylsulfonylamino, etc.); $C_{6-14}$ arylcarbonyloxy which may have substituents (preferably, 1 to 3 optionally halogenated $C_{1-6}$ alkoxy, etc.) (preferably 4-methoxybenzoyloxy, etc.); oxo; carboxy-$C_{1-6}$ alkyl (preferably carboxyethyl, etc.); $C_{1-6}$ alkoxy-carbonyl-$C_{1-6}$ alkyl (preferably methoxycarbonylmethyl, etc.); $C_{7-19}$ aralkyl which may have substituents (preferably 1 to 3 halogen atom) (preferably benzyl, 2,4-dichlorobenzyl, etc.); aromatic hetero ring-$C_{1-6}$ alkoxy (preferably 2-qunolylmethoxy, etc.); cyano, etc.

When "cyclic group" in "cyclic group which may have substituents" for $Ar^1$ is a non-aromatic cyclic hydrocarbon group or a non-aromatic heterocyclic group, $C_{6-14}$ aryl which may have substituents (preferably, 1 to 3 substituents selected from halogen atom, $C_{1-3}$ alkylenedioxy, optionally halogenated $C_{1-6}$ alkyl, optionally halogenated $C_{1-6}$ alkoxy, etc.) (preferably phenyl, 4-fluorophenyl, 1,3-benzodioxol-5-yl, 4-chlorophenyl, 4-methylphenyl, 4-methoxyphenyl), hydroxy, $C_{7-19}$ aralkyloxy-carbonyl (preferably benzyloxy-carbonyl), $C_{7-19}$ aralkyl (preferably benzyl), etc., can be used as a preferable substituent.

$Ar^1$ is preferably phenyl, biphenylyl (preferably 4-biphenylyl, 2-biphenylyl), phenyl-pyridyl (preferably 6-phenyl-3-pyridyl, 5-phenyl-2-pyridyl), phenyl-furyl (preferably 5-phenyl-2-furyl), phenyl-isoxazolyl (preferably 3-phenyl-isoxazol-5-yl), diphenyl-oxazolyl (preferably 2,4-diphenyl-1,3-oxazol-5-yl), pyridyl-phenyl (preferably 4-(4-pyridyl)phenyl, 4-(3-pyridyl)phenyl), phenyl-pyrimidinyl (preferably 2-phenyl-5-pyrimidinyl), benzofuranyl-phenyl (preferably 4-(2-benzofuranyl)phenyl), furyl-phenyl (preferably 4-(2-furyl)phenyl), terphenyl (preferably 4,4'-terphenyl), thienyl-phenyl (preferably 4-(2-thienyl)phenyl), indolyl (preferably 2-indolyl, 3-indolyl), naphthyl-oxadiazolyl (preferably 3-(2-naphthyl)-1,2,4-oxadiazol-5-yl), benzofuranyl-oxadiazole (preferably 3-(2-benzofuranyl)-1,2,4-oxadiazol-5-yl), benzothienyl (preferably 2-benzothienyl), benzofuranyl (preferably 2-benzofuranyl), fluorenyl (preferably 2-fluorenyl), pyridyl-pyrrolyl (preferably 3-(4-pyridyl)pyrrolyl), thioxanthenyl;

each of which may have 1 to 3 (preferably 1 or 2) substituents selected from the group consisting of halogen atom (preferably fluorine, chlorine, bromine, etc.); nitro; $C_{1-3}$ alkylenedioxy (preferably methylenedioxy, etc.); optionally halogenated $C_{1-6}$ alkyl (preferably methyl, ethyl, propyl, trifluoromethyl, etc.); hydroxy-$C_{1-6}$ alkyl (preferably hydroxymethyl, etc.); optionally halogenated $C_{3-6}$ cycloakyl (preferably cyclohexyl, etc.); optionally halogenated $C_{1-6}$ alkoxy (preferably methoxy, ethoxy, etc.); optionally halogenated $C_{1-6}$ alkylthio (preferably methylthio, etc.); hydroxy; $C_{7-19}$ aralkyloxy which may have substituents (preferably, 1 to 3 substituents selected from halogen atom, optionally halogenated $C_{1-6}$ alkyl, optionally halogenated $C_{1-6}$ alkoxy, optionally halogenated $C_{1-6}$ alkylthio, etc.) (preferably benzyloxy, 4-methoxybenzyloxy, 3-methoxybenzyloxy, 4-fluorobenzyloxy, 4-methylthiobenzyloxy, 4-methylbenzyloxy, etc.); $C_{6-14}$ aryloxy which may have substituents (preferably, 1 to 3 optionally halogenated $C_{1-6}$ alkoxy, etc.) (preferably phenyloxy, 4-methoxyphenyloxy, etc.); amino; mono-$C_{1-6}$ alkylamino (preferably methylamino, etc.); di-$C_{1-6}$ alkylamino (preferably dimethylamino, etc.); 5 to 7 membered saturated cyclic amino which may have substituents (preferably 1 to 3 oxo) and may be condensed with a benzene ring (preferably 1,3-dioxo-1,3-dihydro-2H-isoindol-2-yl, etc.); 5 to 7 membered non-aromatic heterocyclic groups which may have substituents (preferably 4,5-dihydro-1,3-oxazol-2-yl, etc.); formyl; carboxy; $C_{6-14}$ aryl-carbonyl which may have substituents (preferably benzoyl, etc.); $C_{6-14}$ aryl-carbamoyl which may have substituents (preferably, 1 to 3 optionally halogenated $C_{1-6}$ alkoxy, etc.) (preferably phenylcarbamoyl, 4-methoxyphenylcarbamoyl, 3,4-dimethoxyphenylcarbamoyl, etc.); aromatic hetero ring-carbamoyl which may have substituents (e.g. 2-pyridinylcarbamoyl, 2-quinolinylcarbamoyl, etc.); $C_{1-6}$ alkoxy-carbonyl (preferably methoxycarbonyl, ethoxycarbonyl, etc.); optionally halogenated $C_{1-6}$ alkyl-carboxamide (preferably, methylcarboxamide, trifluoromethylcarboxamide, isopropylcarboxamide, etc.); $C_{6-14}$ aryl-carboxamide which may have substituents (preferably, 1 to 3 optionally halogenated $C_{1-6}$ alkoxy, etc.) (preferably phenylcarboxamide, 2-methoxyphenylcarboxamide, 4-methoxyphenylcarboxamide, etc.); $C_{7-19}$ aralkyl-carboxamide which may have substituents (preferably benzylcarboxamide, etc.); aromatic hetero ring-carboxamide which may have substituents (preferably benzothiophen-2-yl-carboxamide, etc.); N-($C_{6-14}$ aryl-carbonyl which may have substituents (preferably, 1 to 3 optionally halogenated $C_{1-6}$ alkoxy, etc.))-N-$C_{1-6}$ alkylamino (preferably N-4-methoxybenzoyl-N-methylamino, etc.); $C_{6-14}$ arylamino-carbonylamino which may have substituents (preferably phenylaminocarbonylamino, etc.); $C_{6-14}$ arylsulfonylamino which may have substituents (preferably, 1 to 3 optionally halogenated $C_{1-6}$ alkoxy, etc.) (preferably 4-methoxyphenylsulfonylamino, etc.); $C_{6-14}$ aryl-carbonyloxy which may have substituents (preferably, 1 to 3 optionally halogenated $C_{1-6}$ alkoxy, etc.) (preferably 4-methoxybenzoyloxy, etc.); oxo; carboxy-$C_{1-6}$ alkyl (preferably carboxyethyl, etc.); $C_{1-6}$ alkoxy-carbonyl-$C_{1-6}$ alkyl (preferably methoxycarbonylmethyl, etc.); $C_{7-19}$ aralkyl which may have substituents (preferably 1 to 3 halogen atom) (preferably benzyl, 2,4-dichlorobenzyl, etc.); aromatic hetero ring-$C_{1-6}$ alkoxy (preferably 2-qunolylmethoxy, etc.); and cyano.

Further, preferable examples of $Ar^1$ include piperidinyl (preferably piperidino), piperazinyl, pyrrolidinyl, dihydropyridyl, tetrahydropyridyl; each of which may have 1 or 2 substituents selected from the group consisting of oxo, $C_{6-14}$ aryl which may have substituents (preferably, 1 to 3 substituents selected from halogen atom, $C_{1-3}$ alkylenedioxy, optionally halogenated $C_{1-6}$ alkyl, optionally halogenated $C_{1-6}$ alkoxy, etc.) (preferably phenyl, 4-fluorophenyl, 1,3-benzodioxol-5-yl, 4-chlorophenyl, 4-methylphenyl, 4-methoxyphenyl), hydroxy, $C_{7-19}$ aralkyloxy-carbonyl (preferably benzyloxycarbonyl) and $C_{7-19}$ aralkyl (preferably benzyl).

$Ar^1$ is more preferably, phenyl, biphenylyl (preferably 4-biphenylyl) or phenyl-pyridyl (preferably 6-phenyl-3-pyridyl, 5-phenyl-2-pyridyl); each of which may have 1 or 2 substituents selected from the group consisting of halogen atom (preferably fluorine, chlorine, bromine, etc.); optionally halogenated $C_{1-6}$ alkyl (preferably methyl, ethyl, propyl, trifluoromethyl, etc.); optionally halogenated $C_{1-6}$ alkoxy (preferably methoxy, ethoxy, etc.); $C_{7-9}$ aralkyloxy which may have substituents (preferably, 1 to 3 substituents selected from halogen atom, optionally halogenated $C_{1-6}$ alkyl, optionally halogenated $C_{1-6}$ alkoxy, optionally halogenated $C_{1-6}$ alkylthio, etc.) (preferably benzyloxy, 4-methoxybenzyloxy, etc.); $C_{6-14}$ aryloxy which may have substituents (preferably, 1 to 3 optionally halogenated $C_{1-6}$ alkoxy, etc.) (preferably phenyloxy, etc.); $C_{6-14}$ aryl-carbonyl which may have substituents (preferably, 1 to 3 optionally halogenated $C_{1-6}$ alkoxy, etc.) (preferably benzoyl, etc.); $C_{6-14}$ aryl-carbamoyl which may have substituents (preferably, 1 to 3 optionally halogenated $C_{1-6}$ alkoxy, etc.) (preferably phenylcarbamoyl, 4-methoxyphenylcarbamoyl, 3,4-dimethoxyphenylcarbamoyl, etc.); aromatic hetero ring-carbamoyl which may have substituents (e.g. 2-pyridinylcarbamoyl, 2-quinolinylcarbamoyl, etc.); $C_{6-14}$ arylcarboxamide which may have substituents (preferably, 1 to 3 optionally halogenated $C_{1-6}$ alkoxy, etc.) (preferably phenylcarboxamide, 2-methoxyphenylcarboxamide, 4-methoxyphenylcarboxamide, etc.); $C_{7-19}$ aralkyl-carboxamide which may have substituents (preferably benzylcarboxamide, etc.); aromatic hetero ring-carboxamide (preferably benzothiophen-2-yl-carboxamide, etc.); N—($C_{6-14}$ arylcarbonyl which may have substituents (preferably, 1 to 3 optionally halogenated $C_{1-6}$ alkoxy, etc.))—N—$C_{1-6}$ alkylamino (preferably N-4-methoxybenzoyl-N-methylamino, etc.); $C_{6-14}$ arylamino-carbonylamino which may have substituents (preferably phenylaminocarbonylamino, etc.); $C_{6-14}$ arylsulfonylamino which may have substituents (preferably, 1 to 6 optionally halogenated $C_{1-6}$ alkoxy, etc.) (preferably 4-methoxyphenyl-N-methylamino, etc.); and $C_{6-14}$ arylcarbonyloxy which may have substituents (preferably, 1 to 3 optionally halogenated $C_{1-6}$ alkoxy, etc.) (preferably 4-methoxybenzoyloxy, etc.).

Further, preferable examples of $Ar^1$ include piperidino, piperazinyl or pyrrolidinyl; each of which may have 1 or 2 substituents selected from the group consisting of oxo and $C_{6-14}$ aryl (preferably phenyl) which may have substituents [preferably halogen atom (preferably fluorine, chlorine, bromine, etc.), optionally halogenated $C_{1-6}$ alkyl (preferably methyl, ethyl, propyl, trifluoromethyl, etc.) or optionally halogenated $C_{1-6}$ alkoxy (preferably methoxy, ethoxy, etc.)].

The "spacer having a main chain of 1 to 6 atoms" means a space in which 1 to 6 atoms are linked. Here, the "number of atoms in the main chain" is counted so that the number of atoms in the main chain is minimum. For instance, the number of atoms of 1,2-cyclopentylene is counted as 2, and the number of atoms of 1,3-cyclopentylene is counted as 3.

Examples of the "spacer having a main chain of 1 to 6 atoms" include a bivalent group consisting of 1 to 3 species selected from —O—, —S—, —CO—, —SO—, —SO$_2$—, —NR$^8$— ($R^8$ is hydrogen atom, optionally halogenated $C_{1-6}$ alkyl, optionally halogenated $C_{1-6}$ alkyl-carbonyl, optionally halogenated $C_{1-6}$ alkylsulfonyl), bivalent $C_{1-6}$ non-cyclic hydrocarbon groups which may have substituents, and bivalent $C_{5-8}$ monocyclic non-aromatic hydrocarbon groups.

Here, as "optionally halogenated $C_{1-6}$ alkyl", those exemplified as "substituents" in the above "cyclic group which may have substituents" can be used.

As "optionally halogenated $C_{1-6}$ alkyl-carbonyl" and "optionally halogenated $C_{1-6}$ alkylsulfonyl", those exemplified as "substituents" in the above "$C_{7-19}$ aralkyl which may have substituents" can be used.

Examples of "bivalent $C_{1-6}$ non-cyclic hydrocarbon groups" in the "bivalent $C_{1-6}$ non-cyclic hydrocarbon groups which may have substituents" include (1) $C_{1-6}$ alkylene (e.g. —CH$_2$—, —(CH$_2$)$_2$—, —(CH$_2$)$_3$—, —(CH$_2$)$_4$—, —(CH$_2$)$_5$—, —(CH$_2$)$_6$—, —CH(CH$_3$)—, —C(CH$_3$)$_2$—, —(CH(CH$_3$))$_2$—, —(CH$_2$)$_2$C(CH$_3$)$_2$—, —(CH$_2$)$_3$C(CH$_3$)$_2$—, etc.);

(2) $C_{2-6}$ alkenylene (e.g. —CH=CH—, —CH$_2$—CH=CH—, —C(CH$_3$)$_2$—CH=CH—, —CH$_2$—CH=CH—CH$_2$—, —CH=CH—CH$_2$—, —CH$_2$—CH$_2$—CH=CH—, —CH=CH—CH=CH—, —CH=CH—CH$_2$—CH$_2$—, etc.);

(3) $C_{2-6}$ alkynylene (e.g. —C≡C—, —CH$_2$—C≡C—, —CH$_2$—C≡C—CH$_2$—CH$_2$—, etc.)

each of which may have 1 to 5, preferably 1 to 3, halogen atoms (e.g. fluorine, chlorine, bromine, iodine, etc., The "bivalent $C_{1-6}$ non-cyclic hydrocarbon groups" may have 1 to 5, preferably 1 to 3 substituents at a substitutable position. Examples of such substituents include halogen atom (e.g. fluorine, chlorine, bromine, iodine, etc.), hydroxy, $C_{1-6}$ alkyl-carbonyloxy (e.g., acetoxy, etc.).

As the "bivalent $C_{5-8}$ monocyclic non-aromatic hydrocarbon groups", for instance, bivalent groups formed by removing an optional two hydrogen atoms from $C_{5-8}$ cycloalkane or $C_{5-8}$ cycloalkene, can be mentioned. Concrete examples include 1,2-cyclopentylene; 1,3-cyclopentylene; 1,2-cyclohexylene; 1,3-cyclohexylene; 1,4-cyclohexylene; 1,2-cyclohentylene; 1,3-cycloheptylene; 1,4-cycloheptylene; 3-cyclohexen-1,4-ylene; 3-cyclohexen-1,2-ylene; 2,5-cyclohexadien-1,4-ylene. Especially, $C_{5-8}$ cycloalkylene is preferable.

The "spacer having a main chain of 1 to 6 atoms" is preferably a bivalent group consisting of 1 to 3 species selected from —O—, —S—, —CO—, —SO—, —SO$_2$—, —NR$^8$— ($R^8$ has the same meaning as defined above) and optionally halogenated bivalent $C_{1-6}$ non-cyclic hydrocarbon groups.

Preferred examples of the "spacer having a main chain of 1 to 6 atoms" include (1) $C_{1-6}$ alkylene (e.g. —CH$_2$—, —(CH$_2$)$_2$—, —(CH$_2$)$_3$—, —(CH$_2$)$_4$—, —(CH$_2$)$_5$—, —(CH$_2$)$_6$—, —CHCH$_3$—, —C(CH$_3$)$_2$—, —CH(CF$_3$)—, —(CH(CH$_3$))$_2$—, —(CF$_2$)$_2$—, —(CH$_2$)$_2$C(CH$_3$)$_2$—, —(CH$_2$)$_3$ C(CH$_3$)$_2$—, etc.);

(2) $C_{2-6}$ alkenylene (e.g. —CH=CH—, —CH$_2$—CH=CH—, —CH$_2$—CH=CH—, —C(CH$_3$)$_2$—CH=CH—, —CH$_2$—CH=CH—CH$_2$—, —CH$_2$—CH$_2$—CH=CH—, —CH=CH—CH=CH—, —CH=CH—CH$_2$—CH$_2$—CH$_2$—, etc.);

(3) $C_{2-6}$ alkynylene (e.g. —C≡C—, —CH$_2$—C≡C—, —CH$_2$—C≡C—CH$_2$—CH$_2$—, etc.);

(4) —(CH$_2$)$_{w1}$O(CH$_2$)$_{w2}$—, —(CH$_2$)$_{w1}$S(CH$_2$)$_{w2}$—, —(CH$_2$)$_{w1}$CO(CH$_2$)$_{w2}$—, —(CH$_2$)$_{w1}$SO(CH$_2$)$_{w2}$—, —(CH$_2$)$_{w1}$SO$_2$(CH$_2$)$_{w2}$—, —(CH$_2$)$_{w1}$NR$^8$ (CH$_2$)$_{w2}$—;

(5) —(CH$_2$)$_{w3}$CONR$^8$(CH$_2$)$_{w4}$—, —(CH$_2$)$_{w3}$NR$^8$CO(CH$_2$)$_{w4}$—, —(CH$_2$)$_{w3}$SO$_2$NR$^8$(CH$_2$)$_{w4}$—, —(CH$_2$)$_{w3}$NR$^8$SO$_2$(CH$_2$)$_{w4}$—, —(CH$_2$)$_{w3}$COO(CH$_2$)$_{w4}$—;

(6) —(CH$_2$)$_{w5}$NR$^8$CONR$^8$ (CH$_2$)$_{w6}$—;

(7) —(CH$_2$)$_{w7}$CONR$^8$—(CH$_2$)$_{w8}$—CONR$^{8b}$—(CH$_2$)$_{w9}$—;

—CH=CH—CONR$^8$—; —CH=CH—SO$_2$NR$^8$—;

wherein $R^8$ has the same meaning as defined above; $R^{8b}$ has the same meaning as $R^8$; w1 and w2 is an integer of 0 to 5, and w1+w2 is 0 to 5; w3 and w4 is an integer of 0 to 4, and w3+w4 is 0 to 4; w5 and w6 is an integer of 0 to 3, and w5+w6 is 0 to 3; w7, w8 and w9 is an integer of 0 to 2, and w7+w8+w9 is 0 to 2.

The "spacer having a main chain of 1 to 6 atoms" for X, is preferably —(CH$_2$)$_{w1}$O(CH$_2$)w$_2$— (symbols have the same meaning as defined above), —CONR$^{8c}$—, —NR$^{8c}$CO, —CH=CH— CONR$^{8c}$—, —SO$_2$NR$^{8c}$— ($R^8$ is hydrogen atom or $C_{1-6}$ alkyl); more preferably —CONR$^{8c}$—, —NR$^{8c}$CO—, —CH=CH—CONR$^{8c}$—, —SO$_2$NR$^{8c}$— ($R^8$ has the same meaning as defined above); especially preferably —CONH—, —NHCO—, etc.

The "spacer having a main chain of 1 to 6 atoms" for Y, is preferably optionally halogenated bivalent $C_{1-6}$ non-cyclic hydrocarbon groups, —(CH$_2$)$_{w3}$CONH(CH$_2$)$_{w4}$—, —(CH$_2$)$_{w3}$COO(CH$_2$)$_{w4}$— (symbols have the same meaning as defined above); more preferably $C_{1-3}$ alkylene (e.g. —CH$_2$—, —(CH$_2$)$_2$—, —(CH$_2$)$_3$—, etc.), —(CH$_2$)$_{w3}$CONH(CH$_2$)$_{w4}$—, —(CH$_2$)$_{w3}$COO(CH$_2$)$_{w4}$— (symbols have the same meaning as defined above); especially preferably $C_{1-3}$ alkylene (e.g. —CH$_2$—, —(CH$_2$)$_2$—, —(CH$_2$)$_3$—, etc.), etc.

As "substituents" and "monocyclic aromatic rings" in "monocyclic aromatic rings which may be condensed with 4 to 8 membered non-aromatic rings, and may have further substituents" for Ar, those exemplified as "substituents" and "cyclic group" in the "cyclic group which may have substituents" for the above $Ar^1$ can be used. The number of substituents is, for instance, 1 to 5, preferably 1 to 3. When the number of substituents is 2 or more, each substituents can be the same or different.

The substituents are preferably formyl, optionally halogenated $C_{1-6}$ alkyl-carbonyl, optionally halogenated $C_{1-6}$ alkylsulfonyl, etc.

Here, as "optionally halogenated $C_{1-6}$ alkyl-carbonyl" and "optionally halogenated $C_{1-6}$ alkylsulfonyl", those exemplified as "substituents" in "$C_{7-19}$ aralkyl which may have substituents" can be used respectively.

Examples of "4 to 8 membered non-aromatic rings" in the "monocyclic aromatic rings which may be condensed with 4 to 8 membered non-aromatic rings, and may have further substituents" include $C_{4-8}$ monocyclic non-aromatic hydrocarbon rings, 4 to 8 membered monocyclic non-aromatic hetero rings.

Examples of the "$C_{4-8}$ monocyclic non-aromatic hydrocarbon rings" include $C_{4-8}$ cycloalkane and $C_{4-8}$ cycloalkene. Concrete examples include cyclobutane, cyclopentane, cyclohexane, cycloheptane, cyclooctane, cyclopentene, cyclohexene, cycloheptene. Especially, cyclopentane, cyclohexane, cyclobutane, etc. are preferable.

Examples of the "4 to 8 membered monocyclic non-aromatic hetero rings" include azetidine, pyrrolidine, pyrroline, pyrazolidine, 2- or 3-pyrazoline, imidazoline, piperidine, piperazine, azepine, azocane, oxane, oxine, oxepane, oxazolidine, 2-oxazoline, thiazolidine, 2-thioazoline, morpholine, thiomorpholine.

The above "4 to 8 membered non-aromatic rings" may have 1 to 3 substituents at a substitutable position. Examples of such substituents include optionally halogenated $C_{1-6}$ alkyl (e.g., methyl, ethyl, propyl, isopropyl, butyl, isobutyl, sec-butyl, tert-butyl, pentyl, hexyl, etc.), cyano, hydroxy.

Regarding Ar, concrete examples of "monocyclic aromatic rings which may be condensed with 4 to 8 membered non-aromatic rings, and may have further substituents" include

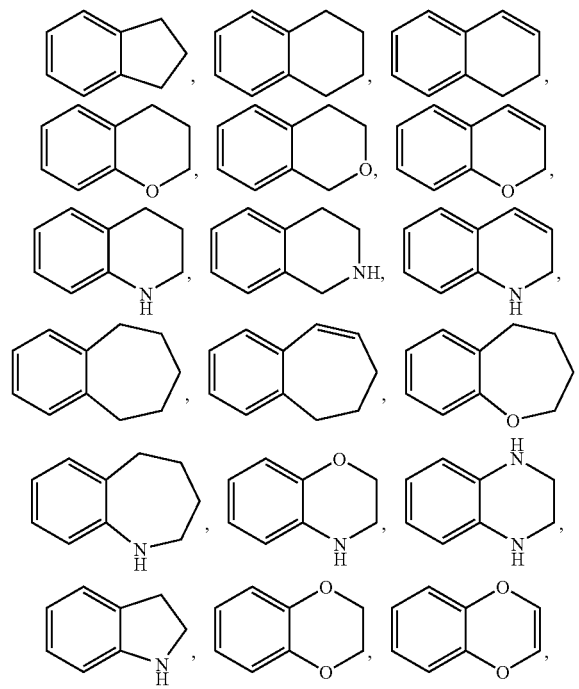

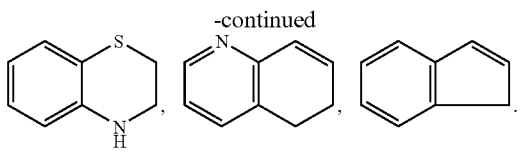

Ar is preferably benzene, pyridine, or rings of the formulae:

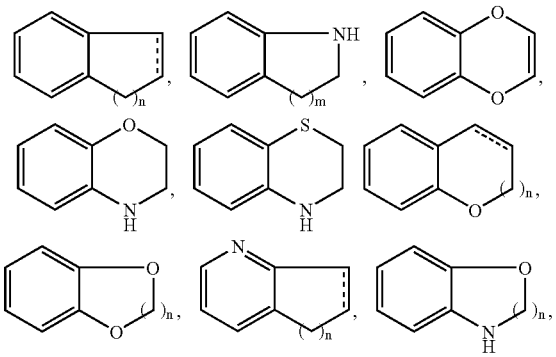

wherein ====is a single bond or double bond; each of m and n is an integer of 1 to 4.

Ar is more preferably benzene, pyridine, rings of the formulae:

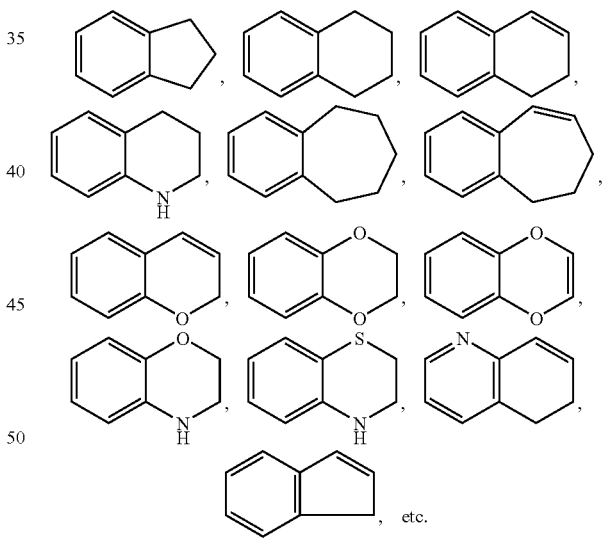

, etc.

As the "hydrocarbon groups which may have substituents" for $R^1$ and $R^2$, those exemplified as the above $R^3$ can be used.

The "hydrocarbon groups which may have substituents" are preferably "$C_{1-6}$ alkyl which may have substituents".

Here, examples of "$C_{1-6}$ alkyl" in the "$C_{1-6}$ alkyl which may have substituents" include methyl, ethyl, propyl, isopropyl, butyl, isobutyl, sec-butyl, tert-butyl, pentyl, hexyl. Especially, methyl, ethyl, propyl, etc. are preferable.

Examples of "substituents" in the "$C_{1-6}$ alkyl which may have substituents" include halogen atom (e.g. fluorine, chlorine, bromine, iodine, etc.), $C_{1-3}$ alkylenedioxy (e.g. methylenedioxy, ethylenedioxy etc.), nitro, cyano, optionally halogenated $C_{3-6}$ cycloakyl optionally halogenated $C_{1-6}$ alkoxy, optionally halogenated $C_{1-6}$ alkylthio, hydroxy, amino, mono-$C_{1-6}$ alkylamino (e.g. methylamino, ethylamino, propylamino, isopropylamino, butylamino, etc.), di-$C_{1-6}$ alkylamino (e.g. dimethylamino, diethylamino, dipropylamino, dibutylamino, ethylmethylamino, etc.), formyl, carboxy, carbamoyl, thiocarbamoyl, optionally halogenated $C_{1-6}$ alkyl-carbonyl, optionally halogenated $C_{1-6}$ alkoxycarbonyl (e.g. methoxycarbonyl, ethoxycarbonyl, propoxycarbonyl, tertbutoxycarbonyl, etc.), mono-$C_{1-6}$ alkyl-carbamoyl (e.g. methylcarbamoyl, ethylcarbamoyl, etc.), di-$C_{1-6}$ alkylcarbamoyl (e.g. dimethylcarbamoyl, diethylcarbamoyl, ethylmethylcarbamoyl etc.), optionally halogenated $C_{1-6}$ alkylsulfonyl, formylamino, optionally halogenated $C_{1-6}$ alkyl-carboxamide, $C_{1-6}$ alkoxy-carboxamide (e.g. methoxycarboxamide, ethoxycarboxamide, propoxycarboxamide, butoxycarboxamide, etc.), $C_{1-6}$ alkylsulfonylamino (e.g. methylsulfonylamino, ethylsulfonylamino, etc.), $C_{1-6}$ alkyl-carbonyloxy (e.g. acetoxy, propanoyloxy, etc.) $C_{1-6}$ alkoxycarbonyloxy (e.g. methoxycarbonyloxy, ethoxycarbonyloxy, propoxycarbonyloxy, butoxycarbonyloxy, etc.), mono-$C_{1-6}$ alkyl-carbamoyloxy (e.g. methylcarbamoyloxy, ethylcarbamoyloxy, etc.), di-$C_{1-6}$ alkyl-carbamoyloxy(e.g. dimethylcarbamoyloxy, diethylcarbamoyloxy, etc.), and aromatic groups which may have substituents. The number of substituents is, for instance, 1 to 5, preferably 1 to 3. When the number of substituents is 2 or more, each substituents can be the same or different.

Here, as "optionally halogenated $C_{3-6}$ cycloalkyl," "optionally halogenated $C_{1-6}$ alkoxy" and "optionally halogenated $C_{1-6}$ alkylthio", those exemplified as "substituents" in the above "cyclic group which may have substituents" can be used.

As "optionally halogenated $C_{1-6}$ alkyl-carbonyl" "optionally halogenated $C_{1-6}$ alkylsulfonyl" and "optionally halogenated $C_{1-6}$ alkyl-carboxamide", those exemplified as "substituents" in the above "$C_{7-19}$ aralkyl which may have substituents" can be used.

As "substituents" and "aromatic groups" in the "aromatic groups which may have substituents", those exemplified as "substituents" and "aromatic groups" in the "cyclic group which may have substituents" for the above $Ar^1$ can be used. The number of substituents is, for instance, 1 to 5, preferably 1 to 3. When the number of substituents is 2 or more, each substituents can be the same or different.

Examples of "nitrogen-containing hetero rings" in the "nitrogen-containing hetero rings which may have substituents" formed by $R^1$ and $R^2$ together with the adjacent nitrogen atom, include 3 to 8 membered nitrogen-containing hetero rings which contain at least one nitrogen atom in addition to carbon atoms, and which may further contain 1 to 3 hetero atoms selected from nitrogen, sulfur and oxygen atom. Concrete examples include aziridine, azetidine, morpholine, thiomorpholine, piperidine, piperazine, pyrrolidine, hexamethyleneimine, heptamethyleneimine, hexahydropyrimidine, 1,4-diazepan, 4,5-dihydro-imidazole, and their unsaturated cyclic amines (e.g. 1,2,5,6-tetrahydropyridine, etc.) can be mentioned. Especially, morpholine, piperidine, piperazine, pyrrolidine.

As "substituents" in the "nitrogen-containing hetero rings which may have substituents", for instance, those exemplified as "substituents" in the above "5 to 7 membered saturated cyclic amino which may have substituents" can be used. The number of substituents is, for instance, 1 to 5, preferably 1 to 3. When the number of substituents is 2 or more, each substituents can be the same or different.

$R^1$ and $R^2$ are preferably $C_{1-6}$ alkyl, more preferably methyl, ethyl, propyl, etc.

Also, it is preferable that $R^1$ and $R^2$, together with the adjacent nitrogen atom, form piperidino, pyrrolidin-1-yl, piperazin-1-yl etc.

And, it is preferable that at least one of $R^1$ and $R^2$ is $C_{1-6}$ alkyl which may have substituents. It is especially preferable that both. $R^1$ and $R^2$ is $C_{1-6}$ alkyls which may have substituents.

$R^2$ can form a spiro ring together with Ar. For instance, Ar is a ring of the formula:

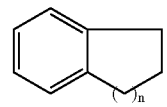

wherein n is an integer of 1 to 4; and Y is methylene; $R^2$ can form a spiro ring together with Ar. Examples of the spiro ring include

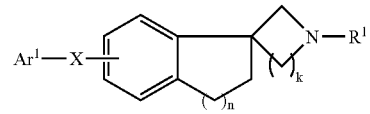

wherein k (ring Ar and N are connected by —$(CH_2)_k$—.) is an integer of 1 to 4; and other symbols have the same meaning as defined above.

$R^2$ may form, together with the adjacent nitrogen atom and Y, a nitrogen-containing hetero ring which may have substituents. Examples of the "nitrogen-containing hetero ring which may have substituents" include those exemplified as the "nitrogen-containing hetero rings which may have substituents formed by $R^1$ and $R^2$ together with the adjacent nitrogen atom.

In formula (I), preferable examples of the partial structural formula: Ar—Y—N($R^1$)$R^2$ (symbols have the same meanings as defined above) include

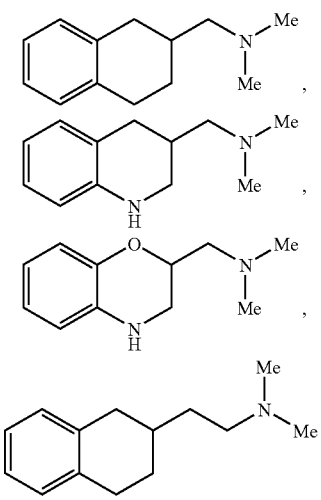

-continued
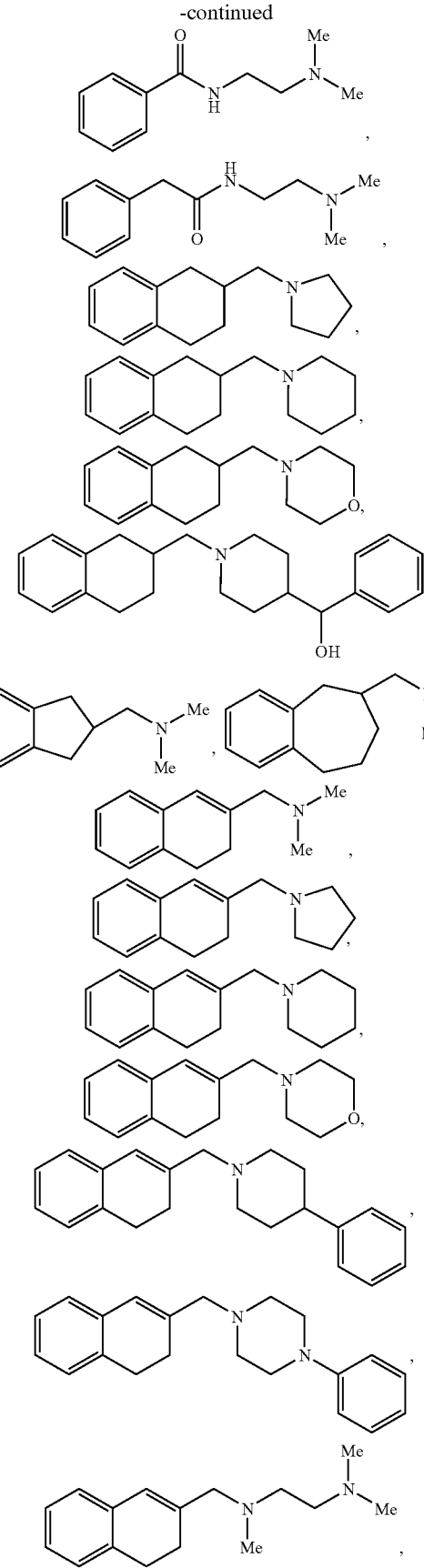
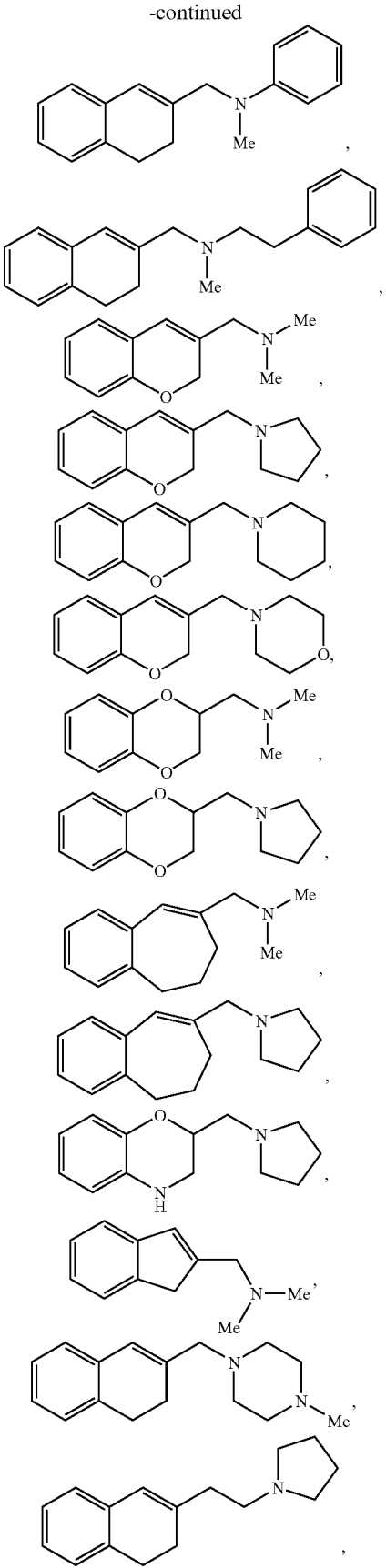

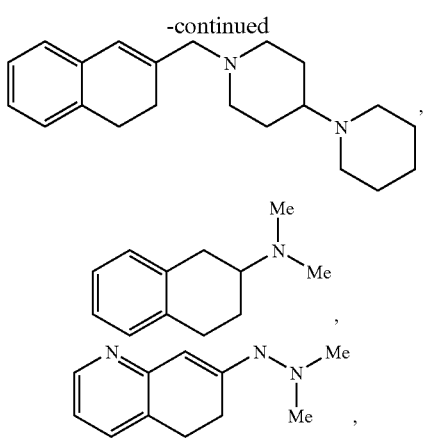

etc.

Among the compounds of the formula (I), a compound wherein Ar is a ring of the formula:

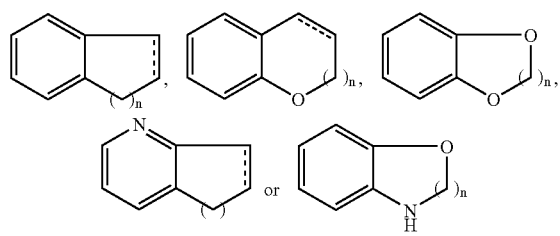

wherein ==== is a single bond or double bond, n is an integer of 1 to 4, and each ring may have substituents;

x is —CONR$^{8c}$—, —NR$^{8c}$CO—, —CH═CH—CONR$^{8c}$— or —SO$_2$NR$^{8c}$— where R$^8$ is hydrogen atom or C$_{1-6}$ alkyl;

Y is a spacer having a main chain of 1 to 6 atoms; provided that Ar is a ring of the formulae:

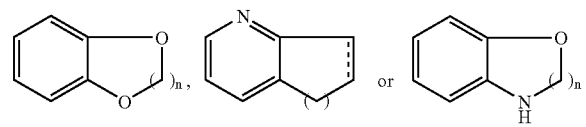

wherein symbols have the same meanings as defined above, and each ring may have substituents, when X is —SO$_2$NH—; and provided that Ar$^1$ is not biphenylyl which may be substituted; when X is —CONH— and Ar is any one of benzopyran, dihydrobenzopyran, dihydrobenzoxazine, dihydrobenzoxazole or tetrahydrobenzoxazepine;

(excluding N-(2-(N,N-dimethylamino)methyl-6-tetralinyl]-4-biphenylylcarboxamide);

namely compound of the formula (I') (excluding N-[2-(N,N-dimethylamino)methyl-6-tetralinyl]-4-biphenylylcarboxamide) is a novel compound.

Preferred examples of compound of the formula (I') include compound of the formula (I'-1), (I'-2), (I'-3), (I'-4), (I'-5), (I'-6), (I'-7), (I'-8), (I'-9) or (I'-10).

In the above formulae (I'), (I'-1), (I'-2), (I'-3), (I'-4), (I'-5), (I'-6), (I'-7), (I'-8), (I'-9) and (I'-10), a ring of the formula:

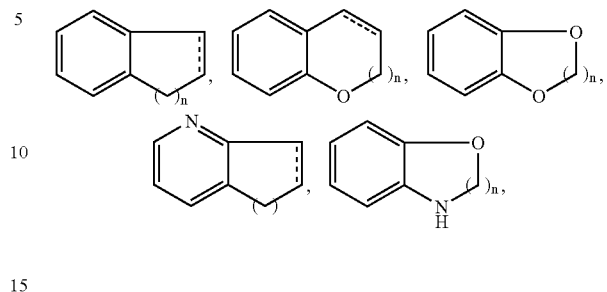

etc.

wherein symbols have the same meanings as above, may have further 1 to 3 substituents at substitutable positions.

Examples of such substituents include "substituents" exemplified in the above Ar. Especially, preferred are formyl, optionally halogenated C$_{1-6}$ alkyl-carbonyl, optionally halogenated C$_{1-6}$ alkylsulfonyl, optionally halogenated C$_{1-6}$ alkyl (e.g., methyl, ethyl, propyl, isopropyl, butyl, isobutyl, sec-butyl, tert-butyl, pentyl, hexyl, etc.), cyano, hydroxy, etc.

Examples of salts of compound (I) or (I') include salts with inorganic bases, ammonium salts, salts with organic bases, salts with inorganic acids, salts with organic acids, and salts with basic or acidic amino acids.

Preferred examples of salts with inorganic bases include alkali metal salts such as sodium salts and potassium salts; alkaline earth metal salts such as calcium salts, magnesium salts, barium salts; and aluminum salts.

Preferred examples of salts with organic bases include salts with trimethylamine, triethylamine, pyridine, picoline, ethanolamine, diethanolamine, triethanolamine, dicyclohexylamine, N,N-dibenzylethylenediamine.

Preferred examples of salts with inorganic acids include salts with hydrochloric acid, hydrobromic acid, nitric acid, sulfuric acid, phosphoric acid.

Preferred examples of salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid, 3-chlorobenzoic acid.

Preferred examples of salts with basic amino acids include salts with arginine, lysine, ornithine. Preferred examples of salts with acidic amino acids include salts with aspartic acid, glutamic.

Among these salts, pharmaceutically acceptable salts are preferable. For instance, when compound (I) or (I') possesses an acidic functional group, it can form an inorganic salt such as an alkali metal salt (e.g., sodium salt, potassium salt, etc.), an alkaline earth metal salt (e.g. calcium salt, magnesium salt, barium salt, etc.), and an ammonium salt. When compound (I) or (I') possesses a basic functional group, it can form an inorganic salt such as hydrochloride, sulfate, phosphate, hydrobromate, etc.; or an organic salt such as acetate, maleate, fumarate, succinate, methanesulfonate, p-toluenesulfonate, citrate and tartrate.

Compounds (I) and (I') (hereinafter also abbreviated as a compound of the invention) can be either anhydrides or hydrates. A hydrate may have 0.5 to 3 water molecules.

In addition, a compound of the invention can be labeled using isotopes (e.g. $^3$H, $^{14}$C, and $^{35}$S, etc.).

When a compound of the invention contains optical isomers, stereoisomers, regio isomers, rotational isomers, these are included as a compound of the invention, and each of them can be obtained as a single substance by per se known synthesis methods and separation methods. For instance, when optical isomers exist in a compound of the invention, the optical isomers separated from the compound are included in a compound of the invention.

The optical isomers can be produced using per se known methods. Concretely, the optical isomer can be obtained by using an optically active synthetic intermediate, or subjecting the racemic mixture of the final product to optical resolution in accordance with common method.

Examples of optical resolution methods include per se known methods such as the fractional recrystallization method, chiral column method, diastereomer method, etc., which are described in detail below.

1) Fractional Recrystallization Method

The method which comprises allowing a racemate to form a salt with an optically active compound (e.g. (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.), separating the salt using a fractional recrystallization method, followed by, if desired, neutralizing process to obtain a free optical isomer.

2) Chiral Column Method

This method comprises subjecting a racemate or its salt to a column for separating an optical isomer (chiral column) for separation. For instance, in the case of liquid chromatography, an optical isomer mixture is added to the chiral column such as ENANTIO-OVM [produced by Toso] or CHIRAL series [produced by Daicel], which is developed using water, various buffer solutions (e.g. phosphate buffer), organic solvents (e.g. ethanol, methanol, isopropanol, acetonitrile, trifluoroacetic acid, diethylamine, etc.) as single or mixed solutions, and the optical isomers are separated. Also, in the case of gas chromatography, for instance, separation is conducted using a chiral column such as CP-Chirasil-DeX (produced by G.L.Science Co.).

3) Diastereomer Method

In this method, a racemic mixture is subjected to a chemical reaction with an optically active reagent to give a diastereomer mixture, which is separated into a single substance by an ordinary separation means (e.g. fractional recrystallization, chromatography method, etc.). This single substance is subjecting to removal of the optically active reagent part using chemical processing such as a hydrolysis reaction. For instance, when a compound of the invention possesses hydroxy or primary or secondary amino in its molecule, this compound is subjected to a condensation reaction with an optically active organic acid (e.g. MTPA [α-methoxy-α-(trifluoromethyl)phenylacetic acid], (−)-menthoxyacetic acid, etc.), to give the diastereomer in an ester form or an amide form, respectively. On the other hand, when a compound of the invention possesses carboxylic acid group, this compound is subjected to a condensation reaction with an optically active amine or alcohol reagent, to give the diastereomer in an amide form or an ester form, respectively. The separated diastereomer can be converted to an optical isomer of the original compound, by applying acidic hydrolysis or basic hydrolysis.

A prodrug of compound (I') is a compound which is converted to compound (I') by reactions involving enzymes and gastric acid, etc. under physiological conditions in the living body; in other words, a compound that is changed into compound (I') by enzymatically-caused oxidation, reduction and hydrolysis, and a compound that is changed into compound (I') by hydrolysis caused by gastric acid. Examples of the prodrugs of compound (I') include compounds in which amino groups of compound (I') have been acylated, alkylated, or phosphorylated [e.g. compounds in which amino groups of compound (I') have been eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated, etc.]; compounds in which hydroxyl groups of compound (I') have been acylated, alkylated, phosphorylated, borated (e.g. compounds in which hydroxyl groups of compound (I') have been acetylated, palmitoylated, propanoylated, pivaloylated, succinylated, fumarylated, alanylated, dimethylaminomethylcarbonylated, etc.); compounds in which carboxyl groups of compound (I') have been esterified or amidated [e.g. compounds in which carboxyl groups of compound (I') have been ethylesterified, phenylesterified, carboxylmethylesterified, dimethylaminomethylesterified, pivaloyloxymethylesterified, ethoxycarbonyloxyethylesterified, phthalidylesterified, (5-methyl-2-oxo-1,3-dioxolen-4-yl)methylesterified, cyclohexyloxycarbonylethylesterified, or methylamidated, etc.]. These compounds can be produced from compound (I') using per se known methods.

Also, a prodrug of compound (I') can be a compound which is changed to compound (I') by physiological conditions, as described in pages 163 to 198 of Molecular Design, Volume 7, "Development of Drugs,", published in 1990 by Hirokawa Shoten.

A compound of the invention can be produced in accordance with per se known methods such as methods described in WO9838156, WO9532967, and EP-A533266, etc., or analogous methods thereto.

For instance, a compound of the invention can be produced in accordance with [Production method 1] to [Production method 6] which are described in detail below, or analogous methods thereto.

Compounds (II) to (XI) used as raw materials, can be used in the form of salts. As such salts, those exemplified as salts of the above compound (I) or (I') can be used.

In the following [Production method 1] to [Production method 6], when an alkylation reaction, a hydrolysis reaction, an amination reaction, an esterification reaction, an amidation reaction, an esterification reaction, an etherification reaction, an oxidation reaction, a reduction reaction, etc. are carried out, these reactions are carried out in accordance with per se known methods. Examples of such methods include the methods described in Organic Functional Group Preparations, Second Edition, Academic Press, Inc., published in 1989; Comprehensive Organic Transformations, VCH Publishers Inc., published in 1989. etc.

[Production Method 1]

Compound (Ia) having —$(CH_2)_{w3}CONR^{8a}(CH_2)_{w4}$— for X in formula (I), is produced, for instance, by the following amidation reaction.

(Amidation Reaction)

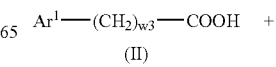

(II)

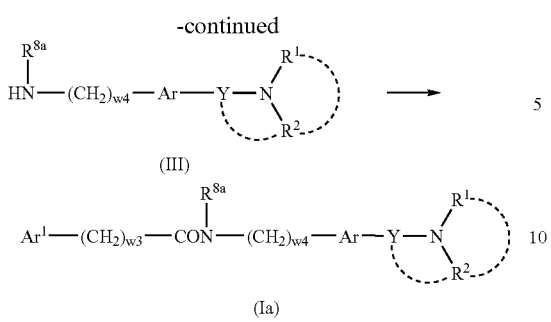

wherein $R^{8a}$ is hydrogen atom or an optionally halogenated $C_{1-6}$ alkyl; other symbols have the same meanings as defined above.

As the "optionally halogenated $C_{1-6}$ alkyl", those exemplified as "substituents" in the above "cyclic group which may have substituents" can be used.

The "amidation reaction" includes the following "method using a dehydration and condensation agent" and "method using a reactive derivative of carboxylic acid".

i) Method Using a Dehydration and Condensation Agent

Compound (III), 1 to 5 equivalents of compound (II), and 1 to 2 equivalents of a dehydration and condensation agent are reacted in an inert solvent. If necessary, the reaction can be carried out with the coexistence of 1 to 1.5 equivalents of 1-hydroxybenzotriazole (HOBT) and (or) catalytic quantity to 5 equivalents of a base.

Examples of the "dehydrating and condensation agent" include dicyclohexylcarbodiimide (DCC), 1-ethyl-3-(3-dimethylaminopropyl)carbodimide hydrochloride (WSC). WSC is particularly preferable.

Examples of the "inert solvent" include nitrile solvents (preferably acetonitrile), amide solvents (preferably DMF), halogenated hydrocarbon solvents (preferably dichloromethane), ether solvents (preferably THF). Two or more kinds of these can be mixed in an appropriate ratio for use.

Examples of the "Base" include 1) for instance, strong bases such as hydrides of alkali metals or alkaline earth metals (e.g. lithium hydride, sodium hydride, potassium hydride, calcium hydride, etc.), amides of alkali metals or alkaline earth metals (e.g. lithium amide, sodium amide, lithium diisopropylamide, lithium dicyclohexylamide, lithium hexamethyldisilazide, sodium hexamethyldisilazide, potassium hexamethyldisilazide, etc.), lower alkoxides of alkali metals or alkaline earth metals (e.g. sodium methoxide, sodium ethoxide, potassium tert-butoxide, etc.);

2) for instance, inorganic bases such as hydroxides of alkali metals or alkaline earth metals (e.g. sodium hydroxide, potassium hydroxide, lithium hydroxide, barium hydroxide, etc.), carbonates of alkali metals or alkaline earth metals (e.g. sodium carbonate, potassium carbonate, cesium carbonate, etc.) and hydrogencarbonates of alkali metals or alkaline earth metals (e.g. sodium hydrogencarbonate, potassium hydrogencarbonate, etc.); and 3) for instance, amines such as triethylamine, diisopropylethylamine, N-methylmorpholine, dimethylaminopyridine, DBU (1,8-diazabicyclo[5.4.0]undec-7-en), DBN (1,5-diazabicyclo[4.3.0]non-5-en); for instance, organic bases such as basic heterocyclic compounds of pyridine, imidazole, 2,6-lutidine, etc.

Among the above bases, triethylamine, 4-dimethylaminopyridine, etc., are preferable.

Reaction temperature is usually room temperature (0° C. to 30° C., hereafter the same). Reaction time is, for instance, 10 to 24 hours.

ii) Method Using a Reactive Derivative of Carboxylic Acid

A reactive derivative of compound (II) and 1 to 5 equivalents (preferably 1 to 3 equivalents) of compound (III) are reacted in an inert solvent. If necessary, the reaction can be carried out with the coexistence of 1 to 10 equivalents, preferably 1 to 3 equivalents of a base.

Examples of the "reactive derivative" of compound (II) include acid halides (e.g., acid chloride, acid bromide, etc.), mixed acid anhydrides (e.g. acid anhydrides with $C_{1-6}$ alkyl-carboxylic acid, $C_{6-10}$ aryl-carboxylic acid or $C_{1-6}$ alkylcarbonate), active esters (e.g. esters with phenol which may have substituents, 1-hydroxybenzotriazole or N-hydroxysuccinimide, etc.).

Examples of the "substituents" in the "phenol which may have substituents" include halogen atom (e.g. fluorine, chlorine, bromine, iodine, etc.), nitro, optionally halogenated $C_{1-6}$ alkyl, optionally halogenated $C_{1-6}$ alkoxy. The number of substituents is, for instance, 1 to 5.

As the "optionally halogenated $C_{1-6}$ alkyl" and "optionally halogenated $C_{1-6}$ alkoxy", those exemplified as "substituents" in the above "cyclic group which may have substituents" can be used.

Concrete examples of "phenol which may have substituents" include phenol, pentachlorophenol, pentafluorophenol, p-nitrophenol. The reactive derivative is, preferably, an acid halide.

Examples of the "inert solvent" include ether solvents, halogenated hydrocarbon solvents, aromatic solvents, nitrile solvents, amide solvents, ketone solvents, sulfoxide solvents, and water. Two or more kinds these can be mixed in an appropriate ratio for use. Especially, acetonitrile, THF, dichloromethane, chloroform, etc. are preferable.

As the "base", the same as above are used. The base is preferably sodium hydride, potassium carbonate, sodium carbonate, sodium hydroxide, potassium hydroxide, sodium hydrogencarbonate potassium hydrogencarbonate, triethylamine, pyridine, etc.

Reaction temperature is usually –20° C. to 50° C., preferably room temperature. Reaction time is usually 5 minutes to 40 hours, preferably 1 to 18 hours.

Compound (III) can be produced by per se known methods. For instance, 6-amino-2-(N,N-dimethylamino)methyltetraline or its salt can be produced in accordance with the methods described in WO9838156. Also, 6-amino-2,3-dihydro-1-(2-dimethylaminoethyl)-1H-indole, 6-amino-3,4-dihydro-4-(2-dimethylaminoethyl)-2H-1,4-benzoxazine, etc., can be produced in accordance with the methods described in WO9532967.

The above "method using a reactive derivative of carboxylic acid" can be also adopted when producing a corresponding sulfonamide derivative or sulfinamide derivative, from the sulfonic acid of the formula: $Ar^1$—$(CH_2)_{w3}$—$SO_2OH$ (symbols have the same meanings as defined above), or the sulfinic formula: $Ar^1$—$(CH_2)_{w3}$—$SOOH$ (symbols have the same meanings as defined above).

[Production Method 2]

Compound (Ib) having —$(CH_2)_{w3}$—$COO(CH_2)_{w4}$— for X in the formula (I), can be produced by the following esterification reaction.

(Esterification Reaction)

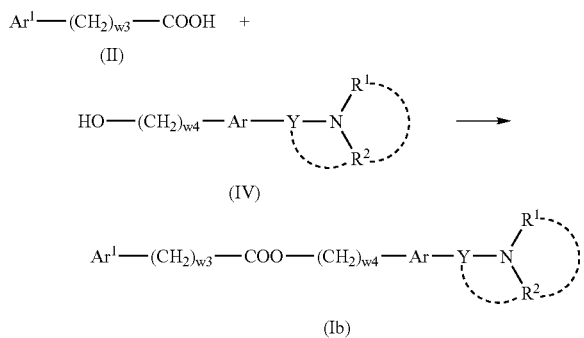

wherein symbols have the same meanings as defined above.

A reactive derivative of compound (II) and 1 to 5 equivalents (preferably 1 to 3 equivalents) of compound (IV) is reacted in an inert solvent. Usually, this reaction is carried out with the coexistence of 1 to 10 equivalents, preferably 1 to 3 equivalents of a base.

As the reactive derivative of compound (II), the same as above is used. Especially, an acid halide is preferable.

Examples of the "inert solvent" include ether solvents, halogenated hydrocarbon solvents, aromatic solvents, nitrile solvents, amide solvents, ketone solvents, sulfoxide solvents. Two or more kinds of these can be mixed in an appropriate ratio for use. Especially, acetonitrile, dichloromethane, chloroform, etc. are preferable.

As the "base", the same one as above can be used. The base is preferably sodium hydride, potassium carbonate, sodium carbonate, sodium hydroxide, potassium hydroxide, sodium hydrogencarbonate, potassium hydrogencarbonate, triethylamine, pyridine, etc.

Reaction temperature is usually −20° C. to 50° C., preferably room temperature. Reaction time is usually 5 minutes to 40 hours, preferably 1 to 18 hours.

[Production Method 3]

Compound (Ic) having —$(CH_2)_{w1}O(CH_2)_{w2}$— for Y in the formula (I), can be produced by, for instance, the following etherification reaction.

(Etherification Reaction)

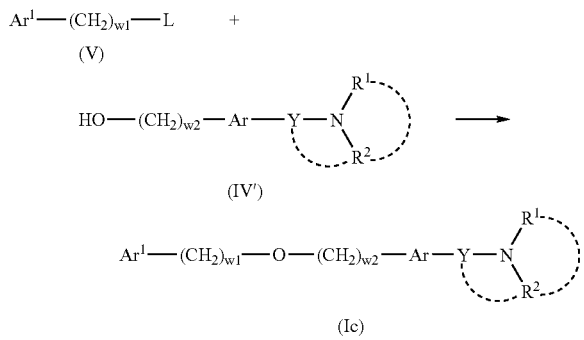

wherein L is a leaving group, and other symbols have the same meanings as defined above.

Examples of the "leaving group" for L include halogen atom (e.g. chlorine, bromine, iodine, etc.), optionally halogenated $C_{1-6}$ alkylsulfonyloxy (e.g. methanesulfonyloxy, ethanesulfonyloxy, trifluoromethanesulfonyloxy, etc.), $C_{6-10}$ arylsulfonyloxy which may have substituents, hydroxy.

Examples of the "substituents" in the "$C_{6-10}$ arylsulfonyloxy which may have substituents" include halogen atom (e.g. chlorine, bromine, iodine, etc.), optionally halogenated $C_{1-6}$ alkyl, $C_{1-6}$ alkoxy. The number of substituents is, for instance, 1 to 3. Concrete examples of the "$C_{6-10}$ arylsulfonyloxy which may have substituents" include benzenesulfonyloxy, p-toluenesulfonyloxy, 1-naphthalenesulfonyloxy, 2-naphthalenesulfonyloxy.

The "leaving group" is preferably halogen atom (e.g. chlorine, bromine, iodine, etc.), methanesulfonyloxy, trifluoromethanesulfonyloxy, p-toluenesulfonyloxy.

Compound (IV') and about 1 to 5 equivalents (preferably 1 to 2 equivalents) of compound (V) are reacted in inert solvent, with the coexistence of base.

As the "base", the same one as above can be used. The base is preferably potassium carbonate, sodium hydrogencarbonate, triethylamine, N-methylmorpholine, pyridine, etc. The amount of the base used is usually about 1 to 5 equivalents relative to compound (V).

Examples of the "inert solvent" include alcohol solvents, ether solvents, halogenated hydrocarbon solvents, aromatic solvents, nitrile solvents, amide solvents, ketone solvents, sulfoxide solvents, water. Two or more kinds of these can be mixed in an appropriate ratio for use. Especially, acetonitrile, N,N-dimethylformamide (DMF), acetone, ethanol, pyridine, etc., are preferable.

Reaction temperature is about −20° C. to 100° C., preferably room temperature to 80° C. Reaction time is, for instance, 5 hours to 1 day.

In the above production method, when the leaving group is hydroxy, Mitsunobu reaction can usually be used. In the Mitsunobu reaction, compound (V) and 0.5 to 5 equivalents (preferably 1 to 1.5 equivalents) of compound (IV') are reacted in inert solvent with the coexistence of 0.5 to 5 equivalents (preferably 1 to 1.5 equivalents) of ethyl acetyldicarboxylate.

Examples of the inert solvent include ether solvents, halogenated hydrocarbon solvents, aromatic solvents, nitrile solvents, amide solvents, ketone solvents, sulfoxide solvents. Two or more kinds of these can be mixed in an appropriate ratio for use. Especially, acetonitrile, dichloromethane, chloroform, etc. are preferable.

Reaction temperature is usually −20° C. to 50° C., preferably room temperature. Reaction time is usually 5 minutes to 40 hours, preferably 1 to 18 hours.

Compound (IV') can be produced by per se known methods. For instance, 3-(N,N-dimethylamino)methyl-1,2,3,4-tetrahydro-7-quinolinol, 2-(N,N-dimethylamino)methyl-6-hydroxytetralin, 6-hydroxy-2-piperidinomethyltetralin, 2-[2-(N,N-dimethylamino)ethyl]-6-hydroxytetralin, 2-(N,N-dimethylamino)methyl-7-hydroxytetralin, 6-hydroxy-2-(N-methylamino)methyltetralin, etc., can be produced in accordance with the methods described in WO9838156.

[Production Method 4]

Compound (Id) having —$(CH_2)_{w3}$ $NR^{8a}CO(CN_2)_{w4}$— for X in the formula (I), can be produced, for instance, by the following amidation reaction.

(Amidation Reacion)

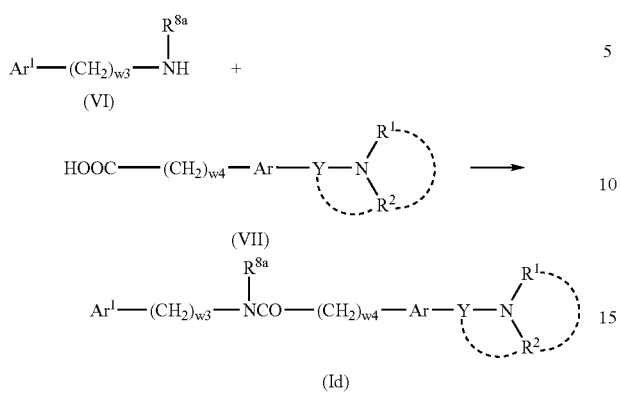

wherein symbols have the same meanings as defined above.

This Production method is carried out in accordance with the above Production method 1.

[Production Method 5]

Compound (Ie) having —$(CH_2)_{w5}NHCONR^{8a}(CN_2)_{w6}$— for X in the formula (I), can be produced, for instance, by the following urea reaction.

(Urea Reaction)

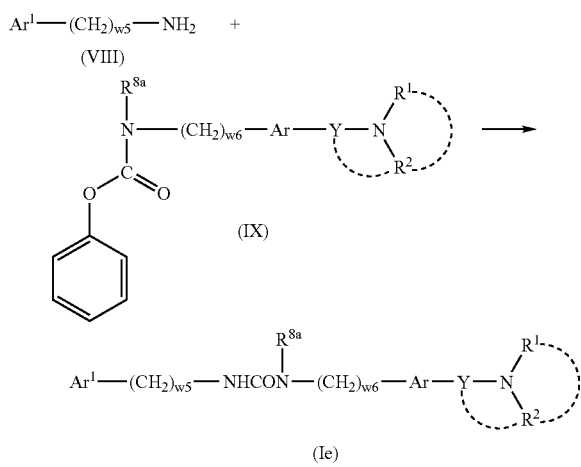

wherein symbols have the same meanings as defined above.

Compound (IX) and 1 to 5 equivalents (preferably 1 to 1.5 equivalents) of compound (VIII) is reacted in an inert solvent with the coexistence of a base.

As the "base", the same one as above can be used. The base is preferably potassium carbonate, sodium carbonate, sodium hydroxide, potassium hydroxide, sodium hydrogencarbonate, potassium hydrogencarbonate, triethylamine, pyridine, etc.

Examples of the "inert solvent" include alcohol solvents, ether solvents, halogenated hydrocarbon solvents, aromatic solvents, nitrile solvents, amide solvents, ketone solvents, sulfoxide solvents, water. Two or more kinds of these can be mixed in an appropriate ratio for use. Especially, acetonitrile, DMF, acetone, ethanol, pyridine, etc. are preferable.

Reaction temperature is usually −20° C. to 100° C., preferably room temperature to 80° C. Reaction time is, for instance, 0.5 hour to 1 day.

[Production Method 6]

Compound (If) having, for $Ar^1$, a ring assembly aromatic group ($Ar^2$—$Ar^3$) which may have substituents in the formula (I), can be produced by, for instance, the following aryl-coupling reaction.

(Aryl-Coupling Reaction)

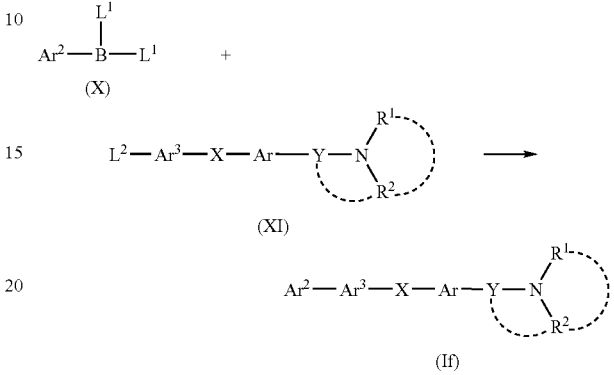

wherein $Ar^2$ and $Ar^3$ are monocyclic aromatic groups or condensed aromatic groups, each of which may have substituents; $L^1$ is hydroxy or $C_{1-6}$ alkyl; $L^2$ is halogen (preferably chlorine, bromine) or trifluoromethanesulfonyloxy; other symbols have the same meanings as defined above.

As "substituents", "monocyclic aromatic groups" and "condensed aromatic groups" in the "monocyclic aromatic groups or condensed aromatic groups, each of which may have substituents for $Ar^2$ and $Ar^3$, those exemplified as the above $Ar^1$ can be used. Especially, it is preferable that both of $Ar^2$ and $Ar^3$ are phenyl groups which may have substituents, and $Ar^2$—$Ar^3$ is biphenylyl which may have substituents.

The aryl-coupling reaction can be carried out in accordance with per se known methods such as the method described in Acta. Chemica Scandinavia, pp. 221–230, 1993, or methods analogous thereto.

Compound (X) and 1 to 3 equivalents (preferably 1 to 1.5 equivalents) of compound (XI) are reacted in an inert solvent in the presence of a base and a transition metal catalyst.

As the base, the same one as above can be used. The base is preferably sodium carbonate, sodium hydrogencarbonate, etc.

The amount of the "base" used is, for instance, about 1 to 10 equivalents relative to compound (XI).

Examples of the "transition metal catalyst" include palladium catalyst, nickel catalyst. Examples of the "palladium catalyst" include tetrakis(triphenylphosphine)palladium (O), palladium acetate, bis (triphenylphosphine) palladium (II) chloride, palladium-carbon. Examples of the "nickel catalyst" include tetrakis(triphenylphosphine) nickel (O).

The amount of the "transition metal catalyst" used is about 0.01 to 1 equivalent, preferably about 0.01 to 0.5 equivalent, relative to compound (XI).

Reaction temperature is room temperature to 150° C., preferably about 80° C. to 150° C. Reaction time is, for instance, about 1 to 48 hours.

Examples of the "inert solvent" include water, alcohol solvents, aromatic solvents. Two or more kinds of these can be mixed in an appropriate ratio for use. Especially, a single solvent such as water, ethanol and toluene; or a mixed solvent of two or more kinds of these is preferable.

Examples of the above "alcohol solvents" include methanol, ethanol, isopropanol, tert-butanol.

Examples of the above "ether solvents" include diethylether, tetrahydrofuran (THF), 1,4-dioxane, 1,2-dimethoxyethane.

Examples of the above "halogenated hydrocarbon solvents" include dichloromethane, chloroform, 1,2-dichloroethane, carbon tetrachloride.

Examples of the above "aromatic solvents" include benzene, toluene, xylene, pyridine.

Examples of the above "hydrocarbon solvents" include hexane, pentane, cyclohexane.

Examples of the above "amide solvents" include N,N-dimethylformamide (DMF), N,N-dimethylacetamide, N-methylpyrrolidone.

Examples of the above "ketone solvents" include acetone, methylethylketone.

Examples of the above "sulfoxide solvents" include dimethylsulfoxide (DMSO).

Examples of the above "nitrile solvents" include acetonitrile, propionitrile.

In a compound of the invention thus obtained, the intramolecular functional group can be converted to a desired functional group by combining per se known chemical reactions. Examples of the chemical reactions include oxidation reaction, reduction reaction, alkylation reaction, hydrolysis reaction, amination reaction, esterification reaction, aryl-coupling reaction, deprotection reaction.

In each of the above reactions, when the raw material compounds possess amino, carboxy, hydroxy, and/or carbonyl as substituents, protecting groups which are generally used in peptide chemicals, etc., can be introduced into these groups, and the desired compound can be obtained by removing the protecting groups after the reaction if necessary.

Examples of the protecting group for amino include formyl, $C_{1-6}$ alkyl-carbonyl (e.g. acetyl, propionyl, etc.), $C_{1-6}$ alkoxy-carbonyl (e.g. methoxycarbonyl, ethoxycarbonyl, tert-butoxycarbonyl, etc.), benzoyl, $C_{7-10}$ aralkyl-carbonyl (e.g. benzylcarbonyl, etc.), $C_{7-14}$ aralkyloxy-carbonyl (e.g. benzyloxycarbonyl, 9-fluorenylmethoxycarbonyl, etc.), trityl, phthaloyl, N,N-dimethylaminomethylene, silyl (e.g. trimethylsilyl, triethylsilyl, dimethylphenylsilyl, tert-butyldimethylsilyl, tert-butyldiethylsilyl, etc.), $C_{2-6}$ alkenyl (e.g. 1-allyl, etc.). These groups may be substituted by 1 to 3 of halogen atom (e.g. fluorine, chlorine, bromine, iodine, etc.), $C_{1-6}$ alkoxy (e.g. methoxy, ethoxy, propoxy, etc.) or nitro, etc.

Examples of the protecting group for carboxy include $C_{1-6}$ alkyl (e.g. methyl, ethyl, propyl, isopropyl, butyl, tert-butyl, etc.), $C_{7-11}$ aralkyl (e.g. benzyl, etc.), phenyl, trityl, silyl (e.g. trimethylsilyl, triethylsilyl, dimethylphenylsilyl, tert-butyldimethylsilyl, tert-butyldiethylsilyl, etc.), $C_{2-6}$ alkenyl (e.g. 1-allyl, etc.). These groups may be substituted by 1 to 3 of halogen atom (e.g. fluorine, chlorine, bromine, iodine, etc.), $C_{1-6}$ alkoxy (e.g. methoxy, ethoxy, propoxy, etc.) or nitro.

Examples of the protective group for hydroxy include $C_{1-6}$ alkyl (e.g. methyl, ethyl, propyl, isopropyl, butyl, tert-butyl, etc.), phenyl, trityl, $C_{7-10}$ aralkyl (e.g. benzyl, etc.), formyl, $C_{1-6}$ alkyl-carbonyl (e.g. acetyl, propionyl, etc.), benzoyl, $C_{7-10}$ aralkyl-carbonyl (e.g. benzylcarbonyl, etc.), 2-tetrahydropyranyl, 2-tetrahydrofuranyl, silyl (e.g. trimethylsilyl, triethylsilyl, dimethylphenylsilyl, tert-butyldimethylsilyl, tert-butyldimethylsilyl, etc.), $C_{2-6}$ alkenyl (e.g. 1-allyl, etc.). These groups may be substituted by 1 to 3 of halogen atom (e.g. fluorine, chlorine, bromine, iodine, etc.), $C_{1-6}$ alkyl (e.g. methyl, ethyl, n-propyl, etc.), $C_{1-6}$ alkoxy (e.g. methoxy, ethoxy, propoxy, etc.) or nitro, etc. can be substituted for these groups.

Examples of the protecting group for carbonyl include cyclic acetal (e.g. 1,3-dioxane, etc.), and non-cyclic acetal (e.g. di-$C_{1-6}$ alkylacetal, etc.).

Removal of the above protecting groups can be carried out in accordance with per se known methods such as those described in Protective Groups in Organic Synthesis, published by John Wiley and Sons (1980). For instance, the methods using acid, base, ultraviolet light, hydrazine, phenylhydrazine, sodium N-methyldithiocarbamate, tetrabutylammonium fluoride, palladium acetate, trialkylsilyl halide (e.g. trimethylsilyl iodide, trimethylsilyl bromide, etc.), and a reduction method, etc. can be used.

A compound of the invention can be isolated and purified by per se known methods such as solvent extraction, changing of liquid properties, transdissolution, crystallization, recrystallization, chromatography, etc. It is also possible to isolate and purify the raw material compounds of a compound of the invention, or their salts using the same known methods as above, but they can also be used as raw materials in the next process as a reaction mixture without being isolated.

A compound of the invention possesses an excellent MCH receptor antagonistic action, therefore, it is useful as an agent for preventing or treating diseases caused by MCH. Also, a compound of the invention is low in toxicity, and is excellent in oral absorbency and intracerebral transitivity.

Therefore, a melanin-concentrating hormone antagonist (hereafter, also abbreviated as "MCH antagonist") comprising a compound of the invention can be safely administered to mammals (e.g. rats, mice, guinea pigs, rabbits, sheep, horses, swine, cattle, monkeys, humans, etc.) as an agent for preventing or treating diseases caused by MCH.

Here, examples of the diseases caused by MCH include obesity (e.g. malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.], hyperphagia, emotional disorders, reproductive function disorders, memory disorders, dementia, hormonal disorders.

A compound of the invention is also useful as an agent for preventing or treating lifestyle diseases such as diabetes, diabetic complications (e.g. diabetic retinopathy, diabetic neuropathy, diabetic nephropathy, etc.), arteriosclerosis, and gonitis.

Further, a compound of the invention is useful as an anorectic agent.

A MCH antagonist and a pharmaceutical composition of the invention can be used in combination with an alimentary therapy (e.g., alimentary therapy for diabetes) and exercise.

A MCH antagonist and a pharmaceutical composition of the invention can be produced by subjecting compound (I) or compound (I') respectively, as it is, or together with a pharmacologically acceptable carrier, to pharmaceutical manufacturing process in accordance with a per se known means.

Here, examples of the pharmacologically acceptable carriers include various organic or inorganic carrier substances which are commonly used as materials for pharmaceutical preparations, such as excipients, lubricants, binders, and disintegrators in solid preparations; solvents, solubilizing agents, suspending agents, isotonizing agents, buffering agents, soothing agents, in liquid preparations. Also, in the pharmaceutical manufacturing process, additives such as antiseptics, antioxidants, coloring agents, sweeteners, absorbents, moistening agents, can be used, if necessary.

Examples of the excipients include lactose, sucrose, D-mannitol, starch, cornstarch, crystalline cellulose, light anhydrous silicic acid.

Examples of the lubricants include magnesium stearate, calcium stearate, talc, colloidal silica.

Examples of the binders include crystalline cellulose, sucrose, D-mannitol, dextrin, hydroxypropylcellulose, hydroxypropylmethylcellulose, polyvinylpyrrolidone, starch, saccharose, gelatin, methylcellulose, carboxymethylcellulose sodium.

Examples of the disintegrators include starch, carboxymethylcellulose, carboxymethylcellulose calcium, crosscarmellose sodium, carboxymethylstarch sodium, low-substituted hydroxypropylcellulose (L-HPC).

Examples of the solvents include distilled water for injection, alcohol, propylene glycol, macrogol, sesame oil, corn oil.

Examples of the solubilizing agents include polyethylene glycol, propylene glycol, D-mannitol, benzyl benzoate, ethanol, trisaminomethane, cholesterol, triethanolamine, sodium carbonate, sodium citrate.

Examples of the suspending agents include surfactants such as stearyltriethanolamine, sodium lauryl sulfate, lauryl amino propionic acid, lecithin, benzalkonium chloride, benzethonium chloride, glyceryl monostearate; or hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose.

Examples of the isotonizing agents include glucose, D-sorbitol, sodium chloride, glycerin, D-mannitol.

Examples of the buffering agents include buffer solutions of phosphate, acetate, carbonate and citrate.

Examples of the soothing agents include benzyl alcohol.

Examples of the antiseptics include paraoxybenzoates, chlorobutanol, benzyl alcohol, phenethylalcohol, dehydroacetic acid, and sorbic acid.

Examples of the antioxidants include sulfite, ascorbic acid.

A MCH antagonist and a pharmaceutical composition of the invention can be safely administered orally or parenterally (e.g. by local, rectal and intravenous administration) in various dosage forms, for instance, as oral drugs such as tablets (including sugar-coated tablets and film-coated tablets), powders, granules, capsules (including soft capsules), solutions; and parenteral preparations such as injections (e.g. subcutaneous injections, intravenous injections, intramuscular injections, intraperitoneal injections, etc.), external preparations (e.g. nasal preparations, percutaneous preparations, ointments, etc.), suppositories (e.g. rectal suppositories, vaginal suppositories, etc.), sustained-release preparations (e.g. sustained-release microcapsules, etc.), pellets, drip infusions, etc.

The content of compound (I) in a MCH antagonist of the invention and the content of compound (I') in a pharmaceutical composition of the invention are, for instance, about 0.1 to 100 weight percent of the MCH antagonist or whole pharmaceutical composition, respectively.

The dose of a MCH antagonist and a pharmaceutical composition of the invention can be appropriately selected depending on the subject of administration, route of administration, disease, etc.

For instance, the dose per day when a MCH antagonist or a pharmaceutical composition of the invention is orally administered to an adult obesity patient (body weight: about 60 kg), is about 0.1 to about 500 mg, preferably about 1 to about 100 mg, more preferably about 5 to about 100 mg, in terms of compound (I) or compound (I'), each of which is an active ingredient. These amounts can be divided into one to several doses per day for administration.

The MCH antagonist and pharmaceutical composition of the invention can be used in combination with other concomitant drugs which do not interfere with the MCH antagonist and pharmaceutical composition of the invention, for the purpose of "strengthening of therapeutic effect against obesity", "reduction of dose of MCH antagonist", etc. Examples of the concomitant drugs include a "agents for treating diabetes", "agents for treating diabetic complications", "agents for treating obesity other than MCH antagonists", "agents for treating hypertension", "agents for treating hyperlipidemia (agents for treating arteriosclerosis)", "agents for treating arthritis", "antianxiety agents", "antidepressant". Two or more kinds of these concomitant drugs can be combined in an appropriate ratio for use.

Examples of the above agents for treating diabetes" include insulin sensitizers, insulin secretion enhancers, biguanides, insulins, $\alpha$-glucosidase inhibitors, $\beta 3$ adrenaline receptor agonists.

Examples of the insulin sensitizers include pioglitazone or its salt (preferably hydrochloride), troglitazone, rosiglitazone or its salt (preferably maleate), JTT-501, GI-26070, MCC-555, YM-440, DRF-2593, BM-13-1258, KRP-297, R-119702.

Examples of the insulin secretion enhancers include sulfonylureas. Concrete examples of the sulfonylureas include tolbutamide, chlorpropamide, trazamide, acetohexamide, glyclopyramide and its ammonium salt, glibenclamide, gliclazide, glimepiride.

Other than the above, examples of insulin secretion enhancers include repaglinide, nateglinide, mitiglinide (KAD-1229), JTT-608.

Examples of biguanides include metformin, buformin, phenformin.

Examples of insulins include animal insulins extracted from bovine or porcine pancreas; semi-synthetic human insulin which is enzymatically synthesized from insulin extracted from porcine pancreas; human insulin synthesized by genetic engineering, using *Escherichi Coli* and yeast. As insulin, also employed are insulin-zinc containing 0.45 to 0.9 (w/w)% of zinc; protamine-insulin-zinc produced from zinc chloride, protamine sulfate and insulin. In addition, insulin can be an insulin fragment or derivative (e.g. INS-1, etc.).

Insulin can also include various types such as ultra immediate action type, immediate action type, two-phase type, intermediate type, prolonged action type, etc., and these can be selected depending on the pathological conditions of patients.

Examples of $\alpha$-glucosidase inhibitors include acarbose, voglibose, miglitol, emiglitate.

Examples of $\beta 3$ adrenaline receptor agonists include AJ-9677, BMS-196085, SB-226552, AZ40140.

Other than the above, examples of the "agents for treating diabetes" include ergoset, pramlintide, leptin, BAY-27-9955.

Examples of the above "agents for treating diabetic complications" include aldose reductase inhibitors, glycation inhibitors, protein kinase C inhibitors Examples of aldose reductase inhibitors include torulestat; eparlestat; imirestat; zenarestat; SNK-860; zopolrestat; ARI-509; AS-3201.

Examples of glycation inhibitors include pimagedine.

Examples of protein kinase C inhibitors include NGF, LY-333531.

Other than the above, examples of "agents for treating diabetic complications" include alprostadil, thiapride hydrochloride, cilostazol, mexiletine hydrochloride, ethyl eicosapentate, memantine, pimagedline (ALT-711).

Examples of the above "agents for treating obesity other than MCH antagonists" include lipase inhibitors and anorectics.

Examples of lipase inhibitors include orlistat.

Examples of anorectics include mazindol, dexfenfluramine, fluoxetine, sibutramine, baiamine, (S)-sibutramine, SR-141716, NGD-95-1.

Other than the above, examples of "agents for treating obesity other than MCH antagonists" include lipstatin.

Examples of the above "agents for treating hypertension" include angiotensin converting enzyme inhibitors, calcium antagonists, potassium channel openers, angiotensin II antagonists.

Examples of angiotensin converting enzyme inhibitors include captopril, enarapril, alacepril, delapril (hydrochloride), lisinopril, imidapril, benazepril, cilazapril, temocapril, trandolapril, manidipine (hydrochloride).

Examples of calcium antagonists include nifedipine, amlodipine, efonidipine, nicardipine.

Examples of potassium channel openers include levcromakalim, L-27152, AL0671, NIP-121.

Examples of angiotensin II antagonists include losartan, candesartan cilexetil, valsartan, irbesartan, CS-866, E4177.

Examples of the above "agents for treating hyperlipidemia (agents for treating arteriosclerosis)" include HMG-COA reductase inhibitors, fibrate compounds.

Examples of HMG-CoA reductase inhibitors include pravastatin, simvastatin, lovastatin, atorvastatin, fluvastatin, lipantil, cerivastatin, itavastatin, ZD-4522, or their salts (e.g. sodium salts, etc.).

Examples of fibrate compounds include bezafibrate, clinofibrate, clofibrate, simfibrate.

Examples of the above "agents for treating arthritis" include ibuprofen.

Examples of the above "antianxiety agents include chlordiazepoxide, diazepam, oxozolam, medazepam, cloxazolam, bromazepam, lorazepam, alprazolam, fludiazepam.

Examples of the above "antidepressants" include fluoxetine, fluvoxamine, imipramine, paroxetine, sertraline.

The timing of administration of the above concomitant drugs is not limited. The MCH antagonist or pharmaceutical composition and the concomitant drugs can be administrated to the subject simultaneously or at staggered times.

The dosages of the concomitant drugs can be determined in accordance with clinically used dosages, and can be appropriately selected according to the subject of administration, route of administration, diseases and combinations of drugs, etc.

The administration forms for the concomitant drugs are not particularly limited as long as a MCH antagonist or a pharmaceutical composition are used in combination with a concomitant drugs at the time of administration. Examples of such administration forms includes 1) administration of a single preparation obtained by simultaneous preparation of MCH antagonist or pharmaceutical composition together with concomitant drugs, 2) simultaneous administration of two kinds of preparations obtained by separate preparation of MCH antagonist or pharmaceutical composition, and concomitant drugs, through the same route of administration, 3) staggered administration of two kinds of preparations obtained by separate preparation of MCH antagonist or pharmaceutical composition, and concomitant drugs, through the same route of administration, 4) simultaneous administration of two kinds of preparations obtained by separate preparation of MCH antagonist or pharmaceutical composition, and concomitant drugs, through different routes of administration, 5) staggered administration of two kinds of preparations obtained by separate preparation of MCH antagonist or pharmaceutical composition, and concomitant drugs, through different routes of administration (for instance, administration of MCH antagonist or pharmaceutical composition; and concomitant drugs in this order; or administration in reverse order).

The ratio of combination of MCH antagonist or pharmaceutical composition with concomitant drugs can be appropriately selected in accordance with the subject of administration, route of administration and diseases, etc.

This invention further relates to "a pharmaceutical comprising a melanin-concentrating hormone antagonist in combination with at least one species selected from the group consisting of an agent for treating diabetes, an agent for treating hypertension and an agent for treating arteriosclerosis".

Here, the "melanin-concentrating hormone antagonist" is not especially limited as long as it is a compound having a melanin-concentrating hormone antagonistic action, and may be either of a peptide compound or a non-peptide compound.

As "an agent for treating diabetes", "an agent for treating hypertension" and "an agent for treating arteriosclerosis", those exemplified as the above concomitant drugs can be mentioned.

These drugs can be used in the same manner as in the above "combination of MCH antagonist of the invention with concomitant drugs".

The pharmaceutical provides excellent effects" such as "strengthening of therapeutic effect against obesity", "reduction of dose of MCH antagonist", etc. as compared to single use of each drug.

BEST MODE FOR CARRYING OUT THE INVENTION

This invention will be explained further in detail by the following Reference Examples, Examples, Preparation Examples, and Experimental Examples. However, these do not limit this invention, and they can be changed within the scope that does not deviate from the scope of this invention.

In the following Reference Examples and Examples, "room temperature" means 0 to 30° C. Anhydrous magnesium sulfate or anhydrous sodium sulfate was used to dry the organic layer. "%" means percent by weight, unless otherwise specified.

Infrared absorption spectra were determined by the diffuse reflectance method, using fourier transform type infrared spectrophotometer.

FABMS (pos) is mass spectrum determined by the (+) method, in Fast Atom Bombardment Mass Spectrometry.

Other symbols used in the description have the following meanings.

| | |
|---|---|
| s: | singlet |
| d: | doublet |
| t: | triplet |
| q: | quartet |
| m: | multiplet |
| br: | broad |
| J: | coupling constant |
| Hz: | Hertz |
| CDCl$_3$: | heavy chloroform |
| DMSO-d$_6$: | heavy dimethylsulfoxide |
| THF: | tetrahydrofuran |
| DMF: | N,N-dimethylformamide |
| DMSO: | dimethylsulf oxide |
| WSCD: | 1-ethyl-3-(3-dimethylaminopropyl)carbodimide |
| WSC: | 1-ethyl-3-(3-dimethylaminopropyl)carbodimide hydrochloride |
| $^1$H-NMR: | proton nuclear resonance (Free substances were usually measured in CDCl$_3$.) |
| IR: | infrared absorption spectrum |
| Me: | methyl |
| Et: | ethyl |
| HOBt: | 1-hydroxy-1H-benzotriazole |
| IPE: | diisopropyl ether |
| DMAP: | 4-dimethylaminopyridine |

In this specification and drawings, when bases and amino acids are shown by codes, these codes are based on those by the IUPAC-IUB Commission on Biochemical Nomenclature or common codes in the concerned fields. Examples of these codes are shown below. Also, where some optical isomers of amino acids can exist, the L form is shown unless otherwise specified.

| | |
|---|---|
| DNA: | deoxyribonucleic acid |
| cDNA: | complementary deoxyribonucleic acid |
| A: | adenine |
| T: | thymine |
| G: | guanine |
| C: | cytosine |
| RNA: | ribonucleic acid |
| mRNA: | messenger ribonucleic acid |
| dATP: | deoxyadenosine triphosphate |
| dTTP: | deoxythymidine triphosphate |
| dGTP: | deoxyguanosine triphosphate |
| dCTP: | deoxycytidine triphosphate |
| ATP: | adenosine triphosphate |
| EDTA: | ethylenediamine tetraacetic acid |
| SDS: | sodium dodecyl sulfate |
| EIA: | enzyme immunoassay |
| Gly: | glycine |
| Ala: | alanine |
| Val: | valine |
| Leu: | leucine |
| Ile: | isoleucine |
| Ser: | serine |
| Thr: | threonine |
| Cys: | cysteine |
| Met: | methionine |
| Glu: | glutamic acid |
| Asp: | aspartic acid |
| Lys: | lysine |
| Arg: | arginine |
| His: | histidine |
| Phe: | phenylalanine |
| Tyr: | tyrosine |
| Tro: | tryptophan |
| Pro: | proline |
| Asn: | asparagine |
| Gln: | glutamine |
| pGl: | pyroglutamine |
| Me: | methyl group |
| Et: | ethyl group |
| Bu: | butyl group |
| Ph: | phenyl group |
| TC: | thiazolidine-4(R)-carboxamide group |

Substituents, protecting groups and reagents frequently used in this specification, are shown by the following symbols.

| | |
|---|---|
| Tos: | p-toluenesulfonyl |
| CHO: | formyl |
| Bzl: | benzyl |
| Cl$_2$Bzl: | 2,6-dichlorobenzyl |
| Bom: | benzyloxymethyl |
| Z: | benxyloxycarbonyl |
| Cl-Z: | 2-chlorobenzyloxycarbonyl |
| Br-Z: | 2-bromobenzyloxycarbonyl |
| Boc: | t-butoxycarbonyl |
| DNP: | dinitrophenol |
| Trt: | trityl |
| Bum: | t-butoxymethyl |
| Fmoc: | N-9-fluorenylmethoxycarbonyl |
| HOBt: | 1-hydroxybenztriazole |
| HOOBt: | 3,4-dihydro-3-hydroxy-4-oxo-1,2,3-benzotriazine |
| HONB: | 1-hydroxy-5-norbornene-2,3-dicarbodiimide |
| DCC: | N,N'-dicyclohexylcarbodiimide |

SEQ ID NO in the SEQUENCE LISTING in the specification of the present application shows the following sequences.

[SEQ ID NO: 1] shows a synthetic DNA used for screening of cDNA coding rat SLC-1.

[SEQ ID NO: 2] shows a synthetic DNA used for screening of cDNA coding rat SLC-1.

[SEQ ID NO: 3] shows an entire amino acid sequence of rat SLC-1.

[SEQ ID NO: 4] shows an entire base sequence of rat SLC-1cDNA wherein Sal I recognition sequence was added to the 5' side, and Spe I recognition sequence was added to the 3' side.

[SEQ ID NO: 5] shows riboprobe used to determine the quantity of SLC-1mRNA expressed in each clone of rat SLC-1 expression CHO cells.

[SEQ ID NO: 6] shows a synthetic DNA used to obtain cDNA for coding of human SLC-1.

[SEQ ID NO: 7] shows a primer used to make double-strand cDNA for coding human SLC-1.

[SEQ ID NO: 8] shows an entire base sequence of cDNA for coding human SLC-1.

[SEQ ID NO: 9] shows an entire amino acid sequence of human SLC-1.

[SEQ ID NO: 10] shows a synthetic DNA used for screening of cDNA for coding human SLC-1(S).

[SEQ ID NO: 11] shows a synthetic DNA used for screening of cDNA for coding human SLC-1(S).

[SEQ ID NO: 12] shows a synthetic DNA used for screening of cDNA for coding human SLC-1(L).

[SEQ ID NO: 13] shows a synthetic DNA used for screening of cDNA for coding human SLC-1(L).

[SEQ ID NO: 14] shows an entire base sequence of human SLC-1(S) cDNA wherein Sal I recognition sequence was added to the 5' side, and Spe I recognition sequence was added to the 3' side.

[SEQ ID NO: 16] shows riboprobe used to determine the quantity of SLC-1mRNA expressed in each clone of human SLC-1(S) expression CHO cells and SLC-1(L) expression CHO cells.

Transformant *Escherichia coli* DH10B/phSLC1L8 transformed by plasmid containing DNA which codes the base sequence shown by SEQ ID NO: 9, obtained in Reference Example 1-6, is on deposit with National Institute of Bioscience and Human-Technology (NIBH), Agency of Industrial Science and Technology, Ministry of International Trade and Industry, as deposit number FERM BP-6632 from Feb. 1, 1999; and with the Institute for Fermentation, Osaka, Japan (IFO), as deposit number IFO 16254 from Jan. 21, 1999.

REFERENCE EXAMPLE 1

2-(R)-[2-(N,N-Dimethylamino)ethyl]-6-(4-[(4-methoxyphenyl)carbonyloxy]benzyloxy)tetralin

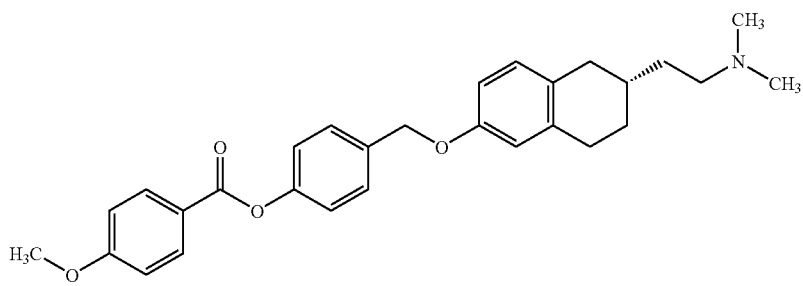

Diethyl azodicarboxylate (40% toluene solution, 0.95 g) was added dropwise to THF solution (6 ml) of 2-(R)-[2-(N,N-dimethylamino)ethyl]-6-hydroxytetralin (300 mg), 4-(hydroxymethyl)phenyl 4-methoxybenzoate (530 mg), and triphenylphosphine (430 mg) under ice-cooling. After stirring for 2 hours at room temperature, the reaction mixture was concentrated. The residue was purified using alumina column chromatography (development solvent; hexane~hexane:ethyl acetate=10:1), and the titled compound (320 mg) was obtained after recrystallization (ethyl acetate-hexane).

Melting point: 111–114° C.
$[\alpha]_D^{20}$=+44.4° (c=0.502, methanol)

REFERENCE EXAMPLE 2

N-Phenyl-4-[[2-(2-piperidinoethyl)-6-tetralinyl]oxymethyl]benzamide

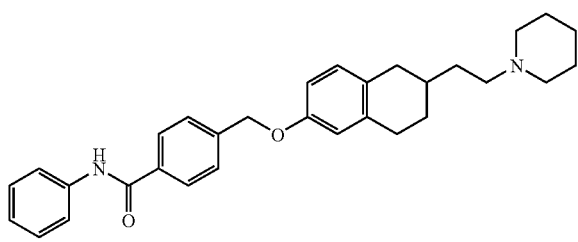

Triethylamine (0.11 ml) was added to THF suspension (3 ml) of 4-[[2-(2-piperidinoethyl)-6-tetralinyl]oxymethyl]benzoate (300 mg). Further, THF solution (0.5 ml) of trimethylacetyl chloride (92 mg) was added dropwise under ice-cooling, which was stirred for 30 minutes. The temperature of the reaction mixture was raised to room temperature, which was stirred for 1 hour. THF solution (0.5 ml) of aniline (85 mg) was added dropwise to the reaction mixture under ice-cooling, which was stirred for 1 hour. After the reaction mixture was stirred for 24 hours at room temperature, saturated sodium bicarbonate solution was added, and extraction was conducted using a mixed solution of ethyl acetate and THF. The organic layer was washed with water and saturated aqueous sodium chloride solution, dried, and then concentrated. The residue was recrystallized from THF-methanol-IPE to give the titled compound (150 mg).

Melting point: 183–185° C.

REFERENCE EXAMPLE 3

4-[[2-(2-Piperidinoethyl)-6-tetralinyl]oxymethyl]-N-(2-pyridinyl)benzamide

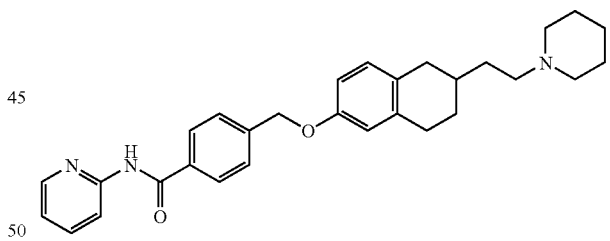

Triethylamine (0.11 ml) was added to THF suspension (6 ml) of 4-[[2-(2-piperidinoethyl)-6-tetraliny]oxymethyl]benzoate (300 mg). Trimethylacetyl chloride (0.095 ml) was added dropwise to the obtained suspension under ice-cooling, which was stirred for 30 minutes. The temperature of the reaction mixture was raised to room temperature, which was stirred for 1 hour. THF solution (1.0 ml) of 2-aminopyridine (110 mg) was added dropwise to the reaction mixture under ice-cooling, which was stirred for 1 hour. Then the reaction mixture was stirred at room temperature for 6 hours, and at 60° C. for 12 hours, which was refluxed with heating for 6 hours. Saturated sodium bicarbonate solution was added to the reaction mixture, and extraction was conducted using ethyl acetate. The organic layer was washed with water and saturated aqueous sodium chloride solution, dried, and then concentrated. The residue was purified using alu- 22mina column chromatography (development solvent: THF), and recrystallized (ethyl acetate-IPE) to give the titled compound (30 mg).

REFERENCE EXAMPLE 4

4-[[2-(2-Piperidinoethyl)-6-tetralinyl]oxymethyl]-N-(2-quinolinyl)benzamide

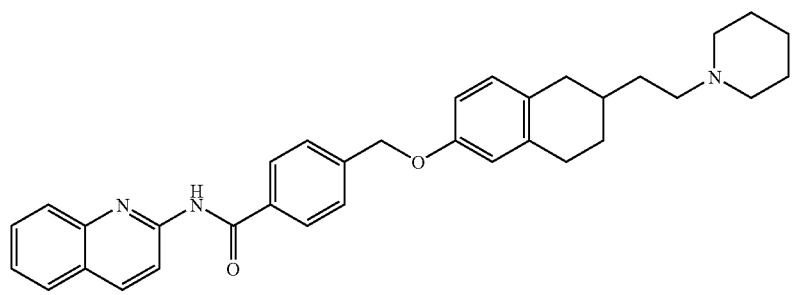

Triethylamine (0.22 ml) was added to THF suspension (6 ml) of 4-[[2-(2-piperidinoethyl)-6-tetralinyl]oxymethyl]benzoate (300 mg). Further, trimethylacetyl chloride (0.095 ml) was added dropwise to under ice-cooling, which was stirred for 30 minutes. The temperature of the reaction mixture was raised to room temperature, which was stirred for 1 hour. THF solution (1.0 ml) of 2-aminoquinoline (170 mg) was added dropwise to the reaction mixture under ice-cooling, which was stirred at room temperature for 12 hours. Saturated sodium bicarbonate solution was added to the reaction mixture, and extraction was conducted using ethyl acetate. The organic layer was washed with water and saturated aqueous sodium chloride solution, dried, and then concentrated. The residue was purified using alumina column chromatography (development solvent: THF), and recrystallized (ethyl acetate-diisopropyl ether) to give the titled compound (45 mg).

Melting point: 135–138° C.

REFERENCE EXAMPLE 5

N-(4-Methoxyphenyl)-4-[[2-(2-piperidinoethyl)-6-tetralinyl]oxymethyl]benzamide

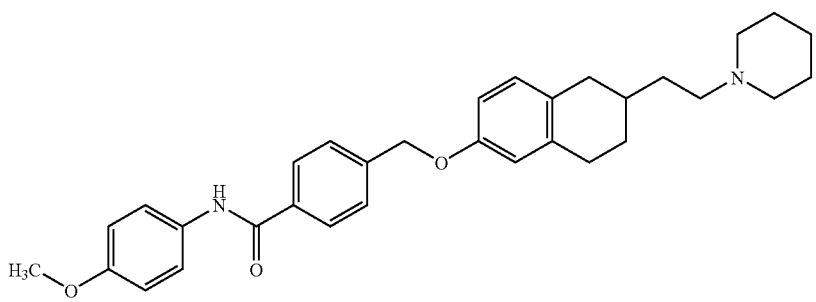

WSCD (0.11 ml) was added to DMF solution (2 ml) of 4-[[2-(2-piperidinoethyl)-6-tetralinyl]oxymethyl]benzoate (170 mg), 4-methoxyaniline (53 mg), HOBt (70 mg) and DMAP (60 mg) at room temperature, which was stirred for 12 hours. 10% aqueous potassium carbonate solution and water was added to the reaction mixture, and extraction was conducted using a mixed solution of THF and ethyl acetate. The organic layer was washed with water and saturated aqueous sodium chloride solution, dried, and then concentrated. The residue was purified using alumina column chromatography (development solvent: THF), and recrystallized (THF-IPE) to give the titled compound (140 mg).

Melting point: 193–196° C.

REFERENCE EXAMPLE 6

N-(3,4-Dimethoxyphenyl)-4-[[2-(2-piperidinoethyl)-6-tetralinyl]oxymethyl]benzamide

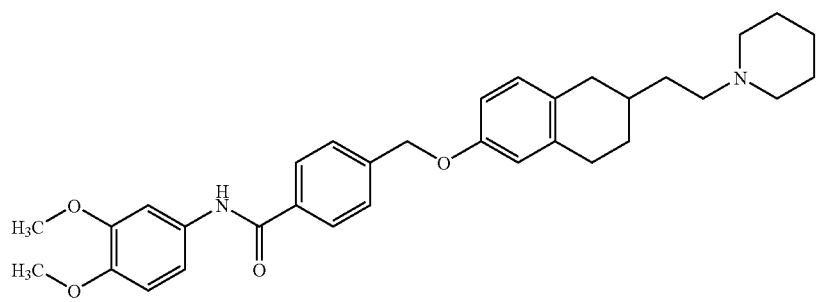

WSCD (free form, 0.2 ml) was added to DMF solution (3 ml) of 4-[[2-(2-piperidinoethyl)-6-tetralinyl]oxymethyl]benzoate (300 mg), 3,4-dimethoxyaniline (120 mg), HOBt (120 mg) and DMAP (100 mg) at room temperature, which was stirred for 12 hours. 10% aqueous potassium carbonate solution was added to the reaction mixture, and the resulting crystals were collected by filtration. The crystals were washed with water, then dried. The crystals were purified using alumina column chromatography (development solvent; THF), and recrystallized (THF-IPE) to give the titled compound (330 mg).

Melting point: 178–180° C.

REFERENCE EXAMPLE 7

6-[4-(Benzoylamino)benzyloxy]-2-(2-piperidinoethyl)tetralin

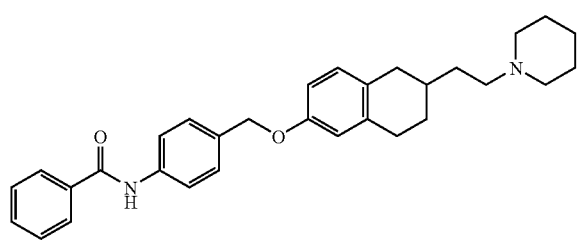

Sodium hydride (60% oily, 85 mg) was added to DMF solution of 6-hydroxy-2-(2-piperidinoethyl)tetralin (500 mg) at room temperature, which was stirred for 1 hour. N-[4-(bromomethyl)phenyl]benzamide (670 mg) was added to the reaction mixture at room temperature, which was stirred for 1 hour. Water was added to the reaction mixture, and extraction was conducted using ethyl acetate. The organic layer was washed with water and saturated aqueous sodium chloride solution, dried, and then concentrated. The residue was purified using alumina column chromatography (development solvent: THF), and recrystallized (ethyl acetate) to give the titled compound (200 mg).

Melting point: 176–179° C.

REFERENCE EXAMPLE 8

2-[(N,N-Dimethylamino)methyl]-6-tetralinyl 4-biphenylylcarboxylate

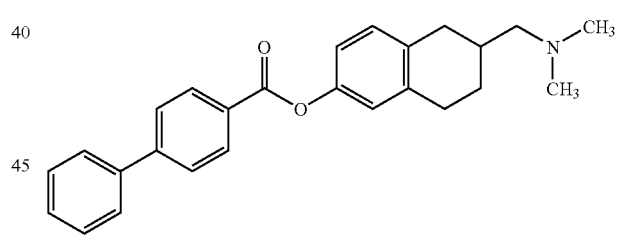

4-Biphenylylcarboxylic acid (580 mg) and WSC (560 mg) were added to pyridine solution (6 ml) of 2-[(N,N-dimethylamino)methyl]-6-hydroxytetralin (300 mg), which was stirred at room temperature for 36 hours. Saturated sodium bicarbonate solution and water were added to the reaction mixture, and extraction was conducted using ethyl acetate. The organic layer was washed with water and saturated aqueous sodium chloride solution, dried, and then concentrated. The residue was purified using alumina column chromatography (development solvent; hexane~hexane:ethyl acetate=10:1), and recrystallized (hexane) to give the titled compound (300 mg).

Melting point: 85–86° C.

REFERENCE EXAMPLE 9

2-[(N,N-Dimethylamino)methyl]-6-[4-[(4-methoxyphenyl)carbonyloxy]benzyloxy]tetralin

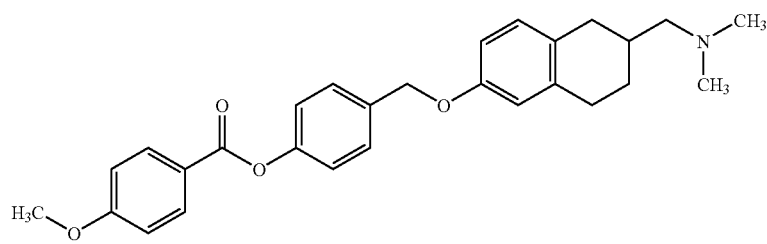

Diethyl azodicarboxylate (40% toluene solution, 950 mg) was added dropwise to THF solution (3 ml) of 2-[(N,N-dimethylamino)methyl]-6-hydroxytetralin (150 mg), 4-(hydroxymethyl)phenyl 4-methoxybenzoate (570 mg) and triphenylphosphine (574 mg) at room temperature, which was stirred for 3 hours. The reaction mixture was concentrated, and the residue was purified using alumina column chromatography (development solvent; hexane~hexane:ethyl acetate=6:1), and recrystallized (ethyl acetate-hexane) to give the titled compound (175 mg).

Melting point: 119–121° C.

REFERENCE EXAMPLE 10

2-[(N,N-Dimethylamino)methyl]-6-[4-[(4-methoxybenzyl)oxy]benzyloxy]tetralin

Diethyl azodicarboxylate (40% toluene solution, 1.91 g) was added dropwise to THF solution (6 ml) of 2-[(N,N-dimethylamino)methyl]-6-hydroxytetralin (300 mg), 4-[(4-methoxybenzyl)oxy]benzylalcohol (1.07 g) and triphenylphosphine (1.15 g) at room temperature, which was stirred for 12 hours. The reaction mixture was concentrated, and the residue was purified using alumina column chromatography (development solvent; hexane~hexane:ethyl acetate=10:1), and recrystallized (ethyl acetate-hexane) to give the titled compound (260 mg).

Melting point: 106–111° C.

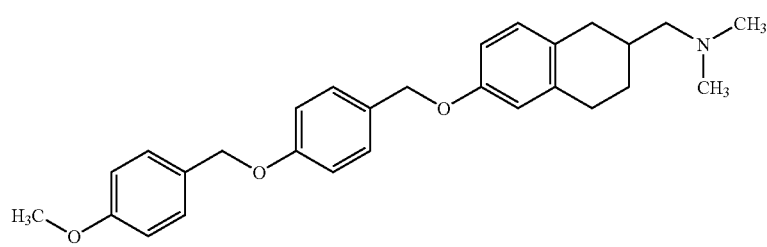

REFERENCE EXAMPLE 11

6-[4-[(1-Benzothiophen-2-yl)carbonylamino]benzyloxy]-2-[(N,N-dimethylamino)methyl]tetralin

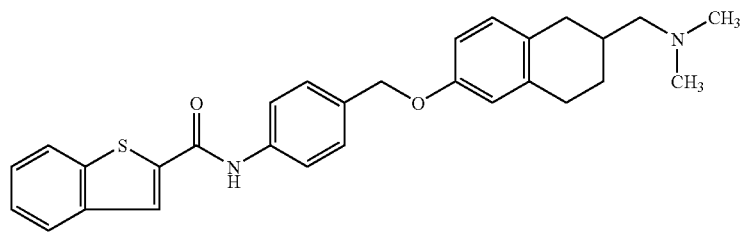

One drop of DMF was added to THF solution (4 ml) of 1-benzothiophene-2-carboxylic acid (230 mg), and oxalyl chloride (0.23 ml) was further added under ice-cooling, which was stirred for 30 minutes at room temperature. The reaction mixture was concentrated, which was dissolved in THF (1 ml). The obtained solution was added dropwise to pyridine solution (6 ml) of 6-(4-aminobenzyloxy)-2-[(N,N-dimethylamino)methyl]tetralin (300 mg), which was stirred for 15 minutes. After stirring at room temperature for another 15 minutes, 10% aqueous potassium carbonate solution was added to the reaction mixture, and extraction was conducted using ethyl acetate. The organic layer was washed with water and saturated aqueous sodium chloride solution, dried, and then concentrated. The residue was purified using alumina column chromatography (development solvent; ethyl acetate), and recrystallized (THF-IPE) to give the titled compound (250 mg).
Melting point: 165–169° C.

REFERENCE EXAMPLE 12

2-[(N,N-Dimethylamino)methyl]-6-[4-[(4-methoxyphenyl) sulfonylamino)benzyloxy]tetralin

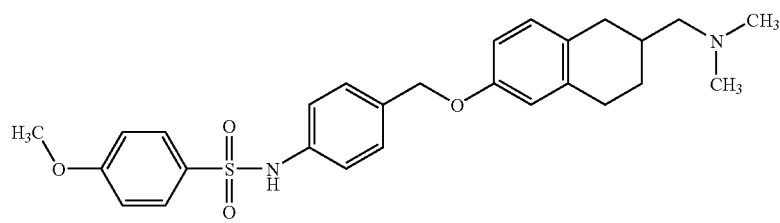

THF solution (1 ml) of 4-methoxybenzenesulfonyl chloride (270 mg) was added dropwise to pyridine solution (6 ml) of 6-[(4-aminobenzyl)oxy]-2-[(N,N-dimethylamino)methyl]tetralin (300 mg) under ice-cooling, which was stirred for 15 minutes. After stirring at room temperature for further 15 minutes, 10% aqueous potassium carbonate solution was added to the reaction mixture, and extraction was conducted using ethyl acetate. The organic layer was washed with water and saturated aqueous sodium chloride solution, dried, and then concentrated. The residue was purified using alumina column chromatography (development solvent: ethyl acetate), and recrystallized (ethyl acetate-IPE) to give the titled compound (260 mg).
Melting point: 137–140° C.

REFERENCE EXAMPLE 13

6-[4-(Benzylcarbonylamino)benzyloxy]-2-[(N,N-dimethylamino)methyl]tetralin

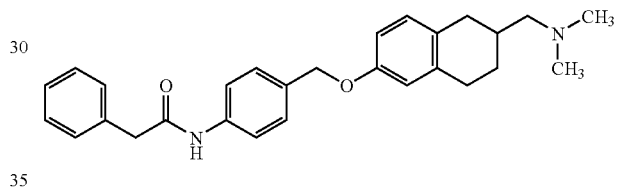

THF solution (1 ml) of phenylacetyl chloride (200 mg) was added dropwise to pyridine solution (6 ml) of 6-[(4-aminobenzyl)oxy]-2-[(N,N-dimethylamino)methyl]tetralin (300 mg) under ice-cooling, which was stirred for 15 minutes. After stirring at room temperature for further 15 minutes, saturated sodium bicarbonate solution was added to the reaction mixture, and extraction was conducted using ethyl acetate. The organic layer was washed with water and saturated aqueous sodium chloride solution, dried, and then concentrated. The residue was purified using alumina column chromatography (development solvent; hexane~hexane:ethyl acetate=2:1), and recrystallized to give the titled compound (175 mg).
Melting point: 130–135° C.

REFERENCE EXAMPLE 14

6-[4-(Benzoylamino)benzyloxy]-2-[(N,N-dimethylamino)methyl]tetralin

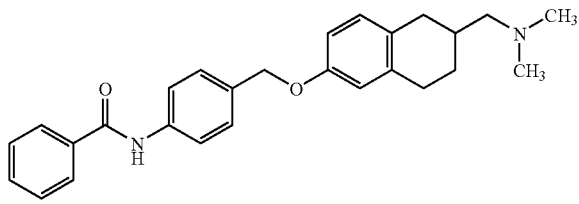

Benzoyl chloride (0.14 ml) was added dropwise to pyridine solution (6 ml) of 6-[(4-aminobenzyl)oxy]-2-[(N,N-dimethylamino)methyl]tetralin (300 mg) under ice-cooling, which was stirred at room temperature for 30 minutes. 10% aqueous potassium carbonate solution was added to the reaction mixture, and extraction was conducted using ethyl acetate. The organic layer was washed with water and saturated aqueous sodium chloride solution, dried, and then concentrated. The residue was purified using alumina column chromatography (development solvent; ethyl acetate), and recrystallized (THF-IPE) to give the titled compound (240 mg).

Melting point: 128–133° C.

REFERENCE EXAMPLE 15

2-[(N,N-Dimethylamino)methyl]-6-[4-[(4-methoxybenzoyl)amino]benzyloxy]tetralin

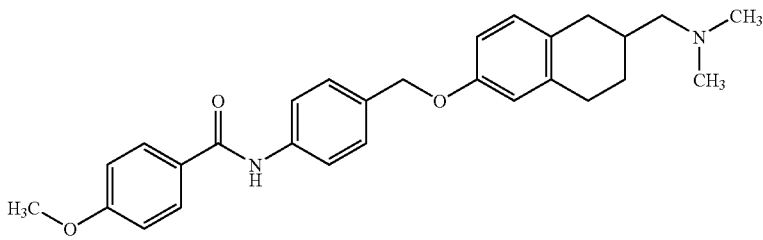

p-Anisoyl chloride (0.20 ml) was added dropwise to pyridine solution (6 ml) of 6-[(4-aminobenzyl)oxy]-2-[(N,N-dimethylamino)methyl]tetralin (300 mg) under ice-cooling, which was stirred at room temperature for 30 minutes. 10% aqueous potassium carbonate solution was added to the reaction mixture, and extraction was conducted using ethyl acetate. The organic layer was washed with water and saturated aqueous sodium chloride solution, dried, and then concentrated. The residue was purified using alumina column chromatography (development solvent: ethyl acetate), and recrystallized (THF-IPE) to give the titled compound (300 mg).

Melting point: 155–159° C.

REFERENCE EXAMPLE 16

2-[(N,N-Dimethylamino)methyl]-6-[4-[(2-methoxybenzoyl]amino]benzyloxy]tetralin

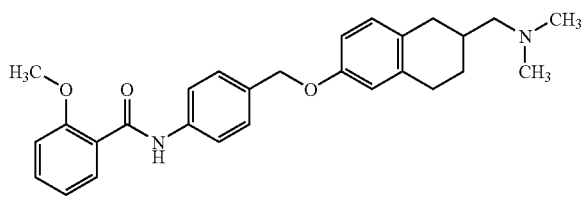

o-Anisoyl chloride (0.15 ml) was added dropwise to pyridine solution (4 ml) of 6-[(4-aminobenzyl)oxy]-2-[(N,N-dimethylamino)methyl]tetralin (200 mg) under ice-cooling, which was stirred at room temperature for 30 minutes. 10% aqueous potassium carbonate solution was added to the reaction mixture, and extraction was conducted using ethyl acetate. The organic layer was washed with water and saturated aqueous sodium chloride solution, dried, and then concentrated. The residue was purified using alumina column chromatography (development solvent; THF), and recrystallized (ethyl acetate-hexane) to give the titled compound (200 mg).

Melting point: 106–108° C.

REFERENCE EXAMPLE 17

6-[4-[N-(4-Methoxybenzoyl)-N-methylamino]benzyloxy]-2-[(N,N-dimethylamino)methyl]tetralin

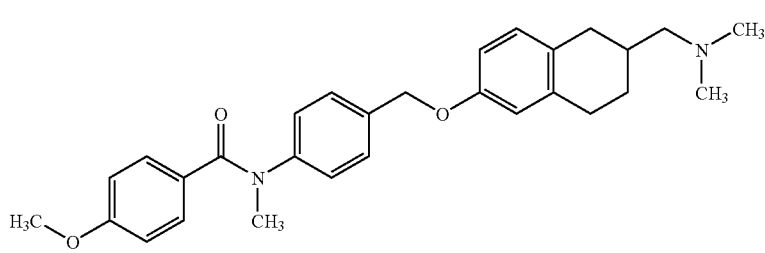

Diethyl azodicarboxylate (40% toluene solution, 960 mg) was added dropwise to THF solution (3 ml) of 2-[(N,N-dimethylamino)methyl]-6-hydroxytetralin (150 mg), N-[4-(hydroxymethylphenyl]-4-methoxy-N-methylbenzamide (600 mg) and triphenylphosphine (570 mg) at room temperature, which was stirred for 12 hours. After the reaction mixture was concentrated, the residue was purified using silca gel column chromatography (development solvent; hexane~ethyl acetate~ethyl acetate:methanol=1:2), and then purified using alumina column chromatography (development solvent; hexane~hexane:ethyl acetate=2:1) to give the titled compound (185 mg).

$^1$H-NMR (CDCl$_3$) δ: 1.20–1.50 (1H, m), 1.80–2.46 (5H, m), 2.25 (6H, s), 2.68–2.86 (3H, m), 3.47 (3H, s), 3.74 (3H, s), 4.95 (2H, s), 6.52–6.76 (4H, m), 6.84–7.14 (3H, m), 7.22–7.38 (4H, m).

REFERENCE EXAMPLE 18

N-[4-[[[2-(Diethylamino)ethyl]amino]carbonyl]phenyl] 4-biphenylylcarboxamide

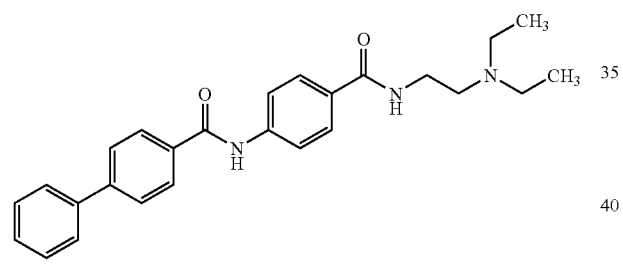

Oxalyl chloride (0.46 ml) and DMF (1 drop) were added to THF solution (15 ml) of 4-biphenylylcarboxylic acid (0.879 g) under ice-cooling. The reaction mixture was stirred at room temperature for 30 minutes, and concentrated. The residue was dissolved in THF (10 ml), which was added dropwise to THF (20 ml) suspension of procaineamide hydrochloride (1.078 g) and triethylamine (1.4 ml) at 0° C. After stirring at 0° C. for 30 minutes, 10% aqueous potassium carbonate solution was added to the reaction mixture, and extraction was conducted using ethyl acetate. The organic layer was washed with water and saturated aqueous sodium chloride solution, dried, and then concentrated. The residue was recrystallized using methanol to give the titled compound (1.147 g).

Melting point: 237–240° C. (decomposition)

REFERENCE EXAMPLE 19

4-(4-Biphenylylmethoxy)-N-[2-(isopropylamino)ethyl]benzamide

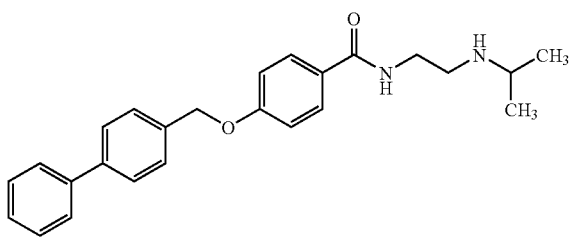

WSC (0.708 g), HOBt (0.521 g), N-isopropyl ethylenediamine (0.353 g) and triethylamine (1 ml) were added to a mixed solution of 4-(4-biphenylylmethoxy) benzoate (1.007 g) in THF (30 ml) and acetonitrile (30 ml). After stirring at room temperature for 18 hours, water was added to the reaction mixture, and extraction was conducted using ethyl acetate. The organic layer was washed with 10% aqueous potassium carbonate solution and saturated aqueous sodium chloride solution, dried, and then concentrated. The residue was recrystallized using ethanol to give the titled compound (0.806 g).

Melting point: 150–154° C.

REFERENCE EXAMPLE 20

2-(N,N-Diethylamino)ethyl 4-(4-biphenylylcarbonylamino)benzoate

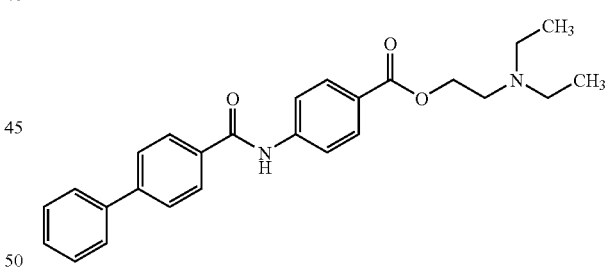

Oxalyl chloride (0.39 ml) and DMF (1 drop) were added to THF solution (15 ml) of 4-biphenylylcarboxylic acid (1.091 g) under ice-cooling, which was stirred at room temperature for 30 minutes, and concentrated. The residue was dissolved in THF (10 ml), which was added dropwise to THF suspension (30 ml) of procaine hydrochloride (1.091 g) and triethylamine (0.67 ml) at 0° C. After stirring at 0° C. for 30 minutes, 10% aqueous potassium carbonate was added to the reaction mixture, and extraction was conducted using ethyl acetate. The organic layer was washed with saturated aqueous sodium chloride solution, dried, and then concentrated. The residue was recrystallized using ethyl acetate/hexane to give the titled compound (0.728 g).

Melting point: 146–149° C.

REFERENCE EXAMPLE 21

N-[4-[[[2-(Dimethylamino)ethyl]amino]carbonyl]phenyl] 4-biphenylylcarboxamide

WSC (0.248 g), HOBt (0.156 g), N,N-dimethyl ethylenediamine (0.097 g) and triethylamine (0.21 ml) were added to a mixed solution of 4-(4-biphenylylcarbonylamino)benzoate (0.323 g) in THF (15 ml) and acetonitrile (15 ml). After stirring at room temperature for 18 hours, water was added to the reaction mixture, and extraction was conducted using ethyl acetate. The organic layer was washed with 10% aqueous potassium carbonate and saturated aqueous sodium chloride solution, dried, and then concentrated. The residue was recrystallized using methanol/diethyl ether to give the titled compound (0.100 g).

Melting point: 261–264° C. (decomposition)

The compounds described in the following Reference Examples 22 to 25 were produced in the same manner as in Reference Example 21.

REFERENCE EXAMPLE 22

N-[4-[[2-(Piperidinoethyl)amino]carbonyl]phenyl] 4-biphenylylcarboxamide

Melting point: 247–252° C. (decomposition)

REFERENCE EXAMPLE 23

N-[4-[[2-(1-Pyrrolidinyl)ethyl]amino]carbonyl]phenyl] 4-biphenylylcarboxamide

Melting point: 241–245° C. (decomposition)

REFERENCE EXAMPLE 24

N-[2-(N,N-Dimethylamino)methyl-6-tetralinyl]-4-biphenylylcarboxamide

Melting point: 164–166° C.

REFERENCE EXAMPLE 25

N-[2-(N,N-Dimethylamino)methyl-6-tetralinyl]-4-biphenylylcarboxamide hydrochloride Melting point: >250° C.

$^1$H-NMR δ: 1.24–1.54 (1H, m), 1.84–2.10 (2H, m), 2.20–2.50 (3H, m), 2.26 (6H, s), 2.79–3.01 (3H, m), 7.10 (H, d, J=8 Hz), 7.28–7.54 (5H, m), 7.60–7.82 (5H, m), 7.94 (2H, d, J=8 Hz).

IR(KBr) 3028, 2910, 2640, 1658, 1538, 1417, 746, 701 cm$^{-1}$

REFERENCE EXAMPLE 26

N-[3-[(N,N-Dimethylamino)methyl]-1,2,3,4-tetrahydo-7-quinolinyl]-4-biphenylylcarboxamide One drop of DMF was added to THF solution of 4-biphenylylcarboxylic acid (145 mg), and oxalyl chloride (0.1 ml) was added dropwise to the solution under ice-cooling, which was stirred at room temperature for 30 minutes. After the reaction mixture was concentrated, the residue was dissolved in THF (1 ml), which was added dropwise to pyridine solution (1.5 ml) of 7-amino-3-[(N,N-dimethylamino)methyl]-1,2,3,4-tetrahydroquinoline (150 mg) under ice-cooling, and the reaction mixture was stirred for 30 minutes. After the temperature of the reaction mixture was raised to room temperature, 10% aqueous potassium carbonate was added to the reaction mixture, and extraction was conducted using a mixed solution of THF and ethyl acetate. The organic layer was washed with water and saturated aqueous sodium chloride solution, dried, and then concentrated. The residue was recrystallized using THF-IPE to give the titled compound (180 mg).

Melting point: 206–211° C.

REFERENCE EXAMPLE 27

4-[N-[(Benzyloxy)carbonyl]-N-methylamino]-N-[3-[(N,N-dimethylamino)methyl]-1,2,3,4-tetrahydo-7-quinolinyl]benzamide

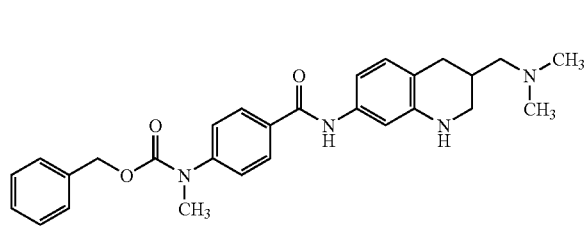

One drop of DMF was added dropwise to THF solution (2 ml) of 4-[N-[(benzyloxy)carbonyl]-N-methylamino]benzoic acid (210 mg), and then oxalyl chloride (0.1 ml) was added dropwise under ice-cooling, which was stirred at room temperature for 30 minutes. After the reaction mixture was concentrated, the residue was dissolved in THF (1 ml), which was added dropwise to pyridine solution (1.5 ml) of 7-amino-3-[(N,N-dimethylamino)methyl]-1,2,3,4-tetrahydroquinoline (150 mg) under ice-cooling. The reaction mixture was then stirred for 30 minutes. After the temperature of the reaction mixture was raised to room temperature, 10% aqueous potassium carbonate solution was added, and extraction was conducted using a mixed solution of THF and ethylacetate. The organic layer was washed with water and saturated aqueous sodium chloride solution, dried, and then concentrated. The residue was recrystallized using THF-IPE to give the titled compound (220 mg).

Melting point: 167–172° C.

REFERENCE EXAMPLE 28

N-[3-[(N,N-Dimethylamino)methyl]-1-formyl-1,2,3,4-tetrahydo-7-quinolinyl]-4-biphenylylcarboxamide

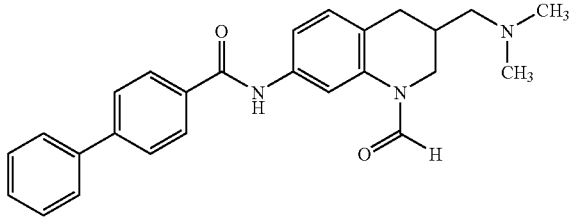

Anhydrous acetic acid (0.1 ml) was added to formic acid (1 ml), which was stirred at 55° C. for 2 hours. N-[3-[(N,N-dimethylamino)methyl]-1,2,3,4-tetrahydo-7-quinolinyl]-4-biphenylylcarboxamide (80 mg) was added to the reaction mixture under ice-cooling, which was stirred at room temperature for 72 hours. 10% aqueous potassium carbonate solution was added to the reaction mixture to make the mixture alkaline, and extraction was conducted using ethyl acetate. The organic layer was washed with water and saturated aqueous sodium chloride solution, dried, and then concentrated. The residue was recrystallized using THF-IPE to give the titled compound (80 mg).

Melting point: 134–138° C.

REFERENCE EXAMPLE 29

N-[1-Acetyl-3-[(N,N-dimethylamino)methyl]-1,2,3,4-tetrahydo-7-quinolyl]-4-biphenylylcarboxamide

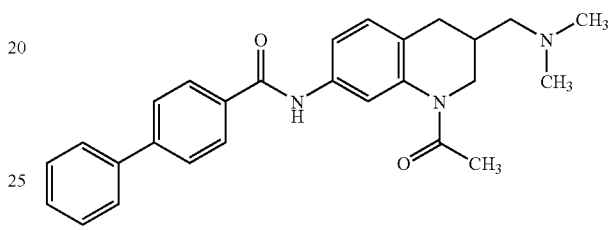

Acetyl chloride (0.02 ml) was added to pyridine solution (1 ml) of N-[3-[(N,N-dimethylamino)methyl[-1,2,3,4-tetrahydro-7-quinolinyl]-4-biphenylylcarboxamide (80 mg) under ice-cooling, which was stirred for 15 minutes, and then stirred at room temperature for 15 minutes. 10% aqueous potassium carbonate solution was added to the reaction mixture, and extraction was conducted using ethyl acetate. The organic layer was washed with water and saturated aqueous sodium chloride solution, dried, and then concentrated. The residue was recrystallized using THF-IPE to give the titled compound (64 mg).

Melting point: 167–173° C.

REFERENCE EXAMPLE 30

N-[3-[(N,N-Dimethylamino)methyl]-1-methylsulfonyl-1,2,3,4-tetrahydro-7-quinolinyl]-4-biphenylylcarboxamide

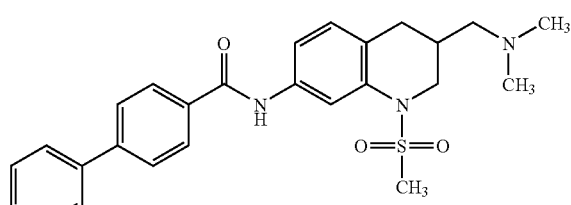

Methanesulfonyl chloride (0.02 ml) was added to pyridine solution (1 ml) of N-[3-[(N,N-dimethylamino)methyl]-1,2,3,4-tetrahydro-7-quinolinyl]-4-biphenylcarboxamide (80 mg) under ice-cooling, which was stirred at room temperature for 1 hour. Further, methanesulfonyl chloride (0.02 ml) was added to the reaction mixture under ice-cooling, which was stirred at room temperature for 12 hours. 10% aqueous potassium carbonate solution was added to the reaction mixture, and extraction was conducted using ethyl acetate. The organic layer was washed with water and saturated aqueous sodium chloride solution, dried, and then concentrated. The residue was recrystallized using THF-IPE to give the titled compound (64 mg).

Melting point: 184–188° C.

REFERENCE EXAMPLE 31

2-(R)-[2-(N,N-Dimethylamino)ethyl]-6-(4-hydroxyphenyl) methoxytetralin

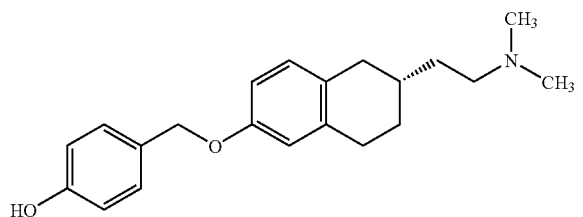

THF solution (2 ml) of 2-(R)-[2-(N,N-dimethylamino) ethyl]-6-[4-(4-methoxyphenylcarbonyloxy) phenylmethoxy]tetralin (330 mg) was added dropwise to THF suspension (4 ml) of lithium aluminum hydride (60 mg) under ice-cooling. 1N aqueous sodium hydroxide solution was added the reaction mixture to make the mixture basic, and the precipitate was removed by celite filtration. After the filtrate was concentrated, the residue was purified using silica gel chromatography (development solvent; ethyl acetate-methanol), and recrystallized (ethyl acetate-hexane) to give the titled compound (70 mg).

Melting point: 132–135° C.

$[\alpha]_D^{20}$=+56.9° (c=0.505, methanol)

REFERENCE EXAMPLE 32

2-(6-Methoxy-2-tetralinyl)-1-piperidino-1-ethanone

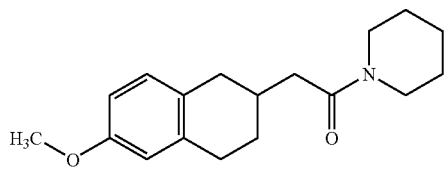

2-(6-Methoxy-2-tetralinyl)acetic acid (8.8 g) was dissolved in a mixed solution of THF (150 ml) and acetonitrile (50 ml), then piperidine (5.2 g), WSC (12 g), HOBt (6.0 g) and triethylamine (17 ml) were added to the solution, which was stirred at room temperature for 12 hours. Water was added to the reaction mixture, and extraction was conducted using ethyl acetate. The organic layer was washed with 1N hydrochloric acid, water, saturated sodium bicarbonate solution, water, and saturated aqueous sodium chloride solution, dried, and then concentrated. The residue was purified using silica gel chromatography (development solvent; ethyl acetate) to give the titled compound (10.3 g). Recrystallization from hexane gave crystals of the following melting points.

Melting point: 59–61° C.

REFERENCE EXAMPLE 33

6-Methoxy-2-(2-piperidinoethyl)tetralin hydrochloride

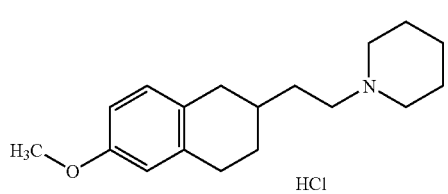

THF solution (50 ml) of 2-(6-methoxy-2-tetralinyl)-1-piperidino-1-ethanone (9.80 g) was added dropwise to THF suspension (100 ml) of lithium aluminum hydride (1.94 g) under ice-cooling. The temperature of the reaction mixture was raised to 60° C. over 30 minutes, which was stirred for 30 minutes. After the reaction mixture was cooled to room temperature, 1N aqueous sodium hydroxide solution was added to make the reaction mixture basic, and the precipitate was removed by celite filtration. The filtrate was concentrated and the residue was made into a hydrochloride, which was then recrystallized from ethanol-IPE to give the titled compound (9.80 g).

Melting point: 189–191° C.

REFERENCE EXAMPLE 34

6-Hydroxy-2-(2-piperidinoethyl)tetralin

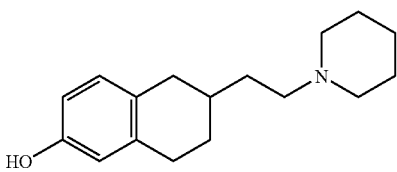

6-Methoxy-2-(2-piperidinoethyl)tetralin hydrochloride (9.3 g) was added to 48% hydrobromic acid (50 ml), which was refluxed with heating for 4 hours. After the reaction mixture was concentrated under reduced pressure, saturated sodium bicarbonate solution was added to the residue to make the water layer alkaline, and the water layer was extracted using a mixed solution of THF and ethyl acetate. The organic layer was washed with water and saturated aqueous sodium chloride solution, dried, and then concentrated. The resulting crystal was washed with IPE to give the titled compound (5.8 g).

Melting point: 154–157° C.

REFERENCE EXAMPLE 35

Methyl 4-[[2-(2-piperidinoethyl)-6-tetralinyl]oxymethyl]benzoate hydrochloride

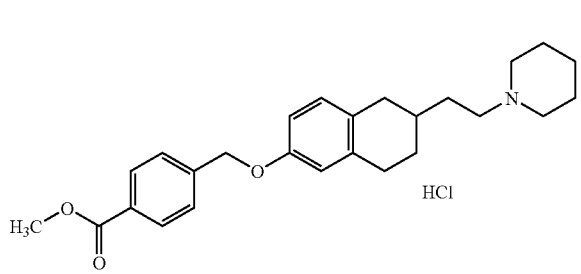

Diethyl azodicarboxylate (40% toluene solution, 5.10 g) was added dropwise to THF solution (15 ml) of 6-hydroxy-2-(2-piperidinoethyl)tetralin (1.50 g), methyl 4-(hydroxymethyl)benzoate (1.44 g), and triphenylphosphine (2.60 g) at room temperature, which was stirred for 12 hours, and then concentrated. The residue was purified using aluminum column chromatography (development solvent; hexane~hexane:ethyl acetate=15:1), which was made into a hydrochloride. The hydrochloride was recrystallized (methanol-IPE) to give the titled compound (1.36 g).

Melting point: 190–193° C.

REFERENCE EXAMPLE 36

4-[[2-(2-Piperidinoethyl)-6-tetralinyl]oxymethyl]benzoic acid

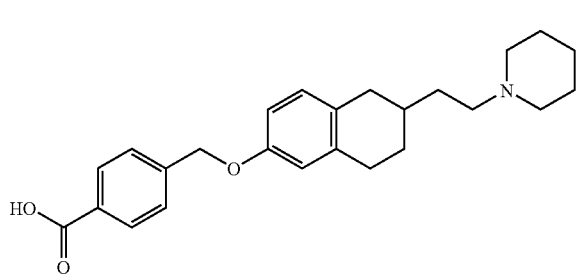

3N Aqueous sodium hydroxide solution (1.8 ml) was added to methanol solution (20 ml) of methyl 4-[[2-(2-piperidinoethyl)-6-tetralinyl]oxymethyl]benzoate hydrochloride (1.06 g), which was refluxed with heating for 6 hours. After the reaction mixture was concentrated, water was added to the reaction mixture. Further, 1N hydrochloric acid was added to make the pH of the mixture about 7. The resulting crystals were filtered to give the titled compound (0.93 g). Recrystallization from ethanol gave crystals of the following melting points.

Melting point: 105–108° C.

REFERENCE EXAMPLE 37

4-[N-(4-Methoxybenzoyl)-N-methylamino]benzoic acid

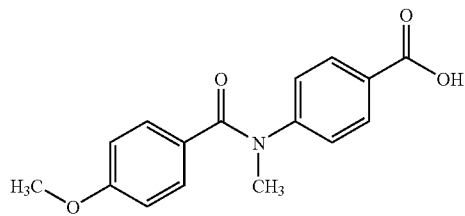

Aqueous solution (50 ml) of sodium carbonate (23 g) was added to THF solution (50 ml) of 4-(methylamino)benzoic acid (5.0 g), and p-anisoyl chloride (5.6 g) was added dropwise to the solution under ice-cooling, which was stirred for 15 minutes, and then stirred at room temperature for 30 minutes. Concentrated hydrochloric acid was added to the reaction mixture under ice-cooling to make the water layer acidic, and extraction was conducted using ethyl acetate. The organic layer was washed with water and saturated aqueous sodium chloride solution, dried, and then concentrated. The residue was purified using silica gel column chromatography (development solvent; hexane~hexane:ethyl acetate=1:2), and recrystallized (ethyl acetate-hexane) to give the titled compound (4.8 g).

Melting point: 157–160° C.

REFERENCE EXAMPLE 38

N-[4-(Hydroxymethyl)phenyl]-4-methoxy-N-methylbenzamide

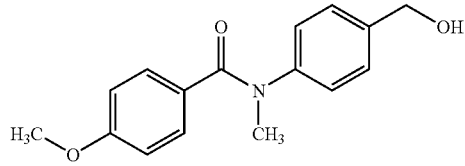

THF solution (1M, 16 ml) of borane was added dropwise to THF solution (10 ml) of 4-[N-(4-methoxybenzoyl)-N-methylamino]benzoic acid (1.14 g) under ice-cooling, which was stirred for 15 minutes, and then stirred at room temperature for 1 hour. After water was added to the reaction mixture, 1N hydrochloric acid was further added, and extraction was conducted using ethyl acetate. The organic layer was washed with water and saturated sodium bicarbonate, and saturated aqueous sodium chloride solution, dried, and then concentrated. The residue was purified using silica gel chromatography (development solvent; hexane~hexane:ethyl acetate=1:2), and recrystallized (ethyl acetate-hexane) to give the titled compound (770 mg).

Melting point: 85–90° C.

REFERENCE EXAMPLE 39

Methyl 4-(4-biphenylylcarbonylamino)benzoate

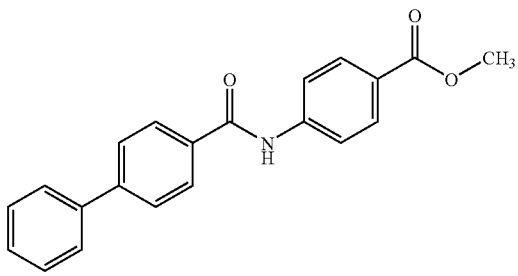

Oxalyl chloride (1.2 ml) and DMF (0.04 ml) were added to THF solution (30 ml) of 4-biphenylylcarboxylic acid (2.184 g) under ice-cooling. The reaction mixture was stirred at room temperature for 30 minutes, which was concentrated. The residue was dissolved in THF (15 ml), which was added dropwise to THF solution (30 ml) of methyl 4-aminobenzoate (1.512 g) and triethylamine (2.1 ml) at 0° C. After the reaction mixture was stirred at 0° C. for 30 minutes, 10% citric acid solution was added to the reaction mixture, and extraction was conducted using ethyl acetate. The organic layer was washed with water and saturated aqueous sodium chloride solution, dried, and then concentrated. The resulting crude crystal was washed with diethyl ether to give the titled compound (2.179 g).

Melting point: 247–251° C.

REFERENCE EXAMPLE 40

4-(4-Biphenylylcarbonylamino)benzoic acid

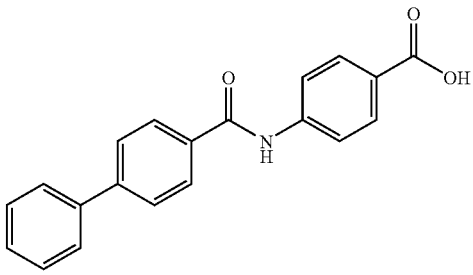

1N Aqueous sodium hydroxide solution (8 ml) was added to a mixed solution of methyl 4-(4-biphenylylcarbonylamino)benzoate (1.998 g) in THF (60 ml) and methanol (20 ml), which was stirred at room temperature for 18 hours. 1N Hydrochloric acid (10 ml) was added to the reaction mixture, and extraction was conducted using ethyl acetate. The organic layer was washed with water and saturated aqueous sodium chloride solution, dried, and then concentrated. The resulting crude crystals were washed with diethyl ether to give the titled compound (1.760 g).

Melting point: >320° C.

$^1$H NMR (DMSO-$d_6$) δ: 7.37–7.57 (3H, m), 7.77 (2H, d), 7.85 (2H, d), 7.95 (4H, s), 8.08 (2H, d), 10.56 (1H, s)

REFERENCE EXAMPLE 41

2-[(N,N-Dimethylamino)methyl]-6-(4-nitrobenzyloxy)tetralin

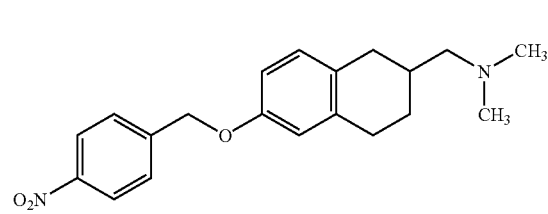

Diethyl azodicarboxylate (40% toluene solution, 9.53 g) was added dropwise to THF solution (15 ml) of 2-[(N,N-dimethylamino)methyl]-6-hydroxytetralin (1.5 g), 4-nitrobenzylalcohol (3.35 g), and triphenylphosphine (5.74 g) at room temperature, which was stirred for 24 hours. The reaction mixture was concentrated, and the residue was purified using alumina column chromatography (development solvent; hexane~hexane:ethyl acetate=8:1), and recrystallized (ethyl acetate-hexane) to give the titled compound (1.29 g).

Melting point: 83–89° C.

REFERENCE EXAMPLE 42

6-(4-Aminobenzyloxy)-2-[(N,N-dimethylamino)methyl]tetralin

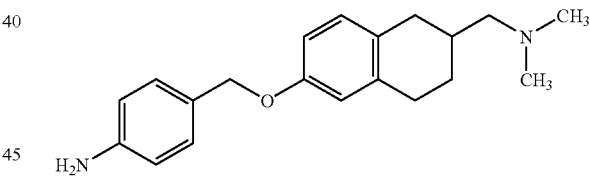

After acetic acid (6 ml) was added to THF solution (12 ml) of 2-[(N,N-dimethylamino)methyl]-6-(4-nitrobenzyloxy)tetralin (1.91 g) under ice-cooling, zinc powder (3.67 g) was further added, which was stirred for 6 hours. The reaction mixture was filtered, and the filtrate was concentrated. 10% aqueous potassium carbonate solution and ethyl acetate were added to the residue, the precipitate was removed by celite filtration, and the filtrate was extracted using ethyl acetate. The organic layer was washed with water and saturated aqueous sodium chloride solution, dried, and then concentrated. The residue was purified using aluminum column chromatography (development solvent; hexane~hexane:ethyl acetate=4:1) to give the titled compound (1.05 g).

Amorphous Powder:

$^1$H-NMR (CDCl$_3$) δ: 1.18–1.50 (1H, m), 1.70–2.50 (5H, m), 2.24 (6H, s), 2.72–2.86 (3H, m), 3.68 (2H, brs), 4.88 (2H, s), 6.58–6.82 (4H, m), 6.99 (1H, s), 7.14–7.30 (2H, m).

REFERENCE EXAMPLE 43

Methyl 4-anilinocarbonylbenzoate

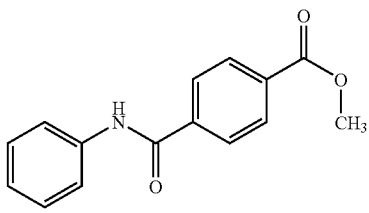

4-Methoxycarbonyl benzoic acid (540 mg), aniline (0.27 ml), WSC (863 mg) and triethylamine (0.84 ml) were added to THF (20 ml). After the reaction mixture was stirred at room temperature for 20 hours, the reaction mixture was placed in water, and extraction was conducted using ethyl acetate-THF (1:1). The organic layer was washed with water, saturated sodium bicarbonate solution, and saturated aqueous sodium chloride solution, dried, and then concentrated. The resulting crude crystals were recrystallized from ethyl acetate-hexane to give the titled compound (659 mg).

Melting point: 189–190° C.

REFERENCE EXAMPLE 44

4-Anilinocarbonylbenzoic acid

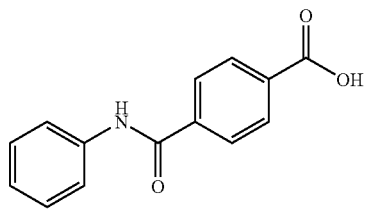

8 mol of aqueous sodium hydroxide solution (8 ml) was added to methanol (16 ml)-THF (6 ml) solution of 4-methyl anilinocarbonylbenzoate (511 mg), which was stirred at room temperature for 1 hour. 1 mol of hydrochloric acid was added to the reaction mixture to make the pH of the mixture to 5, extraction was conducted using ethyl acetate-THF (1:1). The organic layer was washed with water and saturated aqueous sodium chloride solution, dried, and then concentrated. The resulting residue was washed with hexane to give the titled compound (480 mg).

Melting point: 305–307° C.

REFERENCE EXAMPLE 45

4-(2-Benzo[b]furanyl)benzoic acid

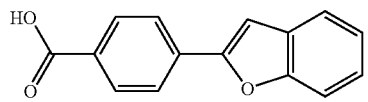

Benzofuranyl-2-boric acid (2.1 g), palladium tetratriphenylphosphine (200 mg) and 2M aqueous sodium carbonate solution were added to toluene (40 ml)-ethanol (10 ml) solution of ethyl 4-bromobenzoate (2.3 g), which was refluxed at 80° C. for 5 hours under an argon atmosphere. The reaction mixture was diluted with water, and extraction was conducted using ethyl acetate. The organic layer was washed with water and saturated aqueous sodium chloride solution, dried, and then concentrated. The resulting residue was purified using silica gel chromatography (development solvent; ethyl acetate:hexane=1:4), and concentrated, which was dissolved in methanol (10 ml)-THF (10 ml). 8 mol of aqueous sodium hydroxide solution (8 ml) was added to the resulting solution at room temperature, which was stirred for 2 hours. After 1 mol of hydrochloric acid was added to the reaction mixture to make the mixture acidic, extraction was conducted using ethyl acetate-THF (1:1). The organic layer was washed with water and saturated aqueous sodium chloride solution, dried, and then concentrated. The resulting residue was washed with hexane to give the titled compound (2.272 g).

Melting point: 292–294° C.

REFERENCE EXAMPLE 46

3'-Acetylamino-4-biphenylylcarboxyic acid

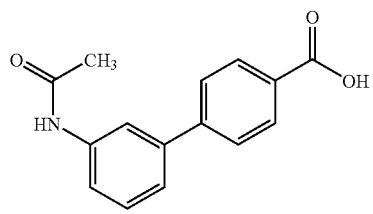

The titled compound was produced in the same manner as in Reference Example 45.

Melting point: 300–301° C.

REFERENCE EXAMPLE 47

N-[2-[(E)-(Dimethylamino)methylidene]-1-oxo-2,3-dihydro-1H-inden-5-yl]acetamide

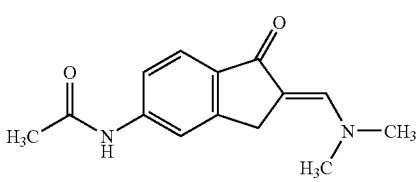

Dimethylformamide dimethylacetal was added to 5-acetamido-1-indanone (2.5 g, 13.2 mmol), which was stirred at 100° C. for 3.5 hours, and cooled to room temperature. The precipitated crude products were collected, which was washed with ethyl acetate to give the titled compound (2.73 g).

$^1$H NMR (DMSO-$d_6$) δ: 2.08 (3H, s), 3.13 (6H, s), 3.87 (2H, s), 7.31 (1H, s), 7.52 (2H, m), 7.86 (1H, s), 10.16 (1H,

REFERENCE EXAMPLE 48

N-[2-[(Dimethylamino)methyl]-2,3-dihydro-1H-inden-5-yl]acetamide

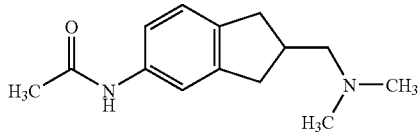

N-[2-[(E)-(Dimethyamino)methylidene]-1-oxo-2,3-dihydro-1H-inden-5-yl]acetamide (2.70 g, 12.3 mmol) obtained in Reference Example 47 and 10% palladium-carbon (0.3 g) were added to a mixed solution of methanol (60 ml) and acetic acid (6 ml), which was stirred at 40° C. under a hydrogen atmosphere for 1 day. After the catalyst was filtered, the filtrate was distilled out under reduced pressure. 1N hydrochloric acid (15 ml) was added to the reaction mixture, which was washed with ethyl acetate. Then, potassium carbonate was added to the mixture, and extraction was conducted using ethyl acetate. The extract was washed with saturated aqueous sodium chloride solution, dried using anhydrous sodium sulfate, and then the solvent was distilled out under reduced pressure. The resulting residue was purified using aluminum column chromatography (development solvent: ethyl acetate) to give the titled compound.

$^1$H NMR (CDCl$_3$) δ: 2.15 (3H, s), 2.25 (6H, s), 2.28 (2H, m), 2.61 (3H, m), 3.02 (2H, m), 7.11 (2H, m), 7.26 (1H, s), 7.39 (1H, s).

REFERENCE EXAMPLE 49

N-[6-[(E)-(Dimethylamino)methylidene]-5-oxo-6,7,8,9-tetrahydro-5H-benzo[a]cyclohepten-2-yl]acetamide

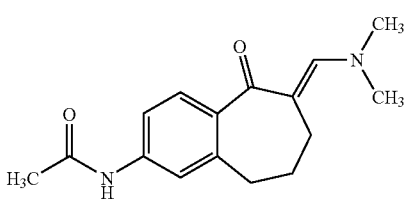

The titled compound was obtained by carrying out the same operation as in Reference Example 47, using N-(5-oxo-6,7,8,9-tetrahydro-5H-benzo[a]cyclohepten-2-yl)acetamide.

$^1$H-NMR (CDCl$_3$) δ: 1.78–1.90 (2H, m), 2.17 (3H, s), 2.34 (2H, t, J=6.6 Hz), 2.74 (2H, t, J=6.8 Hz), 3.11 (6H, s), 7.21 (1H, d, J=8.1 Hz), 7.48–7.63 (3H, m), 7.73 (1H, s).

Melting point: 177–180° C. (crystallization solvent: ethyl acetate-diethyl ether)

REFERENCE EXAMPLE 50

8-[(Dimethylamino)methyl]-6,7-dihydro-5H-benzo[a]cyclohepten-3-amine

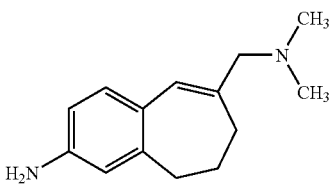

The titled compound was obtained as an oily substance by carrying out the same operation as in Example 41-2), using N-[6-[(E)-(dimethylamino)methylidene]-5-oxo-6,7,8,9-tetrahydro-5H-benzo[a]cyclohepten-2-yl]acetamide obtained in Reference Example 49.

$^1$H-NMR (CDCl$_3$) δ: 1.90–2.01 (2H, m), 2.22 (6H, s), 2.35 (2H, t, J=6.3 Hz), 2.72 (2H, t, J=5.4 Hz), 2.91 (2H, s), 3.7 (2H, br, NH$_2$), 6.28 (1H, s), 6.40–6.50 (2H, m), 6.94 (1H, d, J=7.8 Hz).

REFERENCE EXAMPLE 51

6-[(Dimethylamino)methyl]-6,7,8,9-tetrahydro-5H-benzo[a]cyclohepten-2-amine

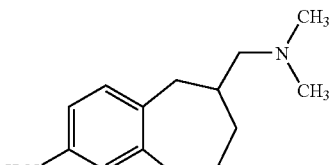

The titled compound was obtained as an oily substance, by carrying out the same operation as in Reference Example 48, using 8-[(dimethylamino)methyl]-6,7-dihydro-5H-benzo[a]cyclohepten-3-amine.

$^1$H-NMR (CDCl$_3$) δ: 1.30–1.63 (3H, m), 1.65–2.22 (10H, m), 2.44–2.80 (4H, m), 3.5 (2H, br, NH$_2$), 6.35–6.48 (2H, m), 6.92 (1H, d, J=7.8 Hz).

REFERENCE EXAMPLE 52

6-(1-Piperidinylmethyl)-7,8-dihydro-2-naphthalenamine

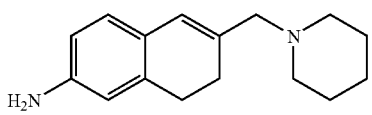

1) A mixture of 6-acetamido-2-(N,N-dimethylaminomethylidene)-1-tetralone (11 g) obtained in Example 41-1) and piperidine (100 ml) was refluxed with heating for 24 hours. After excess piperidine was distilled out under reduced pressure, the resulting residue was crystallized using tetrahydrofuran-isopropyl ether to give 6-acetamido-2-(1-piperidinylmethylidene)-1-tetralone (7 g) as a light yellow powder.

2) The titled compound was obtained as an amorphous powder by carrying out the same operations as in Example 41-2), using 6-acetamido-2-(1-piperidinylmethylidene)-1-tetralone obtained in above 1).

$^1$HNMR (CDCl$_3$) δ: 1.44–1.57 (6H, m), 2.25–2.34 (6H, m), 2.72 (2H, t, J=8.0 Hz), 2.98 (2H, s), 3.59 (2H, s), 6.23 (1H, s), 6.45–6.47 (2H, m), 6.81 (1H, d, J=8.7 Hz).

REFERENCE EXAMPLE 53

6-(1-Piperidinylmethyl)-5,6,7,8-tetrahydro-2-naphthalenamine

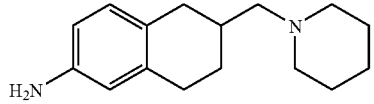

The titled compound was obtained as an amorphous powder by carrying out the same operations as in Reference Example 48, using 6-(1-piperidinylmethyl)-7,8-dihydro-2-naphthalenamine obtained in Reference Example 52.

$^1$H NMR (CDCl$_3$) δ: 1.25–2.82 (19H, m), 3.36 (2H, bs), 6.44–6.49 (2H, m), 6.88 (1H, d, J=8.1 Hz).

REFERENCE EXAMPLE 54

6-(1-Pyrrolidinylmethyl)-7,8-dihydro-2-naphthalenamine

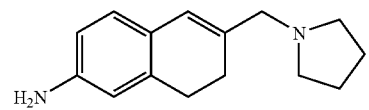

The titled compound was obtained as an amorphous powder by carrying out the same operations as in Reference Example 52, using 6-acetamido-2-(N,N-dimethylaminomethylidene)-1-tetralone obtained in Example 41-1).

$^1$H NMR (CDCl$_3$) δ: 1.76–1.80 (4H, m), 2.30 (2H, t, J=7.8 Hz), 2.47–2.49 (4H, m), 2.74 (2H, t, J=7.8 Hz), 3.13 (2H, s), 3.59 (2H, brs), 6.26 (1H, s), 6.45–6.47 (2H, m), 6.82 (1H, d, J=8.6 Hz).

REFERENCE EXAMPLE 55

6-(1-Pyrrolidinylmethyl)-5,6,7,8-tetrahydo-2-naphthalenamine

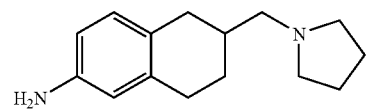

The titled compound was obtained as an amorphous powder by carrying out the same operations as in Reference Example 48, using 6-(1-pyrrolidinylmethyl)-7,8-dihydro-2-naphthalenamine obtained in Reference Example 54.

$^1$H NMR (CDCl$_3$) δ: 1.45–1.90 (1H, m), 1.55–2.80 (16H, m), 3.48 (2H, brs), 6.44 (1H, s), 6.47 (2H, d, J=8.1 Hz), 6.88 (2H, d, J=8.1 Hz).

REFERENCE EXAMPLE 56

4'-Chloro-N-[6-(chloromethyl)-7,8-dihydro-2-naphthalenyl] [1,1'-biphenyl]-4-carboxamide

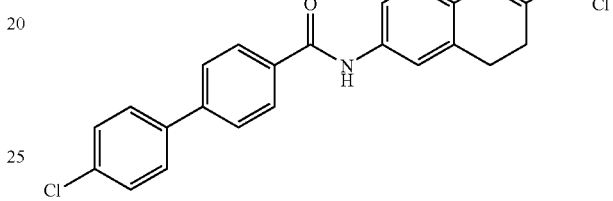

After 1-chloroethyl chloroformate (0.23 ml) was added to tetrahydrofuran solution (30 ml) of 4'-chloro-N-[6-(dimethylamino) methyl]-7,8-dihydro-2-naphthalenyl][1,1'-biphenyl]-4-carboxamide (750 mg) at −78° C., the temperature of the solution was raised to room temperature over 30 minutes. The solvent was distilled out under reduced pressure. The resulting residue was crystallized using tetrahydrofuran-n-hexane to give the titled compound (600 mg).

Melting point: 179–181° C. (crystallization solvent: tetrahydrofuran-n-hexane)

REFERENCE EXAMPLE 57

6-(4-Morpholinylmethyl)-5,6,7,8-tetrahydro-2-naphthalenamine

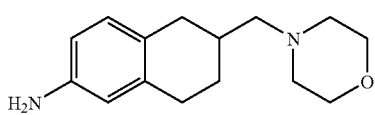

The titled compound was obtained as an amorphous powder by carrying out, in order, the same operations as in Reference Example 52 and Reference Example 48, using 6-acetamido-2-(N,N-dimethylaminomethylidene)-1-tetralone obtained in Example 41-1).

$^1$H NMR (CDCl$_3$) δ: 1.22–1.41 (1H, m), 1.80–1.82 (2H, m), 2.22–2.34 (10H, m), 3.50 (2H, s), 3.69–3.72 (1H, m), 6.40 (1H, s), 6.44 (1H, d, J=8.1 Hz), 6.85 (1H, d, J=8.1 Hz).

REFERENCE EXAMPLE 58

N-[6-(Chloromethyl)-7,8-dihydro-2-naphthalenyl][1,1'-biphenyl]-4-carboxamide

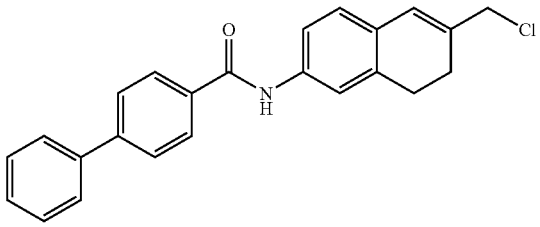

The titled compound was obtained by carrying out the same operations as in Reference Example 56, using N-[6-[(dimethylamino)methyl]-7,8-dihydro-2-naphthalenyl][1,1'-biphenyl]-4-carboxamide obtained in Example 47.

Melting point: 163–165° C. (crystallization solvent: tetrahydofuran-n-hexane)

REFERENCE EXAMPLE 59

3-[(N,N-Dimethylamino)methyl]-2H-chromen-7-amine

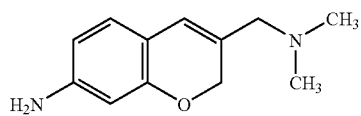

The titled compound was obtained by carrying out, in order, the same operations as in Examples 41-1) and 41-2), using 7-acetylamino-3,4-dihydrochromen-4-on.

$^1$H-NMR (CDCl$_3$) δ: 2.20 (6H, s), 2.94 (2H, s), 3.66 (2H, brs), 4.71 (2H, s), 6.16–6.21 (2H, m), 6.76 (1H, d, J=7.8 Hz).

REFERENCE EXAMPLE 60

6-[(Dimethylamino)methyl]-7,8-dihydro-1-naphthalenamine

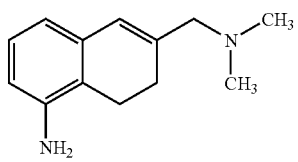

1) Methyl 4-(2-aminophenyl)butanoate hydrochloride (7.20 g, 0.037 mol) synthesized by a known method by documents (Synthetic communications, 26(18), 3443 (1996)) and triethylamine (5.06 g, 0.05 mol) were dissolved in tetrahydrofuran (60 ml). Acetyl chloride (3.51 g, 0.045 mol) was added dropwise to the mixture, which was stirred at room temperature for 30 minutes. Ethyl acetate and 1N hydrochloric acid were added to the reaction mixture, and extraction was conducted. The organic layer was washed with water, concentrated and dried. A mixed solution of ethyl acetate-n-hexane (1:1) was added to the residue. The crystallized product was collected by filtration, to give methyl 4-(2-acetylaminophenyl)butanoate (6.40 g) as a white powder.

$^1$H-NMR (CDCl$_3$) δ: 1.77–1.86 (2H, m), 2.29 (3H, s), 2.41–2.45 (2H, m), 2.59–2.62 (2H, m), 3.74 (3H, s), 7.03 (1H, t, J=7.3 Hz), 7.11–7.12 (1H, m), 7.22 (1H, t, J=7.3 Hz), 8.08 (1H, d, J=8.1 Hz), 8.33 (1H, s).

2) Polyphosphoric acid (100 g) was heated at 130° C., then methyl 4-(2-acetylaminophenyl)butanoate (6.40 g, 0.027 mol) obtained in 1) was added under stirring. After stirring for 1 hour, the reaction mixture was poured into ice water, and ethyl acetate and water were added, then extraction was conducted by adding water. The organic layer was washed with saturated sodium hydrogen carbonate solution and aqueous sodium chloride solution, and concentrated. A mixed solution of ethyl acetate-n-hexane (1:1) was added to the residue, and the crystallized product was collected by filtration, to give 5-acetylamino-1-tetralone (2.80 g) as a white powder.

$^1$H-NMR (CDCl$_3$) δ: 2.10–2.19 (2H, m), 2.24 (3H, s), 2.66 (2H, t, J=6.3 Hz), 2.84 (2H, t, J=5.7 Hz), 7.06 (1H, brs), 7.34 (1H, t, J=7.5 Hz), 7.82 (1H, d, J=7.5 Hz), 7.95 (1H, d, J=7.5 Hz).

3) 5-Acetylamino-1-tetralone (0.6 g, 3.0 mmol) obtained was dissolved in dimethylformamide dimethylacetal (20 ml), which was refluxed with heating for 4 hours. The crystallized product was collected by filtration, which was washed with ethyl acetate, to give 5-acetylamino-2-(dimethylamino)methylidene-1-tetralone (0.58 g) as a yellow powder.

$^1$H-NMR (CDCl$_3$) δ: 2.21 (3H, s), 2.68–2.72 (2H, m), 2.86–2.90 (2H, m), 3.11 (6H, s), 7.26–7.31 (2H, m), 7.62 (1H, m), 7.69 (1H, s), 7.92 (1H, m).

4) Sodium triacetoxyhydroborate (424 mg, 2.0 mmol) was dissolved in a mixed solution of ethyl acetate (5 ml) and tetrahydrofuran (1 ml) under ice-cooling. 5-Acetylamino-2-dimethylaminomethylidene-1-tetralone (129 mg, 0.5 mmol) obtained in 3) was added to the mixture, which was stirred for 15 minutes. The reaction mixture was concentrated, and methanol (10 ml) was added to the residue, and sodium borohydride (38 mg, 1 mmol) was added under ice-cooling. After stirring for 1 hour, the reaction mixture was concentrated. 5N Hydrochloric acid and ethyl acetate were added to the residue, and extraction was conducted. The water layer was refluxed with heating for 2 hours. 4N sodium hydroxide solution and ethyl acetate were added to the reaction mixture, and extraction was conducted. The organic layer was washed with water, and concentrated. The residue was purified by alumina column chromatography (development solvent; ethyl acetate: n-hexane=1:1) to give the titled compound (80 mg) as a colorless oily substance.

$^1$H-NMR (CDCl$_3$) δ: 2.24 (6H, s), 2.37 (2H, t, J=8.1 Hz), 2.63 (2H, t, J=8.1 Hz), 2.97 (2H, s), 3.58 (2H, brs), 6.29 (1H, s,), 6.53 (1H, d, J=8.1 Hz), 6.57 (1H, d, J=8.1 Hz), 6.97 (1H, t, J=8.1 Hz).

REFERENCE EXAMPLE 61

7-[(Dimethylamino)methyl]-5,6-dihydro-2-naphthalenamine

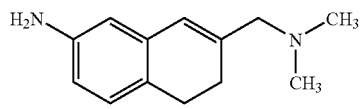

1) 7-Nitro-1-tetralone (8.32 g, 0.044 mol) and concentrated hydrochloric acid (24 ml, 0.29 mol) were dissolved in methanol (100 ml), and an iron powder (7.30 g, 0.13 mol) was gradually added over 1 hour. After stirring for 1 hour, the reaction mixture was concentrated. 4N Sodium hydroxide solution and ethyl acetate were added to the residue, and extraction was conducted. The organic layer was dried, and concentrated. Tetrahydrofuran (100 ml) and triethylamine (5.05 g, 0.05 mol) was added to the residue. Further, acetyl chloride (3.92 g, 0.05 mol) was added under ice-cooling. After stirring for 30 minutes, ethyl acetate and 1N hydrochloric acid were added, and extraction was conducted. The organic layer was concentrated, and the residue was purified with silica gel column chromatography (development solvent: ethyl acetate), to give 7-acetylamino-1-tetralone (7.52 g) as a white powder.

$^1$H-NMR (CDCl$_3$) δ: 2.09–2.18 (2H, m), 2.21 (3H, s), 2.65 (2H, t, J=6.3 Hz), 2.94 (2H, t, J=6.3 Hz), 7.24 (1H, d, J=8.4 Hz), 7.82 (1H, s), 7.98 (1H, brs), 8.15 (1H, d, J=7.5 Hz).

2) 7-Acetylamino-2-[(dimethylamino)methylidene]-1-tetralone (2.95 g) was obtained as a white powder by the same method as in Reference Example 60-3), using 7-acetylamino-1-tetralone (3.00 g, 0.0148 mol) obtained in 1).

$^1$H-NMR (CDCl$_3$) δ: 2.17 (3H, s), 2.78–2.82 (2H, m), 2.88–2.93 (2H, m), 3.14 (6H, s), 7.14 (1H, d, J=8.1 Hz), 7.74 (1H, s), 7.76 (1H, s), 8.09–8.12 (1H, m), 8.24 (1H, s).

3) The titled compound (300 mg) was obtained as a colorless oily substance by the same method as in Reference Example 60-4), using 7-acetylamino-2-[(dimethylamino)methylidene]-1-tetralone (628 mg, 2.43 mmol) obtained in 2).

$^1$H-NMR (CDCl$_3$) δ: 2.23 (6H, s); 2.29 (2H, t, J=8.4 Hz), 2.71 (2H, t, J=8.4 Hz), 2.97 (2H, s), 3.52 (2H, brs), 6.24 (1H, s,), 6.41 (1H, s,), 6.46 (1H, d, J=7.8 Hz), 6.90 (1H, d, J=7.8 Hz).

REFERENCE EXAMPLE 62

N,N-Dimethyl-N-[(7-amino-2,3-dihydro-1,4-benzodioxin-2-yl)methyl]amine

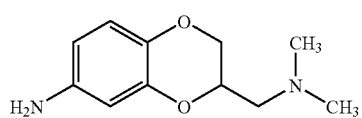

1) 1,2-Dihydroxy-4-nitrobenzene (5.00 g, 0.032 mol), potassium carbonate (9.67 g, 0.07 mol) and epibromohydrin (5.30 g. 0.039 mol) were dissolved in dimethylformamide (100 ml), which was stirred at 100° C. for 1 hour. Water was added to the reaction mixture, and extraction was conducted using ethyl acetate. The organic layer was washed with water, and concentrated. The residue was purified by alumina column chromatography (development solvent: ethyl acetate). The eluent was washed with a mixed solution of ethyl acetate-n-hexane (1:1), to give (7-nitro-2,3-dihydro-1,4-benzodioxin-2-yl)methanol (3.31 g) as a white powder.

$^1$H-NMR (CDCl$_3$) δ: 1.95–1.99 (1H, m), 3.89–3.97 (2H, m), 4.19–4.29 (2H, m), 4.41–4.45 (1H, m), 6.96 (1H, d, J=8.6 Hz), 7.78–7.81 (2H, m).

2) (7-Nitro-2,3-dihydro-1,4-benzodioxin-2-yl)methanol (1.00 g, 4.74 mmol) obtained in 1) and triethylamine (719 mg, 7.10 mmol) were dissolved in dimethylformamide (30 ml), and methanesulfonyl chloride (651 mg, 5.68 mmol) was added, which was stirred at room temperature for 30 minutes. Then, an aqueous dimethylamine solution was added and stirred at 60° C. for 5 hours. Water was added to the reaction mixture, and extraction was conducted using ethyl acetate. The organic layer was washed with water, and concentrated. The residue was purified by alumina column chromatography (development solvent; ethyl acetate: n-hexane=3:7), to give N,N-dimethyl-N-[(7-nitro-2,3-dihydro-1,4-benzodioxin-2-yl)methyl]amine (802 mg) as a colorless oily substance.

$^1$H-NMR (CDCl$_3$) δ: 2.34 (6H, s), 2.50–2.68 (2H, m), 4.02–4.09 (2H, m), 4.30–4.36 (1H, m), 4.39–4.44 (2H, m), 6.94 (1H, d, J=8.9 Hz), 7.76–7.84 (2H, m).

3) N,N-Dimethyl-N-[(7-nitro-2,3-dihydro-1,4-benzodioxin-2-yl)methyl]amine (802 mg, 3.37 mmol) obtained in 2) and concentrated hydrochloric acid (3 ml) was dissolved in methanol (10 ml), and an iron powder (0.80 g, 14 mmol) was quietly added over 1 hour. After stirring for 1 hour, the reaction mixture was concentrated. 4N Sodium hydroxide solution and ethyl acetate were added to the residue, and extraction was conducted. The organic layer was dried, and concentrated. The residue was purified by silica gel column chromatography (development solvent: ethyl acetate-n-hexane 3:7), to give the titled compound (514 mg) as a colorless oily substance.

$^1$H-NMR (CDCl$_3$) δ: 2.32 (6H, s), 2.43–2.64 (2H, m), 3.40 (2H, s), 3.86–3.93 (1H, m), 4.19–4.27 (2H, m), 6.18–6.22 (1H, m), 6.29 (1H, s), 6.67 (1H, d, J=8.7 Hz).

REFERENCE EXAMPLE 63

N,N-Dimethyl-N-[(6-amino-2,3-dihydro-1,4-benzodioxin-2-yl)methyl]amine

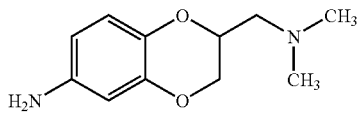

1) 1,2-Dihydroxy-4-nitrobenzene (4.65 g, 0.030 mol), potassium carbonate (8.71 g, 0.063 mol) and methoxymethyl chloride (2.42 g, 0.030 mol) were dissolved in dimethylformamide (50 ml), which was stirred at 40° C. for 30 minutes. Epibromohydrin (7.20 g, 0.045 mol) was added to the mixture, which was stirred at 60° C. for 80 minutes. Then water was added, and extraction was conducted using ethyl acetate. The organic layer was washed with water, and concentrated. The residue was purified by alumina column chromatography (development solvent: ethyl acetate-n-hexane=1:4), to give 2-[[2-(methoxymethoxy)-5-nitrophenoxy]methyl]oxirane (2.61 g) as a white powder.

$^1$H-NMR (CDCl$_3$) δ: 2.79–2.81 (1H, m), 2.93–2.96 (1H, m), 3.41 (1H, m), 3.53 (3H, s), 4.01–4.07 (1H, m), 4.40–4.45 (1H, m), 5.32 (2H, s), 7.22 (1H, d, J=9.0 Hz), 7.82–7.91 (2H, m).

2) 2-[[2-(Methoxymethoxy)-5-nitrophenoxy]methyl]oxirane (4.00 g, 0.016 mol) obtained in 1) was dissolves in methanol (50 ml), and 10% hydrochloric acid-methanol solution (10 ml) was added, which was stirred at room temperature for 30 minutes. The solvent was concentrated, and methanol (30 ml) and potassium carbonate (6.50 g, 0.047 mol) were added to the residue, which was stirred at 60° C. for 1 hour. The solvent was concentrated, water was added, and extraction was conducted using ethyl acetate. The organic layer was washed with water, and concentrated. The residue was purified by alumina column chromatography (development solvent; ethyl acetate), to give (6-nitro-2,3-dihydro-1,4-benzodioxin-2-yl)methanol (2.12 g) as a white powder.

$^1$H-NMR (CDCl$_3$) δ: 1.90–1.94 (1H, m), 3.89–3.97 (2H, m), 4.19–4.28 (2H, m), 4.41–4.45 (1H, m), 6.97 (1H, d, J=8.6 Hz), 7.78–7.8.2 (2H, m).

3) N,N-Dimethyl-N-[(6-nitro-2,3-dihydrodioxin-2-yl)methyl]amine (910 mg) was obtained as a colorless oily substance, by the same method as in Reference Example 62-2), using (6-nitro-2,3-dihydro-1,4-benzodioxin-2-yl)methanol (1.00 g, 4.74 mmol) obtained in 2).

$^1$H-NMR (CDCl$_3$) δ: 2.35 (6H, s), 2.52–2.70 (2H, m), 3.98–4.05 (2H, m), 4.35–4.39 (3H, m), 6.95–6.98 (1H, m), 7.77–7.80 (2H, m).

4) The titled compound (750 mg) was obtained as a colorless oily substance, by the same method as in Reference Example 62-3), using N,N-dimethyl-N-[(6-nitro-2,3-dihydro-1,4-benzodioxin-2-yl)methyl]amine (910 mg, 3.82 mmol) obtained in 3).

$^1$H-NMR (CDCl$_3$) δ: 2.32 (6H, s), 2.43–2.64 (2H, m), 3.40 (2H, s), 3.86–3.92 (1H, m), 4.13–4.27 (2H, m), 6.19–6.28 (2H, m), 6.67–6.70 (1H, m).

REFERENCE EXAMPLE 64

1-[(6-Amino-2,3-dihydro-1,4-benzodioxin-2-yl)methyl]pyrrolidine

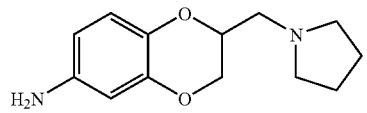

1) 1-[(6-Nitro-2,3-dihydro-1,4-benzodioxin-2-yl)methyl]pyrrolidine (1.30 g) was obtained as a colorless oily substance, by the same method as in Reference Example 0.62–2), using (6-nitro-2,3-dihydro-1,4-benzodioxin-2-yl)methanol (1.12 g, 5.30 mmol) and pyrrolidine (10 ml).

$^1$H-NMR (CDCl$_3$) δ: 1.79–1.83 (4H, m), 2.60–2.62 (4H, m), 2.78 (2H, d, J=5.9 Hz), 4.00–4.07 (1H, m), 4.38–4.42 (2H, m), 6.95–6.98 (1H, m), 7.76–7.80 (2H, m).

2) The titled compound (1.03 g) was obtained as a colorless oily substance, by the same method as in Reference Example 62-3), using 1-[(6-nitro-2,3-dihydro-1,4-benzodioxin-2-yl)methyl]pyrrolidine (1.30 g, 4.92 mmol).

$^1$H-NMR (CDCl$_3$) δ: 1.74–1.83 (4H, m), 2.54–2.63 (4H, m), 2.69–2.72 (2H, m), 3.40 (2H, s), 3.91–3.97 (1H, m), 4.18–4.30 (2H, m), 6.18–6.25 (2H, m), 6.70 (1H, d, J=8.4 Hz).

REFERENCE EXAMPLE 65

N-[(7-Amino-3,4-dihydro-2H-chromen-3-yl)methyl]-N,N-dimethylamine

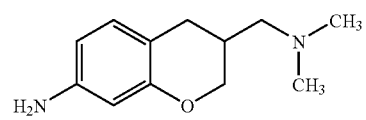

3-[(N,N-Dimethylamino)methyl]-2H-chromen-7-amine (150 mg, 0.73 mmol) obtained in Reference Example 59, 1N hydrochloric acid (0.5 ml) and 10% palladium carbon (40 mg) was dissolved in methanol (5 ml), and catalytic hydrogenation was conducted under normal temperature and normal pressure. After a catalyst was filtered out, the filtrate was concentrated, and the residue was purified by alumina column chromatography (development solvent; ethyl acetate: n-hexane=3:7), to give the titled compound (15 mg) as a colorless oily substance.

$^1$H-NMR (CDCl$_3$) δ: 2.20–2.24 (3H, m), 2.24 (6H, m), 2.30–2.40 (1H, m), 2.75–2.80 (1H, m), 3.60 (1H, m), 3.75–3.80 (2H, m), 4.20–4.25 (1H, m), 6.20 (1H, m), 6.21–6.25 (1H, m), 6.82 (1H, d, J=7.8 Hz).

REFERENCE EXAMPLE 66

6-[(Dimethylamino)methyl]-5-methyl-7,8-dihydro-2-naphthalenamine

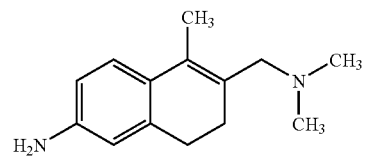

1) 6-Acetylamino-1-tetralone (5.5 g, 0.027 mol) and dimethylmethylenammonium chloride (6.3 g, 0.068 mol) were dissolved in a mixed solution of acetonitrile (100 ml) and tetrahydrofuran (100 ml), which was stirred for 48 hours. The crystallized product was collected by filtration, washed with tetrahydrofuran, and dissolved in ethyl acetate. 0.5N Sodium hydroxide solution was added to the solution for liquid separation. The organic layer was concentrated, to give 6-acetylamino-2-[(dimethylamino)methyl]-1-tetralone (4.48 g) as a colorless oily substance.

2) 6-Acetylamino-2-[(dimethylamino)methyl]-1-tetralone (260 mg, 1.00 mmol) obtained was dissolved in tetrahydrofuran (10 ml). 1M Methyl magnesium bromide tetrahydrofuran solution (3 ml) (3.00 mmol) was added to the solution under ice-cooling, which was stirred at room temperature for 16 hours. Aqueous ammonium chloride solution was added to the reaction mixture, and extraction was conducted using ethyl acetate. The organic layer was concentrated, and 5N hydrochloric acid and ethyl acetate were added to the residue for liquid separation. Concentrated hydrochloric acid was added to the water layer, which was refluxed for 4 hours. The reaction mixture was concentrated, and 1N sodium hydroxide solution and ethyl acetate were added to the residue and extraction was conducted. The organic layer was concentrated, and the residue was purified by alumina column chromatography (development solvent; ethyl acetate n-hexane=3:7), to give the titled compound (83 mg) as a colorless oily substance.

$^1$H-NMR (CDCl$_3$) δ: 2.04 (3H, s), 2.24 (6H, s), 2.28 (2H, t, J=7.4 Hz), 2.66 (2H, t, J=7.4 Hz), 3.04 (2H, s), 3.62 (2H, s), 6.49 (1H, s), 6.51–6.55 (1H, m), 7.10 (1H, d, J=8.1 Hz).

REFERENCE EXAMPLE 67

6-[(Dimethylamino)methyl]-5-ethyl-7,8-dihydro-2-naphthalenamine

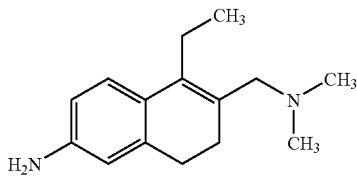

The titled compound was obtained as a colorless oily substance by the same manner as in Reference Example 66-2), using 6-acetylamino-2-(dimethylamino)methyl-1-tetralone obtained in Reference Example 66-1) and ethyl magnesium bromide.

$^1$H-NMR (CDCl$_3$) δ: 1.06 (3H, t, J=7.5 Hz), 2.24 (6H, s), 2.27 (2H, m), 2.52–2.66 (4H, m), 3.04 (2H, s), 3.61 (2H, s), 6.51 (1H, s), 6.51–6.55 (1H, m), 7.11 (1H, d, J=8.1 Hz).

REFERENCE EXAMPLE 68

6-[(Dimethylamino)methyl]-5-isobutyl-7,8-dihydro-2-naphthalenamine

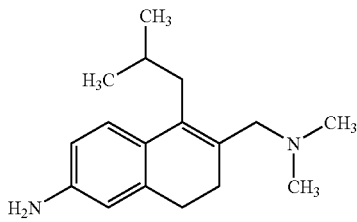

The titled compound was obtained as a colorless oily substance by the same manner as in Reference Example 66-2), using 6-acetylamino-2-[(dimethylamino)methyl]-1-tetralone obtained in Reference Example 66-1) and isobutyl magnesium bromide.

$^1$H-NMR (CDCl$_3$) δ: 0.88 (6H, d, J=6.7 Hz), 1.73–1.79 (1H, m), 2.21 (6H, s), 2.28 (2H, t, J=7.0 Hz), 2.44 (2H, d, J=7.3 Hz), 2.63 (2H, t, J=7.0 Hz), 3.09 (2H, s), 3.60 (2H, s), 6.49 (1H, s), 6.51–6.53 (1H, m), 7.08 (1H, d, J=7.8 Hz).

REFERENCE EXAMPLE 69

5-Methyl-6-(1-pyrrolidinylmethyl)-7,8-dihydro-2-naphthalenamine

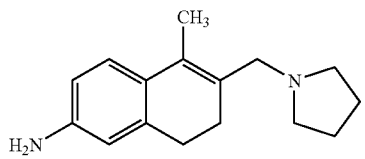

1) 6-Acetylamino-2-[(dimethylamino)methylidene]-1-tetralone (4.90 g, 0.017 mol) obtained in Example 41-1) was suspended in pyrrolidine (25 ml), which was refluxed with heating for 2 hours. The crystallized product was collected by filtration, washed with a mixed solution of ethyl acetate and n-hexane (1:1), to give 6-acetylamino-2-(1-pyrrolidinylmethylidene)-1-tetralone (5.03 g) as yellow crystals.

$^1$H-NMR (CDCl$_3$) δ: 1.75–2.00 (4H, m), 2.19 (3H, s), 2.70–3.00 (4H, m), 3.50–3.70 (4H, m), 7.20–7.25 (1H, m), 7.67 (1H, s), 7.70–7.90 (2H, m), 7.97 (1H, d, J=8.4 Hz).

2) Sodium triacetoxyhydroborate (3.18 g, 0.015 mol) was dissolved in a mixed solution of ethyl acetate (50 ml) and tetrahydrofuran (12.5 ml) under ice-cooling, and 6-acetylamino-2-(1-pyrrolidinylmethylidene)-1-tetralone (2.84 g, 0.01 mol) obtained in 1) was added. After stirring for 1 hour, the reaction mixture was concentrated. 1N Sodium hydroxide solution and ethyl acetate were added to the residue, which was stirred. The crystallized product was collected by filtration, washed with a mixed solution of ethyl acetate and n-hexane (1:1), to give 6-acetylamino-2-(1-pyrrolidinylmethyl)-1-tetralone (2.65 g) as a white powder.

$^1$H-NMR (CDCl$_3$) δ: 1.78 (4H, m), 1.90–2.02 (1H, m), 2.20 (3H, s), 2.35–2.98 (10H, m), 7.20–7.23 (1H, m), 7.57 (1H, s), 7.66 (1H, m), 7.97 (1H, d, J=8.4 Hz).

3) The titled compound was obtained by the same manner as in Reference Example 66-2), using 6-acetylamino-2-(1-pyrrolidinylmethyl)-1-tetralone obtained in 2).

$^1$H-NMR (CDCl$_3$) δ: 1.73–1.79 (4H, m), 2.04 (3H, s), 2.31 (2H, t, J=7.4 Hz), 2.49–2.54 (4H, m), 2.65 (2H, t, J=7.8 Hz), 3.24 (2H, s), 3.60 (2H, brs), 6.48–6.54 (2H, m), 7.09 (1H, d, J=8.1 Hz).

REFERENCE EXAMPLE 70

6-Amino-2-(1-pyrrolidinylmethyl)-3,4-dihydro-1-naphthalenecarbonitrile

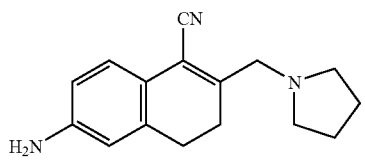

Trimethylsilylnitrile (1.02 ml, 7.68 mmol) and zinc iodide (22 mg, 0.0698 mmol) were added to dichloroethane solution (9 ml) of 6-acetylamino-2-(1-pyrrolidinylmethyl)-1-tetralone (1.00 g, 3.49 mmol) obtained in Reference Example 69-2), which was stirred at room temperature for 2 days. The solvent was distilled out under reduced pressure.

Ethyl acetate was added to the obtained oily substance, which was washed with saturated aqueous sodium chloride solution, dried over anhydrous sodium sulfate, and then the solvent was distilled out under reduced pressure. The resulting residue was purified by alumina column chromatography (development solvent; ethyl acetate), to give trimethylsilyl-cyanohydrin form (1.21 g) as an oily substance. 2.5N Hydrochloric acid was added to the oily substance (978 mg, 2.73 mmol), which was stirred at 100° C. for 1.5 hours. The aqueous solution obtained was washed with ethyl acetate. Potassium carbonate was added to the water layer to make it alkaline, and extraction was conducted using ethyl acetate. The extract was washed with saturated aqueous sodium chloride solution, dried over anhydrous sodium sulfate, and the solvent was distilled out under reduced pressure. The resulting oily substance was purified by alumina column chromatography (development solvent; hexane:ethyl acetate 5:1), to give the titled compound (358 mg).

$^1$H NMR (CDCl$_3$) δ: 1.80 (4H, m), 2.56 (6H, m), 3.73 (2H, m), 3.50 (2H, s), 3.77 (2H, br), 6.46 (1H, s), 6.55 (1H, d, J=8.1 Hz), 7.26 (1H, d, J=8.1 Hz).

REFERENCE EXAMPLE 71

6-Acetamido-2-tetralone

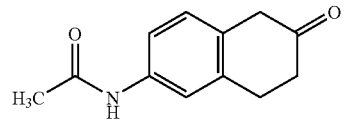

1) Sodium borohydride (931 mg, 24.6 mmol) was added to a methanol solution (60 ml) of 6-acetamido-1-tetralone (5.00 g, 24.6 mmol) under ice-cooling, which was stirred at room temperature for 1 hour. Ethyl acetate was added to the reaction mixture, which was washed with saturated aqueous sodium chloride solution, dried over anhydrous sodium sulfate, and then, the solvent was distilled out under reduced pressure. p-Toluenesulfonic acid (468 mg, 2.46 mmol) and toluene (120 ml) were added to the obtained alcohol form (5.05 g, 24.6 mmol), which was stirred at 100° C. for 1 hour. The solvent was distilled out under reduced pressure. Ethyl acetate was added to the residue, which was washed with saturated aqueous sodium chloride solution, dried over anhydrous sodium sulfate, and then the solvent was distilled out under reduced pressure. The resulting oily substance was purified by silica gel column chromatography (development solvent; hexane:ethyl acetate=1:1), and powdered with hexane to give N-(7,8-dihydro-2-naphthalenyl)acetamide (3.17 g).

$^1$H NMR (CDCl$_3$): 2.16 (3H, s), 2.29 (2H, m), 2.28 (2H, m), 5.97 (1H, m), 6.42 (2H, d, J=9.6 Hz), 6.97 (1H, d, J=8.1 Hz), 7.14 (1H, br), 7.20 (1H, m), 7.32 (1H, s).

2) m-Chloroperbenzoic acid (5.13 g, 20.8 mmol) was added to a chloroform solution (80 ml) of N-(7,8-dihydro-2-naphthalenyl)acetamide (3.00 g, 16.0 mmol) obtained in 1) under ice-cooling, which was stirred at room temperature for 2 hours. Ethyl acetate was added to the reaction mixture, which was washed with saturated sodium hydrogencarbonate solution and saturated aqueous sodium chloride solution, dried over anhydrous sodium sulfate, and then the solvent was distilled out under reduced pressure. The resulting oily substance was purified by alumina B column chromatography (development solvent; hexane:ethyl acetate=1:1). 1N Sodium hydroxide solution (10.7 ml) was added to a methanol solution (100 ml) of the obtained oily substance (3.20 g, 8.89 mmol) under ice-cooling, which was stirred at room temperature for 30 minutes. The solvent was distilled out under reduced pressure. Ethyl acetate was added to the residue, which was washed with saturated aqueous sodium chloride solution, dried over anhydrous sodium sulfate, and then the solvent was distilled out under reduced pressure. The resulting oily substance was purified by alumina B column chromatography (development solvent; ethyl acetate: methanol=10:1). p-Toluenesulfonic acid (50 mg, 0.262 mmol) and toluene (26 ml) were added to the obtained diol (596 mg, 2.62 mmol), which was stirred at 120° C. for 3 hours. The solvent was distilled out under reduced pressure. Ethyl acetate was added to the residue, which was washed with saturated aqueous sodium chloride solution, dried over anhydrous sodium sulfate, and then the solvent was distilled out under reduced pressure. The resulting oily substance was purified by silica gel column chromatography (development solvent; hexane:ethyl acetate=1:3), and powdered with diisopropyl ether, to give the titled compound (231 mg).

$^1$H NMR (CDCl$_3$) δ: 2.18 (3H, s), 2.54 (2H, m), 3.04 (2H, m), 3.76 (2H, s), 7.06 (1H, d, J=8.1 Hz), 7.21 (1H, dd, J=8.1, 2.0 Hz), 7.31 (1H, br), 7.61 (1H, d, J=2.0 Hz).

REFERENCE EXAMPLE 72

N-(6-Oxo-5,6,7,8-tetrahydro-2-naphthalenyl)[1,1'-biphenyl]-4-carboxamide

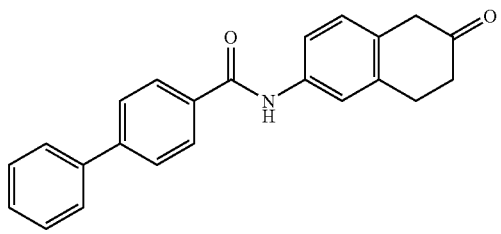

Concentrated hydrochloric acid (1.5 ml) was added to 6-acetamido-2-tetralone (20 mg. 0.098 mmol) obtained in Reference Example 71, which was stirred at 100° C. for 1 hour, and the solvent was distilled out under reduced pressure. Ethyl acetate was added to the residue, which was washed with aqueous potassium carbonate solution and saturated aqueous sodium chloride solution, dried over anhydrous sodium sulfate, and then the solvent was distilled out under reduced pressure. [1,1'-Biphenyl]-4-carbonyl chloride (21.3 mg, 0.098 mmol) was added to a dimethylformamide solution (0.5 ml) of the obtained oily substance and triethylamine (0.014 ml, 0.098 mmol) under ice-cooling, which was stirred at room temperature for 1 hour. Ethyl acetate was added to the reaction mixture, which was washed with 1N hydrochloric acid, aqueous potassium carbonate solution and saturated aqueous sodium chloride solution, dried over anhydrous sodium sulfate, and then the solvent was distilled out under reduced pressure. The resulting residue was purified by silica gel column chromatography (development solvent; hexane:ethyl acetate=1:1), to give the titled compound (10 mg).

$^1$H NMR (CDCl$_3$) δ: 2.56 (2H, t, J=6.6 Hz), 3.08 (2H, t, J=6.6 Hz), 3.57 (2H, s), 7.11 (1H, d, J=8.1 Hz), 7.43 (4H, m), 7.6.4 (2H, m), 7.72 (3H, m), 7.96 (3H, m).

REFERENCE EXAMPLE 73

(E)-3-[4-[([1,1'-biphenyl]-4-ylcarbonyl)amino]phenyl]-2-propenic acid

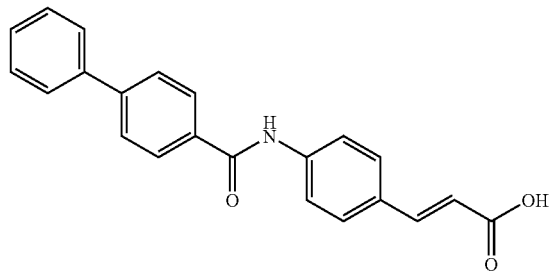

4-Phenylbenzoyl chloride (2.00 g, 9.23 mmol) was added to a mixed solution of 4-aminocinnamic acid (1.51 g, 9.23 mmol) and sodium hydrogen carbonate (2.33 g, 27.7 mmol) in water and diethyl ether under ice-cooling, which was stirred for 5 hours. After the reaction mixture was separated, 5N hydrochloric acid was added to water layer, and the precipitated crude product was washed with water and ethyl acetate, to give the titled compound (1.34 g).

$^1$H NMR (DMSO-$d_6$) δ: 6.84 (1H, d, J=16.0 Hz), 7.43–7.93 (12H, m), 8.09 (2H, d, J=8.4 Hz), 10.51 (1H, s).

REFERENCE EXAMPLE 74

N-[4-[(E)-3-Amino-3-oxo-1-propenyl]phenyl][1,1'-biphenyl]-4-carboxyamide

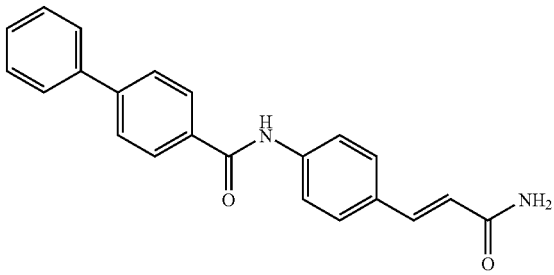

Chloro isobutylcarbonate (0.453 ml, 3.49 mmol) was added to a dimethylformamide suspension of (E)-3-[4-[([1,1'-biphenyl]-4-ylcarbonyl)amino]phenyl]-2-propionic acid (1.00 g, 2.91 mmol) obtained in Reference Example 73 and triethylamine (0.527 ml, 3.79 mmol) under ice-cooling, which was stirred for 30 minute. The solvent was distilled out under reduced pressure. Sodium hydrogencarbonate solution was added to the residue, and the precipitated crude product was washed with water and acetonitrile, to give the titled compound (936 mg).

$^1$H NMR (DMSO-$d_6$) δ: 6.56 (1H, d, J=15.6 Hz), 7.05 (1H, br), 7.52 (7H, m), 7.86 (6H, m), 8.08 (2H, d, J=7.6 Hz).

REFERENCE EXAMPLE 75

N-[4-[(E)-2-Cyanoethenyl]phenyl][1,1'-biphenyl]-4-carboxamide

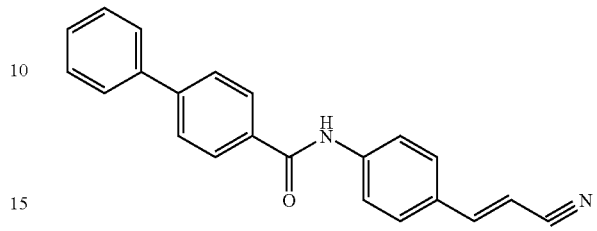

Cyanuric chloride (727 mg, 3.94 mmol) was added to a dimethylformamide suspension of (E)-3-[4-[([1,1'-biphenyl]-4-ylcarbonyl)amino]phenyl]-2-propenic acid (900 mg, 2.63 mmol) obtained in Reference Example 74 at room temperature, which was stirred for 1 hour. After the solvent was distilled out under reduced pressure, the residue was dissolved in chloroform, which was washed with saturated aqueous sodium chloride solution, dried over anhydrous sodium sulfate, and then the solvent was stilled out under reduced pressure. The resulting residue was purified by silica gel column chromatography (development solvent; chloroform:ethyl acetate=20:1), to give the titled compound (561 mg) as a colorless powder from diethyl ether.

$^1$H NMR (DMSO-$d_6$) δ: 6.37 (1H, d, J=16.4 Hz), 7.43–7.51 (4H, m), 7.65–7.93 (8H, m), 8.08 (2H, d, J=8.6 Hz).

REFERENCE EXAMPLE 76

2-[4-[(1-Acetyl-3-piperidinyl)carbonyl]phenyl]-1H-isoindol-1,3(2H)-dione

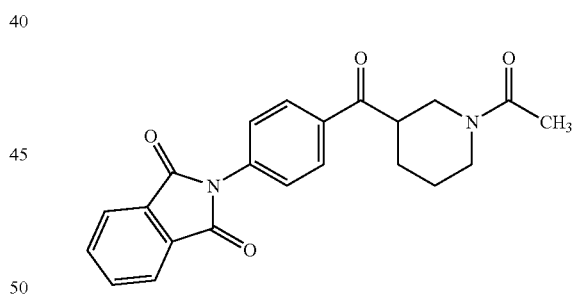

1) Thionyl chloride (2.12 ml, 32.1 mmol) was added to fluorobenzene solution (20 ml) of 1-acetyl-3-piperidinecarboxylic acid (5.00 g, 29.2 mmol) under ice-cooling, which was stirred at room temperature for 30 minutes. Aluminum chloride (9.74 g, 73.0 mmol) was added to the solution, which was stirred at 90° C. for 1 hour. The reaction mixture was poured in ice, and extraction was conducted using ethyl acetate. The extract was washed with saturated aqueous sodium chloride solution, saturated sodium hydrogencarbonate solution, and again saturated aqueous sodium chloride solution, dried over anhydrous sodium sulfate, and then the solvent was distilled out under reduced pressure. The resulting oily substance was purified by silica gel column chromatography (development solvent; hexane:ethyl acetate=1:1), to give (1-acetyl-3-piperidinyl)(4-fluorophenyl)methanone (4.93 g).

$^1$H NMR (CDCl$_3$) δ: 1.61 (2H, m), 1.80 (2H, m), 2.11 and 2.15 (3H, s and s), 2.71 (1H, m), 3.11 and 3.42 (2H, m), 3.87 (1H, m), 4.53 and 4.83 (1H, m), 7.18 (2H, m), 8.02 (2H, m).

2) A dimethylformamide solution (50 ml) of (1-acetyl-3-piperidinyl)(4-fluorophenyl)methanone (4.92 g, 19.7 mmol) obtained in 1) and potassium phthalimide (3.66 g, 19.7 mmol) was stirred at 100° C. for 12 hours under nitrogen atmosphere. The insoluble matters were filtered off, and the solvent was distilled out under reduced pressure. Ethyl acetate was added to the residue, which was washed with 1N hydrochloric acid and saturated aqueous sodium chloride solution, dried over anhydrous sodium sulfate, and then the solvent was distilled out under reduced pressure. The resulting oily substance was purified by silica gel column chromatography (development solvent; ethyl acetate), to give the titled compound (4.18 g) as a colorless powder from ethyl acetate-diisopropyl ether (1:5).

$^1$H NMR (CDCl$_3$) δ: 1.66 (2H, m), 1.86 (2H, m), 2.13 and 2.15 (3H, s and s), 2.74 (1H, m), 3.11 and 3.43 (2H, m), 3.88 (1H, m), 4.54 and 4.85 (1H, m), 7.66 (2H, m), 7.82 (2H, m), 7.99 (2H, m), 8.10 (2H, m).

piperidinyl)methanone (500 mg, 2.45 mmol) obtained in 1) under ice-cooling, which was stirred for 1.5 hours. Ethyl acetate was added to the reaction mixture, which was washed with saturated sodium hydrogencarbonate solution and saturated aqueous sodium chloride solution, dried over anhydrous sodium sulfate, and then the solvent was distilled out under reduced pressure. The resulting oily substance was purified by silica gel column chromatography (development solvent; hexane:ethyl acetate=1:1), to give the titled compound (831 mg).

$^1$H NMR (CDCl$_3$) δ1.47 (9H, s), 1.47–1.52 (2H, m), 1.67–1.74 (2H, m), 2.00 (1H, m), 2.72 (1H, m), 2.90 (1H, m), 3.32 (1H, m), 4.13 (3H, m), 6.66 (2H, d, J=8.4 Hz), 7.84 (2H, d, J=8.4 Hz).

REFERENCE EXAMPLE 78 tert-Butyl 3-[[4-[[(4'-chloro[1,1'-biphenyl]-4-yl)carbonyl]amino]phenyl](hydroxy)methyl]-1-piperidinecarboxylate

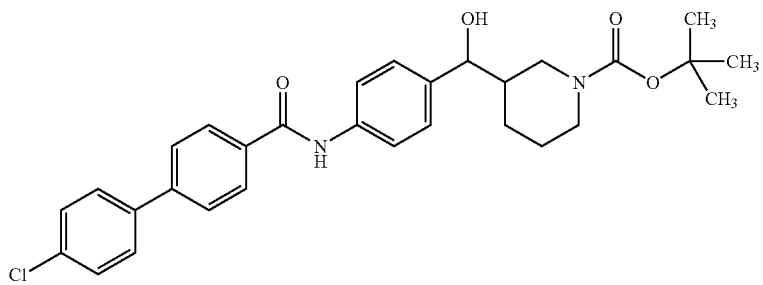

REFERENCE EXAMPLE 77 tert-Butyl 3-(4-aminobenzoyl)-1-piperidinecarboxylate

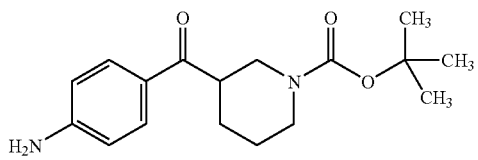

1) Concentrated hydrochloric acid (53 ml) was added to 2-[4-[(1-acetyl-3-piperidinyl)carbonyl]phenyl]-1H-isoindol-1,3(2H)-dione (4.00 g, 10.6 mmol) obtained in Reference Example 76, which was stirred at 100° C. for 16 hours, and then insoluble matters were filtered off. Potassium carbonate was added to the filtrate to make it alkaline, and extraction was conducted using ethyl acetate. The extract was washed with saturated aqueous sodium chloride solution, dried over anhydrous sodium sulfate, and then the solvent was distilled out under reduced pressure. The resulting residue was powdered with diisopropyl ether, to give (4-aminophenyl)(3-piperidinyl)methanone (1.69 g).

$^1$H NMR (CD$_3$OD) δ: 1.59–1.85 (4H, m), 2.68–2.72 (2H, m), 3.30 (2H, m), 3.45 (1H, m), 6.62 (2H, m), 7.74 (2H, m).

2) t-Butyl dicarbonate (0.562 ml, 2.45 mmol) was added to a tetrahydrofuran solution (12 ml) of (4-aminophenyl)(3- tert-Butyl 3-[4-[[(4'-chloro[1,1'-biphenyl]-4-yl)carbonyl]amino]benzoyl]-1-piperidinecarboxylate (506 mg, 0.975 mmol) obtained in Example 127-1) was dissolved in a mixed solution of methanol and tetrahydrofuran (1:1) (10 ml). Sodium borohydride (73.8 mg, 1.95 mmol) was added to the solution under ice-cooling, which was stirred at room temperature for 1 hour. Ethyl acetate was added to the reaction mixture, which was washed with saturated aqueous sodium chloride solution, dried over anhydrous sodium sulfate, and then the solvent was distilled out under reduced pressure. Diisopropyl ether was added to the residue, to give the titled compound (488 mg) as a colorless powder.

FABMS(pos) 521.2 [M+H]+

REFERENCE EXAMPLE 79 tert-Butyl 3-(4-aminobenzyl)-1-piperidinecarboxylate

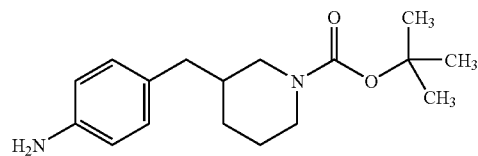

Sodium borohydride (433 mg, 11.5 mmol) was added to a methanol solution (25 ml) of tert-butyl 3-(4-aminobenzoyl)-1-piperidinecarboxylate (1.74 g, 573 mmol) obtained in Reference Example 77 under ice-cooling, which was stirred at room temperature for 1 hour. Ethyl acetate was added to the reaction mixture, which was washed with saturated aqueous sodium chloride solution, dried over anhydrous sodium sulfate, and then the solvent was distilled out under reduced pressure. The resulting oily substance was purified by alumina B column chromatography (development solvent; ethyl acetate), to give an alcohol form. 1N hydrochloric acid (9.79 ml) and 10% palladium carbon (200 mg) were added to a methanol solution (300 ml of the obtained alcohol form (1.00 g, 3.26 mmol), which was stirred for 16 hours under hydrogen atmosphere. The catalyst was filtered off, potassium carbonate was added to the filtrate to make it alkaline, and then the solvent was distilled out under reduced pressure. Ethyl acetate was added to the residue, which was washed with saturated aqueous sodium chloride solution, dried over anhydrous sodium sulfate, and then the solvent was distilled out under reduced pressure. The resulting oily substance was purified by silica gel column chromatography (development solvent; hexane-ethyl acetate=1:1), to give the titled compound (813 mg).

$^1$H NMR (CDCl$_3$) δ: 1.46–1.76 (14H, m), 2.25–2.80 (2H, m), 3.14 (2H, m), 3.76 (4H, m), 6.64 (2H, m), 7.01 (2H, m).

REFERENCE EXAMPLE 80 tert-Butyl 3-[4-[([1,1'-biphenyl]-4-ylcarbonyl)amino]benzyl]-1-piperidinecarboxylate

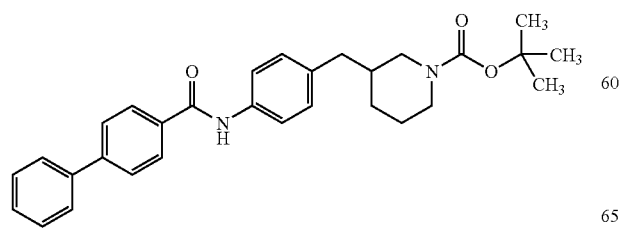

The titled compound was obtained by carrying out the same operation as in Example 1, using tert-butyl 3-(4-aminobenzyl)-1-piperidinecarboxylate obtained in Reference Example 79 and [1,1'-biphenyl]-4-carboxylic acid.

Elemental analysis for C$_{30}$H$_{34}$N$_2$O$_3$.0.5H$_2$O Calcd.: C, 75.13; H, 7.36; N, 5.84. Found: C, 74.83; H, 7.25; N, 5.65.

Melting point: 135–137° C.

REFERENCE EXAMPLE 81 tert-Butyl 3-[4-[[(4'-fluoro[1,1'-biphenyl]-4-yl)carbonyl]amino]benzyl]-1-piperidinecarboxylate

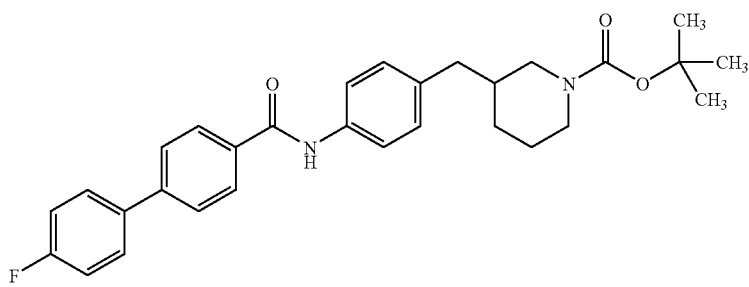

The titled compound was obtained by carrying out the same operation as in Example 1, using tert-butyl 3-(4-aminobenzyl)-1-piperidinecarboxylate obtained in Reference. Example 80 and 4'-fluoro[1,1'-biphenyl]-4-carboxylic acid.

Elemental analysis for C$_{30}$H$_{33}$FN$_2$O$_3$.0.5H$_2$O Calcd.: C, 72.41; H, 6.89; N, 5.63. Found: C, 72.30; H, 7.07; N, 5.60.

Melting point: 138–141° C.

REFERENCE EXAMPLE 82 tert-Butyl 3-[4-[[(4'-chloro[1,1'-biphenyl]-4-yl)carbonyl]amino]benzyl]-1-piperidinecarboxylate

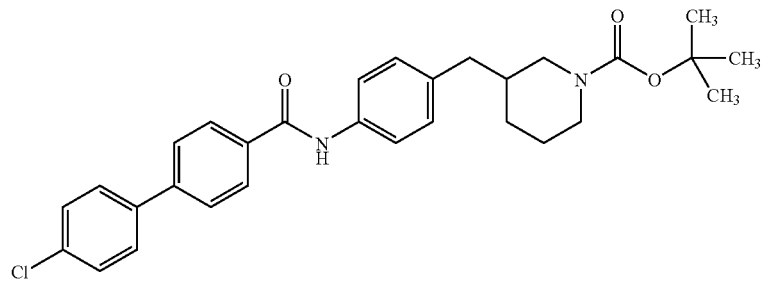

The titled compound was obtained by carrying out the same operation as in Example 1, using tert-butyl 3-(4-aminobenzyl)-1-piperidinecarboxylate obtained in Reference Example 80 and 4'-chloro[1,1'-biphenyl]-4-carboxylic acid.

Elemental analysis for $C_{30}H_{33}ClN_2O_3 \cdot 0.5H_2O$ Calcd.: C, 70.09; H, 6.67; N, 5.45. Found: C, 70.29; H, 6.50; N, 5.38.

Melting point: 173–176° C.

REFERENCE EXAMPLE 83

N-(5,6,7,8-Tetrahydro-3-quinolinyl)acetamide

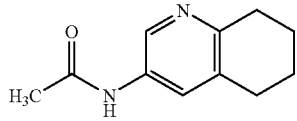

1) Fuming nitric acid (100 ml) was added dropwise to concentrated sulfuric acid solution (200 ml) of 1-methyl-2-pyridone (20.7 g, 190 mmol) at 100° C., which was stirred for 16 hours. The reaction mixture was poured in ice. The resulting precipitate was collected, which was washed with water, to give 1-methyl-3,5-dinitro-2(1H)-pyridinone (3.0 g).

$^1$H NMR (DMSO-$d_6$) δ: 3.68 (3H, s), 9.01 (1H, d, J=3.0 Hz), 9.61 (1H, d, J=3.0 Hz).

2) 1N Methanolic ammonia solution (300 ml) of 1-methyl-3,5-dinitro-2 (1H)-pyridinone (3.00 g, 15.1 mmol) obtained in 1) and 1-morpholino-1-cyclohexene (3.88 ml, 22.6 mmol) was stirred at 70° C. for 3 hours. The solvent was distilled out under reduced pressure. The resulting residue was purified by alumina column chromatography (development solvent; ethyl acetate), to give 3-nitro-5,6,7,8-tetrahydroquinoline (2.42 g) as a powder from methanol-water (1:4).

$^1$H NMR (DMSO-$d_6$) δ: 1.87 (4H, m), 2.90 (4H, m), 8.15 (1H, s), 9.16 (1H, s).

3) 10% Palladium-carbon (200 mg) was added to a methanol solution (68 ml) of 3-nitro-5,6,7,8-tetrahydroquinoline (2.41 g], 13.5 mmol) obtained in 2), which was stirred under hydrogen atmosphere for 16 hours. After a catalyst was filtered off, the solvent was distilled out under reduced pressure. The resulting residue was dissolved in pyridine (35 ml). Anhydrous ethyl acetate (1.91 ml, 20.3 mmol) was added to the solution, which was stirred at room temperature for 1 hour. After completion of the reaction, the solvent was distilled out under reduced pressure. Diisopropyl ether-n-hexane (1:8) was added to the resulting residue, to give the titled compound (2.48 g) as a colorless powder.

$^1$HNMR (CDCl$_3$) δ: 1.80–1.87 (4H, m), 2.18 (3H, s), 2.77 (2H, m), 2.87 (2H, m), 7.72 (1H, br), 7.94 (1H, s), 8.24 (1H, s).

REFERENCE EXAMPLE 84

N-(8-Oxo-5,6,7,8-tetrahydro-3-quinolinyl)acetamide

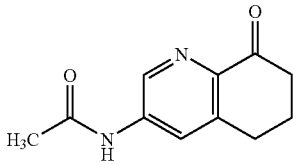

1) m-Chloroperbenzoic acid (3.83 g, 15.5 mmol) was added to a chloroform solution (65 ml) of N-(5,6,7,8-tetrahydro-3-quinolinyl)acetamide (2.46 g, 12.9 mmol) obtained in Reference Example 83 under ice-cooling, which was stirred at room temperature for 16 hours. After the solvent was distilled out under reduced pressure, the residue was powdered with ethyl acetate, to give N-(1-oxide-5,6,7,8-tetrahydro-3-quinolinyl)acetamide (2.00 g).

$^1$H NMR (DMSO-$d_6$) δ: 1.64 (2H, m), 1.75 (2H, m), 2.04 (3H, s), 2.66 (4H, m), 7.13 (1H, s), 8.56 (1H, s), 10.12 (1H, s).

2) Anhydrous ethyl acetate (30 ml) was added to N-(1-oxide-5,6,7,8-tetrahydro-3-quinolinyl)acetamide (1.99 g, 9.65 mmol) obtained in 1), which was stirred at 80° C. for 3 hours. The reaction mixture was cooled to room temperature. The solvent was distilled out under reduced pressure, and the resulting residue was purified by alumina column chromatography (development solvent; ethyl acetate). The resulting oily substance was dissolved in methanol (110 ml). 1N Sodium hydroxide (21.5 ml) was added to the solution under ice-cooling, which was stirred at room temperature for 1 hour. The solvent was distilled out under reduced pressure. Chloroform was added to the residue, which was washed with aqueous potassium carbonate solution and saturated aqueous sodium chloride solution, dried over anhydrous sodium sulfate, and then the solvent was distilled out under reduced pressure. The resulting residue was purified by alumina column chromatography (development solvent; ethyl acetate: methanol=5:1), to give N-(8-hydroxy-5,6,7,8-tetrahydro-3-quinolinyl)acetamide (1.08 g) as a powder from ethyl acetate and diisopropyl ether.

$^1$H NMR (CDCl$_3$) δ: 1.79 (2H, m), 1.96 (1H, m), 2.22 (3H, s), 2.24 (1H, m), 2.82 (2H, m), 4.69 (1H, m), 7.49 (1H, br), 7.92 (1H, s), 8.30 (1H, s).

3) Manganese dioxide (4.47 g, 51.4 mmol) was added to chloroform (26 ml) solution of N-(8-hydroxy-5,6,7,8-tetrahydro-3-quinolinyl)acetamide (1.06 g, 5.14 mmol) obtained in 2), which was stirred at room temperature for 1 day. After completion of the reaction, the insoluble matters were filtered off, and the filtrate was concentrated under reduced pressure. Diisopropyl ether and hexane were added to the resulting residue, to give the titled compound (858 mg) as a colorless powder.

$^1$H NMR (CDCl$_3$) δ: 2.20 (2H, m), 2.26 (3H, s), 2.77 (2H, m), 3.03 (2H, m), 8.10 (1H, br), 8.39 (1H, s), 8.42 (1H, s).

REFERENCE EXAMPLE 85

N-[7-[(Dimethylamino)methylidene]-8-oxo-5,6,7,8-tetrahydro-3-quinolinyl]acetamide

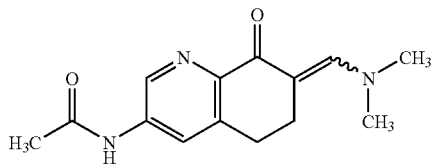

The titled compound was obtained by carrying out the same operation as in Reference Example 47, using N-(8-oxo-5,6,7,8-tetrahydro-3-quinolinyl)acetamide obtained in Reference Example 84.

$^1$H NMR (CDCl$_3$) δ: 2.09 (3H, s), 2.78 (2H, m), 2.85 (2H, m), 3.10 (6H, s), 7.55 (1H, s), 8.01 (1H, s), 8.56 (1H, s).

REFERENCE EXAMPLE 86

N-[(3-Amino-5,6-dihydro-7-quinolinyl)methyl]-N,N-dimethylamine

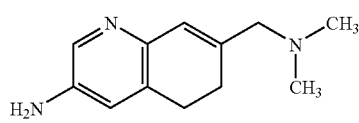

The titled compound was obtained by carrying out the same operation as in Reference Example 41-2), using N-[7-[(dimethylamino)methylidene]-8-oxo-5,6,7,8-tetrahydro-3-quinolinyl]acetamide obtained in Reference Example 85.

$^1$H NMR (CDCl$_3$) δ: 2.23 (6H, s), 2.33 (2H, t, J=8.1 Hz), 2.78 (2H, t, J=8.1 Hz), 2.99 (2H, s), 3.59 (2H, br), 6.43 (1H, s), 6.74 (1H, d, J=2.5 Hz), 7.84 (1H, d, J=2.5 Hz).

REFERENCE EXAMPLE 87

3-(1-Pyrrolidinylmethyl)-2H-chromen-7-amine

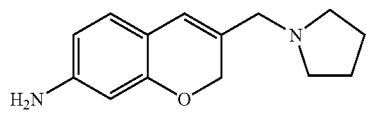

The titled compound was obtained as an oily substance by carrying out the same operations as in Example 41-1), Reference Example 52 and Example 41-2) in this order, using 7-acetylamino-3,4-dihydrochromen-4-one.

$^1$H-NMR (CDCl$_3$) δ: 1.77–179 (4H, m), 2.45–2.47 (4H, m), 3.11 (2H, s), 3.66 (2H, s), 4.74 (2H, s), 6.14–6.21 (3H, m), 6.75 (1H, d, J=7.8 Hz).

REFERENCE EXAMPLE 88

6-[(N-Benzyl-N-methylamino)methyl]-7,8-dihydro-2-naphthalenamine

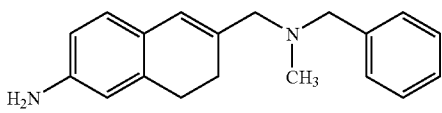

The titled compound was obtained as an oily substance by carrying out the same operation as in Reference Example 52, using 6-acetamido-2-(N,N-dimethylaminomethylidene)-1-tetralone obtained in Example 41-1).

$^1$H-NMR (CDCl$_3$) δ: 2.17 (3H, s), 2.35 (2H, t, J=8.1 Hz), 2.73 (2H, t, J=8.1 Hz), 3.04 (2H, s), 3.48 (2H, s), 3.58 (2H, s), 6.29 (1H, s), 6.44–6.46 (2H, m), 6.82 (1H, d, J=8.1 Hz), 7.03–7.45 (5H, m).

REFERENCE EXAMPLE 89

4'-Chloro-N-[4-(4-piperidinyl)phenyl][1,1'-biphenyl]-4-carboxamide

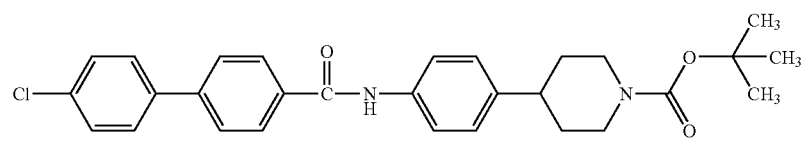

An ethanol solution (30 ml) of tert-butyl 4-(4-nitrophenyl)-1-piperidinecarboxylate (1.7 g) was subjected to catalytic hydrogenation using 10% palladium carbon (0.2 g) as a catalyst under normal temperature and normal pressure. After the catalyst was filtered off, the filtrate was concentrated to give tert-butyl 4-(4-aminophenyl)-1-piperidinecarboxylate as a viscous oily substance. The titled compound (2.2 g) was obtained as colorless crystals, by carrying out the same operation as in Example 1, using the resulting oily substance and 4'-chloro[1,1'-biphenyl]-4-carboxylic acid (1.43 g).

$^1$H-NMR (CDCl$_3$+DMSO-d$_6$) δ: 1.05–1.32 (11H, m), 1.38–1.50 (2H, m), 2.20–2.50 (3H, m), 3.75–3.90 (2H, m), 6.81 (2H, d, J=8.4 Hz), 7.07 (2H, d, J=8.4 Hz), 7.20–7.36 (6H, m), 7.69 (2H, d, J=8.1 Hz), 9.44 (1H, s).

Melting point: 232–233° C. (crystallization solvent ethyl acetate)

REFERENCE EXAMPLE 90

2-[4-[[(Benzyloxy)carbonyl]amino]phenyl]ethyl acetate

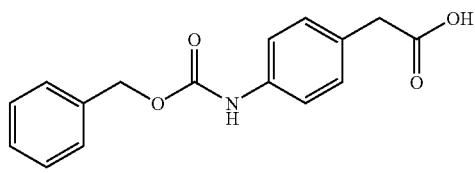

To an ethyl acetate (100 ml) suspension of 4-aminophenylethyl acetate (10 g), saturated aqueous sodium bicarbonate solution (100 ml) was added, and further, benzyloxycarbonyl chloride (12.3 ml) was added dropwise under ice-cooling. After stirring for 1 hour, hydrochloric acid was added to the reaction mixture to make it acidic, and extraction was conducted using ethyl acetate. The organic layer was washed with water and saturated aqueous sodium chloride solution, dried, and then concentrated. The residue was recrystallized from ethyl acetate-hexane, to give the titled compound (17.3 g).

Melting point: 148–149° C.

REFERENCE EXAMPLE 91

2-(4-Aminophenyl)-N-[2-(dimethylamino)ethyl]acetamide

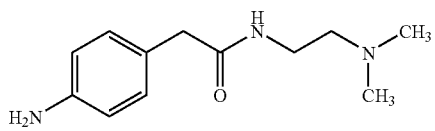

Pd-C (1 g) was added to a methanol (140 ml) solution of benzyl 4-[2-[[2-(dimethylamino)ethyl]amino]-2-oxoethyl]phenylcarbamate (10 g), which was stirred under hydrogen atmosphere for 1 hour. Pd-C was removed, and the filtrate was concentrated. The residue was purified by alumina column chromatography (development solvent; ethyl acetate:hexane=1:1), to give the titled compound (6.63 g) as an oily substance.

$^1$H-NMR(CDCl$_3$) δ: 2.16 (6H, s), 2.05 (3H, s), 2.30–2.36 (2H, t, J=6.2 Hz), 3.23–3.32 (2H, dd, J=11.4, 6.2 Hz), 3.44 (2H, s), 6.00 (1H, s), 6.63–6.67 (2H, m), 7.00–7.07 (2H, m).

REFERENCE EXAMPLE 92

N-Methyl-N-(5-oxo-5,6,7,8-tetrahydro-2-naphthalenyl)acetamide

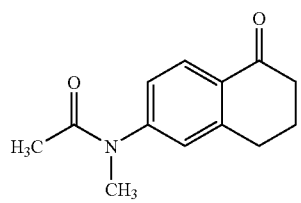

6-Acetamido-1-tetralone (10.0 g, 49.2 mmol) was dissolved in tetrahydrofuran (100 ml). Sodium hydride (oil, 3.0 g) was added to the solution, which was refluxed with heating under nitrogen atmosphere for 2 hours. After cooling, methyl iodide (30 ml) was added to the reaction mixture, which was refluxed with heating under nitrogen atmosphere for 2 hours. The reaction mixture was concentrated. Ethyl acetate and water were added to the residue, and extraction was conducted. The ethyl acetate layer was concentrated, and the residue was purified by alumina column chromatography (development solvent; ethyl acetate:n-hexane=33:67~50:50). The product was concentrated under reduced pressure, and the residue was recrystallized from ethyl acetate diisopropyl ether, to give the titled compound (4.3 g).

$^1$H-NMR (CDCl$_3$) δ: 1.96 (3H, brs), 2.18 (2H, m), 2.69 (2H, t, J=6.1 Hz), 2.99 (2H, t, J=5.9 Hz), 3.29 (3H, s), 7.01–7.15 (2H, m), 8.08 (1H, d, J=8.1 Hz).

REFERENCE EXAMPLE 93

N-[6-[(Dimethylamino)methylidene]-5-oxo-5,6,7,8-tetrahydro-2-naphthalenyl]-N-methylacetamide

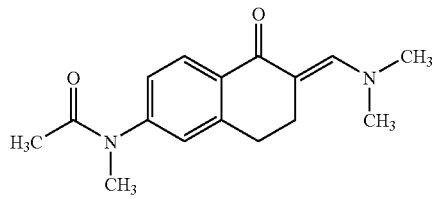

N-Methyl-N-(5-oxo-5,6,7,8-tetrahydro-2-naphthalenyl)acetamide (4.3 g, 19.8 mmol) obtained in Reference Example 92 was dissolved in N,N-dimethylformamide dimethylacetal (50 ml), which was refluxed with heating under nitrogen atmosphere for 15 hours. The reaction mixture was concentrated, and the residue was washed with ethyl acetate and diisopropyl ether, to give the titled compound (3.9 g).

$^1$H-NMR (CDCl$_3$) δ: 1.93 (3H, brs), 2.84 (2H, dd, J=7.5, 5.6 Hz), 2.95 (2H, dd, J=7.5, 5.6 Hz), 3.16 (6H, s), 3.28 (3H, s), 6.99 (1H, s), 7.10 (1H, dd, J=8.1, 2.0 Hz), 7.75 (1H, s), 8.07 (1H, d, J=8.1 Hz).

REFERENCE EXAMPLE 94

N-Methyl-N-[5-oxo-6-[1-pyrrolidinylmethylidene]-5,6,7,8-tetrahydro-2-naphthalenyl]acetamide

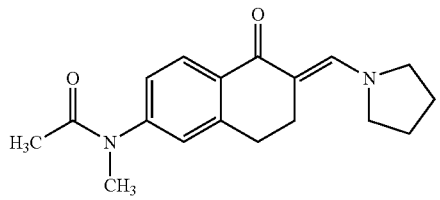

N-[6-[(Dimethylamino)methylidene]-5-oxo-5,6,7,8-tetrahydro-2-naphthalenyl]-N-methylacetamide (5.7 g, 20.9 mmol) obtained in Reference Example 93 was dissolved in pyrrolidine (50 ml), which was refluxed with heating under nitrogen atmosphere for 3.5 hours. Then, ethyl acetate and water were added to the reaction mixture, and extraction was conducted. The ethyl acetate layer was concentrated, and the residue was recrystallized from ethyl acetate-diisopropyl ether, to give the titled compound (4.0 g, yield: 64%).

$^1$H-NMR (CDCl$_3$) δ: 1.94 (7H, m), 2.84 (2H, dd, J=7.0, 5.6 Hz), 2.97 (2H, dd, J=7.0, 5.6 Hz), 3.28 (3H, s), 3.63 (4H, m), 6.98 (1H, s), 7.10 (1H, dd, J=8.1, 2.0 Hz), 7.95 (1H, s), 8.08 (1H, d, J=8.1 Hz).

REFERENCE EXAMPLE 95

N-Methyl-6-(1-pyrrolidinylmethyl)-7,8-dihydro-2-nephthalenamine dihydrochloride

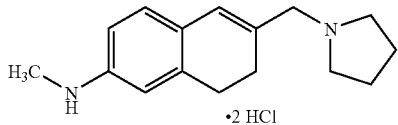

N-Methyl-N-[5-oxo-6-[1-pyrrolidinylmethylidene]-5,6,7,8-tetrahydro-2-naphthalenyl]acetamide (4.0 g, 13.4 mmol) obtained in Reference Example 94 was dissolved in methanol-ethyl acetate (10:1, 220 ml). 10% Palladium carbon (50% wet, 0.4 g) was added to the solution, which was ice cooled. Stirring was began under hydrogen atmosphere, and stirring was conducted for 2 days while returning the temperature of the reaction mixture to room temperature. A catalyst was filtered off, the reaction mixture was concentrated under reduced pressure, and the residue was dissolved in ethyl acetate. Extraction was conducted using 1N hydrochloric acid. The extract was made alkaline with 4N sodium hydroxide solution, and extraction was conducted using ethyl acetate. The extract was concentrated under reduced pressure. The residue was dissolved in tetrahydrofuran (100 ml) and 5N hydrochloric acid (100 ml), which was refluxed with heating for 13 hours. The reaction mixture was concentrated. Ethyl acetate and saturated aqueous sodium carbonate solution were added to the residue, and extraction was conducted. The ethyl acetate layer was concentrated. 4N Hydrogen chloride-ethyl acetate solution was added to the resulting oily substance, which was concentrated. The residue was recrystallized from methanol-ethyl acetate, to give the titled compound (2.8 g, yield: 66%).

$^1$H-NMR (DMSO-d$_6$) δ: 1.98 (4H, m), 2.45 (4H, m), 2.81 (5H, m), 3.01 (2H, brd), 3.44 (2H, brd), 3.86 (2H, d, J=5.0 Hz), 7.02–7.10 (3H, m), 10.89 (1H, brs).

REFERENCE EXAMPLE 96

6-Amino-3,4-dihydro-1-(2H)-naphthalenone

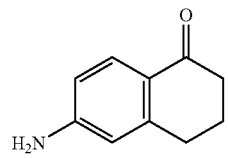

Concentrated hydrochloric acid (250 ml) was added to 6-acetamido-1-tetralone (20.0 g, 98.4 mmol), which was stirred at 100° C. for 1 hour. The solvent was distilled out under reduced pressure. Ethyl acetate was added to the residue, which was washed with aqueous potassium carbonate solution and saturated aqueous sodium chloride solution, dried over anhydrous sodium sulfate, and then the solvent was distilled out under reduced pressure. The residue was powdered with ethyl acetate and isopropyl ether, to give the titled compound (14.5 g).

$^1$H NMR (CDCl$_3$) δ: 2.07 (2H, m), 2.57 (2H, m), 2.83 (2H, m), 4.10 (2H, br), 6.42 (1H, d, J=2.2 Hz), 6.53 (1H, dd, J=2.2, 8.4 Hz), 7.89 (1H, d, J=8.4 Hz).

REFERENCE EXAMPLE 97

4-(4-Fluorophenyl)-N-(5-oxo-5,6,7,8-tetrahydro-2-naphthalenyl)-1-piperidinecarboxamide

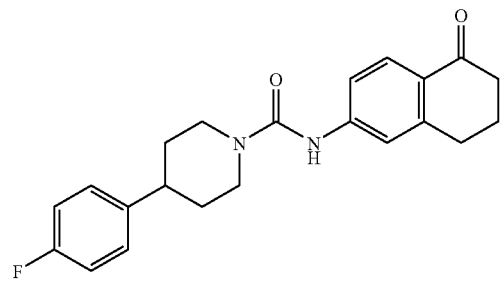

Pyridine(9.95 ml, 123 mmol) and 4-nitrophenyl chloroformate (12.4 g, 61.5 mmol) was added to a tetrahydrofuran (300 ml)solution of 6-amino-3,4-dihydro-1(2H)-naphthalenone(9.92 g, 61.5 mmol)obtained in Reference Example 96, which was stirred at room temperature for 3 hours. The solvent was distilled out under reduced pressure. 1N Hydrochloric acid was added to the residue to powder, which was washed with ethanol. 4N Aqueous sodium hydroxide solution was added to a dimethylsulfoxide (33 ml)solution of the resulting 4-nitrophenyl-5-oxo-5,6,7,8-tetrahydro-2-naphthalenylcarbamate (2.20 g, 6.74 mmol) and 4-(4-fluorophenyl) piperidine hydrochloride (1.60 g, 7.42 mmol), which was stirred at room temperature for 1 hour. Ethyl acetate was added to the reaction mixture, which was washed with 1N hydrochloric acid, aqueous potassium hydrogencarbonate solution and saturated aqueous sodium chloride solution, dried over anhydrous sodium sulfate, and the solvent was distilled out under reduced pressure. The resulting residue was purified by alumina B column chromatography (development solvent ethyl acetate), and powdered with isopropyl ether and hexane, to give the titled compound (1.89 g).

$^1$H NMR (CDCl$_3$) δ: 1.72 (2H, m), 1.92 (2H, m), 2.11 (2H, m), 2.61 (2H, m), 2.72 (1H, m), 2.93 (2H, m), 3.01 (2H, m), 4.23 (2H, m), 6.67 (1H, s), 7.00 (2H, m), 7.12 (3H, m), 7.61 (1H, s), 7.97 (1H, d, J=8.4 Hz).

REFERENCE EXAMPLE 98

[6-(Acetylamino)-1-oxo-3,4-dihydro-2 (1H)-naphthalenylidene]acetic acid

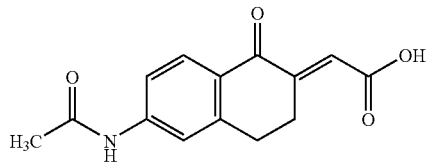

0.5N Aqueous sodium hydroxide solution (190 ml) was added to an aqueous solution(60 ml) of 6-acetamido-1-tetralone (5.00 g, 24.6 mmol) and glyoxylic acid (9.05 g, 98.5 mmol) under ice-cooling, which was stirred at 60 for 16 hours. After cooling, concentrated hydrochloric acid was added to the reaction mixture. The precipitated crystals were collected, which was washed with water, to give the titled compound (3.73 g).

$^1$H NMR (DMSO-d$_6$) δ: 2.10 (3H, s), 2.95 (2H, m), 3.28 (2H, m), 6.63 (1H, s), 7.53 (1H, d, J=8.7 Hz), 7.67 (1H, s), 7.91 (1H, d, J=8.7 Hz), 10.32 (1H, s), 12.89 (1H, br).

REFERENCE EXAMPLE 99

[6-(Acetylamino)-1-oxo-1,2,3,4-tetrahydro-2-naphthalenyl]acetic acid

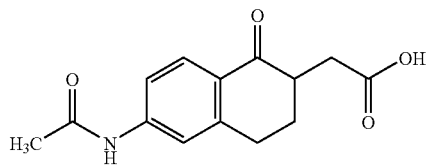

70% Acetic acid-water solution (35 ml) of [6-(acetylamino)-1-oxo-3,4-dihydro-2 (1H)-naphthalenyliden]acetic acid (3.50 g, 13.5 mmol) obtained in Reference Example 98 and zinc powder (2.1 g) was stirred at 100° C. for 30 minutes. After cooling, zinc powder was filtered. Ethyl acetate was added to the filtrate, which was washed with saturated aqueous sodium chloride solution, dried over anhydrous sodium sulfate, and then the solvent was distilled out under reduced pressure. The resulting oily substance was purified by silica gel column chromatography (development solvent; ethyl acetate:methanol=10:1), and powdered with ethyl acetate and isopropyl ether, to give the titled compound (2.51 g).

$^1$H NMR (CDCl$_3$) δ: 1.85–2.15 (2H, m), 2.08 (3H, s), 2.38 (1H, m), 2.71 (1H, m), 2.88 (2H, m), 3.05 (1H, m), 7.46 (1H, d, J=8.7 Hz), 7.60 (1H, s), 7.80 (1H, d, J=8.7 Hz), 10.21 (1H, s), 12.09 (1H, br).

REFERENCE EXAMPLE 100

Methyl [6-(acetylamino)-1-oxo-1,2,3,4-tetrahydro-2-naphthalenyl]acetate

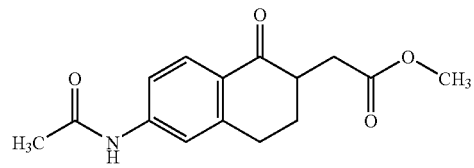

Methyl iodide (0.18 ml, 2.87 mmol) was added to a dimethylformamide solution (10 ml) of [6-(acetylamino)-1-oxo-1,2,3,4-tetrahydro-2-naphthalenyl]acetic acid (500 mg, 1.91 mmol) obtained in Reference Example 99 and potassium carbonate (529 mg, 3.82 mmol), which was stirred at room temperature for 16 hours. Ethyl acetate was added to the reaction mixture, which was washed with aqueous sodium thiosulfate solution and saturated aqueous sodium chloride solution, dried over anhydrous sodium sulfate, and then the solvent was distilled out under reduced pressure. The resulting oily substance was purified by alumina B column chromatography (development solvent; ethyl acetate), to give the titled compound (527 mg).

$^1$H NMR (CDCl$_3$) δ: 1.98 (1H, m), 2.20 (3H, s), 2.23 (1H, m), 2.47 (1H, m), 3.30 (4H, m), 3.73 (3H, s), 7.21 (1H, d, J=8.7 Hz), 7.50–7.80 (2H, m), 7.97. (H, d, J=8.7 Hz).

REFERENCE EXAMPLE 101

Methyl [6-(acetylamino)-3,4-dihydro-2-naphthalenyl]acetate

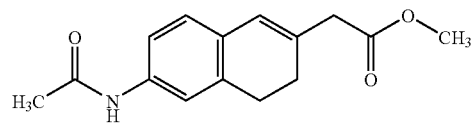

Sodium borohydride (72.4 mg, 1.91 mmol) was added to a methanol solution (10 ml) of methyl [6-(acetylamino)-1-oxo-1,2,3,4-tetrahydro-2-naphthalenyl]acetate (527 mg, 1.91 mmol) obtained in Reference Example 100 under ice-cooling, which was stirred for 1 hour. Ethyl acetate was added to the reaction mixture, which was washed with saturated aqueous sodium chloride solution, dried over anhydrous sodium sulfate, and then the solvent was distilled out under reduced pressure. The resulting oily substance was purified by alumina B column chromatography (development solvent; ethyl acetate). Concentrated sulfuric acid (0.14 ml) was added to an acetic acid solution (7 ml) of the oil (404 mg, 1.46 mmol), which was stirred at 40° C. for 5 hours. The solvent was distilled out under reduced pressure. Ethyl acetate was added to the residue, which was washed with aqueous potassium carbonate solution and saturated aqueous sodium chloride solution, dried over anhydrous sodium sulfate, and then the solvent was distilled out under reduced pressure. The resulting oily substance was purified by silica gel column chromatography (development solvent; hexane:ethyl acetate=1:1), to give the titled compound (251 mg).

¹H NMR (CDCl₃) δ: 2.16 (3H, s), 2.32 (2H, t, J=8.1 Hz), 2.82 (2H, t, J=8.1 Hz), 3.21 (2H, s), 3.71 (3H, s), 6.30 (1H, s), 6.93 (1H, d, J=8.1 Hz), 7.19 (2H, m), 7.33 (1H, s).

REFERENCE EXAMPLE 102

N-[6-(2-Hydroxyethyl)-7,8-dihydro-2-naphthalenyl]acetamide

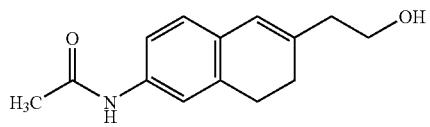

Lithium aluminum hydride (242 mg, 6.38 mmol) was added to a tetrahydrofuran solution (16 ml) of methyl [6-(acetylamino)-3,4-dihydro-2-naphthalenyl]acetate (827 mg, 3.19 mmol) obtained in Reference Example 101 under ice-cooling, which was stirred at room temperature for 1 hour. Ethyl acetate was added to the reaction mixture, which was washed with 1N hydrochloric acid and saturated aqueous sodium chloride solution, dried over anhydrous sodium sulfate, and then the solvent was distilled out under reduced pressure. The residue was powdered with isopropyl ether, to give the titled compound (364 mg).

¹H NMR (CDCl₃) δ: 1.43 (1H, m), 2.16 (3H, s), 2.26 (2H, t, J=8.1 Hz), 2.46 (2H, t, J=6.3 Hz), 2.81 (2H, t, J=8.1 Hz), 3.78 (2H, m), 6.28 (1H, s), 6.94 (1H, d, J=8.1 Hz), 7.08 (1H, br), 7.17 (1H, d, J=8.1 Hz), 7.35 (1H, s).

REFERENCE EXAMPLE 103

N-[6-[2-(1-Pyrrolidinyl)ethyl]-7,8-dihydro-2-naphthalenyl]acetamide

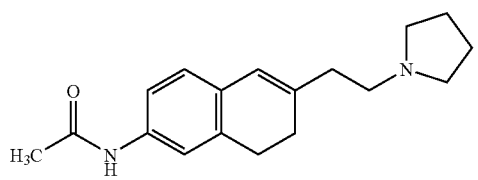

Methanesulfonyl chloride (0.131 ml, 1.69 mmol) was added to a dimethylformamide solution (7 ml) of N-[6-(2-hydroxyethyl)-7,8-dihydro-2-naphthalenyl]acetamide (355 mg, 1.53 mmol) obtained in Reference Example 102 and triethylamine (0.235 ml, 1.69 mmol) under ice-cooling, which was stirred for 30 minutes. Pyrrolidine (0.384 ml, 4.60 mmol) was added to the reaction mixture, which was stirred at 60° C. for 4 hours. The solvent was distilled out under reduced pressure. Ethyl acetate was added to the residue, and extraction was conducted using 1N hydrochloric acid. Potassium carbonate was added to the extract to make it alkaline, and extraction was conducted using ethyl acetate. The extract was washed with saturated aqueous sodium chloride solution, dried over anhydrous sodium sulfate, and the solvent was distilled out under reduced pressure. The resulting residue was purified by alumina column chromatography (development solvent; ethyl acetate), to give the titled compound (294 mg).

¹H NMR (CDCl₃) δ: 1.79 (4H, m), 2.16 (3H, s), 2.25 (2H, m), 2.41 (2H, m), 2.55 (4H, m), 2.62 (2H, m), 2.78 (2H, m), 6.20 (1H, s), 6.91 (1H, d, J=8.1 Hz), 7.18 (1H, d, J=7.8 Hz), 7.32 (2H, m).

REFERENCE EXAMPLE 104

N-[6-[2-(Dimethylamino)ethyl]-7,8-dihydro-2-naphthalenyl]acetamide

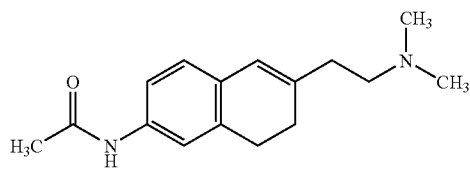

Methanesulfonyl chloride (0.0393 ml, 0.469 mmol) was added to a dimethylformamide solution (2 ml) of N-[6-(2-hydroxyethyl)-7,8-dihydro-2-naphthalenyl]acetamide (102 mg, 0.426 mmol) obtained in Reference Example 102 and triethylamine (0.0652 ml, 0.469 mmol) under ice-cooling, which was stirred for 30 minutes. A tetrahydrofuran solution (0.64 ml) of 2N dimethylamine was added to the reaction mixture, which was stirred at 60° C. for 5 hours. The solvent was distilled out under reduced pressure. Ethyl acetate was added to the residue, and extraction was conducted using 1N hydrochloric acid. Potassium carbonate was added to the extract to make it alkaline, and extraction was conducted using ethyl acetate. The extract was washed with saturated aqueous sodium chloride solution, dried over anhydrous sodium sulfate, and the solvent was distilled out under reduced pressure. The resulting residue was purified by alumina column chromatography (development solvent; ethyl acetate), to give the titled compound (57.5 mg).

¹H NMR (CDCl₃) δ: 2.15 (3H, s), 2.24 (2H, m), 2.29 (6H, s), 2.36 (2H, m), 2.48 (2H, m), 2.78 (2H, m), 6.20 (1H, s), 6.90 (1H, d, J=8.1 Hz), 7.20 (1H, d, J=8.1 Hz), 7.35 (1H, s), 7.76 (1H, br).

REFERENCE EXAMPLE 105

6-Amino-2-[(dimethylamino)methyl]-1,4-benzoxazine

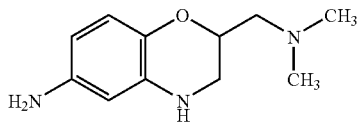

1) 2-Ethoxycarbonyl-6-nitro-1,4-benzoxazine (7.20 g, 0.029 mol) obtained by a known literature method *Journal of Heterocyclic Chemistry*, 19(5), p. 1189 (1982)) was dissolves dissolved in methanol (50 ml). Sodium borohydride (1.08 g, 0.029 mol) was added to the solution, which was stirred for 2 hours. The reaction mixture was concentrated. Ethyl acetate and aqueous potassium hydrogencarbonate solution were added to the residue, and extraction was conducted. The organic layer was washed with water, and concentrated. A mixed solution of ethyl acetate and n-hexane (1:5) was added to the residue for crystallization.

The crystallized product was collected by filtration, to give 2-hydroxymethyl-6-nitro-1,4-benzoxazine (3.10 g) as a red powder.

¹H-NMR (CDCl₃) δ: 1.96 (1H, m), 3.34–3.49 (2H, m), 3.80–3.90 (2H, m), 4.09 (1H, brs), 4.30–4.40 (1H, m), 6.86 (1H, d, J=8.6 Hz), 7.50 (1H, d, J=2.8 Hz), 7.59 (1H, dd, J=2.8, 8.6 Hz).

2) 2-Hydroxymethyl-6-nitro-1,4-benzoxazine (1.00 g, 4.76 mmol) obtained in 1) and triethylamine (708 mg, 7.00 mmol) was dissolves in DMF (30 ml). Methanesulfonyl chloride (545 mg, 4.76 mmol) was added to the solution, which was stirred for 30 minutes. 50% Aqueous dimethylamine solution (3 ml) was added to the reaction mixture, which was stirred at 70° C. for 4 hours. Ethyl acetate and water were added to the mixture, and extraction was conducted. The organic layer was washed, and concentrated. The residue was subjected to alumina column chromatography, and eluted with ethyl acetate: n-hexane (40:60), to give 2-[(dimethylamino)methyl]-6-nitro-1,4-benzoxazine (790 mg) as a colorless oily substance.

¹H-NMR (CDCl₃) δ: 2.33 (6H, s), 2.47–2.67 (2H, m), 3.19–3.25 (1H, m), 3.46–3.52 (1H, m), 4.09 (1H, brs), 4.30–4.35 (1H, m), 6.86 (1H, d, J=8.9 Hz), 7.48 (1H, d, J=2.8 Hz), 7.57 (1H, dd, J=2.8, 8.9 Hz).

3) 2-[(Dimethylamino)methyl]-6-nitro-1,4-benzoxazine (760 mg, 3.2 mmol) obtained in 2) was dissolved in methanol (10 ml). Concentrated hydrochloric acid (3 ml) and iron powder (0.80 g) were added to the solution, which was stirred for 2 hours. The reaction mixture was concentrated. 1N Aqueous sodium hydroxide solution and ethyl acetate was added to the residue, and extraction was conducted. The organic layer was concentrated. The residue was subjected to alumina column chromatography, and eluted with ethyl acetate: n-hexane (20:80), to give the titled compound (430 mg) as a colorless oily substance.

¹H-NMR (CDCl₃) δ: 2.31 (6H, s), 2.41–2.62 (2H, m), 3.12–3.17 (1H, m), 3.36–3.41 (1H, m), 3.30–3.50 (2H, brs), 3.67 (1H, brs), 4.12–4.21 (1H, m), 5.99 (1H, d, J=2.5 Hz), 6.03 (1H, dd, J=2.5, 8.4 Hz), 6.65 (1H, d, J=8.4 Hz).

REFERENCE EXAMPLE 106

6-[(4-Methyl-1-piperazinyl)methyl]-7,8-dihydro-2-naphthalenamine

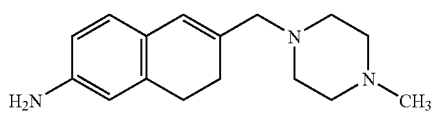

The titled compound was obtained by carrying out the same operation as in Reference Example 52, using 6-acetamido-2-(N,N-dimethylaminomethylidene)-1-tetralone obtained in Example 41-1).

¹H NMR (CDCl₃) δ: 2.27 (2H, t, J=8.1 Hz), 2.29 (3H, s), 2.45 (8H, bs), 2.72 (2H, t, J=8.1 Hz), 3.03 (2H, s), 3.60 (2H, s), 6.26 (1H, s), 6.45–6.47 (2H, m), 6.80–6.83 (–1H, m).

REFERENCE EXAMPLE 107

4-Methyl-3-(1-pyrrolidinylmethyl)-2H-chromen-7-amine

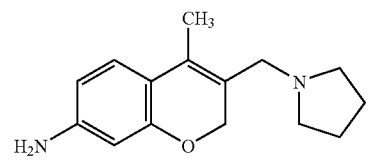

The titled compound was obtained by carrying out the same operations as in Example 41-1) and Reference Example 69 in this order, using 1-acetylamino-3,4-dihydro-chromen-1-one.

¹H NMR (CDCl₃) δ: 1.73–1.83 (4H, m), 1.99 (3H, s), 2.46–2.51 (4H, m), 3.22 (2H, s), 3.70 (2H, bs), 4.66 (2H, s), 6.18 (1H, d, J=2.2 Hz), 6.26 (1H, dd, J=2.2 Hz, 8.1 Hz), 7.00 (1H, d, J=8.1 Hz).

REFERENCE EXAMPLE 108

4-Methyl-3-(4-morpholinylmethyl)-2H-chromen-7-amine

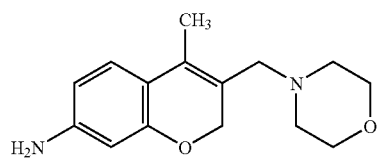

The titled compound was obtained by carrying out the same operations as in Example 41-1) and Reference Example 69 in this order, using 1-acetylamino-3,4-dihydro-chromen-1-one.

¹H NMR (CDCl₃) δ: 1.98 (3H, s), 2.41–2.44 (4H, m), 3.08 (2H, s), 3.66–3.69 (6H, m), 4.62 (2H, s), 6.18 (1H, d, J=2.2 Hz), 6.26 (1H, dd, J=2.2 Hz, 8.1 Hz), 7.00 (1H, d, J=8.1 Hz).

REFERENCE EXAMPLE 109

6-(4-Morpholinylmethyl)-7,8-dihydro-2-naphthalenamine

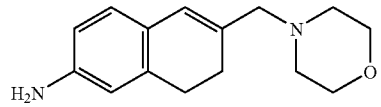

The titled compound was obtained by carrying out the same operations as in Reference Example 52, using 6-acetamido-2-(N,N-dimethylaminomethylidene)-1-tetralone obtained in Example 41-1).

¹H-NMR (CDCl₃) δ: 2.28 (2H, t, J=7.8 Hz), 2.42 (4H, t, J=4.4 Hz), 2.72 (2H, t, J=7.8 Hz), 3.01 (2H, s), 3.60 (2H, brs.), 3.70 (4H, t, J=4.4 Hz), 6.26 (1H, s), 6.46 (2H, m), 6.82 (1H, d, J=8.7 Hz).

REFERENCE EXAMPLE 110

N-Methyl-N-(5-oxo-5,6,7,8-tetrahydro-2-naphthalenyl)acetamide

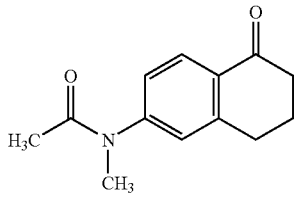

6-Acetamido-1-tetralone (13.7 g, 67.4 mmol) was dissolved in tetrahydrofuran (40 ml). Sodium hydride(oil)(2.40 g, 101 mmol) was added to the solution, which was refluxed with heating for 2.5 hours. After cooling, methyl iodide(20 ml)was added to the reaction mixture, which was stirred at 40° C. for 15 hours. The reaction mixture was poured into a cold water, and extraction was conducted using ethyl acetate. The extract was washed with 1N hydrochloric acid and 1 N aqueous sodium hydroxide solution. The ethyl acetate layer was concentrated. The residue was purified by alumina column chromatography (development solvent; ethyl acetate:n-hexane=50:50 ~100:0). The eluent was concentrated under reduced pressure. The resulting residue was recrystallized from ethyl acetate-diisopropyl ether, to give the titled compound(8.3 g).

$^1$H-NMR (CDCl$_3$) δ: 1.96 (3H, s), 2.19 (2H, m), 2.69 (2H, t, J=6.2 Hz), 2.99 (2H, t, J=5.9 Hz), 3.29 (3H, s), 7.10–7.15 (2H, m), 8.09 (1H, d, J=8.4 Hz).

REFERENCE EXAMPLE 111

N-[6-[(E)-(Dimethylamino)methylidene]-5-oxo-5,6,7,8-tetrahydro-2-naphthalenyl]-N-methylacetamide

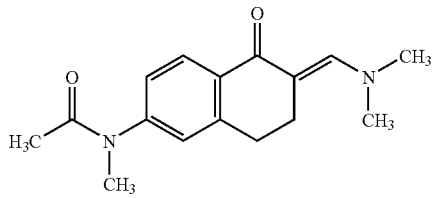

N-Methyl-N-(5-oxo-5,6,7,8-tetrahydro-2-naphthalenyl)acetamide (4.3 g, 19.8 mmol) obtained in Reference Example 110 was dissolved in N,N-dimethylformamide-dimethylacetal(50 ml), which was refluxed with heating under nitrogen atmosphere for 15 hours. The reaction mixture was concentrated under reduced pressure. The resulting residue was washed with ethyl acetate-diisopropyl ether, to give the titled compound(3.9 g).

$^1$H-NMR (CDCl$_3$) δ: 1.93 (3H, s), 2.86 (2H, t, J=7.3 Hz), 2.95 (2H, t, J=7.3 Hz), 3.16 (6H, s), 3.28 (3H, s), 6.99 (1H, s), 7.09 (1H, d, J=8.1 Hz), 7.75 (1H, s), 8.07 (1H, d, J=8.1 Hz).

REFERENCE EXAMPLE 112

N-Methyl-N-[5-oxo-6-((E)-1-pyrrolidinylmethylidene)-5,6,7,8-tetrahydro-2-naphthalenyl]acetamide

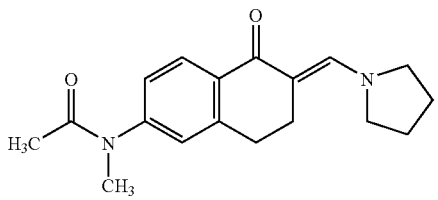

N-[6-[(E)-(Dimethylamino)methylidene]-5-oxo-5,6,7,8-tetrahydro-2-naphthalenyl]-N-methylacetamide (5.7 g, 20.9 mmol) obtained in Reference Example 111 was dissolved in pyrrolidine (50 ml), which was refluxed with heating under nitrogen atmosphere for 3.5 hours. The reaction mixture was poured into cold water, and extraction was conducted using ethyl acetate. The ethyl acetate layer was concentrated. The resulting residue was recrystallized from ethyl acetate-diisopropyl ether, to give the titled compound (4.0 g).

$^1$H NMR (CDCl$_3$) δ: 1.93–1.96 (7H, m), 2.85 (2H, t, J=6.7 Hz), 2.96 (2H, t, J=6.7 Hz), 3.28 (3H, s), 3.63 (4H, m), 6.99 (1H, s), 7.10 (1H, dd, J=8.4, 2.0 Hz), 7.95 (1H, s), 8.08 (1H, d, J=8.4 Hz).

REFERENCE EXAMPLE 113

N-Methyl-6-(1-pyrrolidinylmethyl)-7,8-dihydro-2-naphthalenamine dihydrochloride

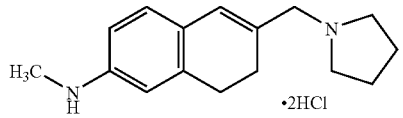

N-Methyl-N-[5-oxo-6-((E)-1-pyrrolidinylmethylidene)-5,6,7,8-tetrahydro-2-naphthalenyl]acetamide (4.0 g, 13.4 mmol) obtained in Reference Example 112 was dissolved in methanol-acetic acid(10:1, 220 ml). 10% Palladium on carbon (0.4 g) was added to the solution, which was stirred under hydrogen atmosphere for 48 hours. The catalyst was filtered off, and the reaction mixture was concentrated under reduced pressure. Ethyl acetate and 1N hydrochloric acid were added to the residue, and extraction was conducted. After the water layer was made alkaline with 4N aqueous sodium hydroxide solution, extraction was conducted using ethyl acetate. The ethyl acetate layer was concentrated. Tetrahydrofuran-5N hydrochloric acid (50:50, 200 ml) was added to the resulting residue, which was refluxed with heating for 13 hours. The reaction mixture was concentrated. Ethyl acetate and saturated aqueous sodium carbonate solution was added to the residue, and extraction was conducted. 4N Hydrogen chloride-ethyl acetate solution was added to the ethyl acetate layer, which was concentrated under reduced pressure. The resulting residue was recrystallized from methanol-ethyl acetate, to give the titled compound(2.8 g).

$^1$H-NMR (DMSO-d$_6$) δ: 1.98 (4H, m), 2.45 (4H, m), 2.81 (5H, m), 3.01 (2H, m), 3.44 (2H, m), 3.85 (1H, s), 3.86 (1H, s), 6.67 (1H, s), 7.02–7.10 (3H, m), 10.90 (1H, brs.).

REFERENCE EXAMPLE 114

6-(1-Piperidinylmethyl)-7,8-dihydro-2-naphthalenamine dihydrochloride

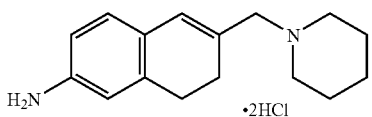

The titled compound was obtained by carrying out the same operation as in Reference Example 52, using 6-acetamido-2-(N,N-dimethylaminomethylidene)-1-tetralone obtained in Example 41-1).

$^1$H-NMR (DMSO-d$_6$) δ: 1.39 (1H, m), 1.80 (5H, m), 2.50 (5H, m), 2.83 (4H, m), 3.35–3.38 (2H, m), 3.79 (2H, s), 6.70 (1H, s), 7.05–7.13 (3H, m), 10.40 (1H, brs).

REFERENCE EXAMPLE 115

5-Methyl-6-[(4-methyl-1-piperazinyl)methyl]-7,8-dihydro-2-naphthalenamine

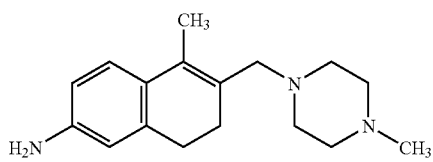

The titled compound was obtained by carrying out the same operation as in Reference Example 69, using 6-acetamido-2-(N,N-dimethylaminomethylidene)-1-tetralone obtained in Example 41-1).

$^1$H NMR (CDCl$_3$) δ: 2.02 (3H, s), 2.27 (2H, t, J=8.1 Hz), 2.27 (3H, s), 2.44 (8H, bs), 2.63 (2H, t, J=8.1 Hz), 3.12 (2H, s), 3.61 (2H, s), 6.48–6.54 (2H, m), 7.08 (1H, d, J=7.8 Hz).

REFERENCE EXAMPLE 116

2-[(Dimethylamino)methyl]-1H-inden-6-amine

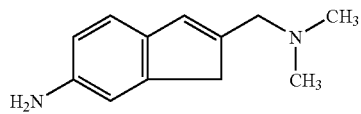

The titled compound was obtained by carrying out the same operation as in Example 41-2), using N-[2-[(E)-(dimethylamino)methylidene]-1-oxo-2,3-dihydro-1H-inden-5-yl]acetamide obtained in Reference Example 47.

$^1$H NMR (CDCl$_3$) δ: 2.24 (6H, s), 3.26 (2H, s), 3.33 (2H, s), ca.3.5 (2H, br), 6.58 (2H, m), 6.81 (1H, s), 7.08 (1H, d, J=8.1 Hz).

REFERENCE EXAMPLE 117

6-Amino-2-(1-pyrrolidinylmethyl)-3,4-dihydro-2H-1,4-benzoxazine

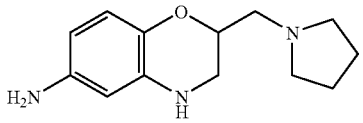

A mixture of 6-nitro-2-(1-pyrrolidinylmethyl)-3,4-dihydro-2H-1,4-benzoxazine and 4-(methylsulfonyl)-6-nitro-2-(1-pyrrolidinylmethyl)-3,4-dihydro-2H-1,4-benzoxazine was obtained by carrying out the same operation as in Reference Example 105-2), using 2-hydroxymethyl-6-nitro-3,4-dihydro-2H-1,4-benzoxazine obtained in Reference Example 105-1).

The titled compound was obtained by carrying out the same operation as in Reference Example 105-3), using the mixture obtained above.

$^1$H-NMR (CDCl$_3$) δ: 1.76–1.81 (4H, m), 2.50–2.70 (4H, m), 2.70 (2H, d, J=6.3 Hz), 3.13–3.20 (1H, m), 3.20–3.40 (2H, brs), 3.39–3.43 (1H, m), 3.66 (1H, brs), 4.11–4.21 (1H, m), 5.99 (1H, d, J=2.7 Hz), 6.03 (1H, dd, J=2.7, 8.4 Hz), 6.64 (1H, d, J=8.4 Hz).

REFERENCE EXAMPLE 118

6-Amino-4-(methylsulfonyl)-2-(1-pyrrolidinylmethyl)-3,4-dihydro-2H-1,4-benzoxazine

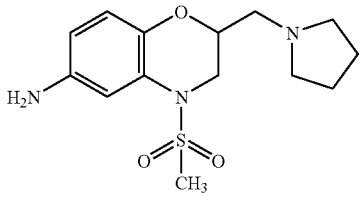

The titled compound was obtained by carrying out the same operation as in Reference Example 105-3), using the mixture of 6-nitro-2-(1-pyrrolidinylmethyl)-3,4-dihydro-2H-1,4-benzoxazine and 4-(methylsulfonyl)-6-nitro-2-(1-pyrrolidinylmethyl)-3,4-dihydro-2H-1,4-benzoxazine obtained in Reference Example 117.

$^1$H-NMR (CDCl$_3$) δ: 1.70–1.80 (4H, m), 2.50–2.70 (4H, m), 2.73 (2H, d, J=6.0 Hz), 2.95 (3H, s), 3.21–3.29 (1H, m), 2.80–3.10 (2H, brs), 4.10–4.21 (1H, m), 4.26–4.32 (1H, m), 6.43 (1H, dd, J=2.7, 8.4 Hz), 6.77 (1H, d, J=8.4 Hz), 7.11 (1H, d, J=2.7 Hz).

EXAMPLE 1

N-[2-(N,N-Dimethylamino)methyl-6-tetralinyl]-(4'-methoxybiphenyl-4-yl)carboxamide

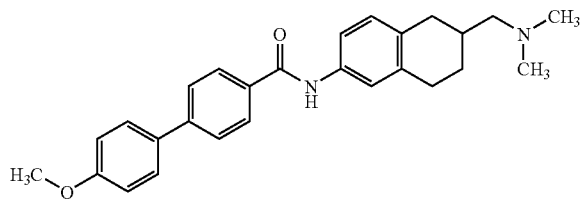

DMF solution (0.25 ml) of 2M HOBt, DMF solution (0.30 ml) of 2M WSCD, triethylamine (0.14 ml) and DMAP (0.132 g) were added to DMF solution (3 ml) of 6-amino-2-(N,N-dimethylamino)methyltetralin (0.139 g) and 4-(4-methoxy phenyl) benzoic acid (0.118 g). After the reaction mixture was stirred at room temperature for 12 hours, 10% potassium carbonate solution was added, and extraction was conducted using ethyl acetate. The organic layer was washed with water and saturated aqueous sodium chloride solution, dried, and then concentrated. The resulting crude crystal was washed with diethyl ether, which was recrystallized using ethyl acetate-hexane, to give the titled compound (0.124 g).

Melting point: 170–175° C.

Compounds described in the following Examples 2 and 3 were produced in the same manner as in Example 1.

EXAMPLE 2

4-Benzoyl-N-[2-(N,N-dimethylamino)methyl-6-tetralinyl]benzamide

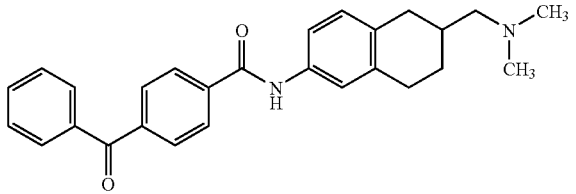

Melting point: 193–196° C. (recrystallization solvent: ethyl acetate-hexane)

EXAMPLE 3

N-[2-(N,N-Dimethylamino)methyl-6-tetralinyl]-4-(1,3-dioxo-1,3-dihydro-2H-isoindol-2-yl) benzamide

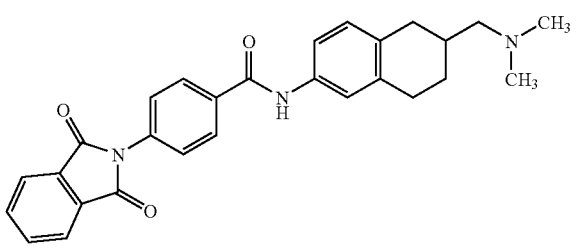

Melting point: 235–240° C. (washed with diethyl ether)

EXAMPLE 4

4-(Benzoylamino)-N-[2-(N,N-dimethylamino)methyl-6-tetralinyl]benzamide

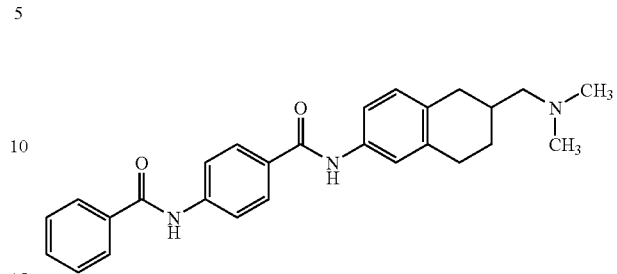

6-Amino-2-(N,N-dimethylamino)methyltetralin hydrochloride (139 mg), 4-benzoylaminobenzoic acid (121 mg), WSCD (0.13 ml), HOBt (92 mg), triethylamine (0.14 ml) and DMAP (61 mg) were added to DMF (4 ml). After the reaction mixture was shaken at room temperature for 20 hours using a shaker, the reaction mixture was poured into water, and extraction was conducted using ethyl acetate-THF (1:1). The organic layer was washed with water, saturated sodium bicarbonate solution and saturated aqueous sodium chloride solution, dried, and then concentrated. The resulting crude crystal was washed with hexane, to give the titled compound (181 mg).

Melting point: 241–242° C.

Washing solvent: hexane

Compounds described in the following Examples 5 to 14 were produced in the same manner as in Example 4.

EXAMPLE 5

4-(Benzyloxy)-N-[2-(N,N-dimethylamino)methyl-6-tetralinyl]benzamide

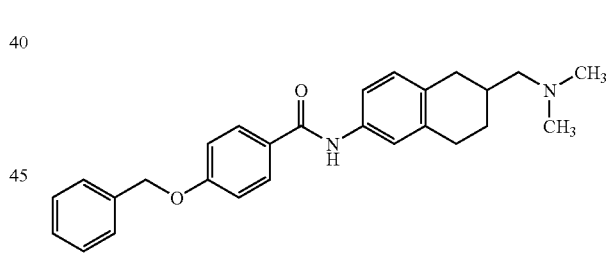

Melting point: 135–136° C.

Washing solvent: hexane

EXAMPLE 6

N-[2-(N,N-Dimethylamino) methyl-6-tetralinyl]-9-oxo-9H-fluoren-2-carboxamide

Melting point: 224–226° C.

Washing solvent: hexane

EXAMPLE 7

N-[2-(N,N-Dimethylamino)methyl-6-tetralinyl]-9,10,10-trioxo-9,10-dihydro-10$1^6$-thioxanthene-3-carboxamide

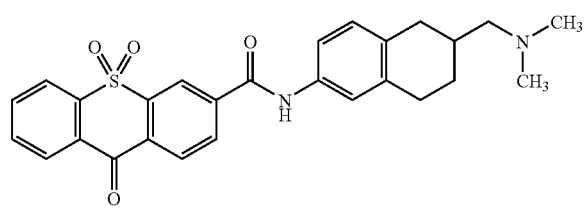

Melting point: 222–223° C. (decomposition)
Washing solvent: hexane

EXAMPLE 8

(4-Anilinocarbonyl)amino-N-[2-(N,N-dimethylamino)methyl-6-tetralinyl]benzamide

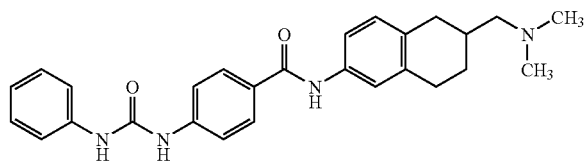

Melting point: 216–217° C. (decomposition)
Washing solvent: hexane

EXAMPLE 9

N-[2-(N,N-Dimethylamino)methyl-6-tetralinyl]-4-phenoxy benzamide

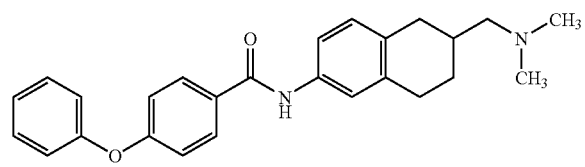

Melting point: 137–139° C.
Washing solvent: hexane

EXAMPLE 10

$N^1$-[2-(N,N-Dimethylamino)methyl-6-tetralinyl]-$N^4$-phenyl terephthalamide

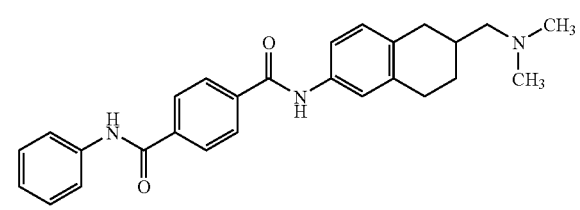

Melting point: 238–240° C. (decomposition)
Washing solvent: hexane

EXAMPLE 11

(4'-Ethylbiphenyl-4-yl)-N-[2-(N,N-dimethylamino)methyl-6-tetralinyl]carboxamide

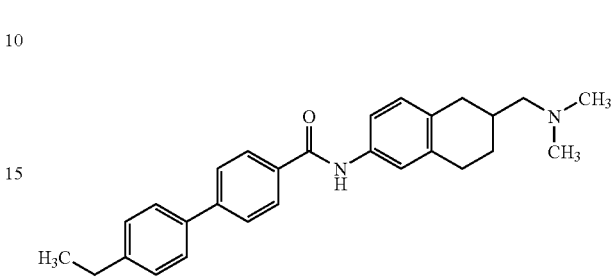

Melting point: 137–138° C.
Washing solvent: hexane

EXAMPLE 12

(4'-Chlorobiphenyl-4-yl)-N-[2-(N,N-dimethylamino)methyl-6-tetralinyl]carboxamide

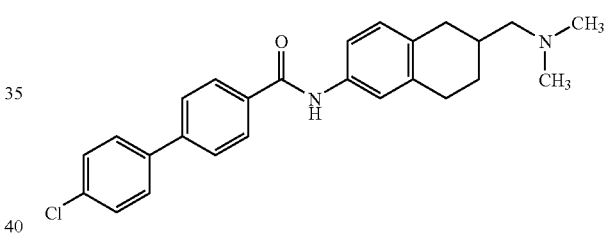

Melting point: 187–189° C.
Washing solvent: hexane

EXAMPLE 13

(4'-Acetylaminobiphenyl-4-yl)-N-[2-(N,N-dimethylamino) methyl-6-tetralinyl]carboxamide

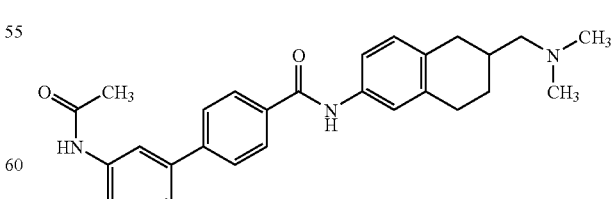

Melting point: 183–186° C.
Washing solvent: hexane

EXAMPLE 14

4-(1,3-Benzodioxol-5-yl)-N-[2-N,N-dimethylamino)methyl-6-tetralinyl]benzamide

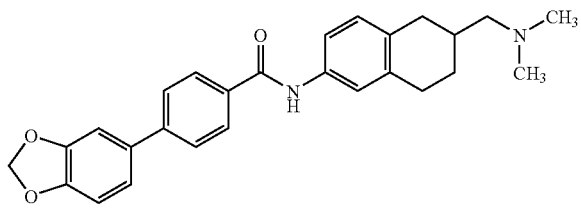

Melting point: 174–176° C.
Washing solvent: hexane

EXAMPLE 15

4-Bromo-N-[6-[(N,N-dimethylamino)methyl]-5,6,7,8-tetrahydro-2-naphthalenyl]benzamide The titled compound was obtained as a white powder by the same method as in Example 1.

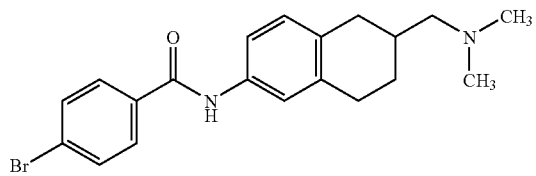

Melting point: 141–143° C. (washing solvent: n-hexane)

EXAMPLE 16

3',4'-Dichloro-N-[6-[(N,N-dimethylamino)methyl]-5,6,7,8-tetrahydro-2-naphthalenyl][1,1'-biphenyl]-4-carboxamide

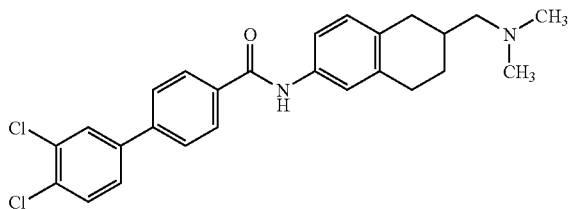

4-Bromo-N-[6-[(N,N-dimethylamino)methyl]-5,6,7,8-tetrahydro-2-naphthalenyl]benzamide (400 mg, 1.03 mmol) obtained in Example 15, 3,4-dichlorophenylboric acid (50 wt % THF-H$_2$O solution, 0.473 ml, 1.24 mmol), and 2N sodium carbonate solution (1.03 ml, 2,07 mmol) were dissolved in 50 ml of dimethoxyethane, then palladium tetrakistriphenylphosphine (35.8 mg, 0.031 mmol) was added under nitrogen atmosphere, which was stirred at 90° C. for 15 hours.

Ethyl acetate was added to the reaction mixture, which was washed with saturated aqueous sodium chloride solution, dried using anhydrous magnesium sulfate, and the solvent was distilled out under reduced pressure. The residue was refined by alumina column chromatography (development solvent; n-hexane:ethyl acetate=3:1), and pulverized with n-hexane to give the titled compound (204 mg) a white powder.

$^1$H-NMR (CDCl$_3$) δ: 1.41 (1H, m), 1.95 (2H, m), 2.26 (6H, s), 2.26–2.45 (3H, m), 2.83–2.99 (3H, m), 7.10 (1H, d, J=8.1 Hz), 7.26–7.77 (8H, m), 7.94 (2H, d, J=8.4 Hz).

Elemental analysis for C$_{26}$H$_{26}$Cl$_2$N$_2$O.0.1H$_2$O Calcd.: C, 68.60; H, 5.80; N, 6.15. Found: C, 68.42; H, 5.60; N, 5.92.

Melting point: 143–145° C. (crystallization solvent: ethyl acetate-hexane)

EXAMPLE 17

N-[6-[(N,N-Dimethylamino)methyl]-5,6,7,8-tetrahydro-2-naphthalenyl]-4'-phenyl[1,1'-biphenyl]-4-carboxamide hydrochloride

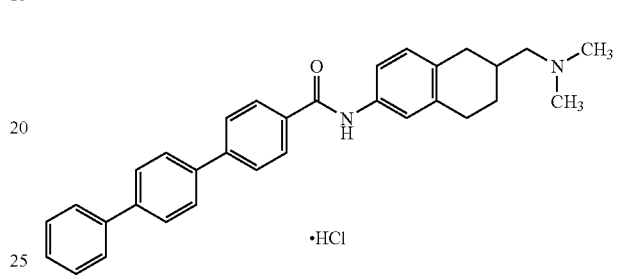

The free basic substance (35 mg) of the titled compound was obtained in the same manner as in Example 16, using 4-bromo-N-[6-[(N,N-dimethylamino)methyl]-5,6,7,8-tetrahydro-2-naphthalenyl]benzamide (400 mg, 1.03 mmol) obtained in Example 15, and 4-biphenylboric acid (1.25 g, 1.25 mmol). The resulting free basic substance (30 mg) was dissolved in 10 ml of methanol, then 100 ml of 1N hydrochloric acid was added, and the reaction mixture was stirred. The reaction mixture was concentrated, and pulverized using diethyl ether, to give the titled compound (35.3 mg) as a white powder.

$^1$H-NMR (DMSO-d$_6$, free base) δ: 1.32 (1H, m), 1.93 (2H, m), 2.15 (6H, s), 2.15–2.36 (3H, m), 2.74–2.94 (3H, m), 7.05 (1H, d, J=8.4 Hz), 7.40–7.55 (5H, m), 7.73–7.91 (8H, m), 8.07 (2H, d, J=8.4 Hz), 10.14 (1H, s).

Elemental analysis for C$_{32}$H$_{32}$N$_2$O.HCl.2H$_2$O Calcd.: C, 72.10; H, 7.00; N, 5.25. Found: C, 71.81; H, 6.57; N, 5.08.

Melting point: 220° C. (decomposition) (crystallization solvent: methanol-diethyl ether)

EXAMPLE 18

N-[6-[(N,N-Dimethylamino)methyl]-5,6,7,8-tetrahydro-2-naphthalenyl]-2'-methoxy[1,1'-biphenyl]-4-carboxamide

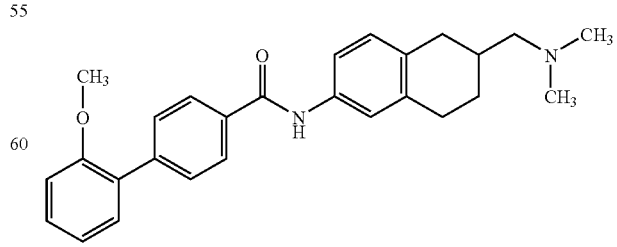

The titled compound (208 mg) was obtained as a white powder by the same method as in Example 16, using 4-bromo-N-[6-[(N,N-dimethylamino)methyl]-5,6,7,8-tetrahydro-2-naphthalenyl]benzamide (250 mg, 0.645 mmol) obtained in Example 15, and 2-methoxyphenylboric acid (118 mg, 0.775 mmol).

$^1$H-NMR (CDCl$_3$) δ: 1.42 (1H, m), 1.96 (2H, m), 2.23 (6H, s), 2.23–2.47 (3H, m), 2.85 (3H, m), 3.83 (3H, s), 7.05 (3H, m), 7.34 (3H, m), 7.47 (1H, s), 7.64 (2H, d, J=8.4 Hz), 7.79 (1H, s), 7.90 (2H, d, J=8.4 Hz).

Elemental analysis for C$_{27}$H$_{30}$N$_2$O$_2$.0.1H$_2$O Calcd.: C, 77.89; H, 7.31; N, 6.73. Found: C, 77.86; H, 7.18; N, 6.79.

Melting point: 155–1570° C. (crystallization solvent: ethyl acetate-hexane)

EXAMPLE 19

Sodium salt of N-[6-[(N,N-dimethylamino)methyl]-5,6,7,8-tetrahydro-2-naphthalenyl]-4'-oxy[1,1'-biphenyl]-4-carboxamide

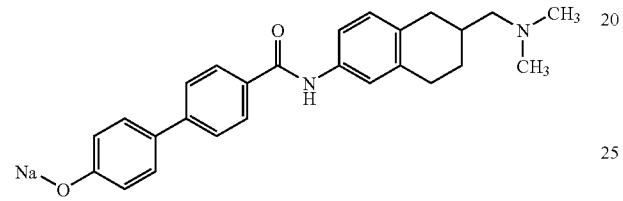

The titled compound (117 mg) was obtained as a white powder by the same method as in Example 16, using 4-bromo-N-[6-[(N,N-dimethylamino)methyl]-5,6,7,8-tetrahydro-2-naphthalenyl]benzamide (250 mg, 0.645 mmol) and 4-hydroxyphenylboric acid (107 mg, 0.775 mmol).

$^1$H-NMR (DMSO-d$_6$) δ: 1.36 (1H, m), 1.89 (2H, m), 2.15 (6H, s), 2.15–2.35 (3H, m), 2.77 (3H, m), 6.88 (2H, d, J=8.4 Hz), 7.02 (1H, d, J=8.4 Hz), 7.48 (1H, d, J=8.4 Hz), 7.53 (1H, s), 7.59 (2H, d, J=8.4 Hz), 7.73 (2H, d, J=8.4 Hz), 8.00 (2H, d, J=8.4 Hz), 10.07 (1H, s).

Elemental analysis for C$_{26}$H$_{27}$N$_2$O$_2$Na.0.2H$_2$O Calcd. C, 73.29; H, 6.48; N, 6.59. Found: C, 73.25; H, 6.18; N, 6.36.

Melting point: 246–248° C. (crystallization solvent: ethyl acetate-diethyl ether)

EXAMPLE 20

N-[6-[(N,N-Dimethylamino)methyl]-5,6,7,8-tetrahydro-2-naphthalenyl]-4'-formyl[1,1'-biphenyl]-4-carboxamide

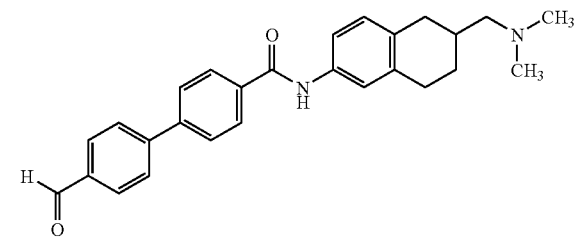

The titled compound (205 mg) was obtained as a white powder by the same method as in Example 16, using 4-bromo-N-[6-[(N,N-dimethylamino)methyl]-5,6,7,8-tetrahydro-2-naphthalenyl]benzamide (250 mg, 0.645 mmol) and 4-formylphenylboric acid (145 mg, 0.968 mmol).

$^1$H-NMR (CDCl$_3$) δ: 1.41 (1H, m), 1.95 (2H, m), 2.26 (6H, s), 2.26–2.42 (3H, m), 2.85–2.94 (3H, m), 7.09 (2H, d, J=8.1 Hz), 7.32 (1H, d, J=8.4 Hz), 7.47 (1H, m), 7.63–7.94 (3H, m), 7.87–7.99 (4H, m)., 8.13 (1H, s), 10.11 (1H, s).

Elemental analysis for C$_{27}$H$_{28}$N$_2$O$_2$.0.2H$_2$O Calcd.: C, 77.93; H, 6.88; N, 6.73. Found: C, 77.89; H, 6.75; N, 6.71.

Melting point: 130–132° C. (crystallization solvent: ethyl acetate-diethyl ether)

EXAMPLE 21

N-[6-[(N,N-Dimethylamino)methyl]-5,6,7,8-tetrahydro-2-naphthalenyl]-4'-(hydroxymethyl)[1,1'-biphenyl]-4-carboxamide

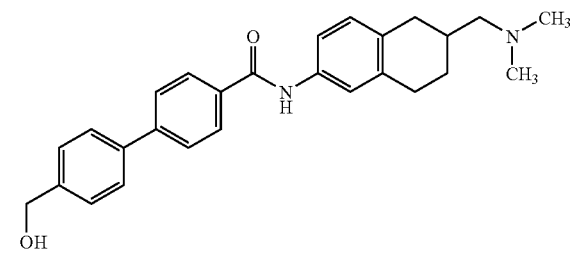

N-[6-[(N,N-Dimethylamino)methyl]-5,6,7,8-tetrahydro-2-naphthalenyl]-4'-formyl[1,1'-biphenyl]-4-carboxamide (100 mg, 0.242 mmol) was dissolved in tetrahydrofuran-methanol (1:1) solution (2.4 ml), then sodium borohydride (18.3 mg, 0.485 mmol) was added, which was stirred for 2 hours. Ethyl acetate was added to the reaction mixture, which was washed with saturated aqueous sodium chloride solution, dried using anhydrous magnesium sulfate, and the solvent was distilled out under reduced pressure. The residue was pulverized using ether-n-hexane, to give the titled compound (86 mg) as a white powder.

$^1$H-NMR (CDCl$_3$) δ: 1.39 (1H, m), 1.94 (2H, m), 2.25 (6H, s), 2.25–2.44 (3H, m), 2.82–2.95 (3H, m), 4.78 (2H, s), 7.07 (1H, d, J=8.4 Hz), 7.31 (1H, d, J=8.4 Hz), 7.38–7.56 (4H, m), 7.64–7.70 (3H, m), 7.85 (1H, s), 7.93 (2H, d, J=8.4 Hz).

Elemental analysis for C$_{27}$H$_{30}$N$_2$O$_2$.0.2H$_2$O Calcd.: C, 77.56; H, 7.33; N, 6.70. Found: C, 77.53; H, 7.27; N, 6.55.

Melting point: 138–139° C. (crystallization solvent: ethyl acetate-diethyl ether)

EXAMPLE 22

N-[6-[(N,N-Dimethylamino)methyl]-5,6,7,8-tetrahydro-2-naphthalenyl]-4'-propyl[1,1'-biphenyl]-4-carboxamide

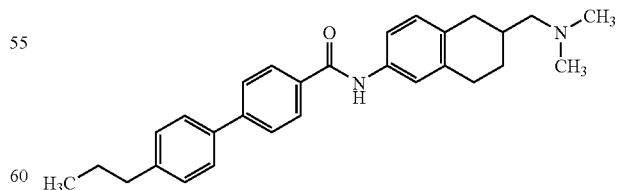

The titled compound (158 mg) was obtained as a white powder by the same method as in Example 1, using N-[(6-amino-1,2,3,4-tetrahydro-2-naphthalenyl)methyl]-N,N-dimethylamine (102 mg, 0.499 mmol), and 4-(4-propyl)benzoic acid (144 mg, 0.599 mmol).

¹H-NMR (CDCl₃) δ: 0.98 (3H, t, J=7.5 Hz), 1.40 (1H, m), 1.69 (2H, m), 1.94 (2H, m), 2.25 (6H, s), 2.25–2.45 (3H, m), 2.64 (2H, t, J=7.5 Hz), 2.85 (3H, m), 7.08 (1H, d, J=7.8 Hz), 7.26 (3H, m), 7.46 (1H, s), 7.54 (2H, d, J=8.1 Hz), 7.67 (2H, d, J=8.1 Hz), 7.81 (1H, s), 7.91 (2H, d, J=8.4 Hz).

Elemental analysis for C₂₉H₃₄N₂O Calcd.: C, 81.65; H, 8.03; N, 6.57. Found: C, 81.30; H, 7.94; N. 6.40.

Melting point: 186–188° C. (crystallization solvent: ethyl acetate-diethyl ether)

EXAMPLE 23

4-Bromo-2-chloro-N-[6-[(N,N-dimethylamino)methyl]-5,6,7,8-tetrahydro-2-naphthalenyl]benzamide

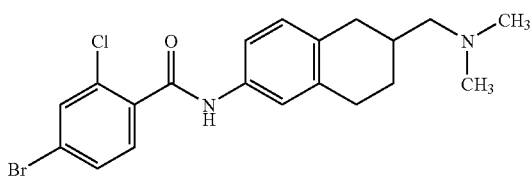

The titled compound (483 mg) was obtained as a white powder by the same method as in Example 1, using N-[(6-amino-1,2,3,4-tetrahydro-2-naphthalenyl)methyl]-N,N-dimethylamine (300 mg, 1.47 mmol) and 4-bromo-2-chloro benzoic acid (415 mg, 1.76 mmol).

¹H-NMR (CDCl₃) δ: 1.40 (1H, m), 1.94 (2H, m), 2.25 (6H, s), 2.25–2.44 (3H, m), 2.94 (3H, m), 7.08 (1H, d, J=8.4 Hz), 7.28 (1H, m), 7.41 (1H, s), 7.50 (1H, m), 7.61 (2H, m), 7.81 (1H, s).

Elemental analysis for C₂₀H₂₂BrClN₂O Calcd.: C, 56.96; H, 5.26; N, 6.64. Found: C, 57.09; H, 5.37; N, 6.55.

Melting point: 130–1320° C. (crystallization solvent: ethyl acetate-diethyl ether)

EXAMPLE 24

4-Bromo-N-[6-[(N,N-dimethylamino)methyl]-5,6,7,8-tetrahydro-2-naphthalenyl]-2-methylbenzamide

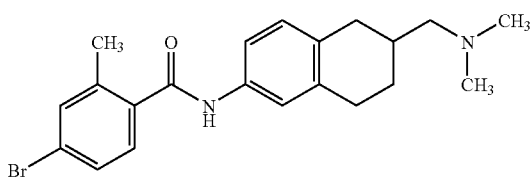

The titled compound (418 mg) was obtained as a white powder by the same method as in Example 1, using N-[(6-amino-1,2,3,4-tetrahydro-2-naphthalenyl)methyl]-N,N-dimethylamine (293 mg, 1.43 mmol) and 4-bromo-2-methyl benzoic acid (370 mg, 1.72 mmol).

¹H-NMR (CDCl₃) δ: 1.40 (1H; m), 2.04 (2H, m), 2.25 (6H, s), 2.25–2.40 (3H, m), 2.46 (3H, s), 2.88 (3H, m), 7.07 (1H, d, J=7.8 Hz), 7.21–7.41 (6H, m).

Elemental analysis for C₂₁H₂₅BrN₂O Calcd.: C, 62.85; H, 6.28; N, 6.98. Found: C, 63.10; H, 6.11; N, 6.97.

Melting point: 140–142° C. (crystallization solvent: ethyl acetate-hexane)

EXAMPLE 25

4-Bromo-N-[6[(N,N-dimethylamino)methyl]-5,6,7,8-tetrahydro-2-naphthalenyl]-3-methylbenzamide

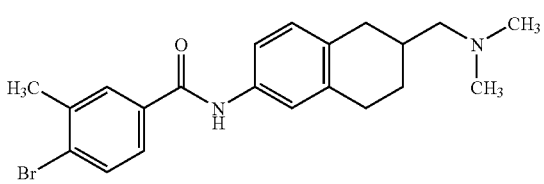

The titled compound (434 mg) was obtained as a white powder by the same method as in Example 1, using N-[(6-amino-1,2,3,4-tetrahydro-2-naphthalenyl)methyl]-N,N-dimethylamine (300 mg, 1.47 mmol) and 4-bromo-3-methyl benzoic acid (379 mg, 1.76 mmol).

¹H-NMR (CDCl₃) δ: 1.40 (1H, m), 1.93 (2H, m), 2.25 (6H, s), 2.25–2.40 (3H, m), 2.46 (3H, s), 2.87 (3H, m), 7.07 (1H, d, J=7.8 Hz), 7.29 (1H, m), 7.40 (1H, s), 7.49 (1H, m), 7.61 (1H, d, J=8.1 Hz), 7.72 (2H, s-like).

Elemental analysis for C₂₁H₂₅BrN₂O Calcd.: C, 62.85; H, 6.28; N, 6.98. Found: C, 62.84; H, 6.05; N, 6.93.

Melting point: 154–155° C. (crystallization solvent: ethyl acetate-hexane)

EXAMPLE 26

3,4'-Dichloro-N-[6-[(N,N-dimethylamino)methyl]-5,6,7,8-tetrahydro-2-naphthalenyl][1,1'-biphenyl]-4-carboxamide

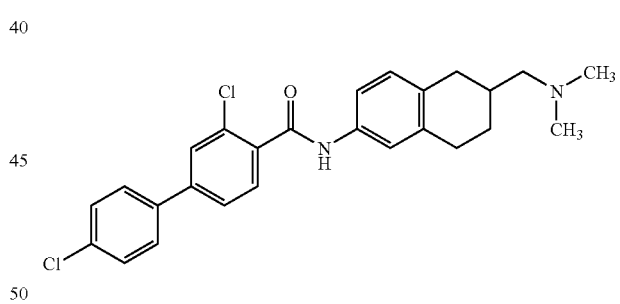

The titled compound (122 mg) was obtained as a white powder by the same method as in Example 16, using 4-bromo-2-chloro-N-[6-[(N,N-dimethylamino)methyl]-5,6,7,8-tetrahydro-2-naphthalenyl)benzamide (250 mg, 0.607 mmol) obtained in Example 23, and 4-chlorophenyl boric acid (114 mg, 0.729 mmol).

¹H-NMR (CDCl₃) δ: 1.41 (1H, m), 1.95 (2H, m), 2.26 (6H, s), 2.26–2.42 (3H, m), 2.85 (3H, m), 7.10 (1H, d, J=8.4 Hz), 7.31 (1H, m), 7.43–7.63 (8H, m), 7.87 (1H, d, J=8.1 Hz).

Elemental analysis for C₂₆H₂₆Cl₂N₂O Calcd.: C, 68.87; H, 5.78; N, 6.18. Found: C, 68.61; H, 5.49; N, 6.10.

Melting point: 177–179° C. (crystallization solvent: ethyl acetate-diethyl ether)

EXAMPLE 27

4'-Chloro-N-[6-[(N,N-dimethylamino)methyl]-5,6,7,8-tetrahydro-2-naphthalenyl]-3-methyl[1,1'-biphenyl]-4-carboxamide

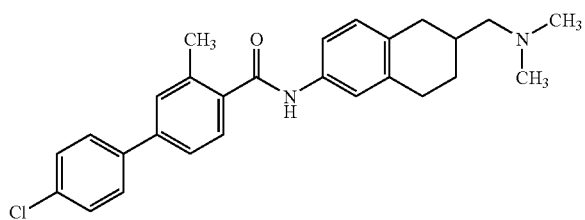

The titled compound (129 mg) was obtained as a white powder by the same method as in Example 16, using 4-bromo-N-[6-[(N,N-dimethylamino)methyl]-5,6,7,8-tetrahydro-2-naphthalenyl)-2-methylbenzamide (250 mg, 0.623 mmol) obtained in Example 24, and 4-chlorophenylboric acid (117 mg, 0.747 mmol).

$^1$H-NMR (CDCl$_3$) δ: 1.42 (1H, m), 1.96 (2H, m), 2.37 (6H, s), 2.37–2.47 (3H, m), 2.56 (3H, s), 2.90 (3H, m), 7.08 (1H, d, J=8.1 Hz), 7.26 (1H, m), 7.41 (6H, m), 7.53 (3H, m).

Elemental analysis for C$_{27}$H$_{29}$ClN$_2$O.H$_2$O Calcd.: C, 71.90; H, 6.93; N, 6.21. Found: C, 71.92; H, 6.52; N, 5.92.

Melting point: 163–165° C. (crystallization solvent: ethyl acetate-diethyl ether)

EXAMPLE 28

4'-Chloro-N-[6-[(N,N-dimethylamino)methyl]-5,6,7,8-tetrahydro-2-naphthalenyl]-2-methyl[1,1'-biphenyl]-4-carboxamide

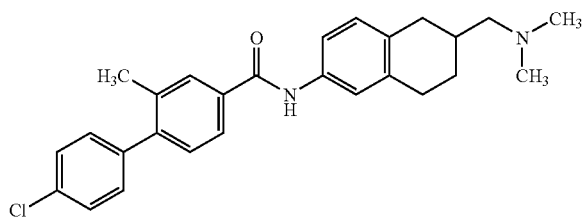

The titled compound (168 mg) was obtained as a white powder by the same method as in Example 16, using 4-bromo-N-[6-[(N,N-dimethylamino)methyl]-5,6,7,8-tetrahydro-2-naphthalenyl)-3-methylbenzamide (250 mg, 0.623 mmol) obtained in Example 25, and 4-chlorophenylboric acid (117 mg, 0.747 mmol).

$^1$H-NMR (CDCl$_3$) δ: 1.41 (1H, m), 1.95 (2H, m), 2.26 (6H, s), 2.24–2.42 (3H, m), 2.33 (3H, s), 2.85 (3H, m), 7.09 (1H, d, J=8.4 Hz), 7.26 (4H, m), 7.43 (3H, m), 7.73 (3H, m).

Elemental analysis for C$_{27}$H$_{29}$ClN$_2$O.0.2H$_2$O Calcd.: C, 74.28; H, 6.79; N, 6.42. Found: C, 74.27; H, 6.73; N, 6.27.

Melting point: 193–195° C. (crystallization solvent: ethyl acetate-diethyl ether)

EXAMPLE 29

N-[6-[(N,N-Dimethylamino)methyl]-5,6,7,8-tetrahydro-2-naphthalenyl]-4'-(trifluoromethyl)[1,1'-biphenyl]-4-carboxamide

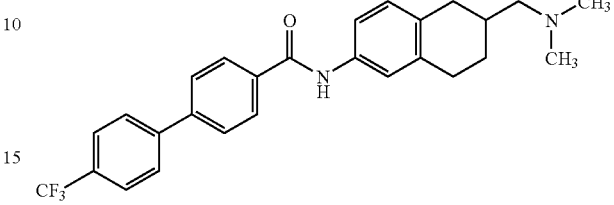

The titled compound (194 mg) was obtained as a white powder by the same method as in Example 16, using 4-bromo-N-[6-[(N,N-dimethylamino)[methyl]-5,6,7,8-tetrahydro-2-naphthalenyl)benzamide (250 mg, 0.645 mmol) obtained in Example 15, and 4-trifluoromethylphenylboric acid (147 mg, 0.775 mmol).

$^1$H-NMR (CDCl$_3$) δ: 1.41 (1H, m), 1.95 (2H, m), 2.25 (6H, s), 2.25–2.45 (3H, m), 2.89 (3H, m), 7.09 (1H, d, J=8.1 Hz), 7.31 (1H, d, J=8.1 Hz), 7.46 (1H, s), 7.70 (6H, m), 7.80 (1H, m), 7.96 (2H, d, J=8.4 Hz).

Elemental analysis for C$_{27}$H$_{27}$F$_3$N$_2$O Calcd.: C, 71.66; H, 6.01; N, 6.19. Found: C, 71.44; H, 6.05; N, 6.09.

Melting point: 205–206° C. (crystallization solvent: ethyl acetate-diisopropyl ether)

EXAMPLE 30

N-[6-[(N,N-Dimethylamino)methyl]-5,6,7,8-tetrahydro-2-naphthalenyl]-4-(3-pyridinyl)benzamide

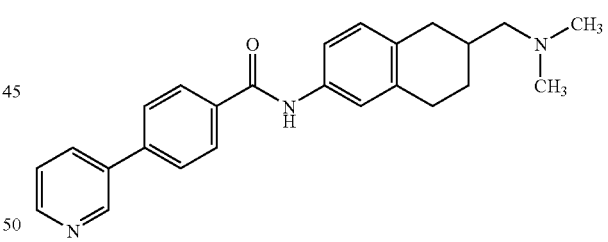

The titled compound (194 mg) was obtained as a white powder by the same method as in Example 16, using 430 bromo-N-[6-[(N,N-dimethylamino)methyl]-5,6,7,8-tetrahydro-2-naphthalenyl)benzamide (250 mg, 0.645 mmol) obtained in Example 15, and 2-(3-pyridyl)-1,3,2,-dioxaborinane (126 mg, 0.775 mmol).

$^1$H-NMR (CDCl$_3$) δ: 1.41 (1H, m), 1.95 (2H, m), 2.26 (6H, s), 52.26–2.42 (3H, m), 2.85 (3H, m), 7.09 (1H, d, J=7.8 Hz), 7.30–7.47 (3H, m), 7.69 (2H, d, J=8.4 Hz), 7.86–7.99 (4H, m), 8.64 (1H, m), 8.87 (1H, m).

Elemental analysis for C$_{25}$H$_{27}$N$_3$O.0.1H$_2$O Calcd.: C, 77.53; H, 7.08; N, 10.85. Found: C, 77.42; H, 7.05; N, 10.58.

Melting point: 177–178° C. (crystallization solvent: ethyl acetate-diisopropyl ether)

EXAMPLE 31

N-[6-[(N,N-Dimethylamino)methyl]-5,6,7,8-tetrahydro-2-naphthalenyl]-4'-[(trifluoroacetyl)amino][1,1'-biphenyl]-4-carboxamide

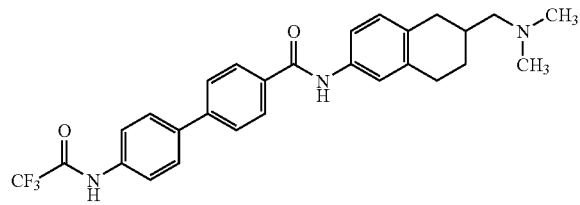

The titled compound (1.02 g) was obtained as a white powder by the same method as in Example 16, using 4-bromo-N-[6-[(N,N-dimethylamino)methyl]-5,6,7,8-tetrahydro-2-naphthalenyl]benzamide (1.00 g, 2.58 mmol) obtained in Example 15, and 4-trifluoroacetamidophenylboric acid (722 mg, 3.10 mmol).

$^1$H-NMR (CDCl$_3$) δ: 1.41 (1H, m), 2.05 (2H, m), 2.26 (6H, s), 2.26–2.42 (3H, m), 2.89 (3H, m), 7.09 (1H, d, J=8.4 Hz), 7.29 (2H, m), 7.46 (1H, s), 7.69 (7H, m), 7.94 (2H, d, J=8.1 Hz).

Elemental analysis for C$_{28}$H$_{28}$F$_3$N$_3$O$_2$ Calcd.: C, 67.87; H, 5.70; N, 8.48. Found: C, 67.70; H, 5.53; N, 8.42.

Melting point: 235–237° C. (crystallization solvent: ethyl acetate-diisopropyl ether)

EXAMPLE 32

N-[6-[(N,N-Dimethylamino)methyl]-5,6,7,8-tetrahydro-2-naphthalenyl]-4'-(4,4-dimethyl-4,5-dihydro-1,3-oxazole 2-yl)[1,1'-biphenyl]-4-carboxamide

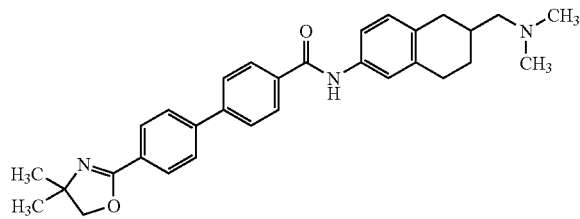

The titled compound (238 mg) was obtained as a white powder by the same method as in Example 16, using 4-bromo-N-[6-[(N,N-dimethylamino)methyl-5,6,7,8-tetrahydro-2-naphthalenyl]benzamide (250 mg, 0.645 mmol) obtained in Example 15, and 4-(4,4-dimethyl-4,5-dihydro-1,3-oxazol-2-yl)phenylboronic acid (170 mg, 0.775 mmol).

$^1$H-NMR (CDCl$_3$) δ: 1.41 (7H, m), 1.94 (2H, m), 2.25 (6H, s), 2.25–2.41 (3H, m), 2.84 (3H, m), 4.14 (2H, s), 7.08 (1H, d, J-7.8 Hz), 7.30 (1H, m), 7.46 (1H, s), 7.68 (5H, m), 7.94 (2H, d, J=8.4 Hz), 8.03 (2H, d, J=8.4 Hz).

Elemental analysis for C$_{31}$H$_{35}$N$_3$O$_2$.0.2H$_2$O Calcd.: C, 76.74; H, 7.35; N, 8.66. Found: C, 76.70; H, 7.19; N, 8.49.

Melting point: 185–187° C. (crystallization solvent: ethyl acetate-diisopropyl ether)

EXAMPLE 33

4'-Amino-N-[6-[(N,N-dimethylamino)methyl]-5,6,7,8-tetrahydro-2-naphthalenyl][1,1'-biphenyl]-4-carboxamide

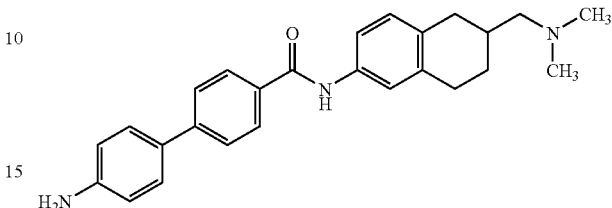

N-[6-[(N,N-Dimethylamino)methyl]-5,6,7,8-tetrahydro-2-naphthalenyl]-4'-[(trifluoroacetyl)amino][1,1'-biphenyl]-4-carboxamide (850 mg, 1.72 mmol) obtained in Example 31 was suspended in a mixed solution of methanol (8 ml) and tetrahydrofuran (4 ml), then 1N sodium hydroxide (3.4 ml) was added, which was stirred at 50° C. for 16 hours. The solvent was distilled out under reduced pressure, and the residue was pulverized using water, to give the titled compound (685 mg) as a white powder.

$^1$H-NMR (CDCl$_3$) δ: 1.31 (1H, m), 1.89 (2H, m), 2.15 (6H, s), 2.15–2.34 (3H, m), 2.83 (3H, m), 5.36 (2H, s), 6.67 (2H, d, J=8.4 Hz), 7.03 (1H, d, J=8.1 Hz), 7.48 (4H, m), 7.68 (2H, d, j=8.1 Hz), 7.96 (2H, d, J=8.4 Hz), 10.02 (1H, s).

Elemental analysis for C$_{26}$H$_{29}$N$_3$O.1.1H$_2$O Calcd.: C, 74.47; H, 7.50; N, 10.02. Found: C, 74.39; H, 7.41; N, 9.82.

Melting point: 148–150° C. (crystallization solvent: methanol-water)

EXAMPLE 34

N-[6-[(N,N-Dimethylamino)methyl]-5,6,7,8-tetrahydro-2-naphthalenyl]-4-(2-thienyl) benzamide

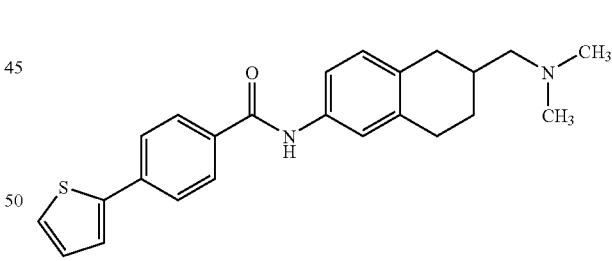

The titled compound (70 mg) was obtained as a white powder by the same method as in Example 16, using 4-bromo-N-[6-[(N,N-dimethylamino)methyl]-5,6,7,8-tetrahydro-2-naphthalenyl]benzamide (250 mg, 0.645 mmol) obtained in Example 15, and 2-thienylboric acid (99.1 mg, 0.775 mmol).

$^1$H-NMR (CDCl$_3$) δ: 1.41 (1H, m), 1.94 (2H, m), 2.25 (6H, s), 2.25–2.45 (3H, m), 2.89 (3H, m), 7.11 (2H, m), 7.29–7.45 (4H, m), 7.71 (3H, m), 7.87 (2H, d, J=8.4 Hz).

Elemental analysis for C$_{24}$H$_{26}$N$_2$OS Calcd.: C, 73.81; H, 6.71; N, 7.17. Found: C, 73.49; H, 6.59; N, 7.14.

Melting point: 165–166° C. (crystallization solvent: ethyl acetate-diisopropyl ether)

EXAMPLE 35

Ethyl 4'-[[[6-[(N,N-dimethylamino)methyl]-5,6,7,8-tetrahydro-2-naphthalenyl]amino]carbonyl][1,1'-biphenyl]-4-carboxylate

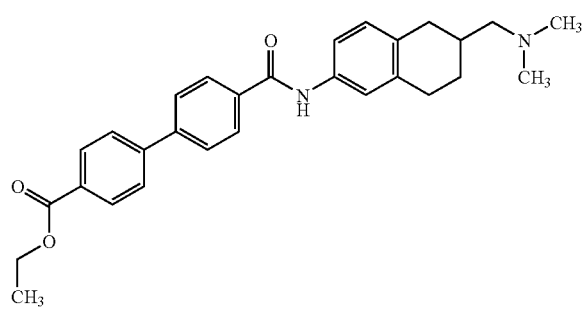

The titled compound (202 mg) was obtained as a white powder by the same method as in Example 16, using 4-bromo-N-[6-[(N,N-dimethylamino)methyl]-5,6,7,8-tetrahydro-2-naphthalenyl]benzamide (250 mg, 0.645 mmol) obtained in Example 15, and 4-ethoxycarbonylphenylboric acid (150 mg, 0.775 mmol).

$^1$H-NMR (CDCl$_3$) δ: 1.42 (4H, m), 1.95 (2H, m), 2.26 (6H, s), 2.26–2.42 (3H, m), 2.89 (3H, m), 4.41 (2H, q, J=7.2 Hz), 7.09 (1H, d, J=8.4 Hz), 7.31 (1H, d, J=8.4 Hz), 7.47 (1H, s), 7.70 (4H, m), 7.80 (1H, s), 7.96 (2H, d, J=8.4 Hz), 8.14 (2H, d, J=8.4 Hz).

Elemental analysis for C$_{29}$H$_{32}$N$_2$O$_3$ Calcd.: C, 76.29; H, 7.06; N, 6.14. Found: C, 76.25; H, 7.07; N, 6.09.

Melting point: 156–158° C. (crystallization solvent: ethyl acetate-diisopropyl ether)

EXAMPLE 36

N-[6-[(N,N-Dimethylamino)methyl]-5,6,7,8-tetrahydro-2-naphthalenyl]-4'-(methylsulfanyl)[1,1'-biphenyl]-4-carboxamide

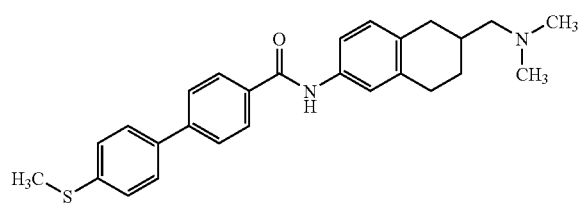

The titled compound (360 mg) was obtained as a white powder by the same method as in Example 16, using 4-bromo-N-[6-[(N,N-dimethylamino)methyl]-5,6,7,8-tetrahydro-2-naphthalenyl]benzamide (500 mg, 1.29 mmol) obtained in Example 15, and 4-methylthiophenylboric acid (260 mg, 1.55 mmol).

$^1$H-NMR (CDCl$_3$) δ: 1.41 (1H, m), 1.94 (2H, m), 2.26 (6H, s), 2.26–2.42 (3H, m), 2.53 (3H, s), 2.94 (3H, m), 7.09 (1H, d, J=8.1 Hz), 7.29–7.36 (3H, m), 7.46 (1H, s), 7.56 (2H, d, J=8.4 Hz), 7.67 (2H, d, J=8.1 Hz), 7.78 (1H, m), 7.92 (2H, d, J=9.0 Hz).

Elemental analysis for C$_{27}$H$_{30}$N$_2$OS.0.2H$_2$O Calcd.: C, 74.69; H, 7.04; N, 6.45. Found: C, 74.63; H, 7.03; N, 6.11.

Melting point: 178–180° C. (crystallization solvent: ethyl acetate-diisopropyl ether)

EXAMPLE 37

4'-(N,N-Dimethylamino)-N-[6-[(N,N-dimethylamino)methyl]-5,6,7,8-tetrahydro-2-naphthalenyl][1,1'-biphenyl)-4-carboxamide

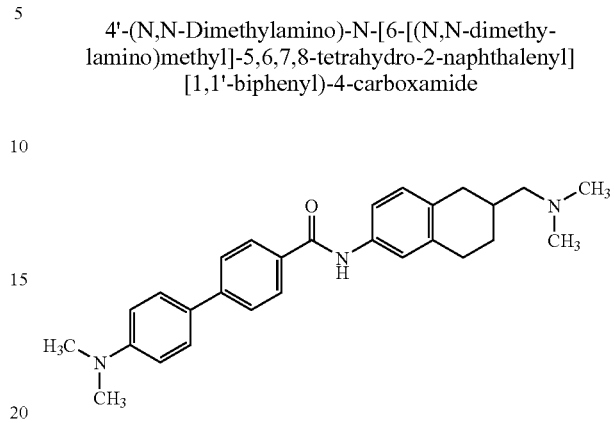

4'-Amino-N-[6-[(N,N-dimethyl)methyl]-5,6,7,8-tetrahydro-2-naphthalenyl][1,1'-biphenyl]-4-carboxamide (150 mg, 0.375 mmol) obtained in Example 33, and paraformaldehyde (45.1 mg, 1.50 mmol) were suspended in mixed solution of methanol (1 ml) and tetrahydrofuran (1 ml). Sodium cyanohydroborate (94.4 mg, 1.50 mmol) was added to the reaction mixture, which was stirred at 40° C. for 18 hours. Ethyl acetate was added to the reaction mixture, which was washed with saturated aqueous sodium chloride solution, dried using anhydrous magnesium sulfate, and the solvent was distilled out under reduced pressure. The residue was refined using alumina column chromatography (development solvent; ethyl acetate), and pulverized using isopropyl ether, to give the titled compound (13 mg) as a white powder.

$^1$H-NMR (DMSO-d$_6$) δ: 1.32 (1H, m), 1.90 (2H, m), 2.15 (6H, s), 2.15–2.35 (3H, m), 2.77 (3H, m), 2.97 (6H, s), 6.82 (2H, d, J=8.4 Hz), 7.03 (1H, d, J=8.4 Hz), 7.48 (1H, d, J=8.1 Hz), 7.53 (1H, s), 7.63 (2H, d, J=8.7 Hz), 7.74 (2H, d; J=7.8 Hz), 7.98 (2H, d, J=8.4 Hz), 10.04 (1H, s).

FABMS(pos) 428.2[M+H]$^+$

Melting point: 212–213° C. (crystallization solvent: ethyl acetate-diisopropyl ether)

EXAMPLE 38 N-[6-[(N,N-Dimethylamino)methyl]-5,6,7,8-tetrahydro-2-naphthalenyl]-4'-(methylamino)[1,1'-biphenyl]-4-carboxamide

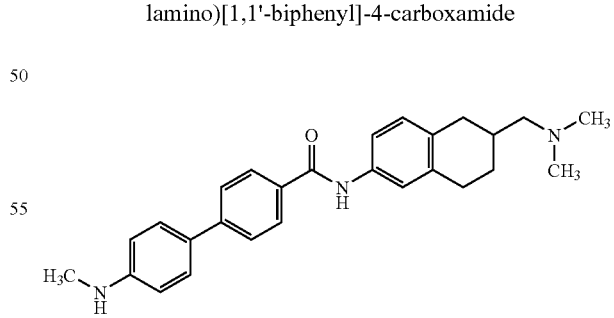

The titled compound was obtained as a white powder by the same method as in Example 37, using 4'-amino-N-[6-[(N,N-dimethyl)methyl]-5,6,7,8-tetrahydro-2-naphthalenyl][1,1'-biphenyl]-4-carboxamide (150 mg, 0.375 mmol) obtained in Example 33, paraformaldehyde (15.0 mg, 0.50 mmol), and sodium cyanohydroborate (31.5 mg, 0.50 mmol).

¹H-NMR (DMSO-d₆) δ: 1.32 (1H, m), 1.89 (2H, m), 2.15 (6H, s), 2.15–2.31 (3H, m), 2.72 (7H, m), 5.94 (1H, m), 6.64 (2H, d, J=9.0 Hz), 7.03 (1H, d, J=8.7 Hz), 7.49 (4H, m), 7.70 (1H, d, J=8.4 Hz), 7.97 (2H, d, J=8.4 Hz), 10.02 (1H, s).

FABMS(pos) 414.3[M+H]⁺

Melting point: 163–165° C. (crystallization solvent: ethyl acetate-diisopropyl ether)

EXAMPLE 39

N-[6-[(N,N-Dimethyl)methyl]-5,6,7,8-tetrahydro-2-naphthalenyl]-4-(2-furyl)benzamide The titled compound (67 mg) was obtained as a white powder by the same method as in Example 16, using 4-bromo-N-[6-[(N,N-dimethyl)methyl]-5,6,7,8-tetrahydro-2-naphthalenyl]benzamide (250 mg, 0.645 mmol) obtained in Example 15, and 2-furylboric acid (86.7 mg, 0.775 mmol).

¹H-NMR (DMSO-d₆) δ: 1.40 (1H, m), 1.94 (2H, m), 2.25 (6H, s), 2.25–2.45 (3H, m), 2.88 (3H, m), 7.08 (1H, d, J=8.1 Hz), 7.26 (4H, m), 7.41 (1H, m), 7.60–7.74 (5H, m).

FABMS(pos) 375.2[M+H]⁺

EXAMPLE 40

4'-[[[6-[(N,N-Dimethylamino)methyl]-5,6,7,8-tetrahydro-2-naphthalenyl]amino]carbonyl][1,1'-biphenyl]-4-carboxylic acid Ethyl-4'-[[[6-[(N,N-dimethyl)methyl]-5,6,7,8-tetrahydro-2-naphthalenyl]amino]carbonyl][1,1'-biphenyl]-4-carboxylate (100 mg, 0.219 mmol) obtained in Example 35 was dissolved in a mixed solution of ethanol (3 ml) and water (0.5 ml). 1N aqueous sodium hydroxide solution (0.329 ml) was added to the reaction mixture at room temperature, which was stirred at 90° C. for 5 hours. After the solvent was distilled out under reduced pressure, water was added to the residue, then 1N hydrochloric acid (0.329 ml) was added and the reaction mixture was stirred. The precipitated crude product collected by filtration, and washed with water to give the titled compound (89 mg) as a white powder.

¹H-NMR (DMSO-d₆) δ: 1.34 (1H, m), 1.91 (2H, m), 2.24 (6H, s), 2.24–2.30 (3H, m), 2.81 (3H, m), 7.05 (1H, d, J=8.4 Hz), 7.49 (1H, d, J=8.4 Hz), 7.55 (1H, s), 7.89 (4H, m), 8.07 (4H, m), 10.18 (1H, s).

Elemental analysis for $C_{27}H_{28}N_2O_3 \cdot 2H_2O$ Calcd.: C, 69.81; H, 6.94; N, 6.03. Found: C, 69.57; H, 7.01; N, 5.93.

Melting point: 143° C. (decomposition) (crystallization solvent: water)

EXAMPLE 41

4'-Chloro-N-[6-[(N,N-dimethyl)methyl]-7,8-dihydro-2-naphthalenyl][1,1'-biphenyl]-4-carboxamide 1) 6-Acetamido-1-tetralone (5.0 g, 0.0246 mol) synthesized according to a known method by documents (Journal of Organic Chemistry 27, 70 (1962)), was dissolved in 50 ml of DMF dimethylacetal, which was stirred at 110° C. for 2 hours. The precipitate was collected by filtration, and washed with ethyl acetate to give 6-acetamido-2-(N,N-dimethylaminomethylidene)-1-tetralone (4.98 g) as a yellow powder.

¹H-NMR (CDCl₃) δ: 2.19 (3H, s), 2.79–2.83, (2H, m), 2.88–2.92 (2H, m), 3.11 (6H, s), 7.14–7.17 (1H, m7.68 (1H, s), 7.69 (1H, s), 7.95 (1H, d, J=8.1 Hz), 7.96 (1H, s).

Melting point: 207–210° C. (crystallization solvent: ethyl acetate)

2) The obtained 6-acetamido-2-(N,N-dimethylaminomethylidene)-1-tetralone (4.50 g, 0.0173 mol) was dissolved in methanol (50 ml), and sodium borohydride (6.56 g, 0.173 mol) was added to the solution under ice-cooling, which was stirred for 2 hours. The reaction mixture was concentrated. Ethyl acetate and sodium hydrogencarbonate solution were added to the residue, and extraction was conducted. The ethyl acetate layer was concentrated, and 30 ml of tetrahydrofuran and 30 ml of 2N hydrochloric acid were added to the residue, which was refluxed with heating for 16 hours. The reaction mixture was concentrated, and ethyl acetate and 2N sodium hydroxide solution were added, and extraction was conducted. The ethyl acetate layer was concentrated, and the residue was refined using alumina column chromatography (development solvent; ethyl acetate:n-hexane=30:70), to give 6-[(N,N-dimethylamino)methyl]-7,8-dihydro-2-naphthaleneamine (1.60 g) as a colorless oily substance.

¹H-NMR (CDCl₃) δ: 2.23 (6H, s), 2.28 (2H, t, J=8.4 Hz), 2.74 (2H, t, J=8.4 Hz), 2.95 (2H, s), 3.57–3.72 (2H, m), 6.25 (1H, s), 6.46–6.48 (2H, m), 6.83 (1H, d, J=8.7 Hz).

3) The titled compound (1.12 g) was obtained as a white powder by the same method as in Example 1, using the obtained 6-[(N,N-dimethylamino)methyl]-7,8-dihydro-2-naphthalenamine (1.00 g, 0.005 mol), and 4-chlorobiphenyl carboxylic acid (2.31 g, 0.01 mol).

¹H-NMR (CDCl₃) δ: 2.25 (6H, s), 2.34 (2H, t, J=7.8 Hz), 2.86 (2H, t, J=7.8 Hz), 2.99 (2H, s), 6.34 (1H, s), 7.03 (1H, d, J=8.7 Hz), 7.39 (1H, d, J=8.1 Hz), 7.45 (2H, d, J=8.7), 7.48 (1H, s), 7.56 (2H, d, J=8.4 Hz), 7.67 (2H, d, J=8.4 Hz), 7.78 (1H, s), 7.94 (2H, d, J=8.4 Hz).

Elemental analysis for $C_{26}H_{25}ClN_2O$ Calcd.: C, 74.90; H, 6.04; N. 6.72. Found: C, 74.64; H, 6.14; N, 6.56.

Melting point: 204–207° C. (crystallization solvent: ethyl acetate-n-hexane)

EXAMPLE 42

4'-Fluoro-N-[6-[(N,N-dimethylamino)methyl]-7,8-dihydro-2-naphthalenyl][1,1'-biphenyl]-4-carboxamide

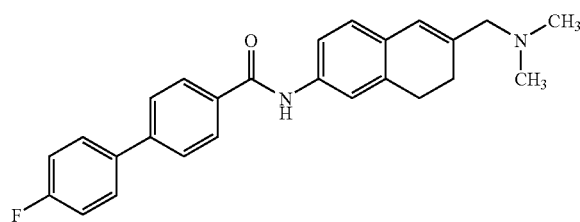

The titled compound (990 mg) was obtained as a white powder by the same method as in Example 1, using 6-[(N,N-dimethylamino)methyl]-7,8-dihydro-2-naphthalenamine (936 mg, 4.62 mmol) obtained in Example 41–2), and 4-fluorobiphenylcarboxyic acid (1.00 g, 4.62 mmol).

$^1$H-NMR (CDCl$_3$) δ: 2.25 (6H, s), 2.34 (2H, t, J=8.1 Hz), 2.85 (2H, t, J=8.1 Hz), 2.99 (2H, s), 6.34 (1H, s), 7.02 (1H, d, J=8.1 Hz), 7.13–7.19 (2H, m), 7.38–7.41 (1H, m), 7.48 (1H, s), 7.56–7.61 (2H, m), 7.65 (2H, d, J=8.4 Hz), 7.80 (1H, s), 7.93 (2H, d, J=8.5 Hz).

Elemental analysis for, $C_{26}H_{25}FN_2O$ Calcd.: C, 77.97; H, 6.29; N, 6.99. Found: C, 77.90; H, 6.23; N, 6.58.

Melting point: 190–193° C. (crystallization solvent: ethyl acetate-n-hexane)

EXAMPLE 43

4'-Chloro-N-[2-[(dimethylamino)methyl]-2,3-dihydro-1H-inden-5-yl][1,1'-biphenyl]-4-carboxamide

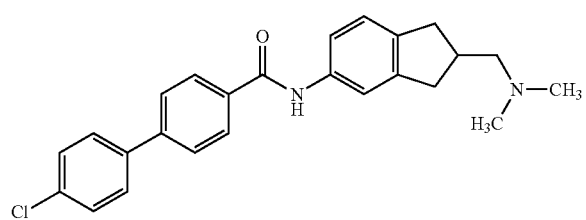

Concentrated hydrochloric acid (1 ml) was added to N-[2-[(dimethylamino)methyl]-2,3-dihydro-1H-inden-5-yl]acetamide (48.9 mg, 0.210 mmol) obtained in Reference Example 48, which was stirred at 110° C. for 2 hours, and the solvent was distilled out under reduced pressure. Ethyl acetate was added to the residue, which was washed with potassium carbonate solution and saturated aqueous sodium chloride solution, dried using anhydrous sodium sulfate, and then the solvent was distilled out under reduced pressure. Using the oily substance obtained, the same operation as in Example 1 was conducted to give the titled compound (30 mg).

$^1$H NMR (DMSO-d$_6$) δ: 2.16 (6H, s), 2.22 (2H, d, J=6.7 Hz), 2.61 (4H, m), 2.97 (1H, m), 7.15 (1H, d, J=8.1 Hz), 7.47 (1H, d, J=8.1 Hz), 7.56 (2H, d, J=8.4 Hz), 8.05 (2H, d, J=8.4 Hz), 10.17 (1H, s).

FAB(pos) 405.1 [M+H]$^+$

Melting point: 192–194° C. (crystallization solvent: ethyl acetate-diisopropyl ether)

EXAMPLE 44

4'-Chloro-N-[8-[(dimethylamino)methyl]-6,7-dihydro-5H-benzo[a]cyclohepten-3-yl][1,1'-biphenyl]-4-carboxamide

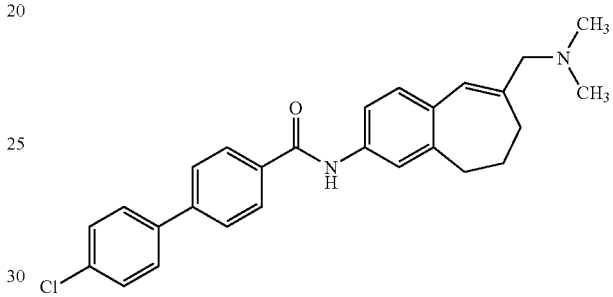

The titled compound was obtained by carrying out the same operation as in Example 1, using 8-[(dimethylamino)methyl]-6,7-dihydro-5H-benzo[a]cyclohepten-3-amine obtained in Reference Example 50.

$^1$H-NMR (CDCl$_3$) δ: 1.96–2.10 (2H, m), 2.25 (6H, s), 2.39 (2H, t, J=6.4 Hz), 2.79–2.85 (2H, m), 2.96 (2H, s), 6.40 (1H, s), 7.15 (1H, d, J=8.6 Hz), 7.40–7.52 (4H, m), 7.56 (2H, d, J=8.4 Hz), 7.67 (2H, d, J=8.1 Hz), 7.81 (1H, s), 7.94 (2H, d, J=8.1 Hz).

Melting point: 183–185° C. (crystallization solvent: ethyl acetate-diethyl ether)

EXAMPLE 45

4'-Fluoro-N-[6-[(dimethylamino)methyl]-6,7,8,9-tetrahydro-5H-benzo[a]cyclohepten-2-yl][1,1'-biphenyl]-4-carboxamide

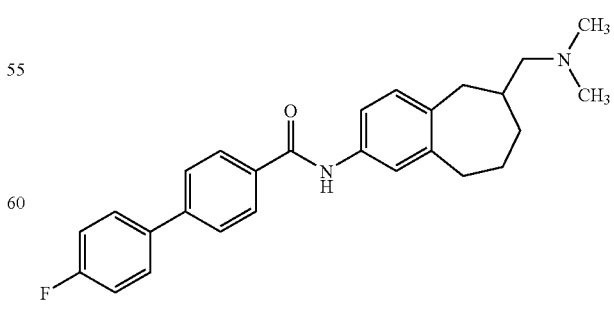

The titled compound was obtained by carrying out the same operation as in Example 1, using 6-[(dimethylamino)

methyl]-6,7,8,9-tetrahydro-5H-benzo[a]cyclohepten-2-amine obtained in Reference Example 51.

¹H-NMR (CDCl₃) δ: 1.40–1.68 (3H, m), 1.85–2.20 (10H, m), 2.55–2.92 (4H, m), 7.13–7.20 (3H, m), 7.35–7.43 (2H, m), 7.56–7.67 (4H, m), 7.77 (1H, s), 7.93 (2H, d, J=8.4 Hz).

Elemental analysis for C₂₇H₂₉FN₂O Calcd.: C, 77.85; H, 7.02; N, 6.73. Found: C, 78.18; H, 7.09; N, 6.74.

Melting point: 167–169° C. (crystallization solvent: diethyl ether)

EXAMPLE 46

4'-Chloro-N-[6-[(dimethylamino)methyl-6,7,8,9-tetrahydro-5H-benzo[a]cyclohepten-2-yl][1,1'-biphenyl]-4-carboxamide

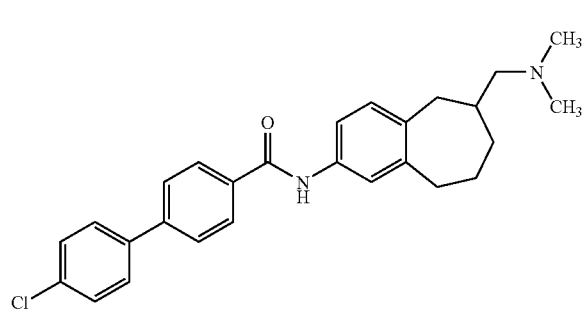

The titled compound was obtained by carrying out the same operation as in Experiment Example 1, using 6-[(dimethylamino) methyl]-6,7,8,9-tetrahydro-5H-benzo[a]cyclohepten-2-amine obtained in Reference Example 51.

¹H-NMR (CDCl₃) δ: 1.40–1.67 (3H, m), 1.85–2.20 (10H, m), 2.55–2.92 (4H, m), 7.15 (1H, d, J=8.1 Hz), 7.35–7.46 (4H, m), 7.56 (2H, d, J=8.4 Hz), 7.66 (2H, d, J=8.1 Hz), 7.77 (1H, s), 7.93 (2H, d, J=8.4 Hz).

Elemental analysis for C₂₇H₂₉ClN₂O Calcd.: C, 74.90; H, 6.75; N, 6.47. Found: C, 74.77; H, 6.65; N, 6.43.

Melting point: 173–175° C. (crystallization solvent: diethyl ether)

EXAMPLE 47

N-[6-[(Dimethylamino)methyl]-7,8-dihydro-2-naphthalenyl][1,1'-biphenyl]-4-carboxamide

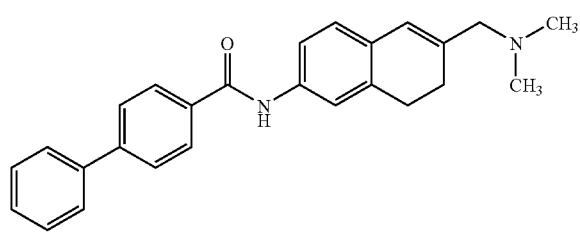

The titled compound was obtained by carrying out the same operation as in Example 1, using 6-[(N,N-dimethylamino)methyl]-7,8-dihydro-2-naphthalenamine obtained in Example. 41-2).

¹H NMR (CDCl₃) δ: 2.25 (6H, s), 2.33 (2H, t, J=5.4 Hz), 2.84 (2H, t, J=5.4 Hz), 2.98 (2H, s), 6.34 (1H, s), 7.01 (1H, d, J=7.8 Hz), 7.32–7.94 (12H, m).

Elemental analysis for C₂₆H₂₆N₂O Calcd.: C, 81.64; H, 6.85; N, 7.32. Found: C, 81.65; H, 6.79; N, 6.91.

Melting point: 173–175° C. (crystallization solvent: tetrahydrofuran-n-hexane)

EXAMPLE 48

N-[6-(1-Piperidinylmethyl)-7,8-dihydro-2-naphthalenyl][1,1'-biphenyl]-4-carboxamide

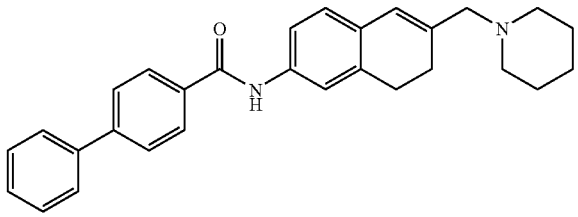

The titled compound was obtained by carrying out the same operation as in Example 1, using 6-(1-piperidinylmethyl)-7,8-dihydro-2-naphthalenamine obtained in Reference Example 52.

¹H NMR (CDCl₃) δ: 1.46–1.59 (6H, m), 2.31–2.36 (6H, m), 2.84 (2H, t, J=8.0 Hz), 3.02 (2H, s), 6.34 (1H, s), 7.02 (1H, d, J=8.1 Hz), 7.37–7.50 (4H, m), 7.63 (2H, d, J=6.9 Hz), 7.71 (2H, d, J=8.1 Hz), 7.79 (1H, s), 7.94 (2H, d, J=8.1 Hz).

Melting point: 156–158° C. (crystallization solvent: tetrahydrofuran-n-hexane)

EXAMPLE 49

N-[6-[(Dimethylamino)methyl]-7,8-dihydro-2-naphthalenyl]-4'-trifluoromethyl[1,1'-biphenyl]-4-carboxamide

The titled compound was obtained by carrying out the same operation as in Example 1, using 6-[(N,N-dimethylamino)methyl]-7,8-dihydro-2-naphthalenamine obtained in Example 41-2).

¹H NMR (CDCl₃) δ: 2.25 (6H, s), 2.34 (d, J=5.1 Hz), 2.86 (2H, d, J=5.1 Hz), 2.99 (2H, s), 6.35 (1H, s), 7.04 (1H, d, J=8.4 Hz), 7.40 (1H, d, J=3.3 Hz), 7.49 (1H, s), 7.70–7.79 (6H, m), 7.87 (2H, d, J=8.4 Hz).

Melting point: 214–216° C. (crystallization solvent: ethyl acetate-diisopropyl ether)

EXAMPLE 50

2'-Chloro-N-[6-[(dimethylamino)methyl]-7,8-dihydro-2-naphthalenyl][1,1'-biphenyl]-4-carboxamide

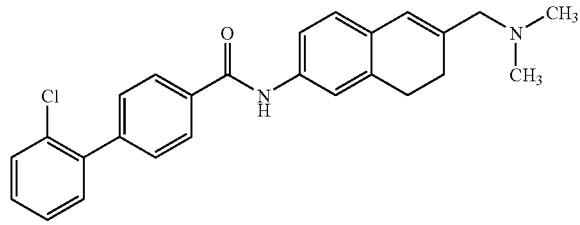

The titled compound was obtained by carrying out the same operation as in Example 1, using 6-[(N,N-dimethylamino)methyl]-7,8-dihydro-2-naphthalenamine obtained in Example 41-2).

$^1$H NMR (CDCl$_3$) δ: 2.25 (6H, s), 2.34 (d, J=5.1 Hz), 2.85 (2H, d, J=5.1 Hz), 3.00 (2H, s), 6.34 (1H, s), 6.69 (1H, s), 7.02 (1H, d, J=8.4 Hz), 7.31–7.57 (8H, m), 7.85 (1H, s), 7.92 (2H, d, J=7.8 Hz).

Elemental analysis for C$_{26}$H$_{25}$ClN$_2$O Calcd.: C, 74.90; H, 6.04; N, 6.72. Found: C, 74.49; H, 5.65; N, 6.06.

Melting point: 145–147° C. (crystallization solvent: ethyl acetate-n-hexane)

EXAMPLE 51

4'-Chloro-N-[6-(1-piperidinylmethyl)-7,8-dihydro-2-naphthalenyl][1,1'-biphenyl]-4-carboxamide

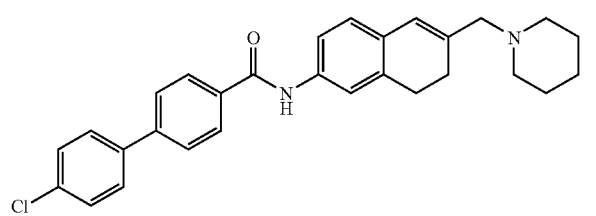

After N,N-dimethylformaldehyde solution (5 ml) of 4'-chloro-N-[6-(chloromethyl)-7,8-dihydro-2-naphthalenyl][1,1'-biphenyl]-4-carboxamide (225 mg) obtained in Reference Example 56, piperidine (0.16 ml), and diisopropylethylamine (0.282 ml) was stirred at room temperature for 15 hours, which was heated at 120° C. for 2 hours. The residue obtained by concentrating the reaction mixture was dissolved in water-ethyl acetate, then extracted using ethyl acetate. The extract was washed with saturated aqueous sodium chloride solution, dried using anhydrous magnesium sulfate, and then the solvent was distilled out under reduced pressure. The resulting residue was refined using alumina column chromatography (development solvent; tetrahydrofuran: n-hexane=1:5), and crystallized using tetrahydrofuran-n-hexane to give the titled compound (110 mg).

$^1$H NMR (CDCl$_3$) δ: 1.26–1.61 (6H, m), 2.30–2.36 (6H, m), 2.83 (2H, t, J=8.4 Hz), 3.02 (2H, s), 6.33 (1H, s), 7.01 (1H, d, J=8.1 Hz), 7.36–7.49 (4H, m), 7.55 (2H, d, J=8.4 Hz), 7.66 (2H, d, J=8.4 Hz), 7.81 (1H, s), 7.93 (2H, d, J=8.1 Hz).

Melting point: 209–211° C. (crystallization solvent: tetrahydrofuran-n-hexane

EXAMPLE 52

4'-Fluoro-N-[6-(1-piperidinylmethyl)-7,8-dihydro-2-naphthalenyl][1,1'-biphenyl]4-carboxamide

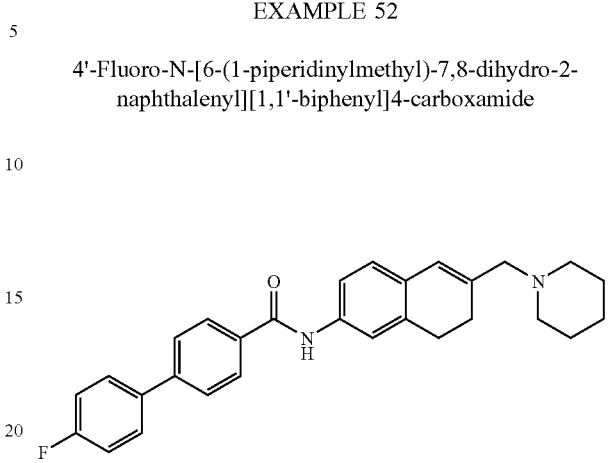

The titled compound was obtained by carrying out the same operation as in Example 1, using the 6-(1-piperidinyl methyl)-7,8-dihydro-2-naphthalene amine obtained in Reference example 52.

$^1$H NMR (CDCl$_3$) δ: 1.45–1.58 (6H, m), 2.29–2.37 (6H, m), 2.82 (2H, t, J=8.0 Hz), 3.01 (2H, s), 6.33 (1H, s), 6.98–7.93 (12H, m).

Melting point: 190–192° C. (crystallization solvent: tetrahydrofuran-n-hexane)

EXAMPLE 53

N-[6-(1-Piperidinylmethyl)-5,6,7,8-tetrahydro-2-naphthalenyl][1,1'-biphenyl]-4-carboxamide

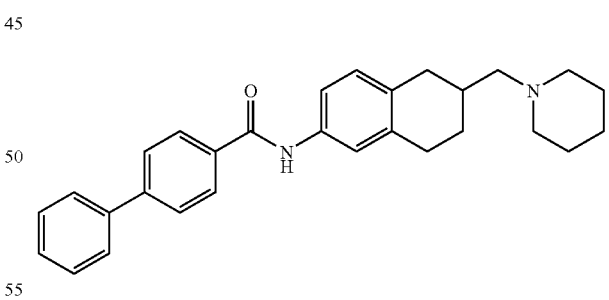

The titled compound was obtained by carrying out the same operation as in Example 1, using 6-(1-piperidinylmethyl)-5,6,7,8-tetrahydro-2-naphthalenamine obtained in Reference Example 53.

$^1$H NMR (CDCl$_3$) δ: 1.37–1.60 (8H, m), 1.96–2.00 (2H, m), 2.24–2.44 (5H, m), 2.82–2.93 (3H, m), 7.09 (1H, d, J=8.3 Hz), 7.30–7.33 (1H, m), 7.38–7.65 (6H, m), 7.70 (2H, d, J=8.4 Hz), 7.76 (1H, s), 7.93 (2H, d, J=8.4 Hz).

Melting point: 160–162° C. (crystallization solvent: tetrahydrofuran-n-hexane)

EXAMPLE 54

4'-Fluoro-N-[6-(1-piperidinylmethyl)-5,6,7,8-tetrahydro-2-naphthalenyl][1,1'-biphenyl]-4-carboxamide

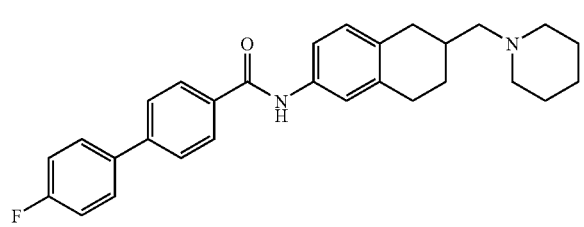

The titled compound was obtained by carrying out the same operation as in Example 1, using 6-(1-piperidinylmethyl)-5,6,7,8-tetrahydro-2-naphthalenamine obtained in Reference Example 53.

$^1$H NMR (CDCl$_3$) δ: 1.36–1.52 (8H, m), 2.29–2.31 (2H, m), 2.24–2.45 (6H, m), 2.82–2.93 (3H, m), 7.08–7.33 (4H, m), 7.44 (1H, s), 7.57–7.66 (4H, m), 7.74 (1H, s), 7.92 (2H, J=8.1 Hz).

Elemental analysis for C$_{29}$H$_{31}$FN$_2$O Calcd.: C, 78.70; H, 7.08; N, 6.33. Found: C, 78.40; H, 7.09; N, 6.09.

Melting point: 179–181° C. (crystallization solvent: ethyl acetate)

EXAMPLE 55

4'-Chloro-N-[6-[1-piperidinylmethyl)-5,6,7,8-tetrahydro-2-naphthalenyl][1,1'-biphenyl]-4-carboxamide

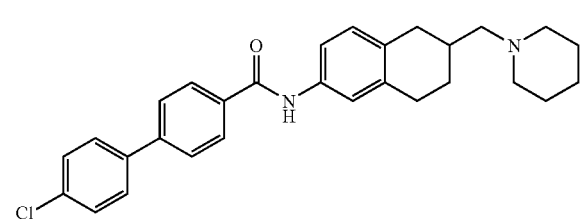

The titled compound was obtained by carrying out the same operation as in Example 1, using 6-(1-piperidinylmethyl)-5,6,7,8-tetrahydro-2-naphthalenamine obtained in Reference Example 53.

$^1$H NMR (CDCl$_3$) δ: 1.25–1.71 (8H, m), 1.95–2.00 (2H, m), 2.25–2.45 (6H, m), 2.83–2.93 (3H, m), 7.09 (1H, d, J=8.3 Hz), 7.30–7.3.2 (1H, m), 7.43–7.45 (3H, m), 7.55 (2H, d, J=8.1 Hz), 7.65 (2H, d, J=8.4 Hz), 7.77 (1H, s), 7.93 (2H, d, J=8.1 Hz).

Melting point: 202–203° C. (crystallization solvent: tetrahydrofuran-n-hexane)

EXAMPLE 56

5-Oxo-1-phenyl-N-[6-(1-piperidinylmethyl)-5,6,7,8-tetrahydro-2-naphthalenyl]-3-pyrrolidinecarboxamide

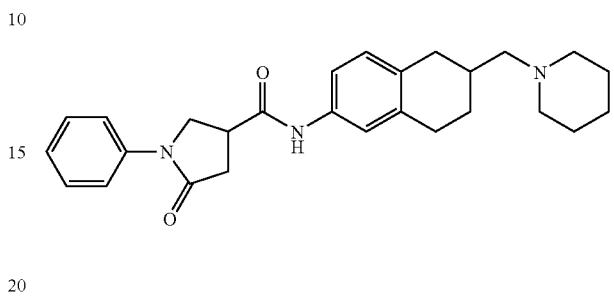

The titled compound was obtained by carrying out the same operation as in Example 1, using 6-(1-piperidinylmethyl)-5,6,7,8-tetrahydro-2-naphthalenamine obtained in Reference Example 53.

$^1$H NMR (CDCl$_3$) δ: 1.03–3.33 (22H, m), 3.97 (1H, t, J=8.4 Hz), 4.21 (1H, dd, J=6.8, 7.1 Hz), 6.91–7.63 (9H, m).

Elemental analysis for C$_{27}$H$_{33}$N$_3$O$_2$ Calcd.: C, 75.14; H, 7.71; N, 9.74. Found: C, 75.01; H, 7.33; N, 9.43.

Melting point: 162–164° C. (crystallization solvent: ethyl acetate)

EXAMPLE 57

6-(4-Chlorophenyl)-N-[6-(1-piperidinylmethyl)-5,6,7,8-tetrahydro-2-naphthalenyl]nicotinamide

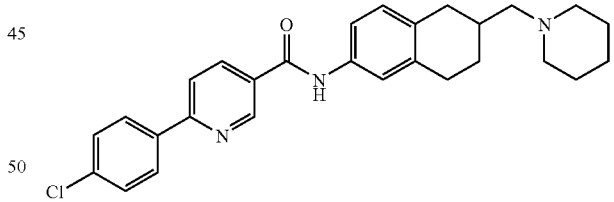

The titled compound was obtained by carrying out the same operation as in Example 1, using 6-(1-piperidinylmethyl)-5,6,7,8-tetrahydro-2-naphthalenamine obtained in Reference Example 53.

$^1$H NMR (CDCl$_3$) δ: 1.30–2.40 (16H, m), 2.82–2.92 (3H, m), 7.09 (1H, d, J=8.1 Hz), 7.26–7.48 (4H, m), 7.80 (2H, d, J=8.7 Hz), 7.99 (2H, d, J=8.7 Hz), 8.23 (d, 1H, J=6.3 Hz), 9.11 (1H, s).

Melting point: 193–195° C. (crystallization solvent: ethyl acetate)

EXAMPLE 58

5-(4-Chlorophenyl)-N-[6-(1-piperidinylmethyl)-5,6,7,8-tetrahydro-2-naphthalenyl]-2-furamide

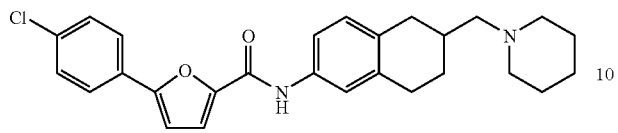

The titled compound was obtained by carrying out the same operation as in Example 1, using 6-(1-piperidinylmethyl)-5,6,7,8-tetrahydro-2-naphthalenamine obtained in Reference Example 53.

$^1$H NMR (CDCl$_3$) δ: 1.23–1.61 (7H, m), 1.96–2.00 (2H, m), 2.24–2.43 (7H, m), 2.80–2.92 (3H, m), 6.75 (1H, d, J=3.6 Hz), 7.07 (1H, d, J=8.4 Hz), 7.27 (1H, d, J=3.6 Hz), 7.32–7.42 (4H, m), 7.66 (2H, d, J=8.4 Hz), 8.32 (1H, s).

EXAMPLE 59

N-[6-(1-Piperidinylmethyl)-5,6,7,8-tetrahydro-2-naphthalenyl]-3-(2,4,5-triethoxyphenyl)-5-isoxazole-carboxamide

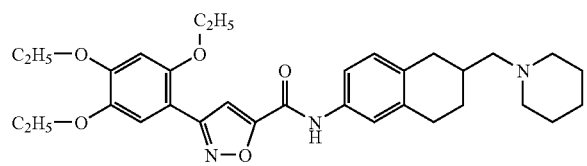

The titled compound was obtained by carrying out the same operation as in Example 1, using 6-(1-piperidinylmethyl)-5,6,7,8-tetrahydro-2-naphthalenamine obtained in Reference Example 53.

$^1$H NMR (CDCl$_3$) δ: 1.42–1.60 (18H, m), 1.97–2.36 (7H, m), 2.80–2.95 (3H, m), 4.06–4.18 (6H, m), 6.58 (1H, s), 7.09 (1H, d, J=8.4 Hz), 7.35 (1H, d, J=8.1 Hz), 7.44 (1H, s), 7.50 (1H, s), 7.55 (1H, s), 8.16 (1H, s).

EXAMPLE 60

4-(4-Chlorophenyl)-2-phenyl-N-[6-(1-piperidinylmethyl)-5,6,7,8-tetrahydro-2-naphthalenyl]-1,3-oxazole-5-carboxamide

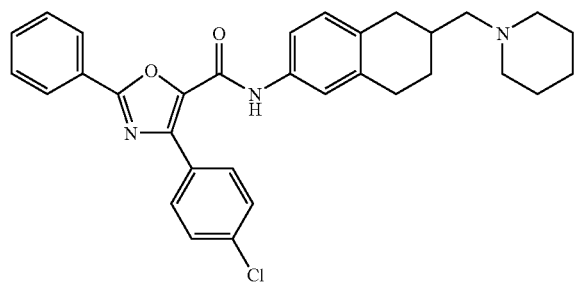

The titled compound was obtained by carrying out the same operation as in Example 1, using 6-(1-piperidinylmethyl)-5,6,7,8-tetrahydro-2-naphthalenamine obtained in Reference Example 53.

$^1$H NMR (CDCl$_3$) δ: 1.26–1.58 (7H, m), 1.90–2.00 (2H, m), 2.22–2.35 (7H, m), 2.70–2.95 (3H, m), 7.06 (1H, d, J=8.1 Hz), 7.25–7.51 (7H, m), 8.04–8.32 (5H, m).

EXAMPLE 61

4'-Chloro-N-[6-(1-pyrrolidinylmethyl)-7,8-dihydro-2-naphthalenyl][1,1-biphenyl]-4-carboxamide

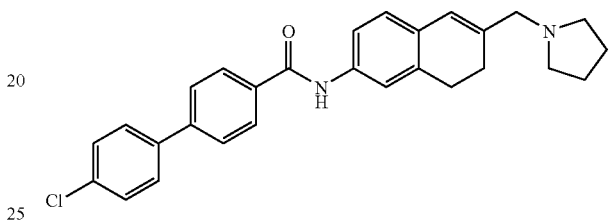

The titled compound was obtained by carrying out the same operation as in Example 51, using 4'-chloro-N-[6-(chloromethyl)-7,8-dihydro-2-naphthalenyl][1,1'-biphenyl]-4-carboxamide obtained in Reference Example 56.

Melting point: 185–187° C. (crystallization solvent: tetrahydrofuran-n-hexane)

$^1$H NMR (CDCl$_3$) δ: 1.83 (4H, s), 2.35 (2H, t, J=8.1 Hz), 2.52 (4H, s), 2.84 (2H, t, J=8.1 Hz), 3.18 (2H, s), 6.36 (1H, s), 7.02 (1H, d, J=8.4 Hz), 7.39–7.56 (6H, m), 7.66 (2H, d, J=7.5 Hz), 7.82 (1H, s), 7.93 (2H, d, J=7.5 Hz).

EXAMPLE 62

5-(4-Chlorophenyl)-N-[6-(1-pyrrolidinylmethyl)-7,8-dihydro-2-naphthalenyl)-2-pyridinecarboxamide

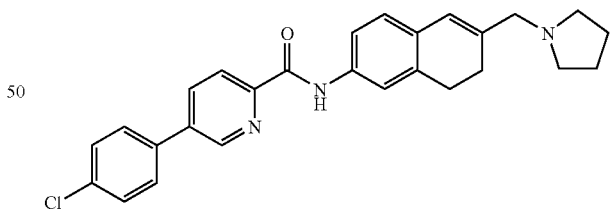

The titled compound was obtained by carrying out the same operation as in Example 51, using 4'-chloro-N-[6-(chloromethyl)-7,8-dihydro-2-naphthalenyl][1,1'-biphenyl]-4-carboxamide obtained in Reference Example 56.

$^1$H NMR (CDCl$_3$) δ: 1.80 (6H, s), 2.37 (2H, t, J=8.1 Hz), 2.52 (4H, s), 2.87 (2H, t, J=8.1 Hz), 3.18(2H, s), 6.37 (1H, s), 7.03 (1H, d, J=7.8 Hz), 7.48–7.61 (6H, m), 8.04 (1H, dd, J=8.1, 2.1 Hz), 8.35 (1H, d, J=8.1 Hz), 8.78 (1H, s), 9.95 (1H, s).

EXAMPLE 63

4-(4-Pyridinyl)-N-[6-(1-pyrrolidinylmethyl)-7,8-dihydro-2-naphthalenyl]benzamide

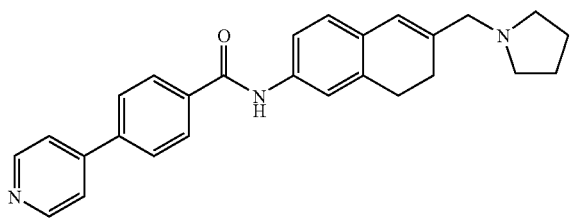

The titled compound was obtained by carrying out the same operation as in Example 1, using 6-(1-pyrrolidinylmethyl)-7,8-dihydro-2-naphthalenamine obtained in Reference Example 54.

$^1$H NMR (CDCl$_3$) δ: 1.79–1.83 (6H, m), 2.35 (2H, t, J=8.1 Hz), 2.53 (4H, s), 2.73 (2H, t, J=8.1 Hz), 3.18 (2H, s), 6.36 (1H, s), 7.02 (1H, d, J=7.8 Hz), 7.38 (1H, d, J=8.1 Hz), 7.48 (1H, s), 7.71–7.78 (4H, m), 7.89 (1H, s), 7.99 (1H, d, J=8.4 Hz), 8.32 (2H, d, J=8.4 Hz).

EXAMPLE 64

4'-Chloro-N-[6-[(4-phenyl-1-piperidinyl)methyl]-7,8-dihydro-2-naphthalenyl][1,1'-biphenyl]-4-carboxamide The titled compound was obtained by carrying out the same operation as in Example 51, using 4'-chloro-N-[6-(chloromethyl)-7,8-dihydro-2-naphthalenyl][1,1'-biphenyl]-4-carboxamide obtained in Reference Example 56.

$^1$H NMR (CDCl$_3$) δ: 1.83–2.10 (6H, m), 2.37 (2H, t, J=8.1 Hz), 2.47–2.54 (1H, m), 2.86 (2H, t, J=8.1 Hz), 3.03–3.10 (2H, m), 3.10 (2H, s), 6.37 (1H, s), 7.03 (1H, d, J=8.4 Hz), 7.19–7.57 (11H, m), 7.66 (2H, d, J=8.4 Hz), 7.81 (1H, s), 7.94 (2H, d, J=8.4 Hz).

Melting point: 228–230° C. (crystallization solvent: tetrahydrofuran-n-hexane)

EXAMPLE 65

4'-Chloro-N-[6-(4-morpholinylmethyl)-7,8-dihydro-2-naphthalenyl][1,1'-biphenyl]-4-carboxamide

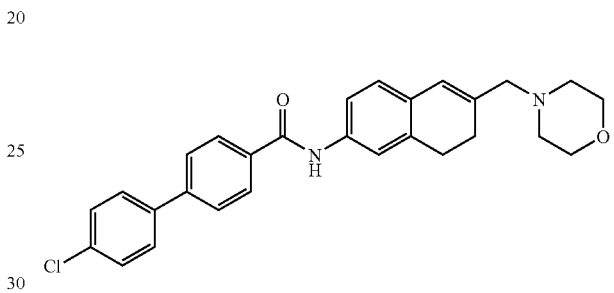

The titled compound was obtained by carrying out the same operation as in Example 51, using 4'-chloro-N-[6-(chloromethyl)-7,8-dihydro-2-naphthalenyl][1,1'-biphenyl]-4-carboxamide obtained in Reference Example 56.

$^1$H NMR (CDCl$_3$) δ: 2.34 (2H, t, J=7.8 Hz), 2.45 (4H, s), 2.84 (2H, t, J=7.8 Hz), 3.06 (2H, s), 3.73 (4H, s), 6.36 (1H, s), 7.02 (1H, d, J=8.1 Hz), 7.36–7.57 (6H, m), 7.67 (2H, d, J=8.4 Hz), 7.80 (1H, s), 7.94 (2H, d, J=8.4 Hz).

Melting point: 194–195° C. (crystallization solvent: tetrahydrofuran-n-hexane)

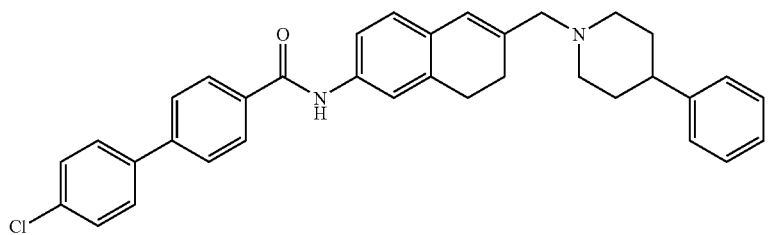

EXAMPLE 66

4'-Chloro-N-(6-[[methyl(2-phenylethyl)amino]methyl]-7,8-dihydro-2-naphthalenyl[1,1'-biphenyl]-4-carboxamide

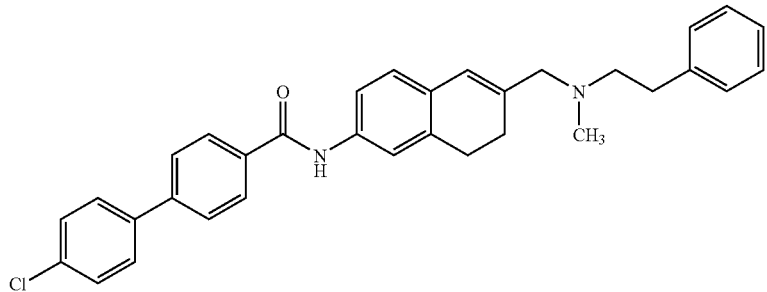

The titled compound was obtained by carrying out the same operation as in Example 51, using 4'-chloro-N-[6-(chloromethyl)-7,8-dihydro-2-naphthalenyl][1,1'-biphenyl]-4-carboxamide obtained in Reference Example 56.

$^1$H NMR (CDCl$_3$) δ: 2.25–2.32 (2H, m), 2.32 (3H, s), 2.60–2.66 (2H, m), 2.77–2.83 (4H, m), 3.10 (2H, s), 6.32 (1H, s), 6.93–7.95 (16H, m).

Melting point: 173–175° C. (crystallization solvent: tetrahydrofuran-n-hexane)

EXAMPLE, 67

4'-Chloro-N-[6-[methylanilino)methyl]-7,8-dihydro-2-naphthalenyl][1,1'-biphenyl]-4-carboxamide

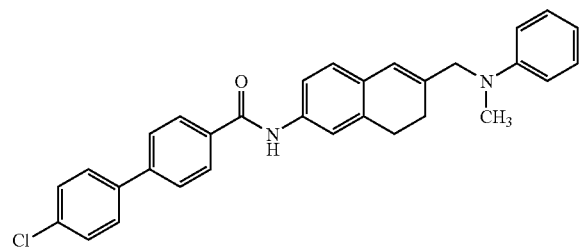

The titled compound was obtained by carrying out the same operation as in Example 51, using 4'-chloro-N-[6-(chloromethyl)-7,8-dihydro-2-naphthalenyl][1,1'-biphenyl]-4-carboxamide obtained in Reference Example 56.

$^1$H NMR (CDCl$_3$) δ: 2.20–2.30 (2H, m), 2.25 (3H, s), 2.85–2.90 (2H, m), 3.00 (2H, s), 6.30 (1H, s), 6.74–7.95 (146H, m).

Melting point: 177–179° C. (crystallization solvent: tetrahydrofuran-n-hexane)

EXAMPLE 68

4'-Chloro-N-[6-[(4-phenyl-1-piperazinyl)methyl]-7,8-dihydro-2-naphthalenyl][1,1'-biphenyl]-4-carboxamide The titled compound was obtained by carrying out the same operation as in Example 51, using 4'-chloro-N-[6-(chloromethyl)-7,8-dihydro-2-naphthalenyl][1,1'-biphenyl]-4-carboxamide obtained in Reference Example 56.

$^1$H NMR (CDCl$_3$) δ: 2.37 (2H, t, J=8.1 Hz), 2.62 (4h, S), 2.86 (2H, t, J=8.4 Hz), 3.13 (2H, s), 3.22 (4H, s), 6.39 (1H, s), 6.85–7.95 (16H, m).

Melting point: 228–230° C. (crystallization solvent: tetrahydrofuran-n-hexane)

EXAMPLE 69

4'-Chloro-N-[6-[[[2-(dimethylamino)ethyl](methyl)amino]methyl]-7,8-dihydro-2-naphthalenyl](1,1'-biphenyl]-4-carboxamide

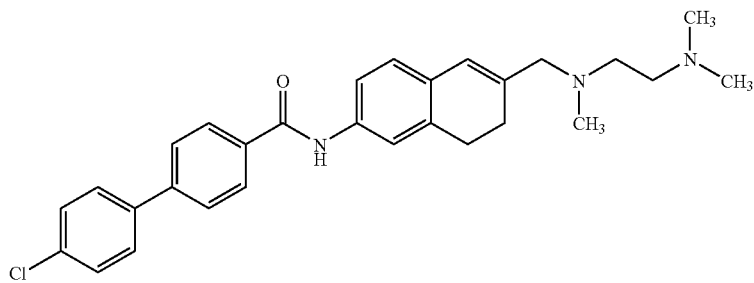

The titled compound was obtained by carrying out the same operation as in Example 51, using 4'-chloro-N-[6-(chloromethyl)-7,8-dihydro-2-naphthalenyl][1,1'-biphenyl]-4-carboxamide obtained in Reference Example 56.

$^1$H NMR (CDCl$_3$) δ: 2.25 (6H, s), 2.26 (3H, s), 2.33 (2H, t, J=8.1 Hz), 2.44–2.50 (4H, m), 2.84 (2H, t, J=8.1 Hz), 3.07 (2H, s), 6.35 (1H, s), 7.02 (1H, d, J=8.4 Hz), 7.37–7.57 (6H, m), 7.67 (2H, d, J=8.1 Hz), 7.80 (1H, s), 7.94 (2H, d, J=8.4 Hz).

Melting point: 156–158° C. (crystallization solvent: tetrahydrofuran-n-hexane)

EXAMPLE 70

4'-Fluoro-N-[6-(4-morpholinylmethyl)-5,6,7,8-tetrahydro-2-naphthalenyl][1,1'-biphenyl]-4-carboxamide

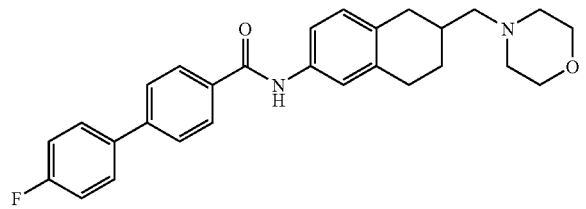

The titled compound was obtained by carrying out the same operation as in Example 1, using 6-(4-morpholinylmethyl)-5,6,7,8-tetrahydro-2-naphthalenamine obtained in Reference Example 57.

$^1$H NMR (CDCl$_3$) δ: 1.40–1.50 (1H, m), 1.90–2.10 (2H, m), 2.29–2.45 (7H, m), 2.80–2.92 (3H, m), 3.72–3.75 (4H, m), 7.07–7.33 (4H, m), 7.46 (1H, s), 7.56–7.66 (4H, m), 7.78 (1H, s), 7.92 (2H, d, J=8.1 Hz).

Melting point: 188–190° C. (crystallization solvent: ethyl acetate)

EXAMPLE 71

4'-Chloro-N-[6-(4-morpholinylmethyl)-5,6,7,8-tetrahydro-2-naphthalenyl][1,1'-biphenyl]-4-carboxamide

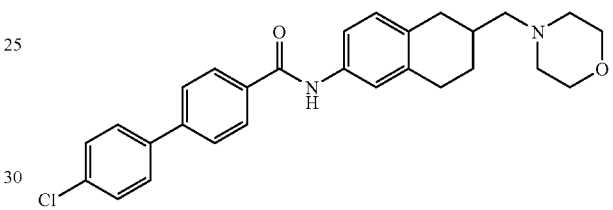

The titled compound was obtained by carrying out the same operation as in Example 1, using 6-(4-morpholinylmethyl)-5,6,7,8-tetrahydro-2-naphthalenamine obtained in Reference Example 57.

$^1$H NMR (CDCl$_3$) δ: 1.40–1.50 (1H, m), 1.90–2.10 (2H, m), 2.32–2.45 (7H, m), 2.80–2.90 (3H, m), 3.70–3.80 (4H, m), 7.10–7.92 (12H, m).

Melting point: 216–218° C. (crystallization solvent: ethyl acetate)

EXAMPLE 72

4-Chloro-N-[6-(0.4-morpholinylmethyl)-5,6,7,8-tetrahydro-2-naphthalenyl]-2-phenyl-5-pyrimidinecarboxamide

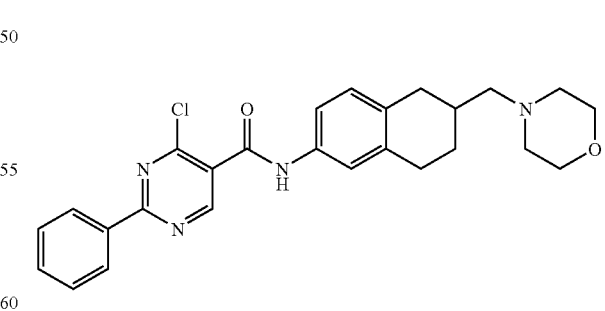

The titled compound was obtained by carrying out the same operation as in Example 1, using 6-(4-morpholinylmethyl)-5,6,7,8-tetrahydro-2-naphthalenamine obtained in Reference Example 57.

$^1$H NMR (CDCl$_3$) δ: 1.40–1.50 (1H, m), 1.95–2.05 (2H, m), 2.29–2.45 (7H, m), 2.80–2.95 (3H, m), 3.73 (4H, t, J=4.5

Hz), 7.10 (1H, d, J=8.1 Hz), 7.32 (1H, d, J=8.1 Hz), 7.42 (1H, s), 7.49–7.56 (3H, m), 8.25 (1H, s), 8.48 (2H, d, J=6.6 Hz), 9.20 (1H, s)

EXAMPLE 73

N-[6-(4-Morpholinylmethyl)-5,6,7,8-tetrahydro-2-naphthalenyl]-2-phenyl-5-pyrimidinecarboxamide

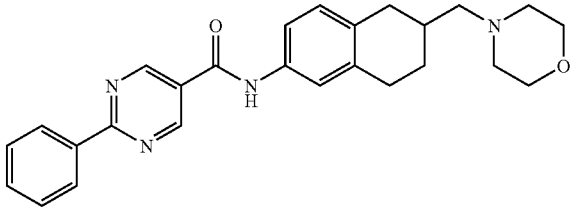

The titled compound was obtained by carrying out the same operation as in Reference Example 48, using 4-chloro-N-[6-(4-morpholinylmethyl)-5,6,7,8-tetrahydro-2-naphthalyl]-2-phenyl-5-pyrimidinecarboxamide obtained in Example 72.

$^1$H NMR (CDCl$_3$) δ: 1.21–1.30 (1H, m), 1.93–2.03 (2H, m), 2.28–2.44 (7H, m), 2.80–2.90 (3H, m), 3.73 (4H, t, J=4.8 Hz), 7.07 (1H, d, J=8.1 Hz), 7.26–7.30 (1H, m), 7.39 (1H, s), 7.51–7.53 (3H, m), 8.00 (1H, s), 8.50 (2H, dd, J=8.1, 2.4 Hz), 9.21 (2H, s)

EXAMPLE 74

N-[6-[(Diethylamino)methyl]-7,8-dihydro-2-naphthalenyl][1,1'-biphenyl]-4-carboxamide

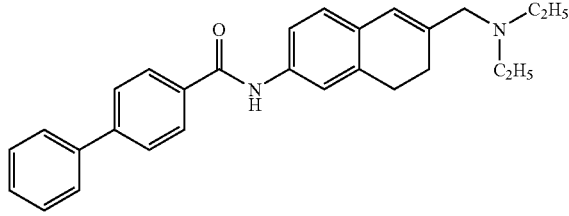

The titled compound was obtained by carrying out the same operation as in Example 51, using N-[6-(chloromethyl)-7,8-dihydro-2-naphthalenyl][1,1'-biphenyl]-4-carboxamide obtained in Reference Example 58.

$^1$H NMR (CDCl$_3$) δ: 1.24 (6H, t, J=7.2 Hz), 2.33 (2H, t, J=5.1 Hz), 2.53 (4H, q, J=7.2 Hz), 2.84 (2H, t, J=5.1 Hz), 3.11 (2H, s), 6.36 (1H, s), 7.02 (1H, d, J=8.1 Hz), 7.37–7.50 (5H, m), 7.63 (2H, d, J=8.7 Hz), 7.71 (2H, d, J=8.4 Hz), 7.79 (1H, s), 7.93 (2H, d, J=8.4 Hz).

Melting point: 153–155° C. (crystallization solvent: tetrahydrofuran-n-hexane)

EXAMPLE 75

4-(2-Benzo[b]furanyl)-N-[2-(N,N-dimethylamino)methyl-6-tetralinyl]benzamide

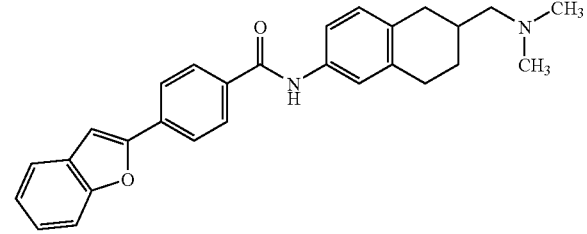

The titled compound was obtained by carrying out the same operation as in Example 4, using 6-amino-2-[(N,N-dimethylamino)methyl]tetralin hydrochloride.

Melting point: 192–194° C. (crystallization solvent: tetrahydrofuran-isopropyl ether)

EXAMPLE 76

4-(3-Methoxybenzyloxy)-N-[2-(N,N-dimethylamino)methyl-6-tetralinyl]benzamide

The titled compound was obtained by carrying out the same operation as in Example 4, using 6-amino-2-[(N,N-dimethylamino)methyl]tetralin hydrochloride.

Melting point: 102–104° C. (crystallization solvent: isopropyl ether)

EXAMPLE 77

4-(4-Fluorobenzyloxy)-N-[2-(N,N-dimethylamino)methy-6-tetralinyl]benzamide

The titled compound was obtained by carrying out the same operation as in Example 4, using 6-amino-2-[(N,N-dimethylamino)methyl]tetralin hydrochloride.

Melting point: 165–167° C. (crystallization solvent: tetrahydrofuran-hexane)

EXAMPLE 78

4-[4-(Methylsulfanyl)benzyloxy]-N-[2-(N,N-dimethylamino)methyl-6-tetralinyl]benzamide

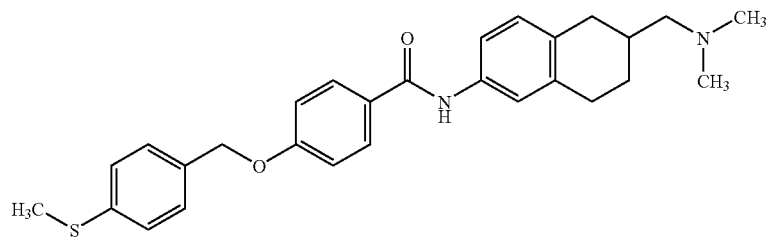

The titled compound was obtained by carrying out the same operation as in Example 4, using 6-amino-2-[(N,N-dimethylamino)methyl]tetralin hydrochloride.

Melting point: 162–163° C. (crystallization solvent: tetrahydrofuran-hexane)

EXAMPLE 79

4-(4-Ethylbenzyloxy)-N-[2-(N,N-dimethylamino)methyl-6-tetralinyl]benzamide

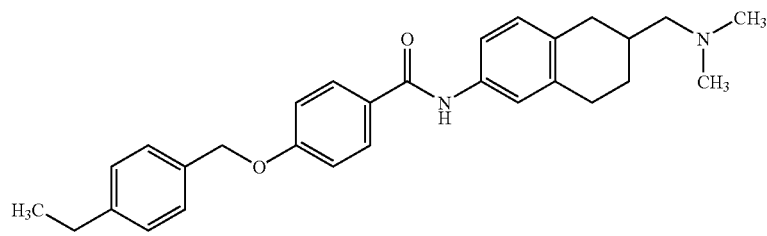

The titled compound was obtained by carrying out the same operation as in Example 4, using 6-amino-2-[(N,N-dimethylamino)methyl]tetralin hydrochloride.

Melting point: 120–122° C. (crystallization solvent: tetrahydrofuran-isopropyl ether)

EXAMPLE 80

(4'-Methylbiphenyl-4-yl)-N-[2-(N,N-dimethylamino)methyl-6-tetralinyl]carboxamide

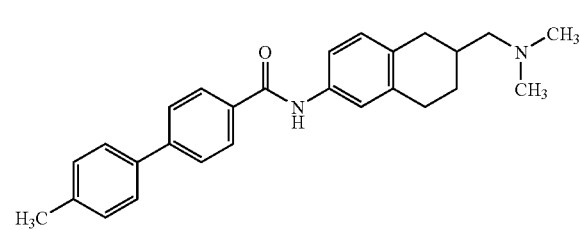

The titled compound was obtained by carrying out the same operation as in Example 4, using 6-amino-2-[(N,N-dimethylamino)methyl]tetralin hydrochloride.

Melting point: 181–1820° C. (crystallization solvent: ethyl acetate-hexane)

EXAMPLE 81

(2',4'-Dichlorobiphenyl-4-yl)-N-[2-(N,N-dimethylamino)methyl-6-tetralinyl]carboxamide

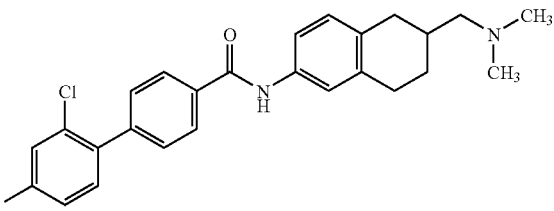

The titled compound was obtained by carrying out the same operation as in Example 4, using 6-amino-2-[(N,N-dimethylamino)methyl]tetralin hydrochloride.

Melting point: 188–189° C. (crystallization solvent: tetrahydrofuran-hexane)

EXAMPLE 82

4-(5-Chloro-2-thienyl-N-[2-(N,N-dimethylamino)methyl-6-tetralinyl]benzamide

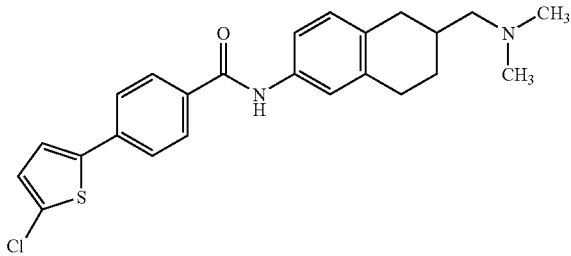

The titled compound was obtained by carrying out the same operation as in Example 4, using 6-amino-2-(N,N-dimethylamino)methyltetraline hydrochloride.

Melting point: 167–169° C. (crystallization solvent: ethyl acetate-hexane)

EXAMPLE 83

(3'-Chlorobiphenyl-4-yl)-N-[2-(N,N-dimethylamino)methyl-6-tetralinyl]carboxamide

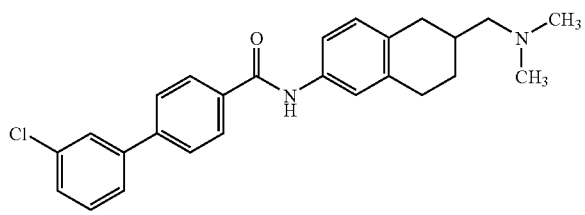

The titled compound was obtained by carrying out the same operation as in Example 4, using 6-amino-2-[(N,N-dimethylamino)methyl]tetralin hydrochloride.

Melting point: 138–139° C. (crystallization solvent: tetrahydrofuran-isopropyl ether)

EXAMPLE 84

(2'-Chlorobiphenyl-4-yl)-N-[2-(N,N-dimethylamino)methyl-6-tetralinyl]carboxamide

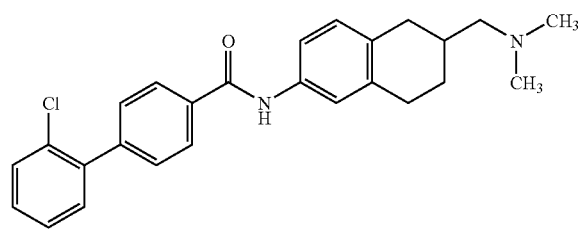

The titled compound was obtained by carrying out the same operation as in Example 4, using 6-amino-2-[(N,N-dimethylamino)methyl]tetralin hydrochloride.

Melting point: 176–177° C. (crystallization solvent: tetrahydrofuran-hexane)

EXAMPLE 85

4'-Methyl-N-[6-[N,N-dimethylamino)methyl]-7,8-dihydro-2-naphthalenyl][1,1'-biphenyl]-4-carboxamide

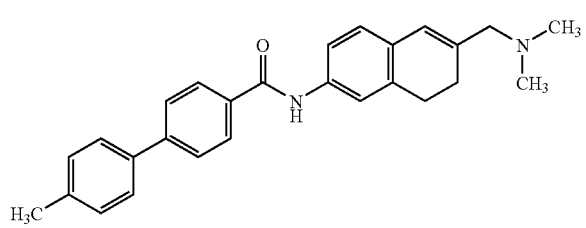

The titled compound was obtained by carrying out the same operation as in Example 1, using 6-[(N,N-dimethylamino)methyl]-7,8-dihydro-2-naphthalenamine obtained in Example 41-2).

$^1$H-NMR (CDCl$_3$) δ: 2.25 (6H, s), 2.33 (2H, t, J=8.1 Hz), 2.41 (3H, s), 2.84 (2H, t, J=8.1 Hz), 2.98 (2H, s), 6.33 (1H, s), 7.01 (1H, d, J=7.8 Hz), 7.39 (1H, d, J=8.4 Hz), 7.48 (1H, s), 7.52 (2H, d, J=7.8 Hz), 7.67 (2H, d, J=8.1 Hz), 7.84 (1H, s), 7.91 (2H, d, J=8.1 Hz).

Elemental analysis for C$_{27}$H$_{28}$N$_2$O Calcd.: C, 81.78; H, 7.12; N, 7.06. Found: C, 81.51; H, 7.22; N, 6.93.

Melting point: 195–196° C. (crystallization solvent: ethyl acetate-diisopropyl ether)

EXAMPLE 86

4-Cyclohexyl-N-[6-[(N,N-dimethylamino)methyl]-7,8-dihydro-2-naphthalenyl]benzamide

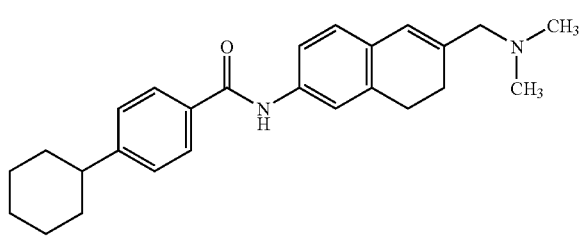

The titled compound was obtained by carrying out the same operation as in Example 1, using the 6-[(N,N-dimethylamino)methyl]-7,8-dihydro-2-naphthalenamine obtained in Example 41-2).

$^1$H-NMR (CDCl$_3$) δ: 1.20–1.52 (4H, m), 1.71–1.96 (6H, m), 2.25 (6H, s), 2.33 (2H, t, J=8.1 Hz), 2.50–2.62 (1H, m), 2.84 (2H, t, J=8.1 Hz), 2.99 (2H, s), 6.33 (1H, s), 7.00 (1H, d, J=7.8 Hz), 7.31 (2H, d, J=8.1 Hz), 7.36 (1H, d, J=7.8 Hz), 7.46 (1H, brs), 7.75 (1H, s), 7.78 (2H, d, J=8.1 Hz).

Melting point: 179–181° C. (crystallization solvent: ethyl acetate-diisopropyl ether)

EXAMPLE 87

6-(2,4-Difluorophenyl)-N-[6-[(1-pyrrolidinyl)methyl]-7,8-dihydro-2-naphthalenyl]nicotinamide

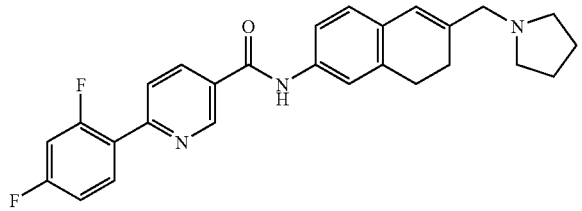

The titled compound was obtained by carrying out the same operation as in Example 1, using 6-(1-pyrrolidinylmethyl)-7,8-dihydro-2-naphthalenamine obtained in Reference Example 54.

$^1$H-NMR (CDCl$_3$) δ: 1.81 (4H, m), 2.37 (2H, t, J=8.1 Hz), 2.54 (4H, m), 2.86 (2H, t, J=8.1 Hz), 3.18 (2H, s), 6.37 (1H, s), 6.93 (1H, m), 7.04 (2H, m), 7.38 (1H, m), 7.47 (1H, s), 7.77 (1H, s), 7.91 (1H, m), 8.13 (1H, m), 8.24 (1H, m), 9.16 (1H, s).

Elemental analysis for C$_{27}$H$_{26}$F$_2$N$_3$O Calcd.: C, 72.79; H, 5.66; N, 9.43. Found: C, 72.65, H, 5.52; N, 9.73.

Melting point: 169–170° C. (crystallization solvent: ethyl acetate-diisopropyl ether)

EXAMPLE 88

4'-Fluoro-N-[6-[(N,N-dimethylamino)methyl]-5,6,7,8-tetrahydro-2-naphthalenyl][1,1'-biphenyl]-4-carboxamide

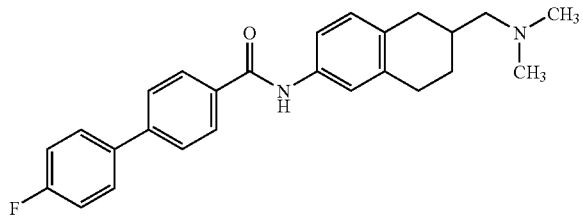

The titled compound was obtained by carrying out the same operation as in Example 4, using 6-amino-2-[(N,N-dimethylamino)methyl]tetralin hydrochloride.

$^1$H-NMR (CDCl$_3$) δ: 1.41 (1H, m), 1.95 (2H, m), 2.25–2.45 (3H, m), 2.36 (6H, s), 2.85–2.94 (3H, m), 7.13 (3H, m), 7.30 (1H, m), 7.46 (1H, s), 7.5.9 (2H, m), 7.65 (2H, d, J=8.1 Hz), 7.74 (1H, s), 7.93 (2H, d, J=8.1 Hz).

Elemental analysis for C$_{26}$H$_{27}$FN$_2$O Calcd.: C, 77.58; H, 6.76; N, 6.96. Found: C, 77.72; H, 6.49; N, 6.79.

Melting point: 184–186° C. (crystallization solvent: ethyl acetate-diisopropyl ether)

EXAMPLE 89

(+)-4'-Fluoro-N-[6-[(N,N-dimethylamino)methyl]-5,6,7,8-tetrahydro-2-naphthalenyl][1,1'-biphenyl]-4-carboxamide, and (−)-4'-fluoro-N-[6-[(N,N-dimethylamino)methyl]-5,6,7,8-tetrahydro-2-naphthalenyl][1,1'-biphenyl]-4-carboxamide Optical resolution of 4'-fluoro-N-[6-[(N,N-dimethylamino)methyl]-5,6,7,8-tetrahydro-2-naphthalenyl][1,1'-biphenyl]-4-carboxamide (2.00 g) obtained in Example 88 was conducted by sample-splitting HPLC using a chiral column (Daicel Co., CHIRALCEL OD 500 mmD×500 mL; moving phase n-hexane:ethanol=85:15), to give (+) form (1.00 g; 99.8% ee) and (−) form (0.89 g; >99.9% ee) as powders. The powders obtained were respectively recrystallized using ethyl acetate—diisopropyl ether, to give the (+) form (855 mg) and (−) form (754 mg) of the titled compounds. The optical rotation of both compounds are shown below. (+)-4'-fluoro-N-[6-[(N,N-dimethylamino)methyl]-5,6,7,8-tetrahydro-2-naphthalenyl][1,1'-biphenyl]-4-carboxamide Optical rotation: [α]$_D$=+50.8° C=0.494% (methanol)

(−)-4'-fluoro-N-[6-[(N,N-dimethylamino)methyl]-5,6,7,8-tetrahydro-2-naphthalenyl][1,1'-biphenyl]-4-carboxamide Optical rotation: [α]$_D$=+51.2° C.=0.492% (methanol)

EXAMPLE 90

4'-Chloro-N-[3-[(N,N-dimethylamino)methyl)-2H-chromen-7-yl][1,1'-biphenyl]-4-carboxamide

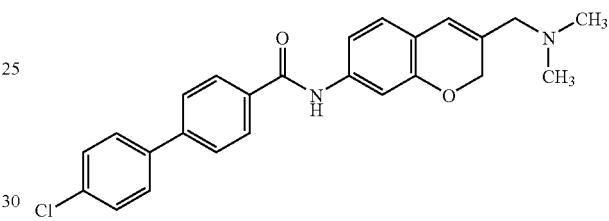

The titled compound was obtained by carrying out the same operation as in Example 1, using 3-[(N,N-dimethylamino)methyl]-2H-chromen-7-amine obtained in Reference Example 59.

$^1$H-NMR (CDCl$_3$) δ: 2.23 (6H, s), 2.97 (2H, s), 4.79 (2H, s), 6.30 (1H, s), 6.96 (1H, d, J=8.1 Hz), 7.13 (1H, s), 7.20 (1H, d, J=8.1 Hz), 7.45 (2H, d, J=8.6 Hz), 7.56 (2H, d, J=8.6 Hz), 7.66 (2H, d, J=8.4 Hz), 7.74 (1H, brs), 7.93 (2H, d, J=8.4 Hz).

Melting point: 199–208° C. (crystallization solvent: diisopropyl ether)

EXAMPLE 91

2',4'-Difluoro-N-[3-[N,N-dimethylamino)methyl]-2H-chromen-7-yl][1,1'-biphenyl]-4-carboxamide

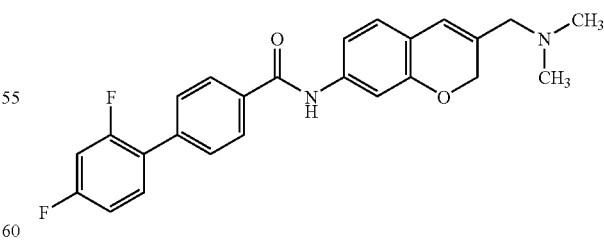

The titled compound was obtained by carrying out the same operation as in Example 1, using 3-[(N,N-dimethylamino)methyl]-2H-chromen-7-amine obtained in Reference Example 59.

$^1$H-NMR (CDCl$_3$) δ: 2.23 (6H, s), 2.97 (2H, s), 4.78 (2H, s), 6.29 (1H, s), 6.80–7.10 (2H, m), 6.96 (1H, d, J=8.1 Hz), 7.13 (1H, s), 7.20 (1H, d, J=8.1 Hz), 7.40–7.50 (1H, m), 7.62 (2H, d, J=8.4 Hz), 7.76 (1H, brs), 7.92 (2H, d, J=8.4 Hz).

Melting point: 200–204° C. (crystallization solvent: diisopropyl ether)

EXAMPLE 92

4'-Chloro-N-[6-[(dimethylamino)methyl]-7,8-dihydro-1-naphthalenyl][1,1'-biphenyl]-4-carboxamide

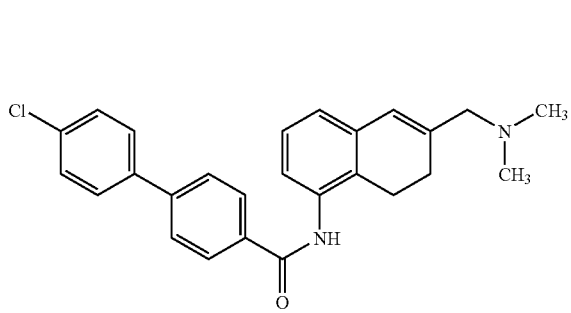

The titled compound was obtained in the same manner as in Example 1, using 6-[(dimethylamino)methyl]-7,8-dihydro-1-naphthalenamine obtained in Reference Example 60.

$^1$H-NMR (CDCl$_3$) δ: 2.34 (6H, s), 2.36 (2H, t, J=8.1 Hz), 2.80 (2H, t, J=8.1 Hz), 3.00 (2H, s), 6.38 (1H, s), 6.94 (1H, d, J=7.8 Hz), 7.21 (1H, t, J=7.8 Hz), 7.45 (2H, d, J=8.6 Hz), 7.56 (2H, d, J=8.6 Hz), 7.61 (2H, m), 7.68 (2H, d, J=8.4 Hz), 7.97 (2H, d, J=8.4 Hz).

Melting point: 193–195° C. (crystallization solvent: diisopropyl ether)

EXAMPLE 93

4'-Chloro-N-[7-[(dimethylamino)methyl]-5,6-dihydro-2-naphthalenyl][1,1'-biphenyl]3-4-carboxamide

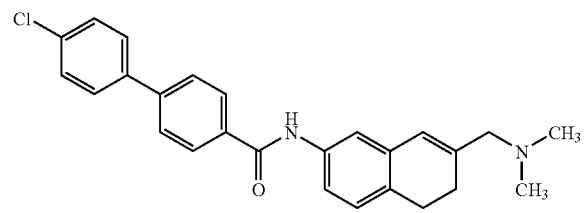

The titled compound was obtained as a white powder by the same method as in Example 1, using 7-[(dimethylamino)methyl]-5,6-dihydro-2-naphthalenamine obtained in Reference Example 61.

$^1$H-NMR (CDCl$_3$) δ: 2.25 (6H, s), 2.34 (2H, t, J=8.1 Hz), 2.82 (2H, t, J=8.1 Hz), 3.00 (2H, s), 6.36 (1H, s), 7.11 (1H, d, J=7.5 Hz), 7.34 (1H, d, J=8.1 Hz), 7.38 (1H, s), 7.44 (2H, d, J=8.4 Hz), 7.56 (2H, d, J=8.4 Hz), 7.66 (2H, d, J=8.4 Hz), 7.78 (1H, brs), 7.97 (2H, d, J=8.4 Hz).

Melting point: 167–169° C. (crystallization solvent diisopropyl ether)

EXAMPLE 94

N-[6-(1-Pyrrolidinylmethyl)-7,8-dihydro-2-naphthalenyl][1,1'-biphenyl]-4-carboxamide

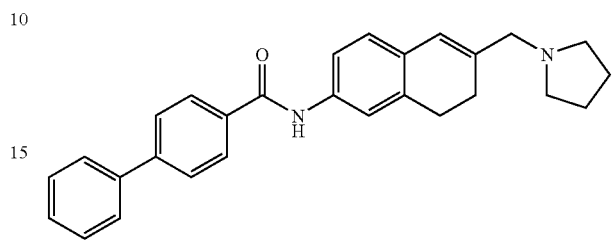

The titled compound was obtained as a white powder in the same manner as in Example 1, using 6-(1-pyrrolidinylmethyl)-7,8-dihydro-2-naphthalenamine obtained in Reference Example 54.

$^1$H-NMR (CDCl$_3$) δ: 1.75–1.90 (4H, m), 2.34 (2H, t, J=8.1 Hz), 2.45–2.60 (4H, m), 2.85 (2H, t, J=8.1 Hz), 3.18 (2H, s), 6.36 (1H, s), 7.02 (1H, d, J=8.1 Hz), 7.27–7.55 (5H, m), 7.63 (2H, d, J=7.3 Hz), 7.70 (2H, d, J=8.4 Hz), 7.82 (1H, s), 7.94 (2H, d, J=8.1 Hz).

Elemental analysis for C$_{28}$H$_{28}$N$_2$O Calcd.: C, 82.32; H, 6.91; N, 6.86. Found: C, 81.99; H, 6.69; N, 6.91.

Melting point: 176–177° C. (crystallization solvent diisopropyl ether)

EXAMPLE 95

4'-Fluoro-N-[6-(1-pyrrolidinylmethyl)-7,8-dihydro-2-naphthalenyl][1,1'-biphenyl]-4-carboxamide

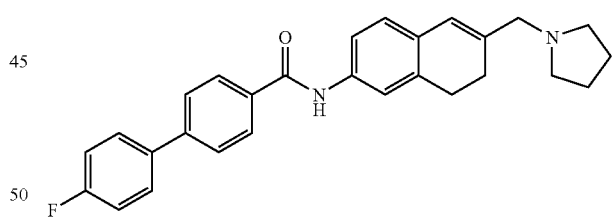

The titled compound was obtained in the same manner as in Example 1, using 6-(1-pyrrolidinylmethyl)-7,8-dihydro-2-naphthalenamine obtained in Reference Example 54.

$^1$H-NMR (CDCl$_3$) δ: 1.75–1.90 (4H, m), 2.35 (2H, t, J=8.2 Hz), 2.45–2.60 (4H, m), 2.84 (2H, t, J=8.2 Hz), 3.18 (2H, s), 6.36 (1H, s), 7.01 (1H, d, J=8.1 Hz), 7.16 (2H, t, J=8.1 Hz), 7.38 (1H, d, J=8.1 Hz), 7.48 (1H, brs), 7.56–7.61 (2H, m), 7.64 (2H, d, J=8.4 Hz), 7.83 (1H, s), 7.93 (2H, d, J=8.4 Hz).

Elemental analysis for C$_{28}$H$_{27}$FN$_2$O Calcd.: C, 78.85; H, 6.38; N, 6.57. Found: C, 78.75; H, 6.39; N, 6.45.

Melting point: 189–192° C. (crystallization solvent diisopropyl ether)

EXAMPLE 96

N-[6-(1-Pyrrolidinylmethyl)-5,6,7,8-tetrahydro-2-naphthalenyl][1,1'-biphenyl]-4-carboxamide

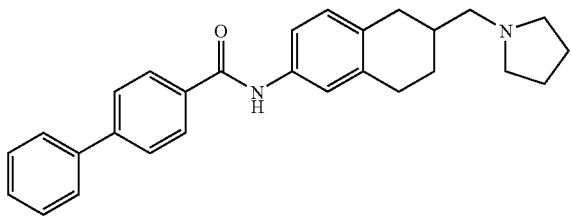

The titled compound was obtained as a white powder in the same manner as in Example 1, using 6-(1-pyrrolidinylmethyl)-5,6,7,8-tetrahydro-2-naphthalenamine obtained in Reference Example 55.

$^1$H-NMR (CDCl$_3$) δ: 1.40–1.50 (1H, m), 1.80 (4H, m), 1.80–2.10 (1H, m), 1.80–2.20 (8H, m), 3.30–4.00 (3H, m), 7.29 (1H, d, J=8.4 Hz), 7.25–7.30 (1H, m), 7.30–7.55 (4H, m), 6.43 (2H, d, J=7.0 Hz), 7.70 (2H, t, J=8.4 Hz), 7.75 (1H, s), 7.94 (2H, d, J=8.4 Hz).

Elemental analysis for C$_{28}$H$_{30}$N$_2$O Calcd.: C, 81.91; H, 7.37; N, 6.82. Found: C, 81.53; H, 7.25; N, 6.86.

Melting point: 144–146° C. (crystallization solvent diisopropyl ether)

EXAMPLE 97

4'-Fluoro-N-[6-(1-pyrrolidinylmethyl)-5,6,7,8-tetrahydro-2-naphthalenyl][1,1'-biphenyl]-4-carboxamide

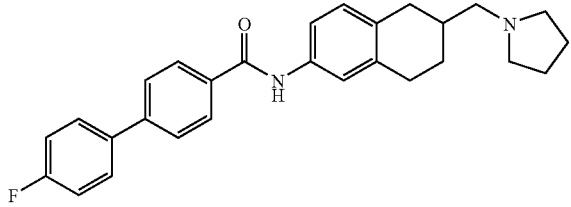

The titled compound was obtained as a white powder in the same manner as in Example 1, using 6-(1-pyrrolidinylmethyl)-5,6,7,8-tetrahydro-2-naphthalenamine obtained in Reference Example 55.

$^1$H-NMR (CDCl$_3$) δ: 1.40–1.50 (1H, m), 1.80 (4H, m), 1.80–2.10 (1H, m), 1.80–2.20 (8H, m), 3.30–4.00 (3H, m), 7.08 (1H, d, J=8.1 Hz), 7.15 (2H, t, J=8.4 Hz), 7.30 (1H, d, J=8.1 Hz), 7.44 (1H, brs), 7.56–7.61 (2H, m), 7.62 (2H, d, J=8.1 Hz), 7.85 (1H, s), 7.92 (2H, d, J=8.1 Hz).

Elemental analysis for C$_{28}$H$_{29}$FN$_2$O Calcd.: C, 78.48; H, 6.82; N, 6.54. Found: C, 78.18; H, 6.60; N, 6.60.

Melting point: 185–189° C. (crystallization solvent diisopropyl ether)

EXAMPLE 98

4'-Chloro-N-[6-(1-pyrrolidinylmethyl)-5,6,7,8-tetrahydro-2-naphthalenyl][1,1'-biphenyl]-4-carboxamide The titled compound was obtained as a white powder in the same manner as in Example 1, using 6-(1-pyrrolidinylmethyl)-5,6,7,8-tetrahydro-2-naphthalenamine obtained in Reference Example 55.

$^1$H-NMR (CDCl$_3$) δ: 1.40–1.50 (1H, m), 1.80 (4H, m), 1.80–2.10 (1H, m), 1.80–2.20 (8H, m), 3.30–4.00 (3H, m), 7.08 (1H, d, J=8.1 Hz), 7.31 (1H, d, J=8.4 Hz), 7.43 (2H, d, J=8.7 Hz), 7.45 (1H, s), 7.54 (2H, d, J=8.7 Hz), 7.64 (2H, d, J=8.4 Hz), 7.80 (1H, s), 7.93 (2H, d, J=8.4 Hz).

Elemental analysis for C$_{28}$H$_{29}$ClN$_2$O Calcd.: C, 75.57; H, 6.57; N, 6.30. Found: C, 75.26; H. 6.68; N. 6.15.

Melting point: 206–209° C. (crystallization solvent diisopropyl ether)

EXAMPLE 99

4-(4-Fluorophenyl)-N-[6-(1-piperidinylmethyl)-7,8-dihydro-2-naphthalenyl]-1-piperidinecarboxamide 6-(1-Pyrrolidinylmethyl)-7,8-dihydro-2-naphthalenamine obtained in Reference Example 54 (50 mg, 0.22 mmol) and pyridine (35 mg, 0.44 mmol) were dissolved in tetrahydrofuran (3 ml). Phenyl chlorocarbonate (38 mg, 0.24 mol) was added to the solution under ice-cooling, which was stirred for 10 minutes. The reaction mixture was concentrated, and dimethylsulfoxide (5 ml) was added to the residue. 4-(4-Fluorophenyl)piperidine hydrochloride (57 mg, 0.26 mmol) and 4N aqueous sodium hydroxide solution (0.066 ml, 0.26 mmol) were added to the reaction mixture at room temperature while stirring, which was stirred for 30 minutes. Ethyl acetate and water were added to the mixture, and extraction was conducted. The organic layer was washed with water, and concentrated. Diisopropyl ether was added to the residue. The crystallized product was collected by filtration, washed with diisopropyl ether, to give 4-(4-fluorophenyl)-N-[6-(1-piperidinylmethyl)-7,8-dihydro-2-naphthalenyl]-1-piperidinecarboxamide (48 mg) as a white powder.

$^1$H-NMR (CDCl$_3$) δ: 1.60–1.70 (2H, m), 1.79 (4H, m), 1.80–1.90 (2H, m), 2.33 (2H, t, J=7.8 Hz), 2.51 (4H, m), 2.60–2.70 (1H, m), 2.80 (2H, t, J=7.8 Hz), 2.90–3.10 (2H, m), 3.16 (2H, s), 4.18–4.23 (2H, m), 6.32 (1H, s), 6.32 (1H, s), 6.92–7.09 (4H, m), 7.15–7.20 (3H, m).

Melting point: 182–185° C. (crystallization solvent: diisopropyl ether)

EXAMPLE 100

4-(4-Fluorophenyl)-N-[6-(1-pyrrolidinylmethyl)-7,8-dihydro-2-naphthalenyl]-1-piperazinecarboxamide

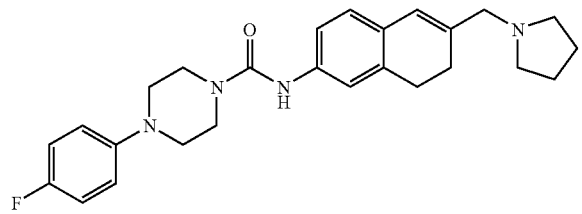

The titled compound was obtained as a white powder in the same manner as in Example 99, using 6-(1-pyrrolidinylmethyl)-7,8-dihydro-2-naphthalenamine obtained in Reference Example 54 and 4-fluorophenylpiperazine.

$^1$H-NMR (CDCl$_3$) δ: 1.79 (4H, m), 2.32 (2H, t, J=7.8 Hz), 2.51 (4H, m), 2.80 (2H, t, J=7.8 Hz), 3.13–3.16 (4H, m), 3.16 (2H, s), 3.63–3.66 (4H, m), 6.30 (1H, s), 6.32 (1H, s), 6.88–7.08 (6H, m), 7.19 (1H, s).

Elemental analysis for C$_{26}$H$_{31}$FN$_4$O Calcd.: C, 71.86; H, 7.19; N, 12.89. Found: C, 71.68; H, 7.35; N, 12.65.

Melting point: 179–181° C. (crystallization solvent: diisopropyl ether)

EXAMPLE 101

N-(4-Bromophenyl)-6-[(dimethylamino)methyl]-7,8-dihydro-2-naphthalenecarboxamide

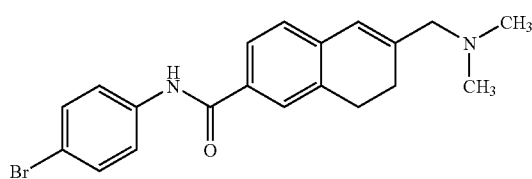

1) 6-Cyano-1-tetralone (1.30 g, 7.59 mmol) synthesized by a known literature method (*Synthetic Communications*, 23(21), 2965 (1993)) was dissolved in a mixed solution of concentrated hydrochloric acid (10 ml) and acetic acid (20 ml), which was stirred at 120° C. for 16 hours. The reaction mixture was concentrated. Ethyl acetate and water were added to the residue, and extraction was conducted. The organic layer was washed with water, and concentrated. The residue was washed with ethyl acetate-n-hexane (1:1), to give 5-oxo-5,6,7,8-tetrahydro-2-naphthalenecarboxylic acid (1.10 g) as a white powder.

$^1$H-NMR (CDCl$_3$) δ: 2.15–2.23 (2H, m), 2.70–2.75 (2H, m), 3.04–3.07 (2H, m), 8.01–8.03 (1H, m), 8.03 (1H, s), 8.13 (1H, d, J=8.7 Hz).

3) N-(4-Bromophenyl)-5-oxo-5,6,7,8-tetrahydro-2-naphthalenecarboxamide (1.10 g, 3.19 mmol) obtained in 2) was dissolved in dimethylformamide diethylacetal (30 ml), which was refluxed with heating for 4 hours. The crystallized product was collected by filtration, washed with ethyl acetate, to give N-(4-bromophenyl)-6-[(dimethylamino)methylidene]-5-oxo-5,6,7,8-tetrahydro-2-naphthalenecarboxamide (1.21 g) as a yellow powder.

$^1$H-NMR (CDCl$_3$) δ: 2.80–2.87 (4H, m), 3.07 (6H, m), 7.46–7.72 (7H, m), 7.91 (1H, d, J=8.4 Hz), 8.53 (1H, s).

4) Sodium triacetoxyhydroborate (398 mg, 1.87 mmol) was dissolved in a mixed solution of acetic acid (40 ml) and tetrahydrofuran (10 ml) under ice-cooling. N-(4-Bromophenyl)-6-[(dimethylamino)methylidene]-5-oxo-5,6,7,8-tetrahydro-2-naphthalenecarboxamide (500 mg, 1.25 mmol) obtained in 3) was added to the solution, which was stirred for 1 hour. The reaction mixture was concentrated under reduced pressure at room temperature. 2-Propanol (50 ml) was added to the residue, and sodium borohydride (142 mg, 3.75 mmol) was further added under ice-cooling. After stirring for 2 hours, the reaction mixture was concentrated. Sodium hydrogencarbonate solution and ethyl acetate was added to the residue for liquid separation. The organic layer was concentrated. The residue was dissolved in a mixed solution of acetic acid (20 ml) and concentrated hydrochloric acid (20 ml), which was stirred at 70° C. for 5 hours. The reaction mixture was concentrated. 4N aqueous sodium hydroxide solution and ethyl acetate were added to the residue, and extraction was conducted. The organic layer was washed with water, and concentrated. The residue was purified by alumina column chromatography (development solvent:ethyl acetate), and the eluent was washed with diisopropyl ether, to give the titled compound (234 mg) as a white powder.

$^1$H-NMR (CDCl$_3$) δ: 2.26 (6H, s), 2.38 (2H, t, J=8.1 Hz), 2.89 (2H, t, J=8.1 Hz), 3.02 (2H, s), 6.42 (1H, s), 7.10 (1H, d, J=8.6 Hz), 7.47 (2H, d, J=8.9 Hz), 7.55 (2H, d J=8.9 Hz), 7.61 (1H, s), 7.62 (1H, d, J=6.7 Hz), 7.76 (1H, s).

Elemental analysis for C$_{20}$H$_{21}$BrN$_2$O Calcd.: C, 62.35; H, 5.49; N, 7.27. Found: C, 61.98; H, 5.43; N, 7.07.

Melting point: 175–179° C. (crystallization solvent diisopropyl ether)

EXAMPLE 102

6-[(Dimethylamino)methyl]-N-(4'-fluoro[1,1'-biphenyl]-4-yl)-7,8-dihydro-2-naphthalenecarboxamide

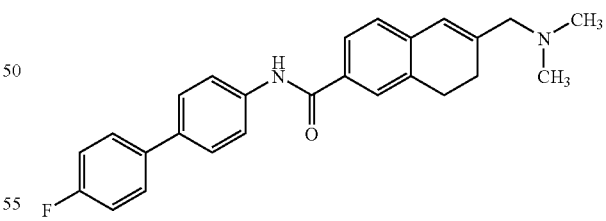

The titled compound was obtained as a white powder, by the same method as in Example 16, using N-(4-bromophenyl)-6-[(dimethylamino)methyl]-7,8-dihydro-2-naphthalenecarboxamide (170 mg, 0.44 mmol) obtained in Example 101 and 4-fluorophenylboric acid (74 mg, 0.53 mmol).

$^1$H-NMR (CDCl$_3$) δ: 2.27 (6H, s), 2.39 (2H, t, J=8.4 Hz), 2.91 (2H, t, J=8.4 Hz), 3.02 (2H, s), 6.43 (1H, s), 7.09–7.16 (3H, m), 7.52–7.73 (8H, m), 7.81 (1H, s).

Melting point: 200–204° C. (crystallization solvent diisopropyl ether)

EXAMPLE 103

2',4'-Difluoro-N-[6-(1-pyrrolidinylmethyl)-7,8-dihydro-2-naphthalenyl][1,1'-biphenyl]-4-carboxamide

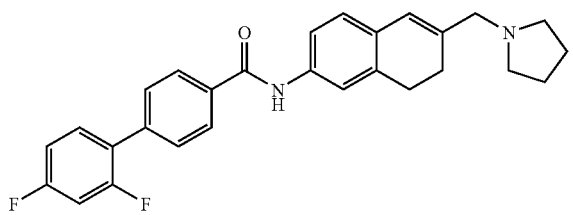

The titled compound was obtained as a white powder by the same method as in Example 1, using 6-(1-pyrrolidinylmethyl)-7,8-dihydro-2-naphthalenamine obtained in Reference Example 54.

$^1$H-NMR (CDCl$_3$): 1.75–1.90 (4H, m), 2.36 (2H, t, J=8.1 Hz), 2.45–2.60 (4H, m), 2.85 (2H, t, J=8.1 Hz), 3.18 (2H, s), 6.36 (1H, s), 6.92–7.03 (3H, m), 7.36–7.45 (2H, m), 7.48 (1H, s), 7.62 (2H, d, J=8.4 Hz), 7.78 (1H, s), 7.94 (2H, d, J=8.4 Hz).

Elemental analysis for C$_{28}$H$_{26}$F$_2$N$_2$O Calcd.: C, 75.66; H, 5.90; N, 6.30. Found: C, 75.36; H, 5.92; N, 6.10.

Melting point: 165–167° C. (crystallization solvent diisopropyl ether)

EXAMPLE 104

N-[3-[(Dimethylamino)methyl]-2,3-dihydro-1,4-benzodioxin-6-yl][1,1'-biphenyl]-4-carboxamide

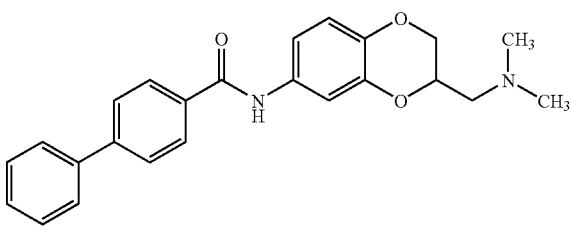

The titled compound was obtained as a white powder by the same method as in Example 1, using N,N-dimethyl-N-[(7-amino-2,3-dihydro-1,4-benzodioxin-2-yl)methyl]amine obtained in Reference Example 62.

$^1$H-NMR(CDCl$_3$) δ: 2.33 (6H, s), 2.48–2.66 (2H, m), 3.93–3.99 (1H, m), 4.27–4.31 (2H, m), 6.86 (1H, d, J=8.6 Hz), 7.03–7.07 (1H, m), 7.31–7.32 (1H, m), 7.37–7.49 (3H, m), 7.62 (2H, d, J=7.0 Hz), 7.68 (2H, d, J=8.4 Hz), 7.76 (1H, s), 7.91 (2H, d, J=8.4 Hz).

Elemental analysis for C$_{24}$H$_{24}$N$_2$O$_3$ Calcd.: C, 74.21; H, 6.23; N, 7.21. Found: C, 74.17; H, 6.23; N, 7.01.

Melting point: 124–126° C. (crystallization solvent diisopropyl ether)

EXAMPLE 105

4'-Chloro-N-[3-[(dimethylamino)methyl]-2,3-dihydro-1,4-benzodioxin-6-yl][1,1'-biphenyl]-4-carboxamide

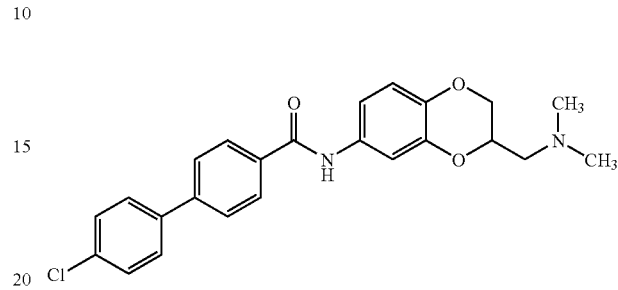

The titled compound was obtained as a white powder by the same method as in Example 1, using N,N-dimethyl-N-[(7-amino-2,3-dihydro-1,4-benzodioxin-2-yl)methyl]amine obtained in Reference Example 62.

$^1$H-NMR(CDCl$_3$) δ: 2.33 (6H, s), 2.50–2.67 (2H, m), 3.94–4.01 (1H, m), 4.28–4.31 (2H, m), 6.86 (1H, d, J=8.7 Hz), 7.03–7.06 (1H, m), 7.31 (1H, m), 7.44 (2H, d, J=8.4 Hz), 7.55 (2H, d, J=8.4 Hz), 7.65 (2H, d, J=8.1 Hz), 7.67 (1H, s), 7.91 (2H, d, J=8.1 Hz).

Melting point: 158–159° C. (crystallization solvent: diisopropyl ether)

EXAMPLE 106

4'-Chloro-N-[2-[(dimethylamino)methyl]-2,3-dihydro-1,4-benzodioxin-6-yl][1,1'-biphenyl]-4-carboxamide

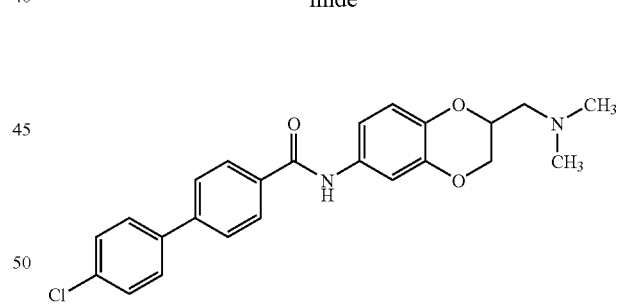

The titled compound was obtained as a white powder by the same method as in Example 1, using N,N-dimethyl-N-[(6-amino-2,3-dihydro-1,4-benzodioxin-2-yl)methyl]amine obtained in Reference Example 63.

$^1$H-NMR (CDCl$_3$) δ: 2.34 (6H, s), 2.46–2.67 (2H, m), 3.94–4.01 (1H, m), 4.28–4.34 (2H, m), 6.91 (1H, d, J=8.6 Hz), 7.02–7.05 (1H, m), 7.30 (1H, m), 7.44 (2H, d, J=8.4 Hz), 7.55 (2H, d, J=8.4 Hz), 7.66 (2H, d, J=8.1 Hz), 7.70 (1H, s), 7.92 (2H, d, J=8.1 Hz).

Elemental analysis for C$_{24}$H$_{23}$ClN$_2$O$_3$ Calcd.: C, 68.16; H, 5.48; N, 6.62. Found: C, 68.09; H, 5.29; N, 6.57.

Melting point: 215–217° C. (crystallization solvent diisopropyl ether)

EXAMPLE 107

2',4'-Difluoro-N-[2-[(dimethylamino)methyl]-2,3-dihydro-1,4-benzodioxin-6-yl][1,1'-biphenyl]-4-carboxamide

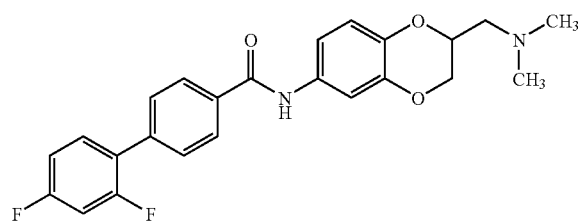

The titled compound was obtained as a white powder by the same method as in Example 1, using N,N-dimethyl-N-[(6-amino-2,3-dihydro-1,4-benzodioxin-2-yl)methyl]amine obtained in Reference Example 63.

$^1$H-NMR (CDCl$_3$) δ: 2.34 (6H, s), 2.50–2.63 (2H, m), 3.94–4.01 (1H, m), 4.28–4.34 (2H, m), 6.91 (1H, d, J=8.6 Hz), 6.91–7.03 (3H, m), 7.30 (1H, m), 7.40–7.50 (1H, m), 7.61 (2H, d, J=8.1 Hz), 7.69 (1H, s), 7.92 (2H, d, J=8.1 Hz).

Elemental analysis for C$_{24}$H$_{22}$F$_2$N$_2$O$_3$ Calcd.: C, 67.91; H, 5.22; N, 6.60. Found: C, 67.75; H, 5.09; N. 6.48.

Melting point: 209–210° C. (crystallization solvent diisopropyl ether)

EXAMPLE 108

6=(4-Chlorophenyl)-N-[2-(1-pyrrolidinylmethyl)-2,3-dihydro-1,4-benzodioxin-6-yl]nicotinamide

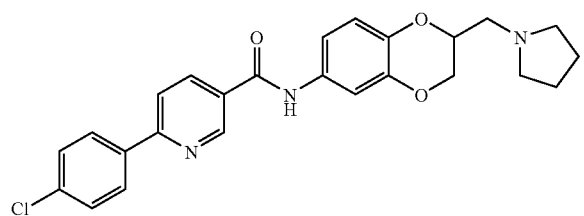

The titled compound was obtained as a white powder by the same method as in Example 1, using 1-[(6-amino-2,3-dihydro-1,4-benzodioxin-2-yl)methyl]pyrrolidine obtained in Reference Example 64.

$^1$H-NMR (CDCl$_3$) 6:1.81 (4H, m), 2.50–2.63 (4H, m), 2.75–2.77 (2H, m), 3.90–4.10 (1H, m), 4.30–4.36 (2H, m), 6.91 (1H, d, J=8.6 Hz), 7.00–7.10 (1H, m), 7.26 (1H, m), 7.48 (2H, d, J=8.6 Hz), 7.72 (1H, s), 7.81 (1H, d, J=7.8 Hz), 8.01 (2H, d, J=8.6 Hz), 8.20–8.25 (1H, m), 9.10 (1H, s).

Elemental analysis for C$_{25}$H$_{24}$ClN$_3$O$_3$ Calcd.: C, 66.74; H, 5.38; N, 9.34. Found: C, 66.66; H, 5.46; N, 9.11.

Melting point: 218–220° C. (crystallization solvent diisopropyl ether)

EXAMPLE 109

N-[3-[(Dimethylamino)methyl]-2H-chromen-7-yl)-4'-fluoro[1,1'-biphenyl]-4-carboxamide

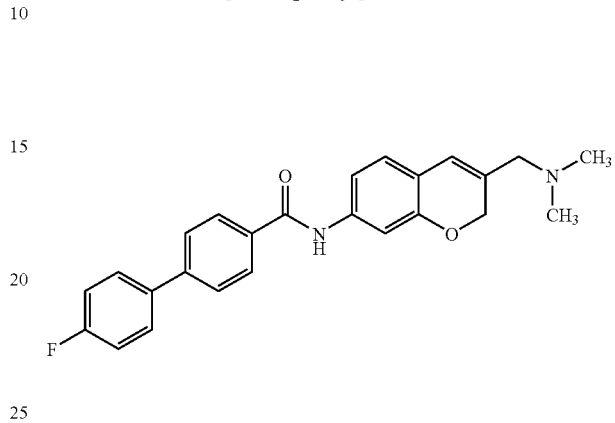

The titled compound was obtained by carrying out the same operation as in Example 1, using 3-[(N,N-dimethylamino)methyl]-2H-chromen-7-amine obtained in Reference Example 59.

$^1$H-NMR (CDCl$_3$) δ: 2.23 (6H, s), 2.97 (2H, s), 4.79 (2H, s), 6.30 (1H, s), 6.96 (1H, d, J=8.1 Hz), 7.13–7.22 (4H, m), 7.56–7.61 (2H, m), 7.65 (2H, d, 3=8.4 Hz), 7.78 (1H, s), 7.92 (2H, d, J=8.4 Hz).

Elemental analysis for C$_{25}$H$_3$FN$_2$O$_2$Calcd.: C, 74.61; H, 5.76; N, 6.96. Found: C, 74.35; H, 5.68; N, 6.74.

Melting point: 192–195° C. (crystallization solvent diisopropyl ether)

EXAMPLE 110

4'-Chloro-N-[3-[(dimethylamino)methyl]-3,4-dihydro-2H-chromen-7-yl][1,1'-biphenyl]-4-carboxamide

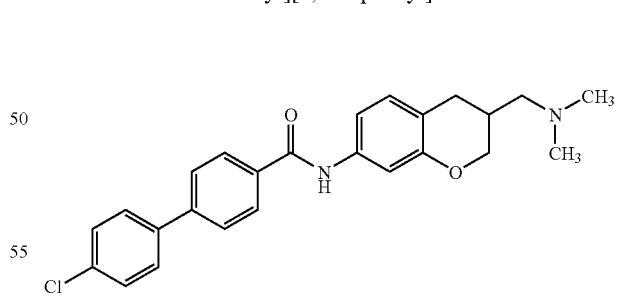

The titled compound was obtained by carrying out the same operation as in Example 1, using N-[(7-amino-3,4-dihydro-2H-chromen-3-yl)methyl]-N,N-dimethylamine obtained in Reference Example 65.

$^1$H-NMR (CDCl$_3$) δ: 2.26 (6H, s), 2.27 (3H, m), 2.47–2.51 (1H, m), 2.83–2.89 (1H, m), 3.82–3.86 (1H, m), 4.28–4.32 (1H, m), 7.04 (1H, d, J=8.1 Hz), 7.12–7.18 (2H, m), 7.44 (2H, d, J=8.4 Hz), 7.56 (2H, d, J=8.4 Hz), 7.67 (2H, d, J=8.4 Hz), 7.71 (1H, s), 7.93 (2H, d, J=8.4 Hz).

EXAMPLE 111

4'-Chloro-N-[6-[(dimethylamino)methyl]-5-methyl-7,8-dihydro-2-naphthalenyl][1,1'-biphenyl]-4-carboxamide

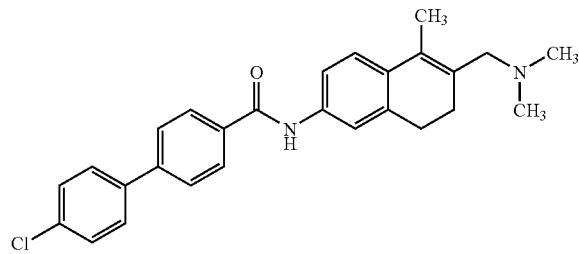

The titled compound was obtained by carrying out the same operation as in Example 1, using 6-[(dimethylamino)methyl]-5-methyl-7,8-dihydro-2-naphthalenamine obtained in Reference Example 66.

$^1$H-NMR (CDCl$_3$) δ: 2.09 (3H, s), 2.27 (6H, s), 2.31–2.37 (2H, m), 2.74–2.79 (2H, m), 3.08 (2H, s), 7.27–7.30 (1H, m), 7.44–7.48 (4H, m), 7.56 (2H, d, J=8.6 Hz), 7.67 (2H, d, J=8.4 Hz), 7.79 (1H, s), 7.95 (2H, d, J=8.4 Hz).

Elemental analysis for C$_{27}$H$_{27}$ClN$_2$O Calcd.: C, 75.25; H, 6.31; N, 6.50. Found: C, 74.86; H, 6.20; N, 6.42.

Melting point: 199–204° C. (crystallization solvent diisopropyl ether)

EXAMPLE 112

4'-Chloro-N-[6-[(dimethylamino)methyl]-S-ethyl-7,8-dihydro-2-naphthalenyl][1,1'-biphenyl]-4-carboxamide

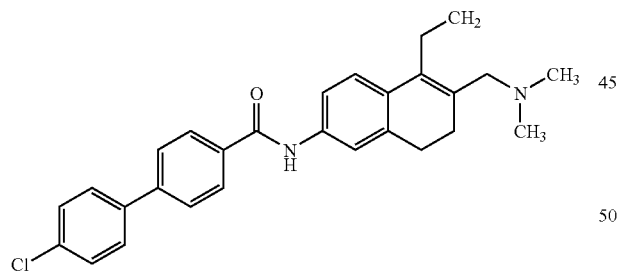

The titled compound was obtained by carrying out the same operation as in Example 1, using 6-[(dimethylamino)methyl]-5-ethyl-7,8-dihydro-2-naphthalenamine obtained in Reference Example 67.

$^1$H-NMR (CDCl$_3$) δ: 1.09 (3H, t, J=7.5 Hz), 2.27 (6H, s), 2.31–2.37 (2H, m), 2.60–2.63 (2H, m), 2.71–2.76 (2H, m), 3.08 (2H, s), 7.31 (1H, d, J=9.2 Hz), 7.43–7.49 (4H, m), 7.56 (2H, d, J=8.7 Hz), 7.67 (2H, d, J=8.6 Hz), 7.80 (1H, s), 7.94 (2H, d, J=8.6 Hz).

Elemental analysis for C$_{28}$H$_{29}$ClN$_2$O Calcd.: C, 75.57; H, 6.57; N, 6.30. Found: C, 75.41; H, 6.34; N, 6.23.

Melting point: 201–204° C. (crystallization solvent diisopropyl ether)

EXAMPLE 113

4'-Chloro-N-(6-[(dimethylamino)methyl)-5-isobutyl-7,8-dihydro-2-naphthalenyl][1,1'-biphenyl]-4-carboxamide

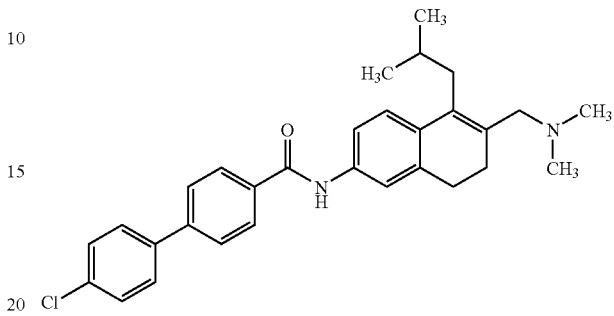

The titled compound was obtained by carrying out the same operation as in Example 1, using 6-[(dimethylamino)methyl]-5-isobutyl-7,8-dihydro-2-naphthalenamine obtained in Reference Example 68.

$^1$H-NMR (CDCl$_3$) δ: 0.90 (6H, d, J=6.4 Hz), 1.73–1.78 (1H, m), 2.23 (6H, s), 2.34 (2H, m), 2.50 (2H, d, J=7.3 Hz), 2.74 (2H, m), 3.13 (2H, s), 7.26–7.30 (1H, m), 7.45–7.48 (4H, m), 7.56 (2H, d, J=8.7 Hz), 7.67 (2H, d, J=8.4 Hz), 7.79 (1H, s), 7.94 (2H, d, J=8.4 Hz).

Elemental analysis for C$_{30}$H$_{33}$ClN$_2$O Calcd.: C, 76.17; H, 7.03; N, 5.92. Found: C, 75.91; H, 7.19; N, 5.72.

Melting point: 159–162° C. (crystallization solvent diisopropyl ether)

EXAMPLE 114

4'-Chloro-N-[5-methyl-6-(1-pyrrolidinylmethyl)-7,8-dihydro-2-naphthalenyl][1,1'-biphenyl]-4-carboxamide

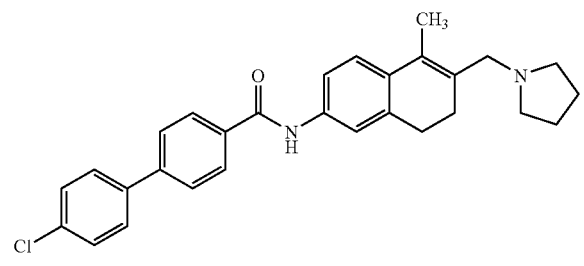

The titled compound was obtained by carrying out the same operation as in Example 1, using 5-methyl-6-(1-pyrrolidinylmethyl)-7,8-dihydro-2-naphthalenamine obtained in Reference Example 69.

$^1$H-NMR (CDCl$_3$) δ: 1.79 (4H, m), 2.11 (3H, s), 2.30–2.40 (2H, m), 2.54 (4H, m), 2.74–2.79 (2H, m), 3.28 (2H, s), 7.26–7.30 (1H, m), 7.45–7.48 (4H, m), 7.56 (2H, d, J=8.6 Hz), 7.67 (2H, d, J=8.4 Hz), 7.81 (1H, s), 7.95 (2H, d, J=8.4 Hz).

Melting point: 190–192° C. (crystallization solvent diisopropyl ether)

EXAMPLE 115

N-[5-Methyl-6-(1-pyrrolidinylmethyl)-7,8-dihydro-2-naphthalenyl][1,1'-biphenyl]-4-carboxamide

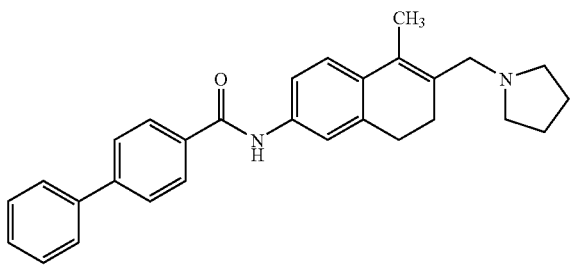

The titled compound was obtained by carrying out the same operation as in Example 1, using 5-methyl-6-(1-pyrrolidinylmethyl)-7,8-dihydro-2-naphthalenamine obtained in Reference Example 69.

$^1$H-NMR (CDCl$_3$) δ: 1.78 (4H, m), 2.10 (3H, s), 2.35–2.40 (2H, m), 2.53 (4H, m), 2.70–2.78 (2H, m), 3.28 (2H, s), 7.26–7.28 (1H, m), 7.40–7.50 (5H, m), 7.62 (2H, d, J=7.0 Hz), 7.70 (2H, d, J=8.4 Hz), 7.87 (1H, s), 7.94 (2H, d, J=8.4 Hz).

Melting point: 169–170° C. (crystallization solvent diisopropyl ether)

EXAMPLE 116

6-(4-Methoxyphenyl)-N-[5-methyl-6-(1-pyrrolidinylmethyl)-7,8-dihydro-2-naphthalenyl]nicotinamide

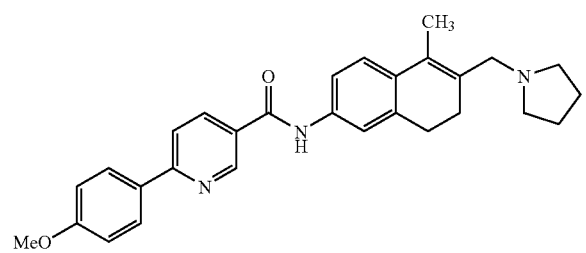

The titled compound was obtained by carrying out the same operation as in Example 1, using 5-methyl-6-(1-pyrrolidinylmethyl)-7,8-dihydro-2-naphthalenamine obtained in Reference Example 69.

$^1$H-NMR(CDCl$_3$) δ: 1.78 (4H, m), 2.09 (3H, s), 2.35–2.40 (2H, m), 2.53 (4H, m), 2.70–2.77 (2H, m), 3.27 (2H, s), 3.88 (3H, s), 7.01 (2H, d, J=8.9 Hz), 7.26 (1H, d, J=8.9 Hz), 7.45–7.47 (2H, m), 7.75 (1H, d, J=8.4 Hz), 7.95 (1H, s), 8.01 (2H, d, J=8.9 Hz), 8.18–8.21 (1H, m), 9.09 (1H, m).

Elemental analysis for C$_{29}$H$_{31}$N$_3$O$_2$ Calcd.: C, 76.79; H, 6.89; N, 9.26. Found: C, 76.46; H, 6.64; N, 9.09.

Melting point: 165–167° C. (crystallization solvent diisopropyl ether)

EXAMPLE 117

4'-Chloro-N-[5-cyano-6-(1-pyrrolidinylmethyl)-7,8-dihydro-2-naphthalenyl][1,1'-biphenyl]-4-carboxamide

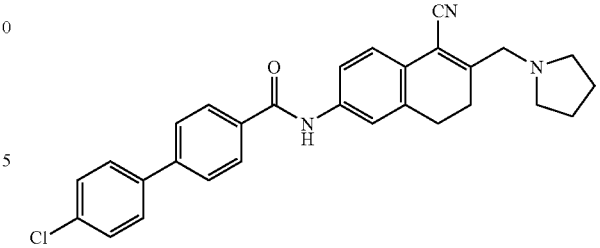

The titled compound was obtained as a colorless powder by carrying out the same operation as in Example 1, using 6-amino-2-(1-pyrrolidinylmethyl)-3,4-dihydro-1-naphthalenecarbonitrile obtained in Reference Example 70 and 4'-chloro[1,1'-biphenyl]-4-carboxylic acid.

$^1$H NMR (DMSO-d$_6$) δ: 1.73 (4H, m), 2.50 (4H, m), 2.56 (2H, m), 2.82 (2H, m), 3.49 (2H, s), 7.32 (1H, d, J=9.0 Hz), 7.57 (2H, d, J=8.4 Hz), 7.56–7.87 (6H, m), 8.07 (2H, d, J=8.4 Hz), 10.40 (1H, s).

FABMS(pos) 468.2 [M+H]

Melting point: 191–192° C. (crystallization solvent diisopropyl ether)

EXAMPLE 118

N-[5-Cyano-6-(1-pyrrolidinylmethyl)-7,8-dihydro-2-naphthalenyl][1,1'-biphenyl]-4-carboxamide

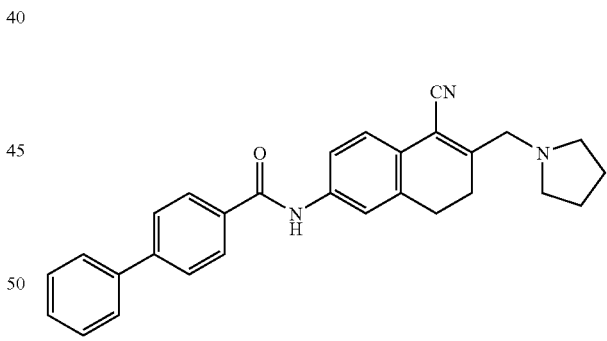

The titled compound was obtained by as a colorless powder carrying out the same operation as in Example 1, using 6-amino-2-(1-pyrrolidinylmethyl)-3,4-dihydro-1-naphthalenecarbonitrile obtained in Reference Example 70 and [1,1'-biphenyl]-4-carboxylic acid.

$^1$H NMR (DMSO-d$_6$) δ: 1.81 (4H, m), 2.62 (6H, m), 2.88 (2H, m), 3.56 (2H, s), 7.41 (2H, m), 7.46 (3H, m), 7.64 (2H, d, J=6.9 Hz), 7.73 (3H, m), 7.88 (1H, s), 7.95 (2H, d, J=8.1 Hz).

FABMS(pos) 434.2 [M+H]$^+$

Melting point: 168–170° C. (crystallization solvent diisopropyl ether)

EXAMPLE 119

3-Bromo-N-[6-[(dimethylamino)methyl]-5,6,7,8-tetrahydro-2-naphthalenyl]benzamide

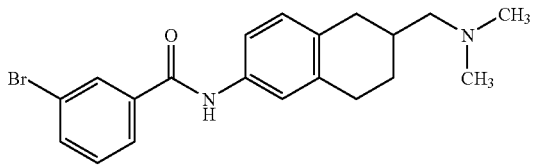

The titled compound was obtained by carrying out the same operation as in Example 1, using 6-amino-2-[(N,N-dimethylamino)methyl]tetralin and 3-bromobenzoic acid.

$^1$H NMR (DMSO-d$_6$) δ: 1.31 (1H, m), 1.89 (2H, m), 2.17 (6H, s), 2.17–2.35 (3H, m), 2.77 (3H, m), 7.04 (1H, d, J=8.4 Hz), 7.49 (3H, m), 7.79 (1H, d, J=8.1 Hz), 7.94 (1H, d, J=7.8 Hz), 8.13 (1H, s), 10.20 (1H, s).

EXAMPLE 120

N-[6-[(Dimethylamino)methyl]-5,6,7,8-tetrahydro-2-naphthalenyl][1,1'-biphenyl]-3-carboxamide

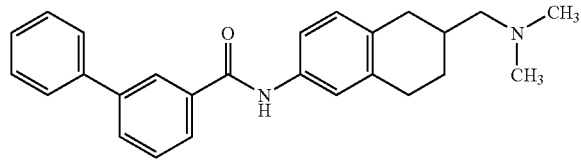

The titled compound was obtained by carrying out the same operation as in Example 16, using 3-bromo-N-[6-[(dimethylamino)methyl]-5,6,7,8-tetrahydro-2-naphthalenyl]benzamide obtained in Example 119 and phenylboronic acid.

$^1$H NMR (DMSO-d$_6$) δ: 1.43 (1H, m), 2.02 (1H, m), 2.21 (1H, m), 2.42 (1H, m), 2.81 (6H, s), 2.88 (3H, m), 3.09 (2H, m), 7.06 (1H, m), 7.42–7.65 (6H, m), 7.78–7.95 (4H, m), 8.22 (1H, s), 10.27 (1H, s).

FABMS(pos) 385.2 [M+H]$^+$

Melting point: 145–148° C. (crystallization solvent: ethyl acetate-diisopropyl ether)

EXAMPLE 121

N-[6-[(Dimethylamino)methyl]-5,6,7,8-tetrahydro-2-naphthalenyl]-2',4'-difluoro[1,1'-biphenyl]-4-carboxamide

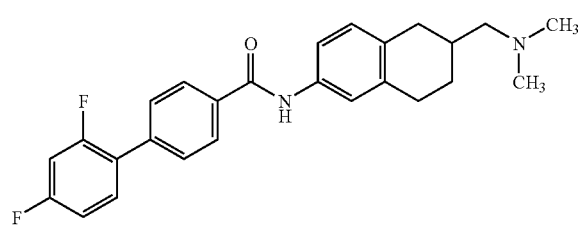

The titled compound was obtained by carrying out the same operation as in Example 1, using 6-amino-2-[(N,N-dimethylamino)methyl]tetralin and 2',4'-difluoro[1,1'-biphenyl]-4-carboxylic acid.

$^1$H NMR (CDCl$_3$) δ: 1.41 (1H, m), 1.94 (2H, m), 2.25 (6H, s), 2.23–2.30 (3H, m), 2.86 (3H, m), 6.96 (2H, m), 7.09 (1H, d, J=8.1 Hz), 7.30 (1H, m), 7.43 (2H, m), 7.61 (2H, m), 7.76 (1H, s), 7.93 (2H, m).

Melting point: 162–163° C. (crystallization solvent: ethyl acetate-diisopropyl ether)

EXAMPLE 122

N-[6-[(Dimethylamino)methyl]-5,6,7,8-tetrahydro-2-naphthalenyl-1H-indole-2-carboxamide

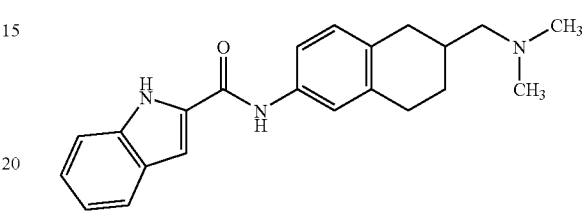

The titled compound was obtained by carrying out the same operation as in Example 1, using 6-amino-2-[(N,N-dimethylamino)methyl]tetralin and 1H-indol-2-carboxylic acid.

$^1$H NMR (DMSO-d$_6$) δ: 1.32 (1H, m), 1.91 (2H, m), 2.16 (6H, s), 2.16–2.35 (3H, m), 2.78 (3H, m), 7.06 (2H, m), 7.21 (1H, m), 7.44 (4H, m), 7.66 (1H, d, J=8.1 Hz), 10.05 (1H, s), 11.68 (1H, s).

FABMS(pos) 348.2 [M+H]$^+$

Melting point: 190–192° C. (crystallization solvent ethyl acetate-diisopropyl-ether)

EXAMPLE 123

N-[6-(Dimethylamino)methyl]-5,6,7,8-tetrahydro-2-naphthalenyl] [1,1'-biphenyl]-4-carboxamide

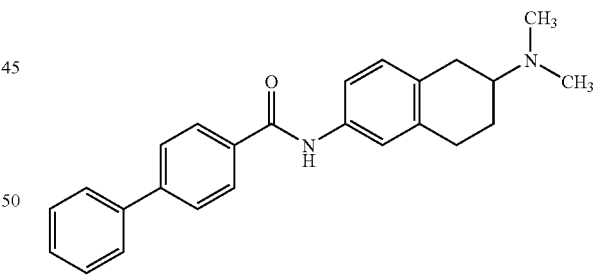

A tetrahydrofuran solution (0.146 ml, 0.293 mmol) of N-(6-oxo-5,6,7,8-tetrahydro-2-naphthalenyl)[1,1'-biphenyl]-4-carboxamide (10 mg, 0.029 mmol) obtained in Reference Example 72 and 2N dimethylamine was added to acetic acid-tetrahydrofuran (1:1) solution (0.5 ml), which was stirred at 50° C. for 15 minutes. After the reaction mixture was cooled at room temperature, sodium triacetoxyhydroborate (31 mg, 0.146 mmol) was added, which was stirred at 50° C. for 2 hours. 1N Hydrochloric acid was added to the reaction mixture, which was washed with ethyl acetate. Sodium carbonate was added to the water layer to make it alkaline, then extraction was conducted using ethyl acetate. The extract was washed with saturated aqueous sodium chloride solution, dried over anhydrous sodium sulfate, and then the solvent was distilled out under reduced pressure. The resulting residue was purified by alumina B column chromatography (development solvent ethyl acetate), to give the titled compound (1.6 mg).

$^1$H NMR (CDCl$_3$) δ: 1.68 (1H, m), 2.27 (1H, m), 2.40 (6H, s), 2.78 (5H, m), 7.11 (1H, d, J=8.1 Hz), 7.32–7.50 (5H, m), 7.62 (2H, m), 7.72 (2H, d, J=8.4 Hz), 7.78 (1H, br), 7.94 (2H, d, J=8.4 Hz).

FABMS(pos) 371.2 [M+H]+

EXAMPLE 124

N-[4-[(E)-2-(4,5-Dihydro-1H-imidazol-2-yl)ethenyl]phenyl][1,1'-biphenyl]-4-carboxamide hydrochloride

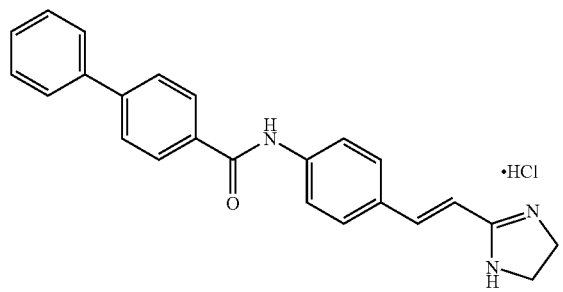

10.1 N Hydrogen chloride-ethanol solution (30 ml) was added to an ethanol suspension of N-[4-[(E)-2-cyanoethenyl]phenyl][1,1'-biphenyl]-4-carboxamide (250 mg, 0.771 mmol) obtained in Reference Example under room temperature, which was stirred for 16 hours. After the solvent was distilled out under reduced pressure, ethanol was again added to the residue, and then ethylenediamine (0.155 ml, 2.31 mmol) was added at room temperature, which was stirred for 16 hours. Sodium hydrogencarbonate solution was added to the reaction mixture, and the precipitated crude product was washed with water and chloroform. This product was dissolved in methanol. 1 N Hydrochloric acid (4 ml) was added to the solution, and the solvent was distilled out under reduced pressure. Small amount of water was added to the resulting residue, to give the titled compound (124 mg) as a colorless powder.

$^1$H NMR (DMSO-d$_6$, free base) δ: 3.33 (4H, m), 6.61 (1H, d, J=16.8 Hz). 7.15 (1H, d, J=16.8 Hz), 7.52 (5H, m), 7.83 (6H, m), 8.07 (2H, d, J=8.4 Hz).

Elemental analysis for C$_{24}$H$_{21}$N$_3$O.HCl.1.5H$_2$O Calcd.: C, 66.89; H, 5.85; N, 9.75. Found: C, 67.16; H, 6.10; N, 10.03.

EXAMPLE 125

N-[4-[2-(4,5-Dihydro-1H-imidazol-2-yl)ethenyl]phenyl][1,1'-biphenyl]-4-carboxamide hydrochloride

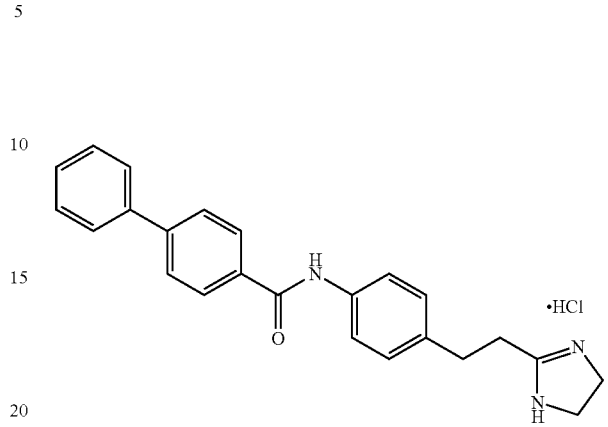

10% Palladium—carbon (200 mg) was added to a methanol suspension of N-[4-[(E)-2-(4,5-dihydro-1H-imidazol-2-yl)ethenyl]phenyl][1,1'-biphenyl]-4-carboxamide hydrochloride (80 mg, 0.198 mmol) obtained in Example 124, which was stirred under hydrogen atmosphere at 60° C. for 2 hours. After a catalyst was filtered off, the solvent was distilled out under reduced pressure. Diethyl ether was added to the resulting residue, to give the titled compound (52 mg) as a colorless powder.

$^1$H NMR (DMSO-d$_6$) δ: 2.73–2.97 (4H, m), 3.37 (4H, s), 7.24 (2H, d, J=8.4 Hz), 7.46 (3H, m), 7.76 (6H, m), 8.08 (2H, d, J=8.4 Hz).

FABMS(pos) 370[M+H]$^+$

EXAMPLE 126

4-Chloro-N-[2-[[6-[(dimethylamino)methyl]-7,8-dihydro-2-naphthalenyl]amino]-2-oxoethyl]benzamide

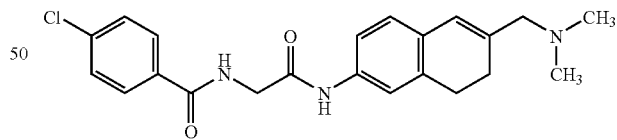

The titled compound was obtained by carrying out the same operation as in Example 1, using 6-[(N,N-dimethylamino)methyl]-7,8-dihydro-2-naphthalenamine obtained in Example 41-2) and 4-chlorobenzoyl glycine.

$^1$H NMR (DMSO-d$_6$) δ: 2.18 (6H, s), 2.21 (2H, m), 2.71 (2H, m), 2.91 (2H, s), 4.05 (2H, d, J=5.6 Hz), 6.30 (1H, s), 6.98 (1H, d, J=8.1 Hz), 7.36 (2H, m), 7.58 (2H, d, J=8.4 Hz), 7.92 (2H, d, J=8.4 Hz), 8.94 (1H, t, J=5.6 Hz), 10.00 (1H, s).

FABMS(pos) 398 [M+H]$^+$

Melting point: 168–171° C. (crystallization solvent diisopropyl ether)

EXAMPLE 127

4'-Chloro-N-[4-(3-piperidinylcarbonyl)phenyl][1,1'-biphenyl]-4-carboxamide hydrochloride

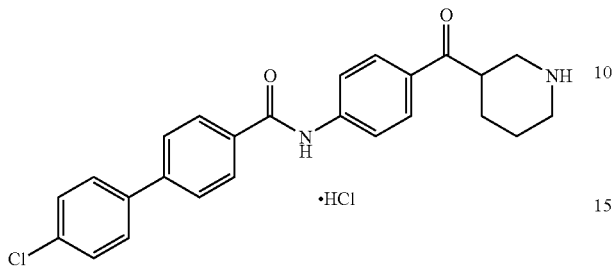

1) tert-Butyl 3-[4-[[(4'-chloro(1,1'-biphenyl]-4-yl)carbonyl]amino]benzoyl]-1-piperidinecarboxylate was obtained by carrying out the same operation as in Example 1, using tert-butyl 3-(4-aminobenzoyl)-1-piperidinecarboxylate obtained in Reference Example 77 and 4'-chloro[1,1'-biphenyl]-4-carboxylic acid.

FABMS(pos) 519.2 [M+H]+

2) 4N Hydrogen chloride-ethyl acetate (1 ml) was added to tert-butyl 3-[4-[[(4'-chloro[1,1'-biphenyl]-4-yl)carbonyl]amino]benzoyl]-1-piperidinecarboxylate (100 mg, 0.193 mmol) obtained in 1). One hour later, the solvent was distilled out under reduced pressure. Diisopropyl ether was added to the residue, to give the titled compound (73.3 mg) as a colorless powder.

$^1$H NMR (DMSO-$d_6$) δ: 1.56 (1H, m), 1.82 (2H, m), 2.02 (1H, m), 2.89 (1H, m), 3.05 (1H, m), 3.33 (2H, m), 3.90 (1H, m), 7.58 (2H, d, J=8.1 Hz), 7.81 (2H, d, J=8.1 Hz), 7.88 (2H, d, J=8.1 Hz), 8.03 (4H, m), 8.11 (2H, d, J=8.0 Hz), 9.04 (2H, br), 10.73 (1H, s).

FABMS(pos) 419.2 [M+H]$^+$

Melting point: 222–225° C. (decomposition)

EXAMPLE 128

4'-Chloro-N-[4-[hydroxy(3-piperidinyl)methyl]phenyl][1,1'-biphenyl]-4-carboxamide hydrochloride

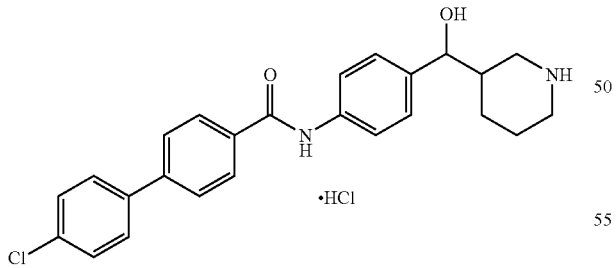

4N Hydrogen chloride-ethyl acetate (1 ml) was added to tert-butyl 3-[[4-[[(4'-chloro[1,1'-biphenyl]-4-yl)carbonyl]amino]phenyl](hydroxy)methyl]-1-piperidinecarboxylate (100 mg, 0.192 mmol) obtained in Reference Example 78. One hour later, the solvent was distilled out under reduced pressure. Diisopropyl ether was added to the residue, to give the titled compound (79.8 mg) as a colorless powder.

FABMSMS(pos) 421.2 [M+H]$^+$

Melting point: 195° C. (decomposition)

EXAMPLE 129

[4-[[(4'-Chloro[1,1'-biphenyl]-4-yl)carbonyl]amino]phenyl](3-piperidinyl)methyl acetate

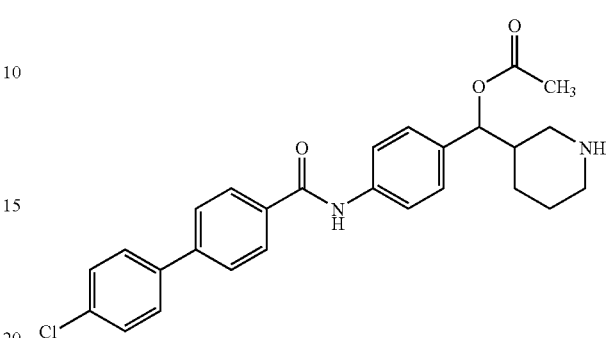

Concentrated sulfuric acid (0.0562 ml) was added to an acetic acid solution (3.5 ml) of tert-butyl 3-[[4-[[(4'-chloro[1,1'-biphenyl]-4-yl)carbonyl]amino]phenyl](hydroxy)methyl]-1-piperidinecarboxylate (366 mg, 0.702 mmol) obtained in Example 128, which was stirred under room temperature for 16 hours. Ethyl acetate was added to the reaction mixture, which was washed with potassium hydrogencarbonate solution and saturated aqueous sodium chloride solution, dried over anhydrous sodium sulfate, and then the solvent was distilled out under reduced pressure. The resulting oily substance was purified by alumina B column chromatography (development solvent; ethyl acetate: methanol=3:1), and powdered with diisopropyl ether, to give the titled compound (210 mg).

FABMS(pos) 403.2 [M+H]$^+$

Melting point: 200–203° C.

EXAMPLE 130

N-[4-(3-Piperidinylmethyl)phenyl[1,1'-biphenyl]-4-carboxamide hydrochloride

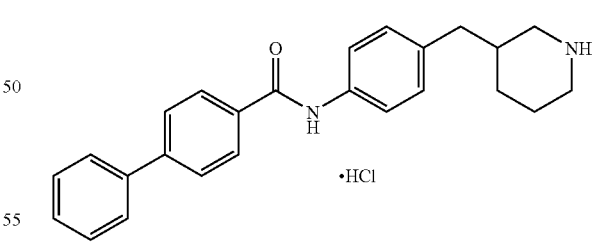

4N Hydrogen chloride-ethyl acetate (2 ml) was added to tert-butyl 3-[4-[([1,1'-biiphenyl]-4-ylcarbonyl)amino]benzyl]-1-piperidinecarboxylate (100 mg, 0.212 mmol) obtained in Reference Example 80. Two hours later, the solvent was distilled out under reduced pressure. Diisopropyl ether was added to the residue for powdering, to give the titled compound (79 mg).

FABMS(pos) 371.3 [M+H]$^+$

Melting point: 218–220° C. (decomposition)

EXAMPLE 131

4'-Fluoro-N-[4-(3-piperidinylmethyl)phenyl][1,1'-biphenyl]-4-carboxamide hydrochloride

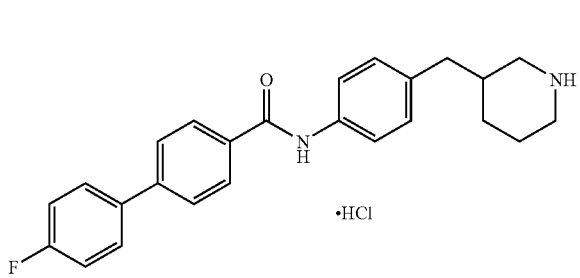

4N Hydrogen chloride-ethyl acetate (3 ml) was added to tert-butyl 3-[4-[[(4'-fluoro[1,1'-biphenyl]-4-yl)carbonyl]amino]benzyl]-1-piperidinecarboxylate (150 mg, 0.307 mmol) obtained in Reference Example 81. Two hours later, the solvent was distilled out under reduced pressure. Diisopropyl ether was added to the residue, to give the titled compound (115 mg) as a colorless powder.

FABMS(pos) 389.3 [M+H]$^+$

Melting point: 205° C. (decomposition)

EXAMPLE 132

4'-Chloro-N-[4-(3-piperidinylmethyl)phenyl][1,1'-biphenyl]-4-carboxamide hydrochloride

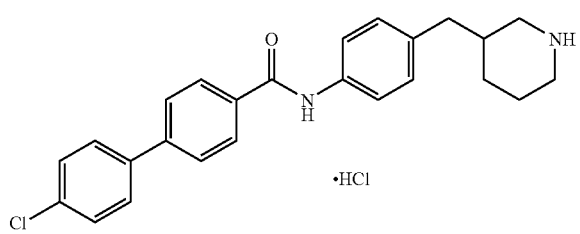

4N Hydrogen chloride-ethyl acetate (3 ml) was added to tert-butyl 3-[4-[[(4'-chloro[1,1'-biphenyl]-4-yl)carbonyl]amino]benzyl]-1-piperidinecarboxylate (150 mg, 0.297 mmol) obtained in Reference Example 82. Two hours later, the solvent was distilled out under reduced pressure. Diisopropyl ether was added to the residue, to give the titled compound (73.3 mg) as a colorless powder.

FABMS(pos) 405.2 [M+H]+

Melting point: 200° C. (decomposition)

EXAMPLE 133

N-[7-[(Dimethylamino)methyl]-5,6-dihydro-3-quinolinyl][1,1'-biphenyl]-4-carboxamide

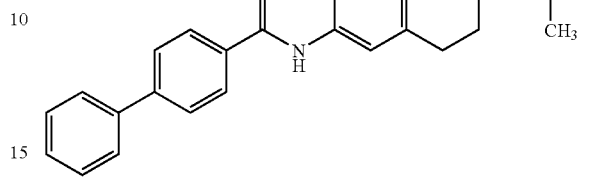

The titled compound was obtained by carrying out the same operation as in Example 1, using N-[(3-amino-5,6-dihydro-7-quinolinyl)methyl]-N,N-dimethylamine obtained in Reference Example 86 and [1,1'-biphenyl]-4-carboxylic acid.

$^1$H NMR (DMSO-$d_6$) δ: 2.16 (6H, s), 2.29 (2H, t, J=8.1 Hz), 2.84 (2H, t, J=8.1 Hz), 2.98 (2H, s), 6.40 (1H, s), 7.42 (1H, m), 7.51 (2H, m), 7.76 (2H, d, J=7.2 Hz), 7.84 (2H, d, J=8.1 Hz), 7.97 (1H, s), 8.06 (2H, d, J=8.4 Hz), 8.65 (1H, s), 10.39 (1H, s).

FABMS(pos) 384.2 [M+H]+

Melting point: 202–203° C.

EXAMPLE 134

4'-Chloro-N-[7-[(dimethylamino)methyl]-5,6-dihydro-3-quinolinyl][1,1'-biphenyl]-4-carboxamide

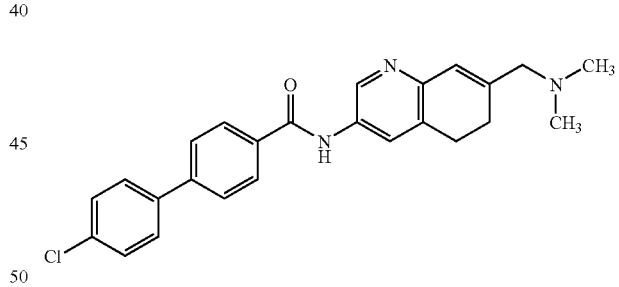

The titled compound was obtained by carrying out the same operation as in Example 1, using N-[(3-amino-5,6-dihydro-7-quinolinyl)methyl]-N,N-dimethylamine obtained in Reference Example 86 and 4'-chloro[1,1'-biphenyl]-4-carboxylic acid.

$^1$H NMR (DMSO-$d_6$) δ: 2.17 (6H, s), 2.31 (2H, t, J=8.1 Hz), 2.85 (2H, t, J=8.1 Hz), 2.99 (2H, s), 6.41 (1H, s), 7.57 (2H, d, J=8.4 Hz), 7.81 (2H, d, J=8.4 Hz), 7.86 (2H, d, J=8.4 Hz), 7.98 (1H, s), 8.08 (2H, d, J=8.4 Hz), 8.66 (1H, s), 10.41 (1H, s).

FABMS(pos) 418.2 [M+H]$^+$

Melting point: 220–222° C.

EXAMPLE 135

4'-Chloro-N-[6-[(4-methyl-1-piperazinyl)methyl]-7,8-dihydro-2-naphthalenyl][1,1'-biphenyl]-4-carboxamide

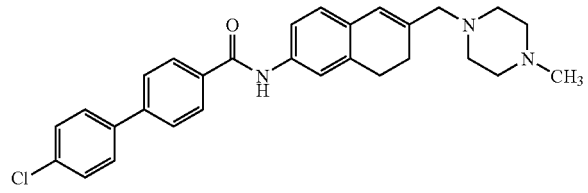

The titled compound was obtained by carrying out the same operation as in Example 51, using 4'-chloro-N-[6-(chloromethyl)-7,8-dihydro-2-naphthalenyl][1,1'-biphenyl]-4-carboxamide obtained in Reference Example 56.

$^1$H-NMR (CDCl$_3$) δ: 2.30 (3H, s), 2.25–2.50 (10H, m), 2.83 (2H, t, J=8.1 Hz), 3.07 (2H, s), 6.35 (1H, s), 7.01 (1H, d, J=8.1 Hz), 7.36 (1H, d, J=7.8 Hz), 7.44 (2H, d, J=8.4 Hz), 7.51 (1H, s), 7.55 (2H, d, J=8.4 Hz), 7.66 (2H, d, J=8.4 Hz), 7.84 (1H, s), 7.93 (2H, d, J=8.4 Hz).

Melting point: 220–222° C. (crystallization solvent tetrahydrofuran-n-hexane)

EXAMPLE 136

4'-Chloro-N-[6-[[methyl[2-(1-piperidinyl)ethyl]amino]methyl]-7,8-dihydro-2-naphthalenyl][1,1'-biphenyl]-4-carboxamide

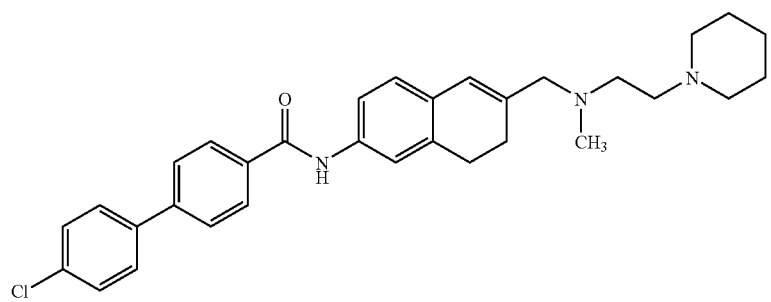

The titled compound was obtained by carrying out the same operation as in Example 51, using 4'-chloro-N-[6-(chloromethyl)-7,8-dihydro-2-naphthalenyl][1,1'-biphenyl]-4-carboxamide obtained in Reference Example 56.

$^1$H-NMR (CDCl$_3$) δ: 1.72–1.77 (6H, m), 2.25–2.36 (2H, m), 2.27 (3H, s), 2.52–2.63 (8H, m), 2.84 (2H, t, J=8.0 Hz), 3.08 (2H, s), 6.35 (1H, s), 7.01 (1H, d, J=8.1 Hz), 7.38 (1H, d, J=8.1 Hz), 7.44 (2H, d, J=8.4 Hz), 7.49 (1H, s), 7.55 (2H, d, J=8.4 Hz), 7.66 (2H, d, J=8.4 Hz), 7.83 (1H, s), 7.93 (2H, d, J=8.4 Hz).

Melting point: 165–167° C. (crystallization solvent: tetrahydrofuran-n-hexane)

EXAMPLE 137

4'-Chloro-N-[6-[[methoxy(methyl)amino]methyl]-7,8-dihydro-2-naphthalenyl][1,1'-biphenyl]-4-carboxamide

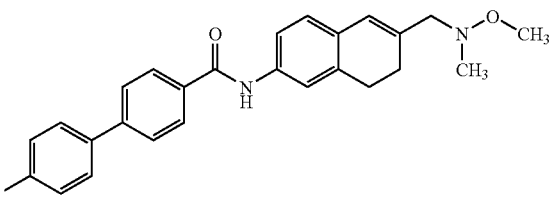

The titled compound was obtained by carrying out the same operation as in Example 51, using 4'-chloro-N-[6-(chloromethyl)-7,8-dihydro-2-naphthalenyl][1,1'-biphenyl]-4-carboxamide obtained in Reference Example 56.

$^1$H-NMR (CDCl$_3$) δ: 2.41 (2H, t, J=8.1 Hz), 2.61 (3H, s), 2.86 (2H, t, J=8.1 Hz), 3.37 (2H, s), 3.52 (3H, s), 6.39 (1H, s), 7.03 (1H, d J=8.1 Hz), 7.36 (1H, d, J=8.1 Hz), 7.44 (2H, d, J=8.4 Hz), 7.53 (1H, s), 7.55 (2H, d, J=8.4 Hz), 7.66 (2H, d, J=8.4 Hz), 7.83 (1H, s), 7.93 (2H, d, J=8.4 Hz).

Melting point: 190–192° C. (crystallization solvent: ethyl acetate-n-hexane)

EXAMPLE 138

4'-Chloro-N-[6-[[4-(1-piperidinyl)-1-piperidinyl]methyl]-7,8-dihydro-2-naphthalenyl][1,1'-biphenyl]-4-carboxamide

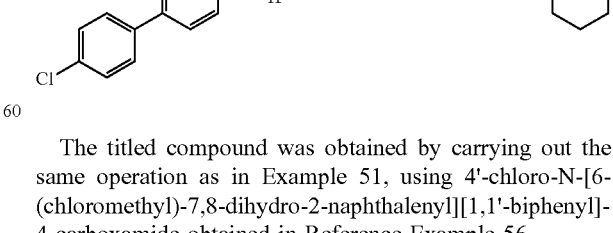

The titled compound was obtained by carrying out the same operation as in Example 51, using 4'-chloro-N-[6-(chloromethyl)-7,8-dihydro-2-naphthalenyl][1,1'-biphenyl]-4-carboxamide obtained in Reference Example 56.

$^1$H-NMR (CDCl$_3$) δ: 1.45–1.96 (12H, m), 2.29–2.34 (3H, m), 2.57 (4H, s), 2.83 (2H, t, J=8.1 Hz), 2.96–3.03 (4H, m), 6.32 (1H, s), 7.00 (1H, d, J=8.1 Hz), 7.38 (1H, d, J=8.1 Hz), 7.44 (2H, d, J=8.4 Hz), 7.50 (1H, s), 7.55 (2H, d, J=8.4 Hz), 7.66 (2H, d, J=8.4 Hz), 7.86 (1H, s), 7.93 (2H, d, J=8.4 Hz).

Melting point: 232–234° C. (crystallization solvent ethyl acetate-n-hexane)

EXAMPLE 139

6-(4-Fluorophenyl)-N-[3-(1-pyrrolidinylmethyl)-2H-chromen-7-yl]nicotineamide

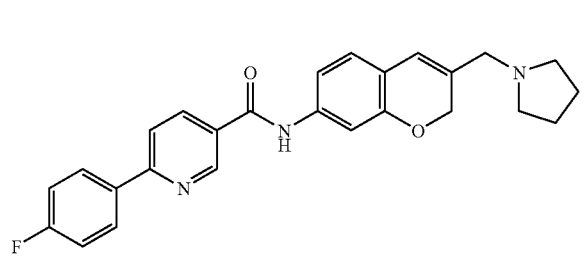

The titled compound was obtained by carrying out the same operation as in Example 1, using 3-(1-pyrroidinylmethyl)-2H-chromen-7-amine obtained in Reference Example 87.

$^1$H-NMR (CDCl$_3$) δ: 1.70 (4H, s), 2.43 (4H, s), 3.12 (2H, s), 4.73 (2H, s), 6.37 (1H, s), 7.03 (1H, d, J=7.8 Hz), 7.29–7.40 (4H, m), 8.15 (1H, d, J=8.4 Hz), 8.22–8.39 (3H, m), 9.15 (1H, s), 10.40 (1H, s).

Melting point: 233–235° C. (crystallization solvent: tetrahydrofuran-n-hexane)

EXAMPLE 140

4-Bromo-N-[6-(1-pyrrolidinylmethyl)-7,8-dihydro-2-naphthalenyl]benzamide

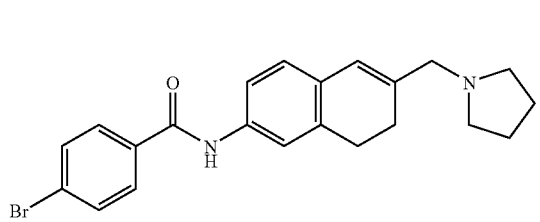

The titled compound was obtained by carrying out the same operation as in Example 1, using 6-(1-pyrrolidinylmethyl)-7,8-dihydro-2-naphthalenamine obtained in Reference Example 54.

$^1$H-NMR (CDCl$_3$) δ: 1.79 (4H, s), 2.35 (2H, t, J=8.1 Hz), 2.52 (4H, s), 2.83 (2H, t, J=8.1 Hz), 3.17 (2H, s), 6.35 (1H, s), 6.99 (1H, d, J=8.1 Hz), 7.34 (1H, d, J=8.1 Hz), 7.43 (1H, s), 7.60 (2H, d, J=8.4 Hz), 7.72 (2H, d, J=8.4 Hz), 7.76 (1H, s).

Melting point: 135–137° C. (crystallization solvent ethyl acetate-n-hexane)

EXAMPLE 141

6-(4-Methoxyphenyl)-N-[3-(1-pyrrolidinylmethyl)-2H-chromen-7-yl]nicotinamide

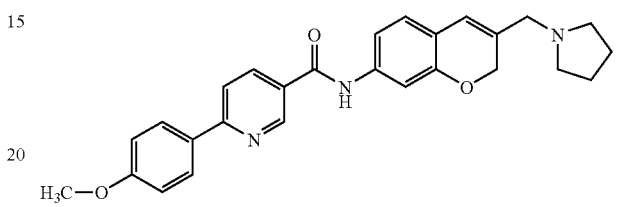

The titled compound was obtained by carrying out the same operation as in Example 1, using 3-(1-pyrrolidinylmethyl)-2H-chromen-7-amine obtained in Reference Example 87.

$^1$H-NMR (CDCl$_3$) δ: 1.70 (4H, s), 2.44 (4H, s), 3.12 (2H, s), 3.84 (3H, s), 4.73 (2H, s), 6.37 (1H, s), 7.03 (1H, d, J=8.1 Hz), 7.09 (2H, t, J=8.7 Hz), 7.29 (1H, d, J=8.4 Hz), 7.31 (1H, s), 8.07 (1H, d, J=8.7 Hz), 8.16 (2H, d, J=8.7 Hz), 8.32 (1H, d, J=8.4 Hz), 9.12 (1H, s), 10.34 (1H, s).

Elemental analysis for C$_{27}$H$_{27}$N$_3$O$_3$ Calcd.: C, 73.45; H, 6.16; N, 9.52. Found: C, 73.02; H, 6.27; N, 9.33.

Melting point: 243–245° C. (crystallization solvent tetrahydrofuran-n-hexane)

EXAMPLE 142

4-(4-Fluorophenyl)-N-[3-(1-pyrrolidinylmethyl)-2H-chromen-7-yl]-1-piperidinecarboxamide

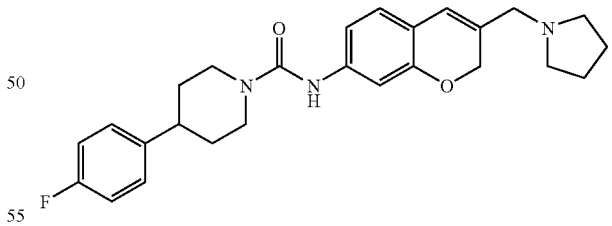

The titled compound was obtained by carrying out the same operation as in Example 99, using 3-(1-pyrrolidinylmethyl)-2H-chromen-7-amine obtained in Reference Example 87.

$^1$H-NMR (CDCl$_3$) δ: 1.69–1.91 (8H, m), 2.49 (4H, s), 2.70 (1H, t, J=12.0 Hz), 2.97 (2H, t, J=12.0 Hz), 3.12 (2H, s), 4.19 (2H, d, J=13.0 Hz), 4.76 (2H, s), 6.26 (1H, s), 6.37 (1H, s), 6.82–7.03 (5H, m), 7.16 (2H, dd, J=5.4, 8.4 Hz).

Melting point: 176–178° C. (crystallization solvent.: ethyl acetate-diisopropyl ether)

EXAMPLE 143

N-[3-(1-Pyrrolidinylmethyl)-2H-chromen-7-yl][1,1'-biphenyl]-4-carboxamide

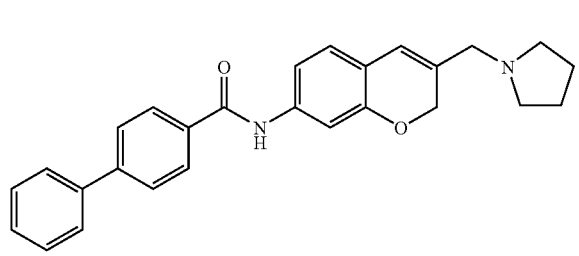

The titled compound was obtained by carrying out the same operation as in Example 1, using 3-(1-pyrrolidinylmethyl)-2H-chromen-7-amine obtained in Reference Example 87.

$^1$H-NMR (CDCl$_3$) δ: 1.79 (4H, s), 2.50 (4H, s), 3.15 (2H, s), 4.81 (2H, s), 6.30 (1H, s), 6.95 (1H, d, J=8.1 Hz), 7.13 (1H, s), 7.20 (1H, d, J=8.1 Hz), 7.39–7.50 (3H, m), 7.61–7.70 (4H, m), 7.82 (1H, s), 7.92 (2H, d, J=8.1 Hz).

Melting point: 198–200° C. (crystallization solvent ethyl acetate)

EXAMPLE 144

N-[6-[(N-Benzyl-N-methylamino)methyl]-7,8-dihydro-2-naphthalenyl]-4'-fluoro[1,1'-biphenyl]-4-carboxamide

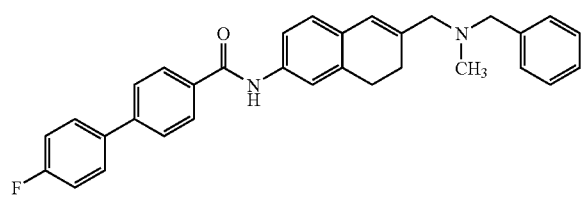

The titled compound was obtained by carrying out the same operation as in Example 1, using 6-[(N-benzyl-N-methylamino)methyl]-7,8-dihydro-2-naphthalenamine obtained in Reference Example 88.

$^1$H-NMR (CDCl$_3$) δ: 2.20 (3H, s), 2.38 (2H, t, J=8.1 Hz), 2.85 (2H, t, J=8.1 Hz), 3.09 (2H, s), 3.52 (2H, s), 6.39 (1H, s), 7.02 (1H, d, J=8.1 Hz), 7.13–7.66 (13H, m), 7.84 (1H, s), 7.93 (2H, d, J=8.4 Hz).

Melting point: 143–145° C. (crystallization solvent ethyl acetate-n-hexane)

EXAMPLE 145

4'-Isobutyrylamino-N-[6-(1-pyrrolidinylmethyl)-7,8-dihydro-2-naphthalenyl][1,1'-biphenyl]4-carboxamide

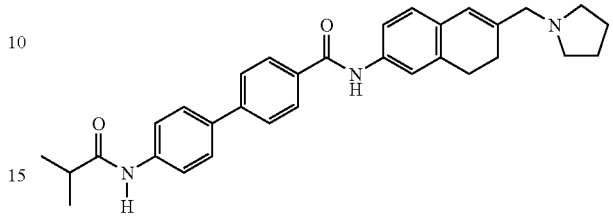

The titled compound was obtained as an amorphous powder by carrying out the same operation as in Example 1, using 6-(1-pyrrolidinylmethyl)-7,8-dihydro-2-naphthalenamine obtained in Reference Example 54.

MS m/z 494.4 (MH$^+$).

EXAMPLE 146

Ethyl 4'-[[[6-(1-pyrrolidinylmethyl)-7,8-dihydro-2-naphthalenyl]amino]carbonyl][1,1'-biphenyl]-3-carboxylate

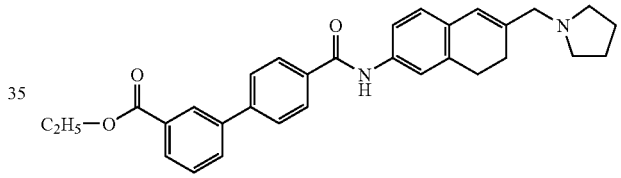

The titled compound was obtained as an amorphous powder by carrying out the same operation as in Example 1, using 6-(1-pyrrolidinylmethyl)-7,8-dihydro-2-naphthalenamine obtained in Reference Example 54.

MS m/z 481.4 (MH$^+$).

EXAMPLE 147

3-[4'-[[[6-(1-Pyrrolidinylmethyl)-7,8-dihydro-2-naphthalenyl]amino]carbonyl][1,1'-biphenyl]-4-yl] propionic acid

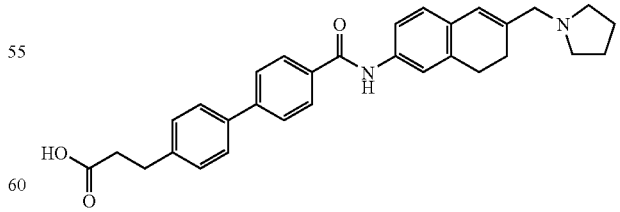

The titled compound was obtained as a powder by carrying out the same operation as in Example 1, using 6-(1-pyrrolidinylmethyl)-7,8—dihydro-2-naphthalenamine obtained in Reference Example 54.

MS m/z 481.4 (MH$^+$).

EXAMPLE 148

4'-Methoxy-N-[6-(1-pyrrolidinylmethyl)-7,8-dihydro-2-naphthalenyl][1,1'-biphenyl]-4-carboxamide

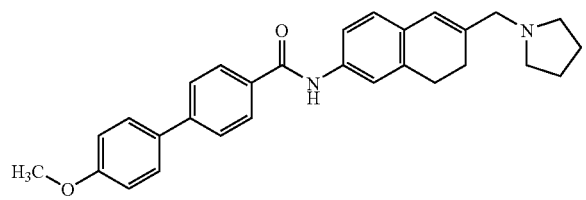

The titled compound was obtained by carrying out the same operation as in Example 1, using 6-(1-pyrrolidinylmethyl)-7,8-dihydro-2-naphthalenamine obtained in Reference Example 54.

$^1$H-NMR (CDCl$_3$) δ: 1.80 (4H, m), 2.36 (2H, t, J=7.8 Hz), 2.52 (4H, m), 2.86 (2H, t, J=7.8 Hz), 3.18 (2H, s), 3.87 (3H, s), 6.36 (1H, s), 7.00–7.03 (3H, m), 7.26 (1H, m), 7.38 (1H, d, J=8.3 Hz), 7.49 (1H, s), 7.58 (2H, d, J=8.6 Hz), 7.67 (1H, d, J=8.2 Hz), 7.78 (1H, s), 7.90 (2H, d, J=8.2 Hz).

Elemental analysis for C$_{29}$H$_{30}$N$_2$O$_2$ Calcd.: C, 79.42; H, 6.89; N, 6.39. Found: C, 79.21; H, 6.88; N, 6.35.

Melting point: 187–188 t (crystallization solvent: ethyl acetate-diisopropyl ether)

EXAMPLE 149

6-(4-Fluorophenyl)-N-[6-[(1-pyrrolidinyl)methyl]-7,8-dihydro-2-naphthalenyl]nicotinamide

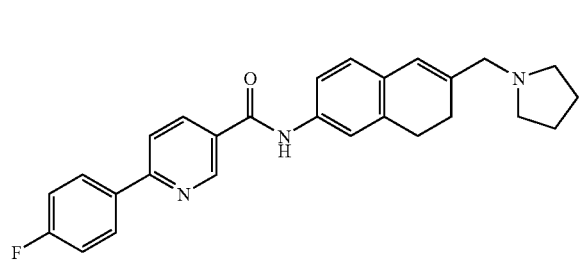

The titled compound was obtained by carrying out the same operation as in Example 1, using 6-(1-pyrrolidinylmethyl)-7,8-dihydro-2-naphthalenamine obtained in Reference Example 54.

$^1$H-NMR (CDCl$_3$) δ: 1.81 (4H, m), 2.36 (2H, t, J=8.1 Hz), 2.53 (4H, m), 2.86 (2H, t, J=8.1 Hz), 3.18 (2H, s), 6.37 (1H, s), 7.03 (1H, d, J=7.8 Hz), 7.16–7.30 (3H, m), 7.47 (1H, s), 7.77–7.82 (2H, m), 8.06 (2H, dd, J=8.9, 5.3 Hz), 8.25 (1H, dd, J=8.4, 2.2 Hz), 9.11 (1H, d, J=2.0 Hz).

Elemental analysis for C$_{27}$H$_{26}$FN$_3$O Calcd.: C, 75.85; H, 6.13; N, 9.83. Found: C, 75.71; H, 5.93; N, 9.75.

Melting point: 225–227° (crystallization solvent: ethyl acetate-diisopropyl ether)

EXAMPLE 150

6-(4-Methylphenyl)-N-[6-[(1-pyrrolidinyl)methyl]-7,8-dihydro-2-naphthalenyl]nicotinamide

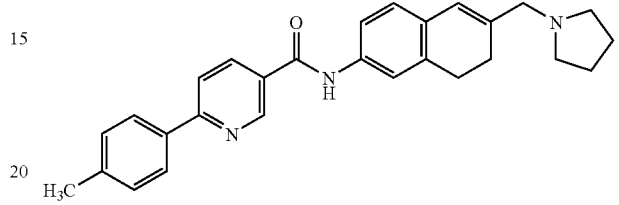

The titled compound was obtained by carrying out the same operation as in Example 1, using 6-(1-pyrrolidinylmethyl)-7,8-dihydro-2-naphthalenamine obtained in Reference Example 54.

$^1$H-NMR (CDCl$_3$) δ: 1.81 (4H, m), 2.36 (2H, t, J=7.8 Hz), 2.43 (3H, s), 2.53 (4H, m), 2.86 (2H, t, J=7.8 Hz), 3.19 (2H, s), 6.37 (1H, s), 7.02 (1H, d, J=8.7 Hz), 7.25–7.39 (3H, m), 7.47 (1H, s), 7.82 (2H, m), 7.96 (2H, d, J=8.1 Hz), 8.23 (1H, dd, J=8.1, 2.3 Hz), 9.12 (1H, d, J=2.3 Hz).

Melting point: 235–236° C. (crystallization solvent: ethyl acetate-diisopropyl ether)

EXAMPLE 151

N-[6-[(Dimethylamino)methyl]-7,8-dihydro-2-naphthalenyl]-6-(4-fluorophenoxy)nicotinamide

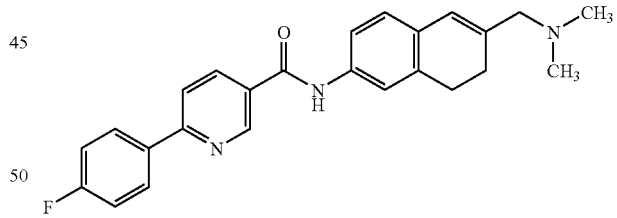

The titled compound was obtained by carrying out the same operation as in Example 1, using 6-[(N,N-dimethylamino)methyl]-7,8-dihydro-2-naphthalenamine obtained in Reference Example 41-2).

$^1$H-NMR (CDCl$_3$) δ: 2.25 (6H, s), 2.34 (2H, t, J=8.1 Hz), 2.86 (2H, t, J=8.1 Hz), 2.99 (2H, s), 6.35 (1H, s), 7.03 (1H, d, J=8.1 Hz), 7.17 (2H, m), 7.26 (1H, m), 7.39 (1H, d, J=8.1 Hz), 7.47 (1H, s), 7.78 (1H, d, J=7.2 Hz), 7.83 (1H, s), 8.06 (1H, dd, J=8.4, 6.7 Hz), 8.25 (1H, d, J=6.7 Hz), 9.12 (1H, s).

Elemental analysis for C$_{25}$H$_{24}$FN$_3$O Calcd.: C, 74.79; H, 6.03; N, 10.47. Found: C, 74.74; H, 5.95; N, 10.24.

Melting point: 216–219° C. (crystallization solvent: ethyl acetate-diisopropyl ether)

EXAMPLE 152

6-(2,4-Difluorophenyl)-N-[6-[(dimethylamino)methyl]-7,8-dihydro-2-naphthalenyl]nicotinamide

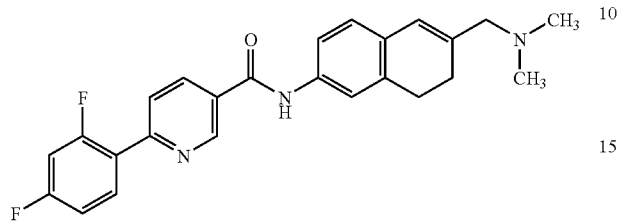

The titled compound was obtained by carrying out the same operation as in Example 1, using 6-[(N,N-dimethylamino)methyl]-7,8-dihydro-2-naphthalenamine obtained in Reference Example 41-2).

$^1$H-NMR (CDCl$_3$) δ: 2.25 (6H, s), 2.34 (2H, t, J=8.1 Hz), 2.85 (2H, t, J=8.1 Hz), 3.00 (2H, s), 6.35 (1H, s), 6.90–7.06 (3H, m), 7.39 (1H, d, J=7.8 Hz), 7.47 (1H, s), 7.80–7.90 (2H, m), 8.10 (1H, dd, J=15.3, 8.8 Hz), 8.23 (1H, dd, J=8.4, 2.3 Hz), 9.15 (1H, d, J=1.7 Hz).

Elemental analysis for C$_{25}$H$_{23}$F$_2$N$_3$O Calcd.: C, 71.58; H, 5.53; N, 10.02. Found: C, 71.50; H, 5.49; N, 9.61.

Melting point: 162–163° C. (crystallization solvent: ethyl acetate-diisopropyl ether)

EXAMPLE 153

6-Phenyl-N-[6-(1-pyrrolidinylmethyl)-7,8-dihydro-2-naphthalenyl]nicotinamide

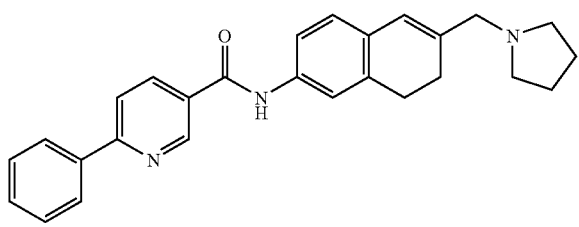

The titled compound was obtained by carrying out the same operation as in Example 1, using 6-(1-pyrrolidinylmethyl)-7,8-dihydro-2-naphthalenamine obtained in Reference Example 54.

$^1$H-NMR (CDCl$_3$) δ: 1.81 (4H, m), 2.36 (2H, t, J=8.1 Hz), 2.53 (4H, m), 2.85 (2H, t, J=8.1 Hz), 3.18 (2H, s), 6.37 (1H, s), 7.02 (1H, d, J=8.1 Hz), 7.37–7.53 (5H, m), 7.83 (1H, d, J=8.1 Hz), 7.86 (1H, d, J=6.2 Hz), 8.04 (1H, s), 8.06 (1H, d, J=1.7 Hz), 8.24 (1H, dd, J=8.4, 2.4 Hz), 9.13 (1H, d, J=2.2 Hz).

Elemental analysis for C$_{27}$H$_{27}$N$_3$O Calcd.: C, 79.19; H, 6.65; N, 10.26. Found: C, 78.93; H, 6.65; N, 10.19.

Melting point: 186–187° C. (crystallization solvent: ethyl acetate-diisopropyl ether)

EXAMPLE 154

6-(4-Methoxyphenyl)-N-[6-(1-pyrrolidinylmethyl)-7,8-dihydro-2-naphthalenyl]nicotinamide

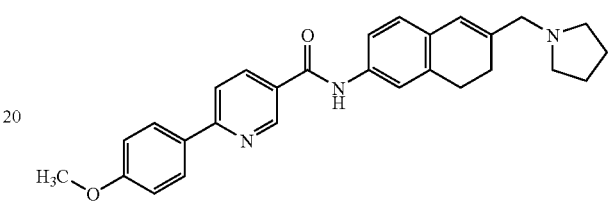

The titled compound was obtained by carrying out the same operation as in Example 1, using 6-(1-pyrrolidinylmethyl)-7,8-dihydro-2-naphthalenamine obtained in Reference Example 54.

$^1$H-NMR (CDCl$_3$) δ: 1.80 (4H, m), 2.36 (2H, t, J=8.1 Hz), 2.52 (4H, m), 2.84 (2H, t, J=8.1 Hz), 3.18 (2H, s), 3.88 (3H, s), 6.36 (1H, s), 7.02 (3H, m), 7.37 (1H, d, J=7.5 Hz), 7.47 (1H, s), 7.78 (1H, d, J=8.1 Hz), 7.79 (1H, s), 8.03 (2H, d, J=8.5 Hz), 8.20 (1H, d, J=8.1 Hz), 9.08 (1H, s).

Melting point: 219–220° C. (crystallization solvent: ethyl acetate-diisopropyl ether)

EXAMPLE 155

4-(4-Methylphenyl)-N-[6-(1-pyrrolidinylmethyl)-7,8-dihydro-2-naphthalenyl]-1-piperidinecarboxamide

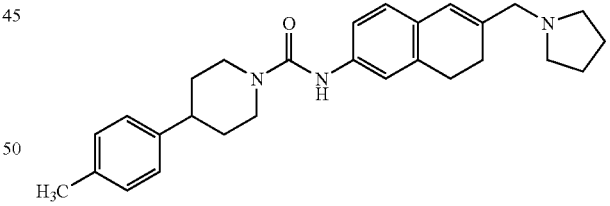

The titled compound was obtained by carrying out the same operation as in Example 99, using 6-(1-pyrrolidinylmethyl)-7,8-dihydro-2-naphthalenamine obtained in Reference Example 54.

$^1$H-NMR (CDCl$_3$) δ: 1.64–1.92 (8H, m), 2.29 (2H, m), 2.32 (3H, s), 2.51 (4H, m), 2.64 (1H, m), 2.80 (2H, t, J=7.8 Hz), 2.97 (2H, dd, J=13.1, 10.7 Hz), 3.15 (2H, s), 4.19 (2H, d, J=13.1 Hz), 6.32 (1H, s), 6.35 (1H, s), 6.42 (1H, d, J=7.8 Hz), 7.06–7.20 (6H, m).

Elemental analysis for C$_{28}$H$_{35}$N$_3$O.0.5H$_2$O Calcd.: C, 76.67; H, 8.27; N, 9.58. Found: C, 76.72; H, 8.03; N, 9.36.

Melting point: 197–198° C. (crystallization solvent: ethyl acetate-diisopropyl ether)

EXAMPLE 156

4-Phenyl-N-[6-(1-pyrrolidinylmethyl)-7,8-dihydro-2-naphthalenyl]-1-piperidinecarboxamide

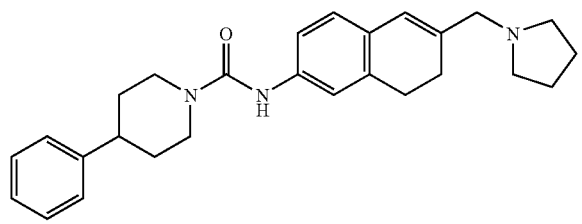

The titled compound was obtained by carrying out the same operation as in Example 99, using 6-(1-pyrrolidinylmethyl)-7,8-dihydro-2-naphthalenamine obtained in Reference Example 54.

$^1$H-NMR (CDCl$_3$) δ: 1.72–1.94 (8H, m), 2.32 (2H, t, J=8.1 Hz), 2.50 (4H, m), 2.72 (1H, m), 2.80 (2H, t, J=8.1 Hz), 2.99 (2H, dd, J=13.4, 10.6 Hz), 3.16 (2H, s), 4.21 (2H, d, J=13.4 Hz), 6.32 (1H, s), 6.34 (1H, s), 6.93 (1H, d, J=8.4 Hz), 7.07 (1H, d, J=8.1 Hz), 7.20–7.35 (6H, m).

Melting point: 184–186° C. (crystallization solvent: ethyl acetate-diisopropyl ether)

EXAMPLE 157

4-(1,3-Benzodioxol-5-yl)-N-[6-(1-pyrrolidinylmethyl)-7,8-dihydro-2-naphthalenyl]-1-piperidinecarboxamide

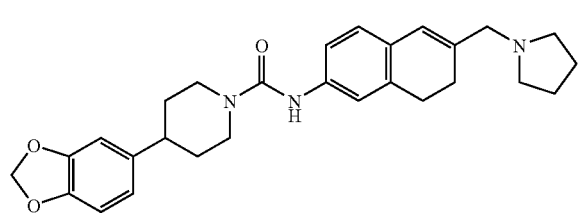

The titled compound was obtained by carrying out the same operation as in Example 99, using 6-(1-pyrrolidinylmethyl)-7,8-dihydro-2-naphthalenamine obtained in Reference Example 54.

$^1$H-NMR (CDCl$_3$) δ: 1.61–1.88 (8H, m), 2.31 (2H, t, J=8.1 Hz), 2.51 (4H, m), 2.59 (1H, m), 2.62 (2H, t, J=8.1 Hz), 2.94 (2H, dd, J=13.1, 11.2 Hz), 3.15 (2H, s), 4.18 (2H, d, J=13.1 Hz), 5.93 (2H, s), 6.31 (1H, s), 6.44 (1H, s), 6.64–6.77 (3H, m), 6.92 (1H, d, J=8.1 Hz), 7.07 (1H, d, J=8.1 Hz), 7.19 (1H, s).

Melting point: 149–150° C. (crystallization solvent: ethyl acetate-diisopropyl ether)

EXAMPLE 158

4-(4-Fluorophenyl)-N-[6-(1-pyrrolidinylmethyl)-7,8-dihydro-2-naphthalenyl]-3,6-dihydro-[(2H)-pyridinecarboxamide

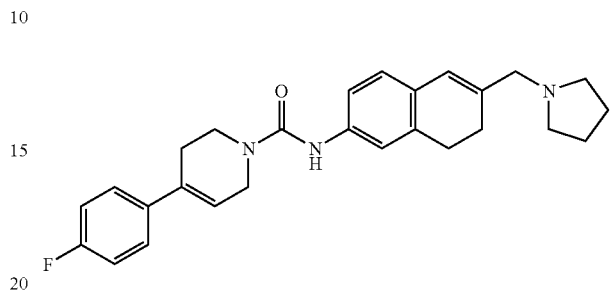

The titled compound was obtained by carrying out the same operation as in Example 99, using 6-(1-pyrrolidinylmethyl)-7,8-dihydro-2-naphthalenamine obtained in Reference Example 54.

$^1$H-NMR (CDCl$_3$) δ: 1.79 (4H, m), 2.32 (2H, t, J=8.1 Hz), 2.50 (4H, m), 2.59 (2H, brt), 2.80 (2H, t, J=8.1 Hz), 3.17 (2H, s), 3.74 (2H, t, J=5.7 Hz), 4.15 (2H, d, J=2.5 Hz), 6.00 (1H, brt), 6.32 (1H, s), 6.32 (1H, s), 6.94 (1H, d, J=8.1 Hz), 7.00–7.32 (6H, m).

Elemental analysis for C$_{27}$H$_{30}$FN$_3$O Calcd.: C, 75.15; H, 7.01; N, 9.74. Found: C, 75.09; H, 6.93; N, 9.77.

Melting point: 206–207° (crystallization solvent: ethyl acetate-diisopropyl ether)

EXAMPLE 159

4-(4-Chlorophenyl)-N-[6-(1-pyrrolidinylmethyl)-7,8-dihydro-2-naphthalenyl]-3,6-dihydro-[(2H)-pyridinecarboxamide

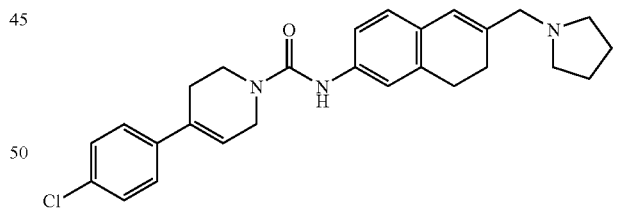

The titled compound was obtained by carrying out the same operation as in Example 99, using 6-(1-pyrrolidinylmethyl)-7,8-dihydro-2-naphthalenamine obtained in Reference Example 54.

$^1$H-NMR (CDCl$_3$) δ: 1.79 (4H, m), 2.32 (2H, t, J=8.1 Hz), 2.50 (4H, m), 2.59 (2H, brt), 2.80 (2H, t, J=8.1 Hz), 3.16 (2H, s), 3.73 (2H, t, J=5.6 Hz), 4.15 (2H, d, J=2.8 Hz), 6.06 (1H, brt), 6.30 (1H, s), 6.32 (1H, s), 6.93 (1H, d, J=7.8 Hz), 7.09 (1H, d, J=7.8 Hz), 7.21–7.31 (5H, m).

Elemental analysis for C$_{27}$H$_{30}$ClN$_3$O Calcd.: C, 72.39; H, 6.75; N, 9.38. Found: C, 72.19; H, 6.75; N, 9.19.

Melting point: 217–218° (crystallization solvent: ethyl acetate-diisopropyl ether)

EXAMPLE 160

4-(4-Chlorophenyl)-4-hydroxy-N-[6-(1-pyrrolidinyl-methyl)-7,8-dihydro-2-naphthalenyl]-1-piperidin-ecarboxamide

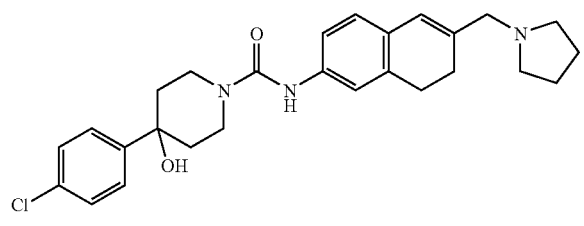

The titled compound was obtained by carrying out the same operation as in Example 99, using 6-(1-pyrrolidinyl-methyl)-7,8-dihydro-2-naphthalenamine obtained in Reference Example 54.

$^1$H-NMR (CDCl$_3$) δ: 1.79 (4H, m), 1.80 (2H, m), 2.04 (1H, dd, J=13.1, 10.8 Hz), 2.06 (1H, dd, J=13.1, 10.8 Hz), 2.31 (2H, t, J=7.8 Hz), 2.50 (1H, brs), 2.51 (4H, m), 2.79 (2H, t, J=7.8 Hz), 3.15 (2H, s), 3.41 (2H, dd, J=12.6, 10.8 Hz), 4.00 (2H, d, J=12.6 Hz), 6.32 (1H, s), 6.37 (1H, s), 6.93 (1H, d, J=8.1 Hz), 7.05–7.42 (6H, m).

Melting point: 181–182° (crystallization solvent: ethyl acetate-diisopropyl ether)

EXAMPLE 161

4-(4-Methylphenyl)-N-[6-(1-pyrrolidinylmethyl)-7,8-dihydro-2-naphthalenyl]-3,6-dihydro-[(2H)-pyridi-necarboxamide

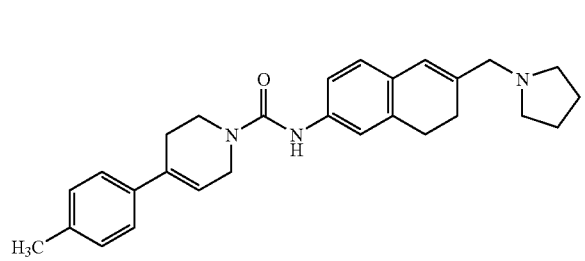

The titled compound was obtained by carrying out the same operation as in Example 99, using 6-(1-pyrrolidinyl-methyl)-7,8-dihydro-2-naphthalenamine obtained in Reference Example 54.

$^1$H-NMR (CDCl$_3$) δ: 1.79 (4H, m), 2.32 (2H, t, J=7.8 Hz), 2.35 (3H, s), 2.50 (4H, m), 2.61 (2H, brt), 2.80 (2H, t, J=7.8 Hz), 3.16 (2H, s), 3.73 (2H, t, J=5.7 Hz), 4.15 (2H, d, J=2.8 Hz), 6.03 (1H, s), 6.29 (1H, s), 6.32 (1H, s), 6.93 (1H, d, J=8.1 Hz), 7.07–7.30(6H, m).

Melting point: 199–202° C. (crystallization solvent: ethyl acetate-diisopropyl ether)

EXAMPLE 162

6-(4-Chlorophenyl)-N-[6-(1-pyrrolidinylmethyl)-7,8-dihydro-2-naphthalenyl]nicotinamide

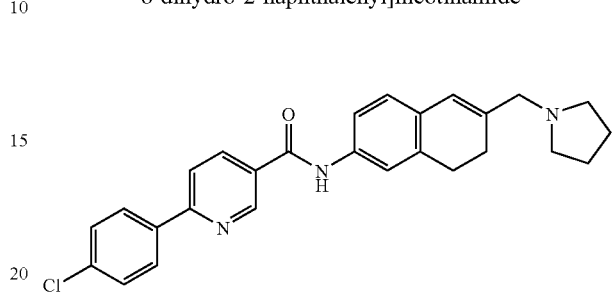

The titled compound was obtained by carrying out the same operation as in Example 1, using 6-(1-pyrrolidinylm-ethyl)-7,8-dihydro-2-naphthalenamine obtained in Reference Example 54.

$^1$H-NMR (CDCl$_3$+DMSO-d$_6$) δ: 1.80 (4H, m), 2.32–2.58 (6H, m), 2.85 (2H, t, J=8.0 Hz), 3.18 (2H, s), 6.36 (1H, s), 7.01 (1H, d, J=8.4 Hz), 7.48 (2H, d, J=8.4 Hz), 7.49 (1H, m), 7.59 (1H, s), 7.83 (1H, d, J=8.4 Hz), 8.04 (2H, d, J=8.4 Hz), 8.35 (1H, dd, J=8.4, 2.2 Hz), 9.25 (1H, d, J=2.2 Hz), 9.42 (1H, s).

Elemental analysis for C$_{27}$H$_{26}$ClN$_3$O Calcd.: C, 73.04; H, 5.90; N, 9.46. Found: C, 73.11; H, 5.71; N, 9.20.

Melting point: 252–253° C. (crystallization solvent: ethyl acetate-diisopropyl ether)

EXAMPLE 163

N-[6-[(Dimethylamino)methyl]-7,8-dihydro-2-naph-thalenyl]-6-(4-methylphenyl)nicotinamide

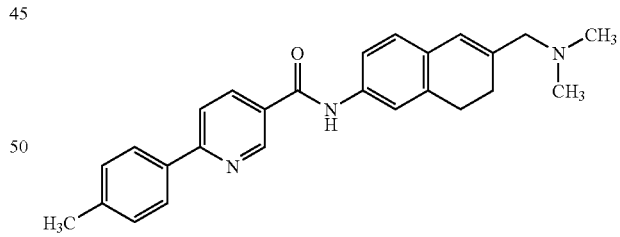

The titled compound was obtained by carrying out the same operation as in Example 1, using 6-[(N,N-dimethy-lamino)methyl]-7,8-dihydro-2-naphthalenamine obtained in Reference Example 41-2).

$^1$H-NMR (CDCl$_3$) δ: 2.25 (6H, s), 2.34 (2H, t, J=8.1 Hz), 2.43 (3H, s), 2.85 (2H, t, J=8.1 Hz), 2.99 (2H, s), 6.34 (1H, s), 7.02 (1H, d, J=8.1 Hz), 7.31 (2H, d, J=8.1 Hz), 7.39 (1H, d, J=8.1 Hz), 7.46 (1H, s), 7.81 (1H, d, J=8.4 Hz), 7.87 (1H, s), 7.96 (2H, d, J=8.1 Hz), 8.22 (1H, dd, J=8.4, 2.3 Hz), 9.11 (1H, d, J=2.3 Hz).

Melting point: 228–230° C. (crystallization solvent: ethyl acetate-diisopropyl ether)

EXAMPLE 164

6-(4-Chlorophenyl)-N-[6-[(dimethylamino)methyl]-7,8-dihydro-2-naphthalenyl]nicotinamide

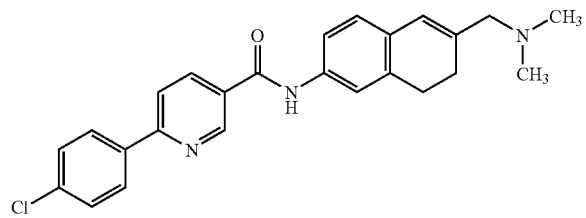

The titled compound was obtained by carrying out the same operation as in Example 1, using 6-[(N,N-dimethylamino)methyl]-7,8-dihydro-2-naphthalenamine obtained in Reference Example 41-2).

$^1$H-NMR (CDCl$_3$) δ: 2.25 (6H, s), 2.35 (2H, t, J=8.1 Hz), 2.86 (2H, t, J=8.1 Hz), 2.99 (2H, s), 6.35 (1H, s), 7.04 (1H, d, J=8.1 Hz), 7.40 (1H, d, J=8.4 Hz), 7.49 (1H, brs), 7.49 (2H, d, J=8.4 Hz), 7.78 (1H, s), 7.84 (1H, d, J=8.4 Hz), 8.02 (2H, d, J=8.4 Hz), 8.26 (1H, dd, J=8.1, 2.2 Hz), 9.13 (1H, d, J=2.2 Hz).

Elemental analysis for C$_{25}$H$_{24}$ClN$_3$O Calcd.: C, 71.85; H, 5.79; N, 10.05. Found: C, 71.88; H, 5.67; N, 9.86.

Melting point: 248–249° C. (crystallization solvent: ethyl acetate-diisopropyl ether)

EXAMPLE 165

4-(4-Chlorophenyl)-N-[6-(1-pyrrolidinylmethyl)-7,8-dihydro-2-naphthalenyl]-1-piperidinecarboxamide

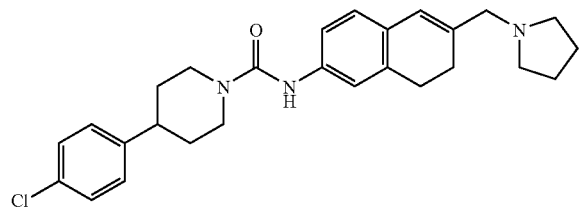

The titled compound was obtained by carrying out the same operation as in Example 99, using 6-(1-pyrrolidinylmethyl)-7,8-dihydro-2-naphthalenamine obtained in Reference Example 54.

$^1$H-NMR (CDCl$_3$) δ: 1.66–1.91 (8H, m), 2.32 (2H, t, J=8.1 Hz), 2.50 (4H, m), 2.70 (1H, m), 2.80 (2H, t, J=8.1 Hz), 2.98 (2H, dd, J=13.7, 12.0 Hz), 3.16 (2H, s), 4.20 (2H, d, J=13.7 Hz), 6.32 (1H, s), 6.32 (1H, s), 6.93 (1H, d, J=8.1 Hz), 7.05–7.30 (6H, m).

Elemental analysis for C$_{27}$H$_{32}$ClN$_3$O Calcd.: C, 72.06; H, 7.17; N, 9.34. Found: C, 72.08; H, 7.23; N, 9.15.

Melting point: 194–195° C. (crystallization solvent:ethyl acetate-diisopropyl ether)

EXAMPLE 166

N-[6-[(Dimethylamino)methyl]-7,8-dihydro-2-naphthalenyl]-4-(4-fluorophenyl)-1-piperidinecarboxamide

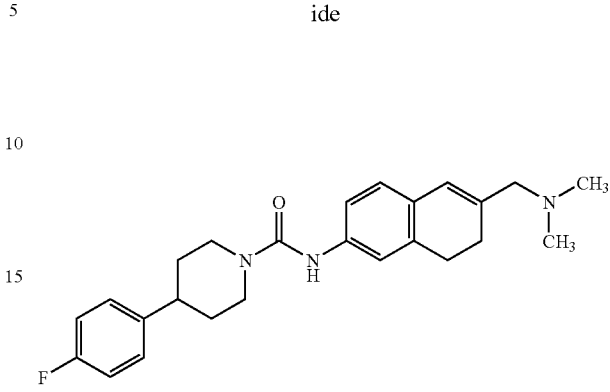

The titled compound was obtained by carrying out the same operation as in Example 99, using 6-[(N,N-dimethylamino)methyl]-7,8-dihydro-2-naphthalenamine obtained in Reference Example 41-2).

$^1$H-NMR (CDCl$_3$) δ: 1.65–1.75 (2H, m), 1.89 (2H, d, J=11.4 Hz), 2.23 (6H, s), 2.30 (2H, t, J=8.1 Hz), 2.70 (1H, m), 2.80 (2H, t, J=8.1 Hz), 2.94–3.01 (4H, m), 4.20 (2H, d, J=13.4 Hz), 6.30 (1H, s), 6.35 (1H, s), 6.92–7.20 (7H, m).

Melting point: 187–188° C. (crystallization solvent: ethyl acetate-diisopropyl ether)

EXAMPLE 167

N-[6-[(Dimethylamino)methyl]-7,8-dihydro-2-naphthalenyl]-4-(4-methylphenyl)-1-piperidinecarboxamide

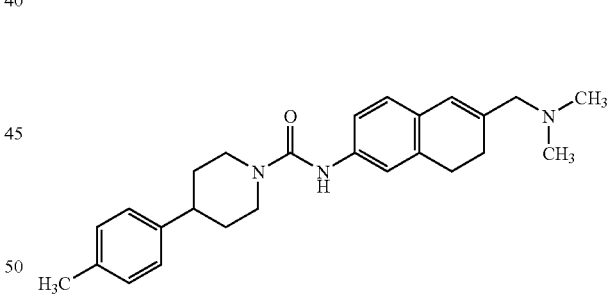

The titled compound was obtained by carrying, out the same operation as in Example 99, using 6-[(N,N-dimethylamino)methyl]-7,8-dihydro-2-naphthalenamine obtained in Reference Example 41-2).

$^1$H-NMR (CDCl$_3$) δ: 1.66–1.74 (2H, m), 1.89 (2H, d, J=11.7 Hz), 2.28 (6H, s), 2.30 (2H, t, J=8.1 Hz), 2.38 (3H, s), 2.68 (1H, m), 2.80 (2H, t, J=8.1 Hz), 2.94–3.02 (4H, m), 4.19 (2H, d, J=12.8 Hz), 6.30 (1H, s), 6.35 (1H, s), 6.93 (1H, d, J=8.1 Hz), 7.07–7.20 (6H, m).

Elemental analysis for C$_{26}$H$_{33}$N$_3$O.0.5H$_2$O Calcd.: C, 75.69; H, 8.31; N, 10.18. Found: C, 75.4.4; H, 8.16; N, 10.05.

Melting point: 200–202° C. (crystallization solvent: ethyl acetate-diisopropyl ether)

EXAMPLE 168

N-[6-[(Dimethylamino)methyl]-5,6,7,8-tetrahydro-2-naphthalenyl][1,1'-biphenyl]-2-carboxamide hydrochloride

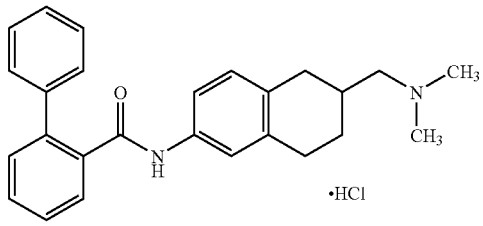

The titled compound was obtained by carrying out the same operation as in Example 1, using 6-amino-2-[(N,N-dimethylamino)methyl)tetralin hydrochloride.

$^1$H-NMR (DMSO-$d_6$) δ: 1.39 (1H, m), 1.99 (1H, m), 2,17 (1H, m), 2.42 (1H, dd, J=16.2, 10.1 Hz), 2.78 (6H, s), 2.88 (1H, dd, J=16.2, 4.5 Hz), 3.06 (2H, t, J=5.7 Hz), 3.38 (2H, s), 6.94–7.62 (1H, m), 7.64 (1H, d, J=1.7 Hz), 10.11 (1H, brs), 10.18 (1H, s).

Melting point: 196–197° C. (crystallization solvent: methanol-ethyl acetate)

EXAMPLE 169

N-[6-[(Dimethylamino)methyl]-5,6,7,8-tetrahydro-2-naphthalenyl]-4'-fluoro[1,1'-biphenyl]-4-carboxamide hydrochloride

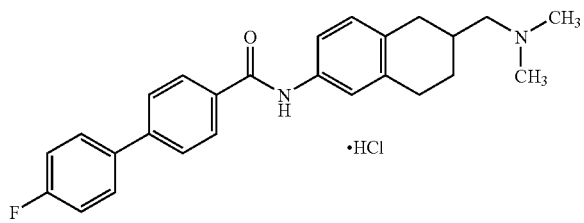

4'-Fluoro-N-[6-[(N,N-dimethylamino)methyl]-5,6,7,8-tetrahydro-2-naphthalenyl][1,1'-biphenyl]-4-carboxamide synthesized in Example 42 was dissolved in ethyl acetate. An excess amount of 4N hydrochloric acid-ethyl acetate solution was added to the solution, which was concentrated under reduced pressure. The resulting residue was recrystallized from methanol-ethyl acetate, to give the titled compound.

$^1$H-NMR (DMSO-$d_6$) δ: 1.43 (1H, m), 2.06 (1H, m), 2.21 (1H, m), 2.45 (1H, m), 2.79 (6H, s), 2.92 (1H, dd, J=16.2, 4.2 Hz), 3.08 (2H, d, J=6.4 Hz), 3.33 (2H, s), 7.05 (1H, d, J=8.4 Hz), 7.34 (2H, dd, J=8.9, 8.9 Hz), 7.53 (1H, d, J=8.4 Hz), 7.59 (1H, s), 7.80 (4H, m), 8.06 (2H, d, J=8.1 Hz), 10.02 (1H, s), 10.03 (1H, brs).

Melting point: δ 240–245° C. (crystallization solvent: methanol-ethyl acetate)

EXAMPLE 170

6-(4-Fluorophenyl)-N-[6-(1-pyrrolidinylmethyl)-7,8-dihydro-2-naphthalenyl]nicotinamide hydrochloride

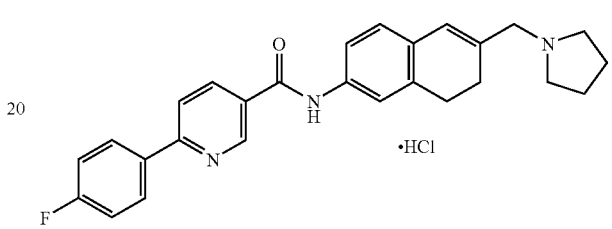

The titled compound was obtained by carrying out the same operation as in Example 1, using 6-(1-pyrrolidinylmethyl)-7,8-dihydro-2-naphthalenamine obtained in Reference Example 54.

$^1$H-NMR (DMSO-$d_6$) δ: 1.70 (4H, m), 2.26 (2H, t, J=8.1 Hz), 2.44 (4H, m), 2.76 (2H, t, J=8.1 Hz), 3.12 (2H, s), 3.34 (1H, s), 6.36 (1H, s), 7.03 (1H, d, J=7.8. Hz), 7.37 (2H, dd, J=8.4, 7.0 Hz), 7.57 (1H, d, J=8.4 Hz), 7.59 (1H, s), 8.13–8.42 (4H, m), 9.19 (1H, s), 10.43 (1H, s).

Melting point: 229–231° C. (crystallization solvent: methanol-ethyl acetate)

EXAMPLE 171

6-(4-Fluorophenyl)-N-[6-(1-pyrrolidinylmethyl)-7,8-dihydro-2-naphthalenyl]nicotinamide dihydrochloride

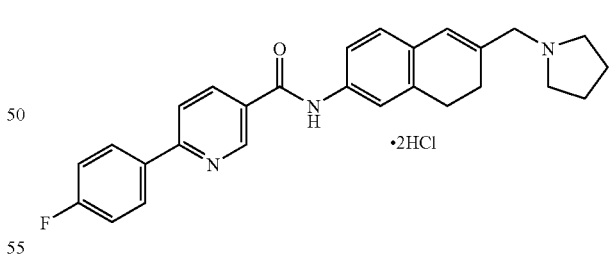

The titled compound was obtained by carrying out the same operation as in Example 1, using 6-(1-pyrrolidinylmethyl)-7,8-dihydro-2-naphthalenamine obtained in Reference Example 54.

$^1$H-NMR (DMSO-$d_6$) δ: 2.00 (4H, m), 2.45 (4H, m), 2.83 (2H, t, J=8.1 Hz), 3.05 (2H, m), 3.47 (2H, m), 3.88 (1H, s), 6.69 (1H, s), 7.13 (1H, d, J=8.1 Hz), 7.38 (2H, dd, J=8.9, 8.6 Hz), 7.64 (1H, d, J=10.6 Hz), 7.66 (1H, s), 8.14–8.42 (4H, m), 9.19 (1H, s), 10.52 (1H, s), 10.60 (1H, brs).

Melting point: 245–248° C. (crystallization solvent: methanol-ethyl acetate)

EXAMPLE 172

N-[6-[(Dimethylnitroyl)methyl]-5,6,7,8-tetrahydro-2-naphthalenyl]-4'-fluoro[1,1'-biphenyl]-4-carboxamide 3-chlorobenzoate

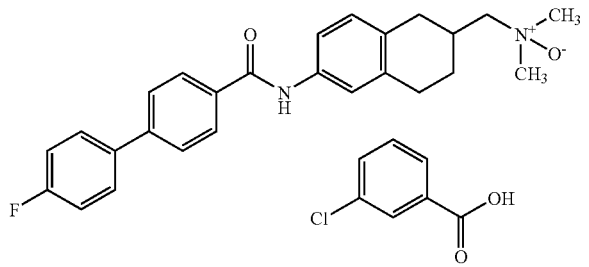

4'-FluoroN-[6-[(N,N-dimethylamino)methyl]-5,6,7,8-tetrahydro-2-naphthalenyl][1,1'-biphenyl]-4-carboxamide (100 mg) obtained in Example 42 was dissolved in acetone (10 ml), which was stirred under ice-cooling. 3-Chloroperbenzoic acid (purity: 50%) (86 mg) was added to the solution, which was stirred under ice-cooling for 1 hour. The reaction mixture was concentrated under reduced pressure, and the residue was washed with diisopropyl ether, to give the titled compound (158 mg).

$^1$H-NMR (DMSO-d$_6$) δ: 1.57 (1H, m), 2.07 (1H, m), 2.61 (1H, m), 2.82 (2H, m), 3.04 (1H, m), 3.33 (1H, m), 3.48 (6H, s), 3.56–3.67 (2H, m), 6.55 (1H, s), 7.03 (1H, d, J=8.4 Hz), 7.30–7.56 (6H, m), 7.78–7.85 (6H, m), 8.04 (2H, d, J=8.4 Hz), 10.17 (1H, s).

FABMS(pos) 419.1 [M+H]+

EXAMPLE 173

N-[6-[(Dimethylamino)methyl]-5,6,7,8-tetrahydro-2-naphthalenyl][1,1'-biphenyl]-4-sulfonamide hydrochloride

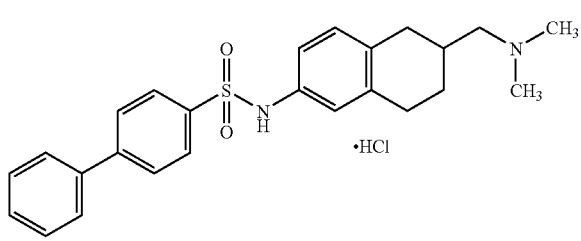

6-[(N,N-Dimethylamino)methyl]-7,8-dihydro-2-naphthalenamine (200 mg, 0.72 mmol) obtained in Example 41-2) was dissolved in acetonitrile (30 ml). Triethylamine (0.401 ml, 2.88 mmol) and [1,1'-biphenyl]-4-sulfonylchloride (200 mg, 0.79 mmol) were added to the solution under ice-cooling, which was stirred for 3 hours. The reaction mixture was concentrated. Ethyl acetate and water were added to the residue, and extraction was conducted. The ethyl acetate layer was concentrated, and the residue was purified by alumina column chromatography (development solvent; ethyl acetate: n-hexane=33:67). 4N Hydrogen chloride-ethyl acetate solution was added to the resulting oily substance, which was concentrated. The residue was recrystallized from methanol-ethyl acetate, to give the titled compound (194 mg).

$^1$H-NMR (DMSO-d$_6$) δ: 1.32 (1H, m), 1.96 (1H, m), 2.11 (1H, m), 2.35 (1H, d, J=15.9, 10.0 Hz), 2.74 (2H, m), 2.78 (7H, m), 3.02 (2H, m), 6.89 (2H, d, J=10.6 Hz), 6.91 (1H, m), 7.40–7.51 (3H, m), 7.70 (2H, d, J=6.7 Hz), 7.85 (4H, m), 9.92 (1H, brs), 10.23 (1H, s).

Melting point: 168–170° C. (crystallization solvent: methanol-ethyl acetate).

FABMS(pos) 421.1 [M+H]+

EXAMPLE 174

4'-Chloro-N-[4-(4-piperidininyl)phenyl][1,1'-biphenyl]-4-carboxamide

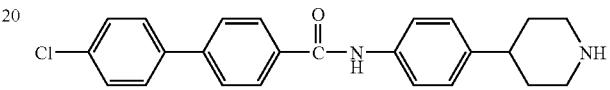

The titled compound was obtained as a colorless powder by carrying out the same operation as in Example 127-2), using 4'-chloro-N-[4-(4-piperidininyl)phenyl][1,1'-biphenyl]-4-carboxamide obtained in Reference Example 89.

$^1$H-NMR (CDCl$_3$+DMSO-d$_6$) δ: 1.40–1.90 (4H, m), 2.60–2.90 (3H, m), 3.18–3.28 (2H, m), 7.19 (2H, d, J=8.1 Hz), 7.49 (2H, d, J=7.0 Hz), 7.67–7.75 (6H, m), 8.07–8.10 (3H, m), 10.16 (1H, s).

Melting point: 276–281° C. (decomposition) (crystallization solvent: ethyl acetate)

EXAMPLE 175

4'-Chloro-N-[4-(1-methyl-4-piperidininyl)phenyl][1,1'-biphenyl]-4-carboxamide

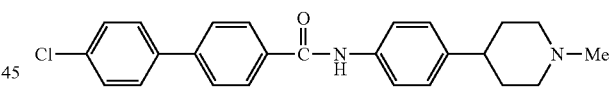

A mixture of 4'-chloro-N-[4-(4-piperidininyl)phenyl][1,1'-biphenyl]-4-carboxamide (0.17 g) obtained in Example 174, 37% aqueous formaldehyde solution (0.05 ml) and formic acid (0.5 ml) was heated at 100° C. for 4 hours. The reaction mixture was cooled to room temperature. Water was added to the mixture, which was made alkaline with 8N aqueous sodium hydroxide solution, and extracted with ethyl acetate-tetrahydrofuran (1:1) mixed solution. The extract was washed with saturated aqueous sodium chloride solution, dried over anhydrous magnesium sulfate, and then the solvent was distilled out under reduced pressure. The resulting solid was washed with ethyl acetate, dried under reduced pressure, to give the titled compound (90 mg).

$^1$H-NMR (CDCl$_3$+DMSO-d$_6$) δ: 1.55–1.80 (2H, m), 1.90–2.10 (2H, m), 2.22 (3H, s), 2.30–2.45 (1H, m), 2.80–3.20 (4H, m), 7.11 (2H, d, J=8.1 Hz), 7.36 (2H, d, J=8.1 Hz), 7.50–7.63 (6H, m), 7.97 (2H, d, J=8.4 Hz), 9.79 (1H, s).

Melting point: 273–277° C. (decomposition) (Washing solvent: ethyl acetate)

EXAMPLE 176

Benzyl 4-[2-[[2-(dimethylamino)ethyl]amino]-2-oxoethyl]phenylcarbamate

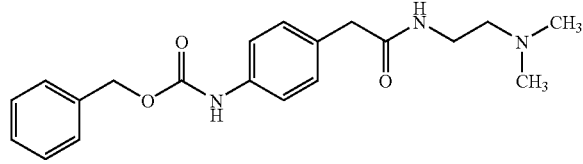

N,N-Dimethylethylenediamine (0.64 ml), WSC (1.31 g), HOBt (1.05 g), and triethylamine (2.4 ml) were added to a tetrahydrofuran (50 ml) solution of 2-[4-[[(benzyloxy)carbonyl]amino]phenyl]acetic acid (1.5 g) obtained in Reference Example 90. After stirring for 20 hours, the reaction mixture was poured into water, and extraction was conducted using ethyl acetate. The organic layer was washed with water, saturated aqueous sodium bicarbonate solution, and saturated aqueous sodium chloride solution, dried and then concentrated. The residue was recrystallized from ethyl acetate-hexane, to give the titled compound (1.72 g).

Melting point: 126–127° C.

EXAMPLE 177

N-[4-[2-[[2-(Dimethylamino)ethyl]amino]-2-oxoethyl]phenyl][1,1'-biphenyl]-4-carboxamide hydrochloride

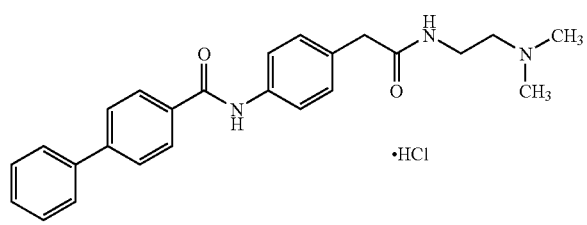

Oxalyl chloride (0.56 ml) was added dropwise to a tetrahydrofuran (45 ml) solution of 4-biphenylcarboxylic acid (1.01 g) under ice-cooling. 9 drops of DMF was added to the mixture, and the temperature of the mixture was raised to room temperature, which was stirred for 40 minutes. The reaction mixture was concentrated and dried. A tetrahydrofuran (50 ml) solution of the residue was added dropwise to a tetrahydrofuran (45 ml) solution of 2-(4-aminophenyl)-N-[2-(dimethylamino)ethyl]acetamide (939 mg) obtained in Reference Example 91 under ice-cooling. Then the temperature of the reaction mixture was raised to room temperature, which was stirred for 2 hours. Saturated aqueous sodium bicarbonate solution was added to the reaction mixture, and extraction was conducted using ethyl acetate. The organic layer was washed with water and saturated aqueous sodium chloride solution, dried over sodium sulfate, and then concentrated. The residue was dissolved in tetrahydrofuran. 4N Hydrochloric acid-ethyl acetate was added to the solution, which was concentrated.

The residue was recrystallized from methanol diisopropyl ether, to give the titled compound (750 mg).

Melting point: 216–217° C.

The above N-[4-[2-[(2-(dimethylamino)ethyl]amino]-2-oxoethyl]phenyl][1,1'-biphenyl]-4-carboxyamide hydrochloride (100 mg) was dissolved in saturated aqueous sodium bicarbonate solution, and extraction was conducted using tetrahydrofuran-ethyl acetate (1:1). The organic layer was washed with saturated aqueous sodium chloride solution, dried over sodium sulfate, and then concentrated. The residue was recrystallized from methanol-diisopropyl ether, to give a free base form (56 mg) of the titled compound.

Melting point: 228–229° C.

EXAMPLE 178

Benzyl 4-[[4-[2-[[2-(dimethylamino)ethyl]amino]-2-oxoethyl]anilino]carbonyl]-1-piperidinecarboxylate

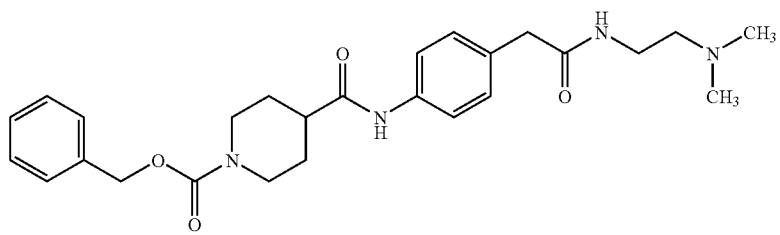

2-(4-Aminophenyl)-N-[2-(dimethylamino)ethyl]acetamide (221 mg), WSC (249 mg), 1-hydroxybenzotriazole (199 mg), triethylamine (0.4 ml), and dimethylaminopyridine (244 mg) were added to a tetrahydrofuran (10 ml) solution of 1-[(benzyloxy)carbonyl]-4-piperidinecarboxylic acid (290 mg), which was stirred for 20 hours. The reaction mixture was poured into water, and extraction was conducted using ethyl acetate. The organic layer was washed with water, saturated aqueous sodium bicarbonate solution, and saturated aqueous sodium chloride solution, dried over sodium sulfate, and then concentrated. The residue was recrystallized from methanol-diisopropyl ether, to give the titled compound (230 mg).

Melting point: 169–170° C.

EXAMPLE 179

N-[4-[2-[[2-(Dimethylamino)ethyl]amino]-2-oxoethyl]phenyl]-3-[3-(2-naphthyl)-1,2,4-oxadiazol-5-yl]propanamide

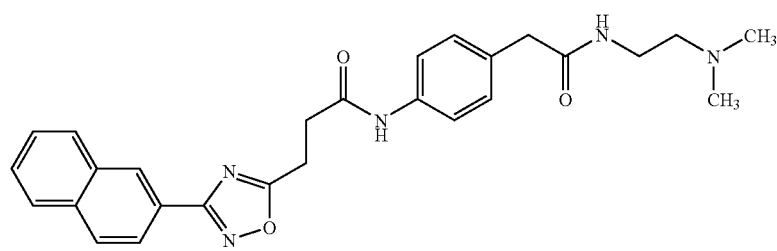

2-(4-Aminophenyl)-N-[2-(dimethylamino)ethyl]acetamide (221 mg), WSC (249 mg), 1-hydroxybenzotrizole (199 mg), triethylamine (0.4 ml), and dimethylaminopyridine (244 mg) were added to a DMF (5 ml) solution of 3-[3-(2-naphthyl)-1,2,4-oxadiazol-5-yl]propionic acid (268 mg), which was stirred for 5 hours. The reaction mixture was poured into water, and extraction was conducted using ethyl acetate. The organic layer was washed with water, saturated aqueous sodium bicarbonate solution, and saturated aqueous sodium chloride solution, dried over sodium sulfate, and then concentrated. The residue was recrystallized from methanol, to give the titled compound (166 mg).

Melting point: 173–174° C.

EXAMPLE 180

N-[4-[2-[[2-(Dimethylamino)ethyl]amino]-2-oxoethyl]phenyl]-2-(4-nitrophenyl)acetamide

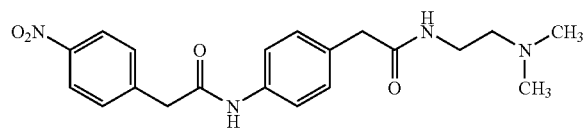

2-(4-Aminophenyl)-N-[2-(dimethylamino)ethyl]acetamide (221 mg), WSC (free form: 0.23 ml), 1-hydroxybenzotriazole (199 mg), and dimethylaminopyridine (244 mg) were added to a DMF (5 ml) solution of 4-nitrophenylacetic acid (181 mg), which was stirred for 4 hours. The reaction mixture was poured into water, and extraction was conducted using ethyl acetate. The organic layer was washed with water, saturated aqueous sodium bicarbonate solution, and saturated aqueous sodium chloride solution, dried over sodium sulfate, and then concentrated. The residue was recrystallized from methanol, to give the titled compound (80 mg).

Melting point: 160–162° C.

EXAMPLE 181

(E)-N-[4-[2-[[2-(Dimethylamino)ethyl]amino]-2-oxoethyl]phenyl)-3-[4-(4-methoxyphenoxy)phenyl]-2-propanamide

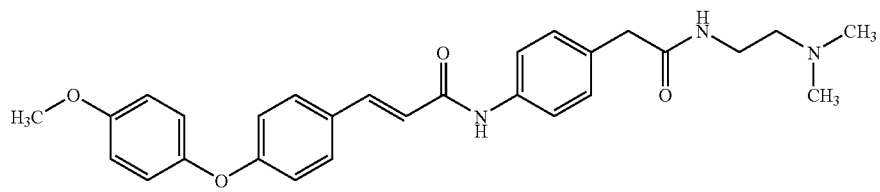

2-(4-Aminophenyl)-N-[2-(dimethylamino)ethyl]acetamide (221 mg), WSC (free form: 0.23 ml), 1-hydroxybenzotriazole (199 mg), triethylamine (0.14 ml) and dimethylaminopyridine (122 mg) were added to a DMF (5 ml) solution of (E)-3-[4-(4-methoxyphenoxy)phenyl]-2-propenoic acid (270 mg), which was stirred for 24 hours. The reaction mixture was poured into water, and extraction was conducted using ethyl acetate-tetrahydrofuran (1:1). The organic layer was washed with water, saturated aqueous sodium bicarbonate solution, and saturated aqueous sodium chloride solution, dried over sodium sulfate, and then concentrated. The resulting crude crystals were washed with diisopropyl ether, to give the titled compound (227 mg).

Melting point: 175–177° C. (decomposition).

Compounds described in the following Example 182 to 198 were produced in the same manner as in Example 181.

EXAMPLE 182

4-[3-(1-Benzofuran-2-yl)-1,2,4-oxadiazol-5-yl]-N-[4-[2-[[2-(dimethylamino)ethyl]amino]-2-oxoethyl]phenyl]butanamide

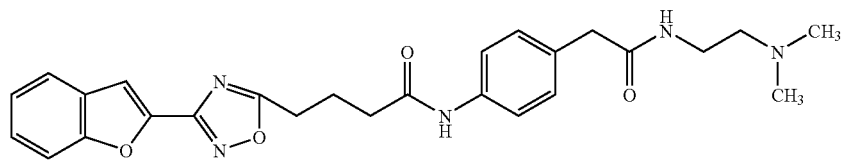

Melting point: 161–163° C.
Washing solvent: diisopropyl ether.

EXAMPLE 183

N-[4-[2-[[2-(Dimethylamino)ethyl]amino]-2-oxoethyl]phenyl]-3-methoxy-4-(2-quinolinylmethoxy)benzamide

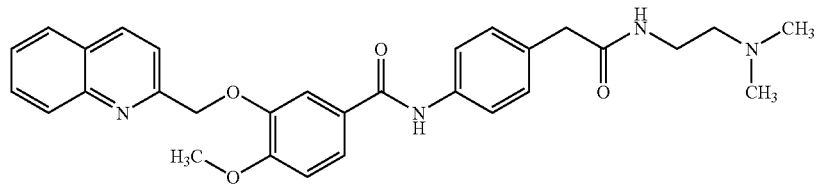

Melting point: 209–210° C. (decomposition).
Washing solvent: diisopropyl ether.

EXAMPLE 184

3-[1-(2,4-Dichlorobenzyl)-1H-indol-3-yl]-N-[4-[2-[[2-(dimethylamino)ethyl]amino]-2-oxoethyl]phenyl]propanamide

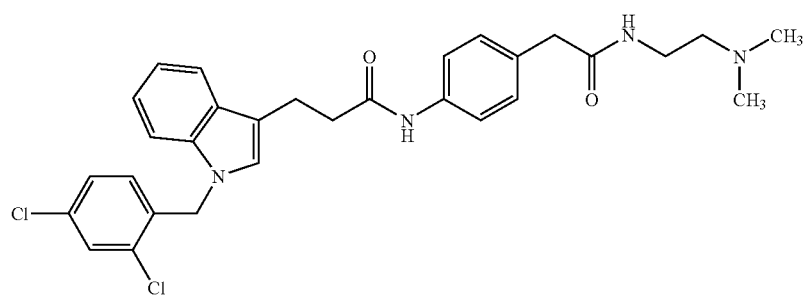

Melting point: δ 123–125° C. (decomposition).
Washing solvent: diisopropyl ether.-

EXAMPLE 185

N-[4-[2-[[2-(Dimethylamino)ethyl]amino]-2-oxoethyl]phenyl]-1-benzothiophen-2-carboxamide

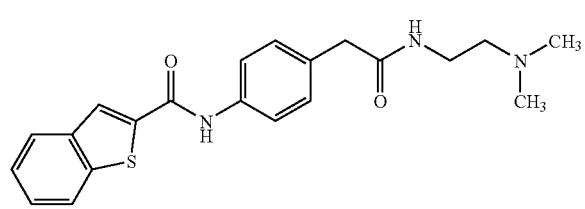

Melting point: 186–187° C. (decomposition).
Washing solvent: diisopropyl ether.

EXAMPLE 186

2-(2-Benzylphenyl)-N-[4-[2-[[2-(dimethylamino)ethyl]amino]-2-oxoethyl]phenyl]acetamide

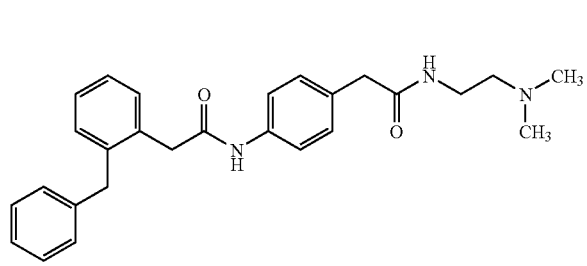

Melting point: 115–117° C.
Washing solvent: diisopropyl ether.

EXAMPLE 187

2-(3,4-dimethoxyphenyl)-N-[4-[2-[[2-(dimethylamino)ethyl]amino]-2-oxoethyl]phenyl]acetamide

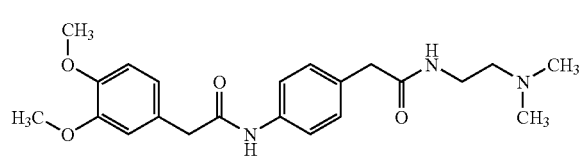

Melting point: 123–124° C.
Recrystallization solvent: methanol-diisopropyl ether.

EXAMPLE 188

N-[4-[2-[[2-(Dimethylamino)ethyl]amino]-2-oxoethyl]phenyl]-2-(5-methoxy-2-methyl-1H-indol-3-yl)acetamide

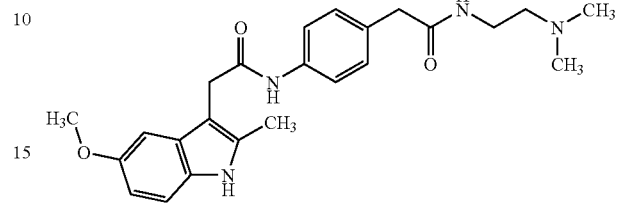

Melting point: 125–126° C.
Recrystallization solvent: methanol-diisopropyl ether.

EXAMPLE 189

N-[4-[2-[[2-(Dimethylamino)ethyl]amino]-2-oxoethyl]phenyl]-4-(1H-indol-3-yl)butanamide

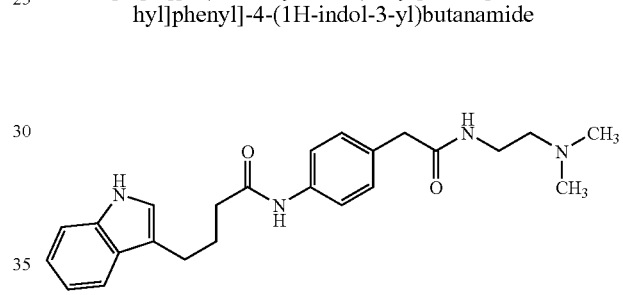

Melting point: 132–133° C.
Washing solvent: diisopropyl ether.

EXAMPLE 190

N-[4-[2-[[2-(Dimethylamino)ethyl]amino]-2-oxoethyl]phenyl]furo[2,3-f][1,3]benzodioxol-6-carboxamide

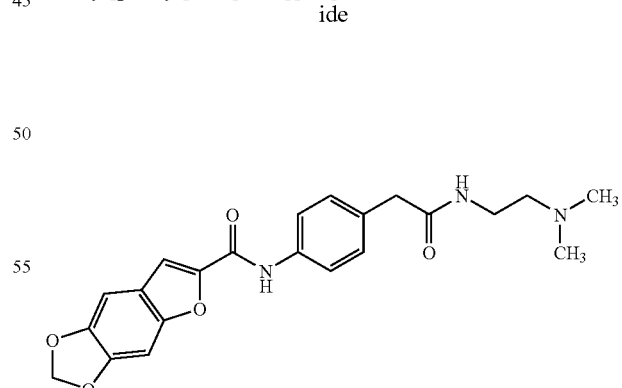

Melting point: δ 173–175° C. (decomposition).
Washing solvent: diisopropyl ether.

EXAMPLE 191

4-([1,1'-Biphenyl]-4-ylmethoxy)-N-[4-[2-[[2-(dimethylamino)ethyl]amino]-2-oxoethyl]phenyl]benzamide

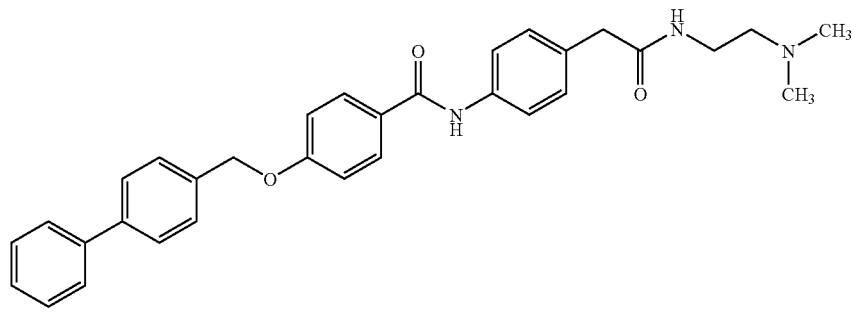

Melting point: 204–208° C.
Washing solvent: diisopropyl ether.

EXAMPLE 192

4-(Benzoylamino)-N-[4-[2-[[2-(dimethylamino)ethyl]amino]-2-oxoethyl]phenyl]benzamide

Melting point: 220–221° C.
Washing solvent: diisopropyl ether.

EXAMPLE 193

N-[4-[2-[[2-(Dimethylamino)ethyl]amino]-2-oxoethyl]phenyl]-4'-methoxy[1,1'-biphenyl]-4-carboxamide

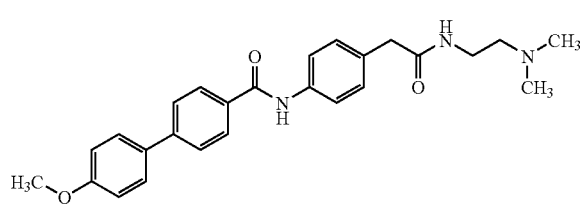

Melting point: 196–198° C. (decomposition).
Washing solvent: diisopropyl ether.

EXAMPLE 194

N-[4-[2-[[2-(Dimethylamino)ethyl]amino]-2-oxoethyl]phenyl]-9,10,10-trioxo-9,10-dihydro-10λ$^6$-thioxanten-3-carboxamide

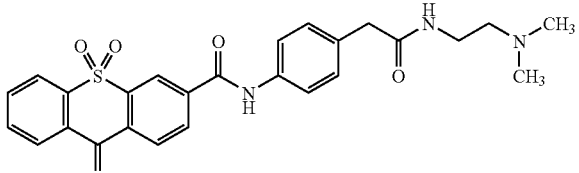

Melting point: 162–163° C. (decomposition).
Washing solvent: diisopropyl ether.

EXAMPLE 195

4-(Benzyloxy-N-[4-[2-[[2-(dimethylamino)ethyl]amino]-2-oxoethyl]phenyl]benzamide

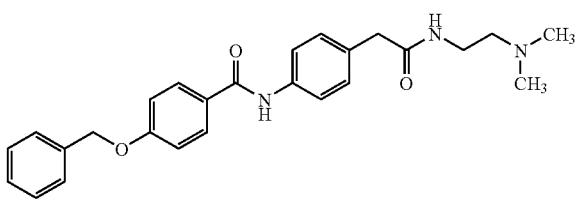

Melting point: 190–192° C. (decomposition).
Washing solvent: diisopropyl ether.

EXAMPLE 196

4-Benzoyl-N-[4-[2-[[2-(dimethylamino)ethyl]amino]-2-oxoethyl)phenyl]benzamide

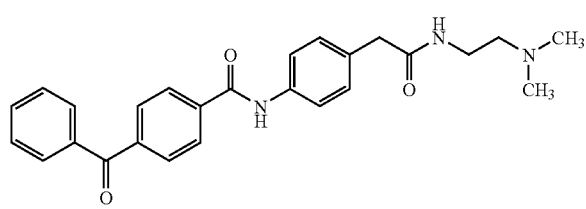

Melting point: 173–175° C. (decomposition).
Washing solvent: diisopropyl ether.

EXAMPLE 197

N-[4-[2-[[2-(Dimethylamino)ethyl]amino]-2-oxoethyl]phenyl]-5-methyl-3-(4-pyridinyl)-1H-pyyrole-2-carboxamide

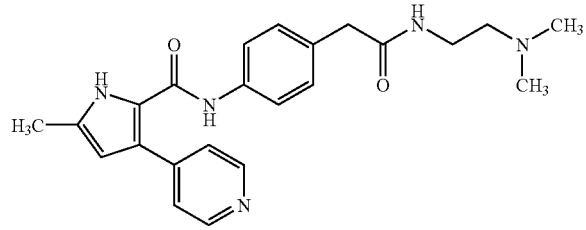

Melting point: 215–218° C. (decomposition).
Washing solvent: diisopropyl ether.

EXAMPLE 198

1-(3,4-Dichlorobenzyl)-N-(4-(2-[[2-(dimethylamino)ethyl]amino]-2-oxoethyl]phenyl]-4-piperidinecarboxamide

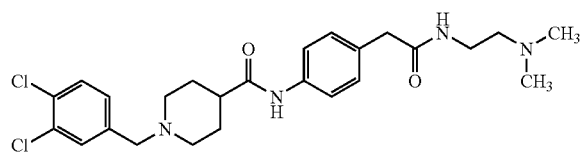

Melting point: δ 182–183° C. (decomposition)
Washing solvent: diisopropyl ether. .

EXAMPLE 199

4-(4-Methoxyphenyl)-N-[6-(1-pyrrolidinylmethyl)-7,8-dihydro-2-naphthalenyl]-1-piperidinecarboxamide

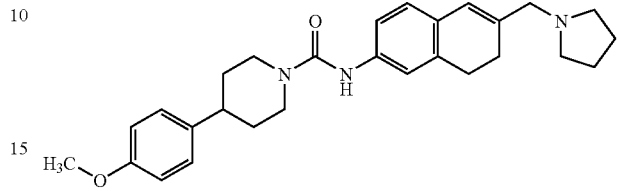

The titled compound was obtained by carrying out the same operation as in Example 99, using 6-(1-pyrrolidinylmethyl)-7,8-dihydro-2-naphthalenamine obtained in Reference Example 54.

$^1$H-NMR (CDCl$_3$) δ: 1.61–1.91 (8H, m), 2.31 (2H, t, J=8.1 Hz), 2.54 (4H, m), 2.73–2.81 (3H, m), 2.98 (2H, t, J=7.8 Hz), 3.16 (2H, s), 3.79 (3H, s), 4.20 (2H, d, J=13.1 Hz), 6.31 (1H, s), 6.36 (1H, s), 6.86 (2H, d, J=8.6 Hz), 7.06–7.20 (5H, m).

Melting point: 175–176° C. (crystallization solvent: ethyl acetate-diisopropyl ether)

EXAMPLE 200

4'-Methoxy-N-[6-(1-pyrrolidinylmethyl)-5-methyl-7,8-dihydro-2-naphthalenyl][1,1'-biphenyl]-4-carboxamide

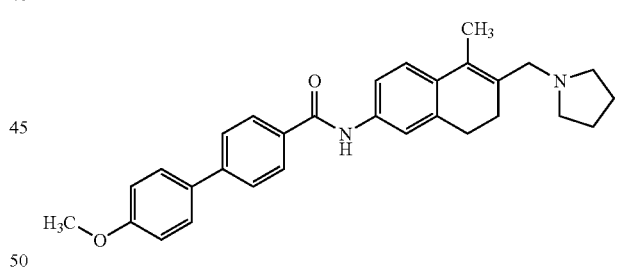

The titled compound was obtained by carrying out the same operation as in Example 1, using 5-methyl-6-(1-pyrrolidinylmethyl)-7,8-dihydro-2-naphthalenamine obtained in Reference Example 69.

$^1$H-NMR (CDCl$_3$) δ: 1.78 (4H, m), 2.10 (3H, s). 2.37 (2H, t, J=8.1 Hz), 2.53 (4H, m), 2.76 (2H, t, J=8.1 Hz), 3.28 (2H, s), 3.87 (3H, s), 7.01 (2H, d, J=8.6 Hz), 7.27 (1H, d, J=7.8 Hz), 7.46 (1H, d, J=7.8 Hz), 7.48 (1H, s), 7.57 (2H, d, J=8.6 Hz), 7.66 (2H, d, J=8.4 Hz), 7.81 (1H, s), 7.92 (2H, d, J=8.4 Hz).

Elemental analysis for C$_{30}$H$_{32}$N$_2$O$_2$ Calcd.: C, 79.61; H, 7.13; N, 6.19. Found: C, 79.35; H, 7.28; N, 6.24.

Melting point: 179–180° C. (crystallization solvent: ethyl acetate-diisopropyl ether)

EXAMPLE 201

4-(4-Methoxyphenyl)-N-[6-(1-pyrrolidinylmethyl)-5-methyl-7,8-dihydro-2-naphthalenyl]-1-piperidinecarboxamide

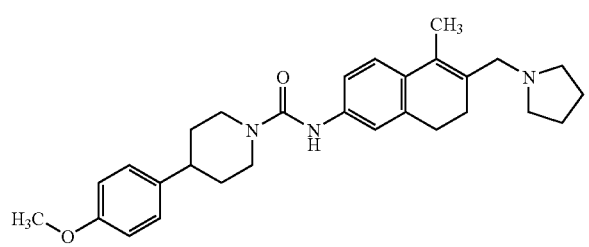

The titled compound was obtained by carrying out the same operation as in Example 99, using 5-methyl-6-(1-pyrrolidinylmethyl)-7,8-dihydro-2-naphthalenamine obtained in Reference Example 69.

$^1$H-NMR (CDCl$_3$) δ: 1.67 (2H, dd, J=13.4, 4.0 Hz), 1.78 (4H, m), 1.89 (2H, d, J=11.4 Hz), 2.07 (3H, s), 2.34 (2H, t, J=7.5 Hz), 2.52 (4H, m), 2.68–2.73 (3H, m), 2.98 (2H, t, J=7.5 Hz), 3.26 (2H, s), 3.80 (3H, s), 4.20 (2H, d, J=13.4 Hz), 6.36 (1H, s), 6.86 (2H, d, J=8.4 Hz), 7.12–7.20 (5H, m).

Elemental analysis for C$_{28}$H$_{37}$N$_3$O$_2$ Calcd.: C, 75.13; H, 8.33; N, 9.39. Found: C, 74.96; H, 8.14; N, 9.10.

Melting point: 163–164° C. (crystallization solvent: ethyl acetate-diisopropyl ether)

EXAMPLE 202

4'-Fluoro-N-methyl-N-[6-(1-pyrrolidinylmethyl)-7,8-dihydro-2-naphthalenyl][1,1'-biphenyl]-4-carboxamide hydrochloride

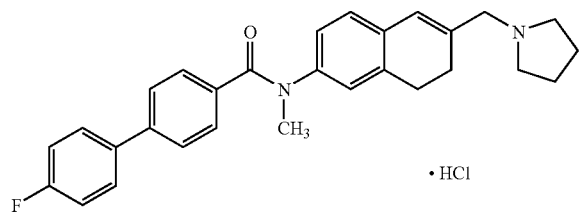

The titled compound was obtained by carrying out the same operation as in Example 1, using N-methyl6-(1-pyrrolidinylmethyl)-7,8-dihydro-2-naphthalenamine hydrochloride obtained in Reference Example 95.

$^1$H-NMR (DMSO-d$_6$) δ: 1.92–1.98 (4H, m), 2.39 (0.2H, t, J=8.1 Hz), 2.73 (2H, t, J=8.1 Hz), 3.00 (2H, m), 3.35 (3H, m), 3.44 (2H, m), 3.83 (2H, d, J=5.6 Hz), 6.62 (1H, s), 6.92–7.01 (2H, m), 7.11 (1H, s), 7.26 (2H, dd, J=8.9, 5.6 Hz), 7.38 (2H, d, J=8.1 Hz), 7.55 (2H, d, J=8.1 Hz), 7.69 (2H, dd, J=8.9, 5.6 Hz), 10.60 (1H, brs).

FABMS(pos) 441.2 [M+H]$^+$

EXAMPLE 203

N-[6-[(Dimethylamino)methyl]-5-hydroxy-5,6,7,8-tetrahydro-2-naphthalenyl]-4-(4-fluorophenyl)-1-piperidinecarboxamide

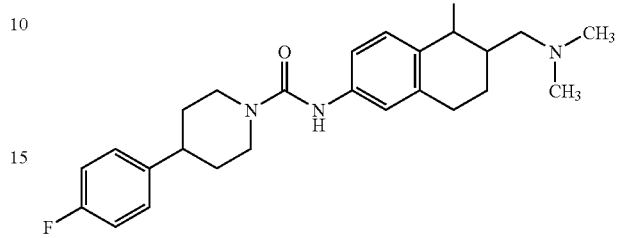

N,N-Dimethylmethylene ammonium chloride(638 mg, 6.82 mmol) was added to a mixed solution of 4-(4-fluorophenyl)-N-(5-oxo-5,6,7,8-tetrahydro-2-naphthalenyl)-1-piperidinecarboxamide (1.00 g, 2.73 mmol) obtained in Reference Example 97 in tetrahydrofuran (10 ml) and acetonitrile (10 ml), which was stirred at room temperature for 1 day. The solvent was distilled out under reduced pressure. Ethyl acetate was added to the residue, which was washed with aqueous potassium carbonate solution and saturated aqueous sodium chloride solution, dried over anhydrous sodium sulfate, and then the solvent was distilled out under reduced pressure. The resulting oily substance was dissolved in methanol (15 ml). Sodium borohydride (103 mg, 2.73 mmol) was added to the solution under ice-cooling, which was stirred for 1 hour. Then, the solvent was distilled out under reduced pressure. 1N Hydrochloric acid was added to the residue, which was washed with ethyl acetate. 4N Sodium hydroxide was added to the water layer to make it alkaline. The reaction mixture was extracted with ethyl acetate, which was washed with saturated aqueous sodium chloride solution, dried over anhydrous sodium sulfate, and then the solvent was distilled out under reduced pressure. The resulting residue was purified by aluminum B column chromatography (development solvent; ethyl acetate), powdered with hexane, to give the titled compound (231 mg).

Melting point: 160–163° C. (crystallization solvent: ethyl acetate-n-hexane)

FAB(pos) 426.3 [M+H]+

EXAMPLE 204

N-[6-[2-(1-Pyrrolidinyl)ethyl]-7,8-dihydro-2-naphthalenyl][1,1'-biphenyl]-4-carboxamide

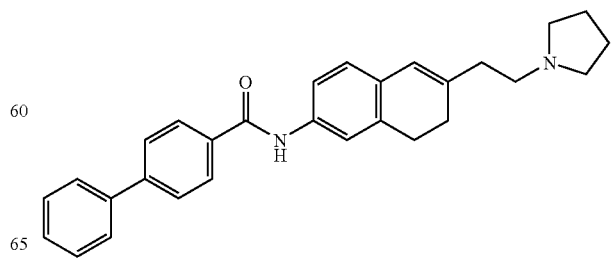

Concentrated hydrochloric acid (2 ml) was added to N-[6-[2-(1-pyrrolidinyl)ethyl]-7,8-dihydro-2-naphthalenyl]acetamide (98.0 mg, 0.345 mmol) obtained in Reference Example 103, which was stirred at 100° C. for 16 hours. The solvent was distilled out under reduced pressure. Ethyl acetate was added to the residue, which was washed with aqueous potassium carbonate solution and saturated aqueous sodium chloride solution, dried over anhydrous sodium sulfate, and then the solvent was distilled out under reduced pressure. WSC (62.5 mg, 0.326 mmol) was added to a dimethylformamide solution (1.5 ml) of the resulting oily substance (79.0 mg, 0.326 mmol), [1,1'-biphenyl]-4-carboxylic acid (64.6 mg, 0.326 mmol) and DMAP (39.8 mg, 0.326 mmol) under ice-cooling, which was stirred at room temperature for 1 day. Ethyl acetate was added to the reaction mixture, washed with aqueous potassium carbonate solution and saturated aqueous sodium chloride solution, dried over anhydrous sodium sulfate, then the solvent was distilled out under reduced pressure. The resulting residue was purified by aluminum column chromatography (development solvent; ethyl acetate), powdered with ethyl acetate and isopropyl ether (1:5), to give the titled compound (36.8 mg).

$^1$H NMR (DMSO-$d_6$) δ: 1.67 (4H, m), 2.23 (2H, m), 2.34 (2H, m), 2.46 (4H, m), 2.57 (2H, m), 2.75 (2H, m), 6.24 (1H, s), 6.98 (1H, d, J=8.1 Hz), 7.40–7.59 (5H, m), 7.76 (2H, d, J=7.5 Hz), 7.82 (2H, d, J=8.4 Hz), 8.05 (2H, d, J=8.4 Hz), 10.19 (1H, s).

Melting point: 184–186° C. (crystallization solvent: ethyl acetate-isopropyl ether)

FAB(pos) 423.2 [M+H]+

EXAMPLE 205

4'-Fluoro-N-[6-[2-(1-pyrrolidinyl)ethyl]-7,8-dihydro-2-naphthalenyl][1,1'-biphenyl]-4-carboxamide

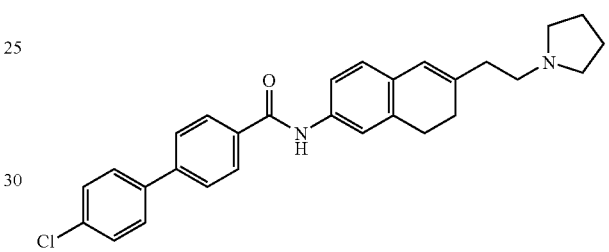

Concentrated hydrochloric acid (2 ml) was added to N-[6-[2-(1-pyrrolidinyl)ethyl]-7,8-dihydro-2-naphthalenyl]acetamide (98.0 mg, 0.345 mmol) obtained in Reference Example 103, which was stirred at 100° C. for 16 hours. The solvent was distilled out under reduced pressure. Ethyl acetate was added to the residue, which was washed with aqueous potassium carbonate solution and saturated aqueous sodium chloride solution, dried over anhydrous sodium sulfate, and then the solvent was distilled out under reduced pressure. WSC (62.5 mg, 0.326 mmol) was added to a dimethylformamide solution (1.5 ml) of the resulting oily substance (79.0 mg, 0.326 mmol), 4'-fluoro-[1,1'-biphenyl]-4-carboxylic acid (64.6 mg, 0.326 mmol) and DMAP (39.8 mg, 0.326 mmol) under ice-cooling, which was stirred at room temperature for 1 day. Ethyl acetate was added to the reaction mixture, which was washed with aqueous potassium carbonate solution and saturated aqueous sodium chloride solution, dried over anhydrous sodium sulfate, and the solvent was distilled out under reduced pressure. The resulting residue was purified by aluminum column chromatography (development solvent; ethyl acetate), powdered with ethyl acetate-isopropyl ether (1:5), to give the titled compound (75.1 mg).

$^1$H NMR (DMSO-$d_6$) δ: 1.68 (4H, m), 2.23 (2H, m), 2.35 (2H, m), 2.50 (4H, m), 2.59 (2H, m), 2.75 (2H, m$^{-1}$), 6.24 (1H, s), 6.98 (1H, d, J=8.1 Hz), 7.34 (2H, m), 7.56 (2H, m), 7.81 (4H, m), 8.04 (2H, d, J=8.4 Hz), 10.19 (1H, s).

Melting point: 187–189° C. (crystallization solvent: ethyl acetate-isopropyl ether)

FAB (pos) 441.3 [M+H]+

EXAMPLE 206

4'-Chloro-N-[6-[2-(1-pyrrolidinyl)ethyl]-7,8-dihydro-2-naphthalenyl][1,1'-biphenyl]-4-carboxamide

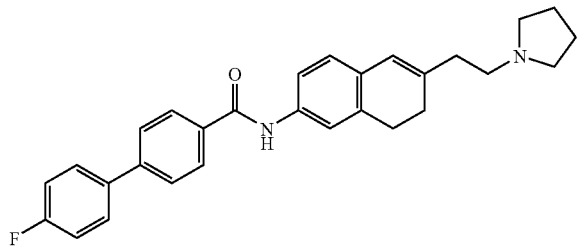

Concentrated hydrochloric acid (2 ml) was added to N-[6-[2-(1-pyrrolidinyl)ethyl]-7,8-dihydro-2-naphthalenyl]acetamide (98.0 mg, 0.345 mmol) obtained in Reference Example 103, which was stirred at 100° C. for 16 hours. The solvent was distilled out under reduced pressure. Ethyl acetate was added to the residue, which was washed with aqueous potassium carbonate solution and saturated aqueous sodium chloride solution, dried over anhydrous sodium sulfate, and then the solvent was distilled out under reduced pressure. WSC (62.5 mg, 0.326 mmol) was added to a dimethylformamide solution (1.5 ml) of the resulting oily substance (79.0 mg, 0.326 mmol), 4'-chloro-[1,1'-biphenyl]-4-carboxylic acid (64.6 mg, 0.326 mmol) and DMAP (39.8 mg, 0.326 mmol) under ice-cooling, which was stirred at room temperature for 1 day. Ethyl acetate was added to the reaction mixture, which was washed with aqueous potassium carbonate solution and saturated aqueous sodium chloride solution, dried over anhydrous sodium sulfate, and then the solvent was distilled out under reduced pressure. The resulting residue was purified by aluminum column chromatography (development solvent; ethyl acetate), powdered with ethyl acetate-isopropyl ether (1:5), to give the titled compound (78.4 mg).

$^1$H NMR (DMSO-$d_6$) δ: 1.67 (4H, m), 2.23 (2H, m), 2.34 (2H, m), 2.45 (4H, m), 2.57 (2H, m), 2.75 (2H, m), 6.24 (1H, s), 6.98 (1H, d, J=8.1 Hz), 7.55 (4H, m), 7.80 (2H, d, J=8.4 Hz), 7.84 (2H, d, J=8.4 Hz), 8.05 (2H, d, J=8.7 Hz), 10.20 (1H, s).

Melting point: 207–209° C. (crystallization solvent: ethyl acetate-isopropyl ether)

FAB (pos) 457.2 [M+H]+

EXAMPLE 207

4'-Cyano-N-[6-[(dimethylamino)methyl]-5,6,7,8-tetrahydro-2-naphthalenyl][1,1'-biphenyl]-4-carboxamide

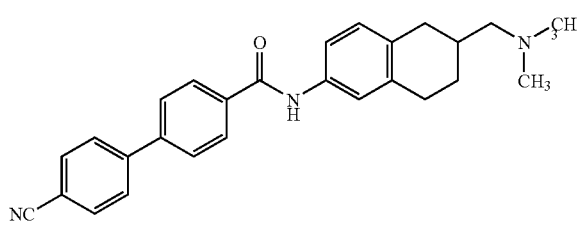

The titled compound was obtained by carrying out the same operation as in Example 1, using N-[(6-amino-1,2,3,4-tetrahydro-2-naphthalenyl)methyl]-N,N-dimethylamine and 4'-cyano-[1,1'-biphenyl]-4-carboxylic acid.

$^1$H NMR (CDCl$_3$) δ: 1.42 (1H, m), 1.95 (2H, m), 2.26 (6H, s), 2.24–2.46 (3H, m), 2.84–2.95 (3H, m), 7.10 (1H, d, J=8.4 Hz), 7.30 (1H, m), 7.46 (1H, s), 7.74 (7H, m), 7.98 (2H, d, J=8.4 Hz).

Melting point: 183–185° C. (crystallization solvent: ethyl acetate-isopropyl ether)

FAB (pos) 410.2 [M+H]+

EXAMPLE 208

N-[6-[2-(Dimethylamino)ethyl]-7,8-dihydro-2-naphthalenyl][1,1'-biphenyl]-4-carboxamide

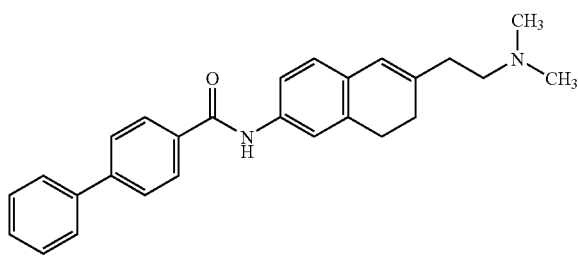

Concentrated hydrochloric acid (1.5 ml) was added to N-[6-[2-(dimethylamino)ethyl]-7,8-dihydro-2-naphthalenyl]acetamide (57.5 mg, 0.223 mmol) obtained in Reference Example 104, which was stirred at 100° C. for 1 hour. The solvent was distilled out under reduced pressure. Ethyl acetate was added to the residue, which was washed with aqueous potassium carbonate solution and saturated aqueous sodium chloride solution, dried over anhydrous sodium sulfate, and then the solvent was distilled out under reduced pressure. WSC (29.2 mg, 0.139 mmol) was added to a dimethylformamide solution (0.7 ml) of the resulting oily substance (30 mg, 0.139 mmol), [1,1'-biphenyl]-4-carboxylic acid (30.2 mg, 0.139 mmol) and DMAP (16.9 mg, 0.139 mmol) under ice-cooling, which was stirred at room temperature for 16 hours. Ethyl acetate was added to the reaction mixture, which was washed with aqueous potassium carbonate solution and saturated aqueous sodium chloride solution, dried over anhydrous sodium sulfate, and then the solvent was distilled out under reduced pressure. The resulting residue was purified by aluminum column chromatography (development solvent; ethyl acetate), powdered with ethyl acetate-isopropyl ether (1:5), to give the titled compound (12.4 mg).

$^1$H NMR (CDCl$_3$) δ: 2.29 (8H., m), 2.41 (2H, m), 2.46 (2H, m), 2.84 (2H, t, J=8.1 Hz), 6.24 (1H, s), 6.98 (1H, d, J=8.4 Hz), 7.34 (1H, m), 7.41 (1H, d, J=6.9 Hz), 7.46 (3H, m), 7.63 (2H, d, J=7.2 Hz), 7.71 (2H, d, J=8.4 Hz), 7.77 (1H, br), 7.94 (2H, d, J=8.4 Hz).

Melting point: 148–150° C. (crystallization solvent: ethyl acetate-isopropyl ether)

FAB (pos) 397.2 [M+H]+

EXAMPLE 209

N-[6-[2-(Dimethylamino)ethyl]-5,6,7,8-tetrahydro-2-naphthalenyl][1,1'-biphenyl]-4-carboxamide

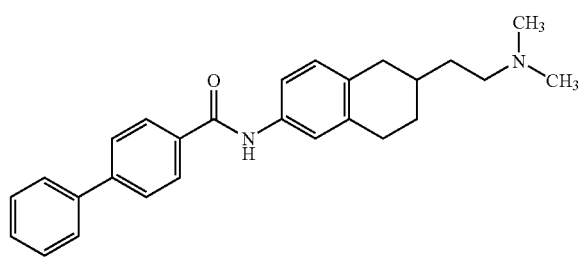

A methanol solution (5 ml) of N-[6-[2-(dimethylamino)ethyl] 7,8-dihydro-2-naphthalenyl][1,1'-biphenyl]-4-carboxamide (20 mg, 0.050 mmol) obtained in Example 208 and palladium carbon (10 mg) was stirred under hydrogen atmosphere for 4 hours. After a catalyst was filtered off, the filtrate was concentrated under reduced pressure. The resulting residue was purified by aluminum B column chromatography (development solvent; ethyl acetate), powdered with ethyl acetate-hexane (1:3), to give the titled compound (4.0 mg).

$^1$H NMR (CDCl$_3$) δ: 1.60 (4H, m), 1.92 (1H, m), 2.26 (6H, s), 2.42 (3H, m), 2.84 (3H, m), 7.06 (1H, d, J=8.1 Hz), 7.32 (1H, m), 7.46 (4H, m), 7.63 (2H, d, J=6.9 Hz), 7.72 (3H, m), 7.94 (2H, d, J=8.1 Hz).

Melting point: 112–114° C. (crystallization solvent: ethyl acetate-isopropyl ether)

FAB(pos) 399.2 [M+H]+

EXAMPLE 210

4'-Chloro-N-[2-[(dimethylamino)methyl]-3,4-dihydro-2H-1,4-benzoxazin-6-yl][1,1'-biphenyl]-4-carboxamide

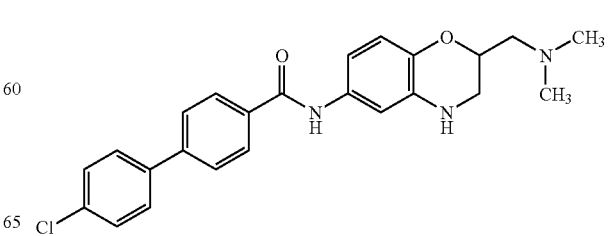

The titled compound was obtained as white powders by the same method as in Example 1, using 6-amino-2-(dimethylamino)methyl-1,4-benzoxazin obtained in Reference Example 105.

$^1$H-NMR (CDCl$_3$) δ: 2.33 (6H, s), 2.44–2.65 (2H, m), 3.15–3.21 (1H, m), 3.41–3.46 (1H, m), 3.87 (1H, brs), 4.24–4.26 (1H, m), 6.61 (1H, dd, J=2.5, 8.6 Hz), 6.81 (1H, d, J=8.6 Hz), 7.28 (1H, d, J=2.5 Hz), 7.43 (2H, d, J=6.5 Hz), 7.54 (2H, d, J=6.5 Hz), 7.64 (2H, d, J=8.4 Hz), 7.71 (1H, s), 7.90 (2H, d, J=8.4 Hz).

Melting point: 227–230° C. (crystallization solvent: diisopropyl ether)

EXAMPLE 211

4'-Methoxy-N-[6-[(4-methyl-1-piperazinyl)methyl]-7,8-dihydro-2-naphthalenyl][1,1'-biphenyl]-4-carboxamide

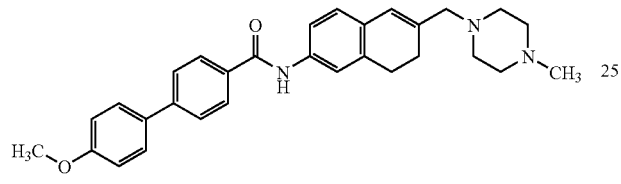

The titled compound was obtained as colorless powders by carrying out the same operation as in Example 1, using 6-[(4-methyl-1-piperazinyl)methyl]-7,8-dihydro-2-naphthalenamine obtained in Reference Example 106.

$^1$H NMR (CDCl$_3$) δ: 2.31 (3H, s), 2.33 (2H, t, J=8.1 Hz), 2.49 (8H, bs), 2.84 (2H, t, J=8.1 Hz), 3.07 (2H, s), 3.87 (3H, s), 6.36 (1H, s), 7.00–7.03 (3H, m), 7.36 (1H, d, J=8.1 Hz), 7.51 (1H, s), 7.58 (2H, d, J=8.4 Hz), 7.67 (2H, d, J=8.4 Hz), 7.78 (1H, s), 7.91 (2H, d, J=8.4 Hz).

Melting point: 208–210° C. (crystallization solvent: ethyl acetate)

EXAMPLE 212

6-(4-Methoxyphenyl)-N-[6-[(4-methyl-1-piperazinyl)methyl]-7,8-dihydro-2-naphthalenyl]nicotinamide

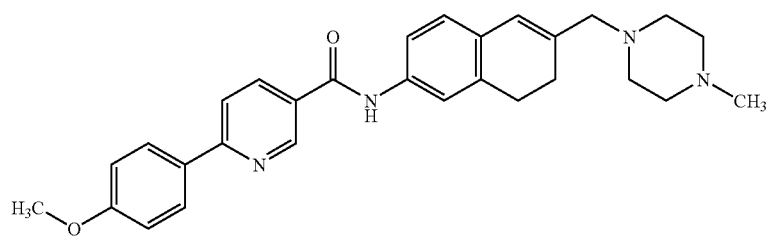

The titled compound was obtained as colorless powders by carrying out the same operation as in Example 1, using 6-[(4-methyl-1-piperazinyl)methyl]-7,8-dihydro-2-naphthalenamine obtained in Reference Example 106.

$^1$H NMR (CDCl$_3$) δ: 2.30 (3H, s), 2.33 (2H, t, J=8.1 Hz), 2.47 (8H, bs), 2.84 (2H, t, J=8.1 Hz), 3.07 (2H, s), 3.89 (3H, s), 6.36 (1H, s), 7.01–7.04 (3H, m), 7.37 (1H, d, J=8.1 Hz), 7.49 (1H, s), 7.78–7.81 (2H, m), 8.03 (2H, d, J=8.4 Hz), 8.21 (1H, dd, J=2.1 Hz, 8.7 Hz), 9.09 (1H, s).

Melting point: 235–237° C. (crystallization solvent: ethyl acetate)

EXAMPLE 213

N-[4-Methyl-3-(1-pyrrolidinylmethyl)-2H-chromen-7-yl][1,1'-biphenyl]-4-carboxamide

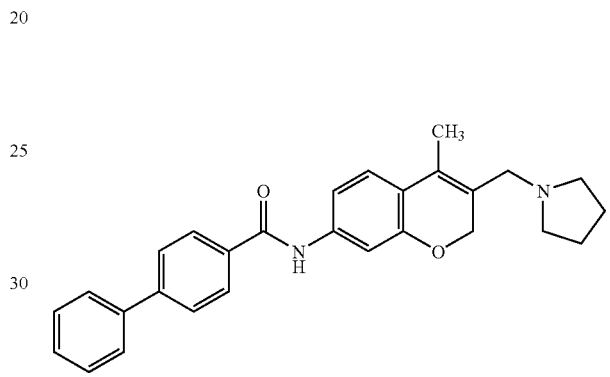

The titled compound was obtained as colorless powders by carrying out the same operation as in Example 1, using 4-methyl-3-(1-pyrrolidinylmethyl)-2H-chromen-7-amine obtained in Reference Example 107.

$^1$H NMR (CDCl$_3$) δ: 1.77 (4H, s), 2.05 (3H, s), 2.51 (4H, s), 3.25 (2H, s), 4.74 (2H, s), 7.14–7.50 (6H, m), 7.63 (2H, d, J=7.2 Hz), 7.71 (2H, d, J=8.4 Hz), 7.79 (1H, s), 7.94 (2H, d, J=8.4 Hz).

Melting point: 176–178° C. (crystallization solvent: ethyl acetate-diisopropyl ether)

EXAMPLE 214

4'-Methoxy-N-[4-methyl-3-(1-pyrrolidinylmethyl)-2H-chromen-7-yl][1,1'-biphenyl]-4-carboxamide

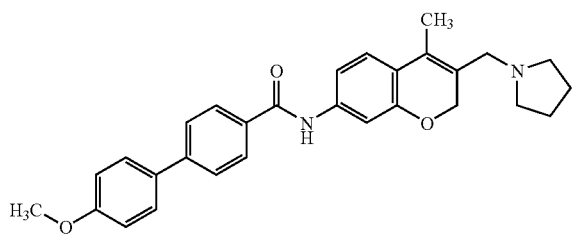

The titled compound was obtained as colorless powders by carrying out the same operation as in Example 1, using 4-methyl-3-(1-pyrrolidinylmethyl)-2H-chromen-7-amine obtained in Reference Example 107.

$^1$H NMR (CDCl$_3$) δ: 1.77 (4H, s), 2.05 (3H, s), 2.51 (4H, s), 3.25 (2H, s), 3.87 (3H, s), 4.74 (2H, s), 7.01 (2H, d, J=8.7 Hz), 7.14–7.31 (3H, m), 7.57 (2H, d, J=8.7 Hz), 7.66 (2H, d, J=8.4 Hz), 7.89 (1H, s), 7.91 (2H, d, J=8.4 Hz).

Melting point: 195–197° C. (crystallization solvent: ethyl acetate-diisopropyl ether)

EXAMPLE 215

N-[4-Methyl-3-(1-pyrrolidinylmethyl)-2H-chromen-7-yl]-6-phenylnicotinamide

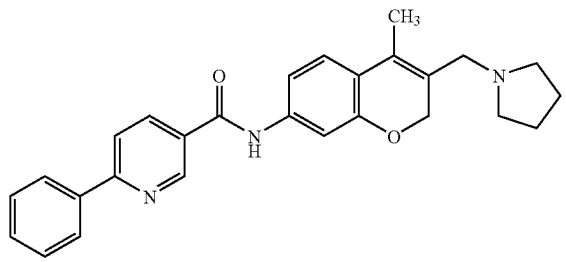

The titled compound was obtained as colorless powders by carrying out the same operation as in Example 1, using 4-methyl-3-(1-pyrrolidinylmethyl)-2H-chromen-7-amine obtained in Reference Example 107.

$^1$H NMR (CDCl$_3$) δ: 1.77 (4H, s), 2.05 (3H, s), 2.51 (4H, s), 3.25 (2H, s), 4.74 (2H, s), 7.14–7.28 (3H, m), 7.47–7.54 (3H, m), 7.81–7.87 (2H, m), 8.06 (2H, d, J=8.4 Hz), 8.27 (1H, d, J=8.4 Hz), 9.13 (1H, s).

Melting point: 192–193° C. (crystallization solvent: ethyl acetate)

EXAMPLE 216

6-(4-Methoxyphenyl)-N-[4-methyl-3-(1-pyrrolidinylmethyl)-2H-chromen-7-yl]nicotinamide

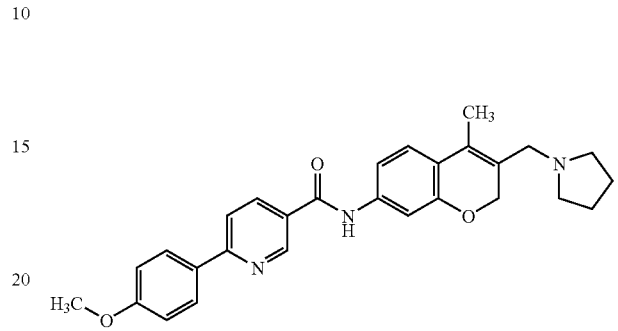

The titled compound was obtained as colorless powders by carrying out the same operation as in Example 1, using 4-methyl-3-(1-pyrrolidinylmethyl)-2H-chromen-7-amine obtained in Reference Example 107.

$^1$H NMR (CDCl$_3$) δ: 1.77 (4H, s), 2.05 (3H, s), 2.51 (4H, s), 3.25 (2H, s), 3.89 (3H, s), 4.74 (2H, s), 7.03 (2H, d, J=8.7 Hz), 7.14–7.26 (3H, m), 7.75–7.81 (2H, m), 8.03 (2H, d, J=8.7 Hz), 8.21 (1H, d, J=6.6 Hz), 9.09 (1H, s).

Melting point: 201–203° C. (crystallization solvent: ethyl acetate)

EXAMPLE 217

N-[4-Methyl-3-(1-pyrrolidinylmethyl)-2H-chromen-7-yl]-4-phenyl-1-piperidinecarboxamide

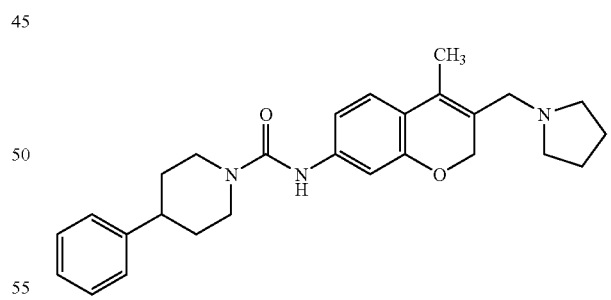

The titled compound was obtained as colorless powders by carrying out the same operation as in Example 99, using 4-methyl-3-(1-pyrrolidinylmethyl)-2H-chromen-7-amine obtained in Reference Example 107.

$^1$H NMR (CDCl$_3$) δ: 1.72–1.95 (8H, m), 2.03 (3H, s), 2.54 (4H, s), 2.63–2.76 (1H, m), 2.95–3.00 (2H, m), 3.27 (2H, s), 4.19–4.23 (2H, m), 4.70 (2H, s), 6.39 (1H, s), 6.83 (1H, s), 7.01–7.32 (7H, m).

Melting point: 125–127° C. (crystallization solvent: ethyl acetate-diisopropyl ether)

EXAMPLE 218

4-(4-Methoxyphenyl)-N-[4-methyl-3-(1-pyrrolidinylmethyl)-2H-chromen-7-yl]-1-piperidinecarboxamide

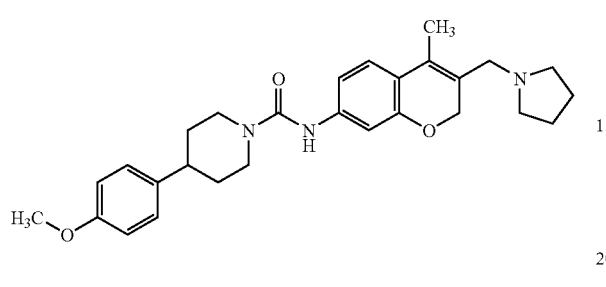

The titled compound was obtained as colorless powders by carrying out the same operation as in Example 99, using 4-methyl-3-(1-pyrrolidinylmethyl)-2H-chromen-7-amine obtained in Reference Example 107.

$^1$H NMR (CDCl$_3$) δ: 1.63–1.91 (8H, m), 2.02 (3H, s), 2.49 (4H, s), 2.61–2.71 (1H, m), 2.93–3.01 (2H, m), 3.23 (2H, s), 3.79 (3H, s), 4.16–4.21 (2H, m), 4.69 (2H, s), 6.34 (1H, s), 6.82–6.91 (3H, m), 6.99–7.02 (1H, m), 7.10–7.15 (3H, m).

Melting point: 144–146° C. (crystallization solvent: ethyl acetate-n-hexane)

EXAMPLE 219

N-[4-Methyl-3-(4-morpholinylmethyl)-2H-chromen-7-yl][1,1'-biphenyl]-4-carboxamide

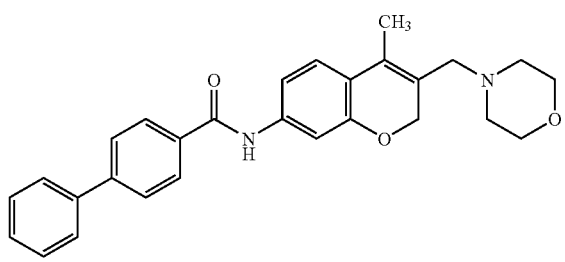

The titled compound was obtained as colorless powders by carrying out the same operation as in Example 1, using 4-methyl-3-(4-morpholinylmethyl)-2H-chromen-7-amine obtained in Reference Example 108.

$^1$H NMR (DMSO-d$_6$) δ: 2.01 (3H, s), 2.37 (4H, s), 3.32 (2H, s), 3.57 (4H, s), 4.63 (2H, s), 7.23 (1H, d, J=8.1 Hz), 7.38–7.54 (5H, m), 7.76 (2H, d, J=7.5 Hz), 7.84 (2H, d, J=8.1 Hz), 8.04 (2H, d, J=8.1 Hz), 10.27 (1H, s).

Melting point: 162–164° C. (crystallization solvent: ethyl acetate-diisopropyl ether)

EXAMPLE 220

4'-Methoxy-N-[4-methyl-3-(4-morpholinylmethyl)-2H-chromen-7-yl][1,1'-biphenyl]-4-carboxamide

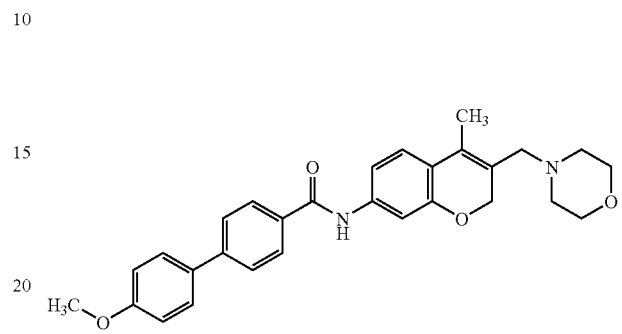

The titled compound was obtained as colorless powders by carrying out the same operation as in Example 1, using 4-methyl-3-(4-morpholinylmethyl)-2H-chromen-7-amine obtained in Reference Example 108.

$^1$H NMR (DMSO-d$_6$) δ: 2.00 (3H, s), 2.37 (4H, s), 3.11 (2H, s), 3.57 (4H, s), 3.82 (3H, s), 4.63 (2H, s),7.07 (2H, d, J=8.7 Hz), 7.23 (1H, d, J=8.1 Hz), 7.38–7.40 (2H, m), 7.72 (2H, d, J=8.7 Hz), 7.79 (2H, d, J=8.4 Hz), 8.01 (2H, d, J=8.4 Hz), 10.23 (1H, s).

Melting point: 198–200° C. (crystallization solvent: ethyl acetate-diisopropyl ether

EXAMPLE 221

N-[6-(4-Morpholinylmethyl)-7,8-dihydro-2-naphthalenyl][1,1'-biphenyl]-4-carboxamide

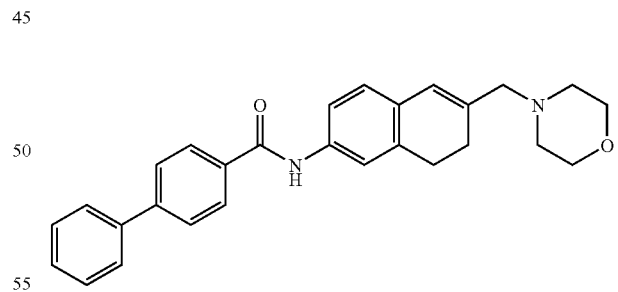

The titled compound was obtained as colorless powders by carrying out the same operation as in Example 1, using 6-(4-morpholinylmethyl)-7,8-dihydro-2-naphthalenamine obtained in Reference Example 109.

$^1$H-NMR (CDCl$_3$) δ: 2.34 (2H, t, J=8.4 Hz), 2.45 (4H, m), 2.85 (2H, t, J=8.4 Hz), 3.06 (2H, s), 3.73 (4H, t, J=4.7 Hz), 6.36 (1H, s), 7.02 (1H, d, J=8.1 Hz), 7.36–7.78 (10H, m), 7.93 (2H, d, J=8.1 Hz).

Melting point: 180–181° C. (crystallization solvent: ethyl acetate-diisopropyl ether)

EXAMPLE 222

6-(4-Methylphenyl)-N-[6-(4-morpholinylmethyl)-7,8-dihydro-2-naphthalenyl]nicotinamide

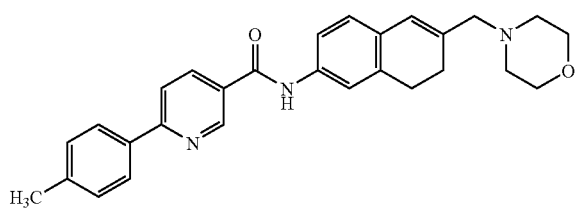

The titled compound was obtained as colorless powders by carrying out the same operation as in Example 1, using 6-(4-morpholinylmethyl)-7,8-dihydro-2-naphthalenamine obtained in Reference Example 109.

$^1$H-NMR (CDCl$_3$) δ: 2.39 (2H, t, J=8.4 Hz), 2.43 (7H, m). 2.85 (2H, t, J=8.4 Hz), 3.06 (2H, s), 3.73 (4H, t, J=4.5 Hz), 6.36 (1H, s), 7.03 (1H, d, J=8.1 Hz), 7.30–7.38 (3H, m), 7.50 (1H, s), 7.76 (1H, s), 7.84 (1H, d, J=8.1 Hz), 7.97 (2H, d, J=8.1 Hz), 8.24 (1H, dd, J=8.4, 2.3 Hz), 9.12 (1H, s).

Melting point: 233–234° C. (crystallization solvent: ethyl acetate-diisopropyl ether)

EXAMPLE 223

4-(4-Methylphenyl)-N-[6-(4-morpholinylmethyl)-7,8-dihydro-2-naphthalenyl]-1-piperidinecarboxamide

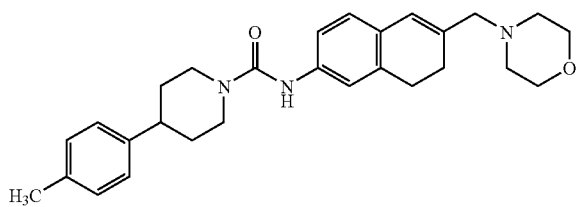

The titled compound was obtained as colorless powders by carrying out the same operation as in Example 99, using 6-(4-morpholinylmethyl)-7,8-dihydro-2-naphthalenamine obtained in Reference Example 109.

$^1$H-NMR (CDCl$_3$) δ: 1.65–1.75 (4H, m), 1.90 (2H, m), 2.27–2.43 (7H, m), 2.72 (1H, m), 2.79 (2H, t, J=7.5 Hz), 2.93–3.04 (4H, m), 3.72 (4H, m), 4.20 (2H, d, J=11.7 Hz), 6.31 (1H, s), 6.39 (1H, s), 6.92 (1H, d, J=8.1 Hz), 7.05–7.26 (6H, m).

Melting point: 231–214° C. (crystallization solvent: ethyl acetate-diisopropyl ether)

EXAMPLE 224

4'-Methyl-N-[6-(4-morpholinylmethyl)-7,8-dihydro-2-naphthalenyl][1,1'-biphenyl]-4-carboxamide

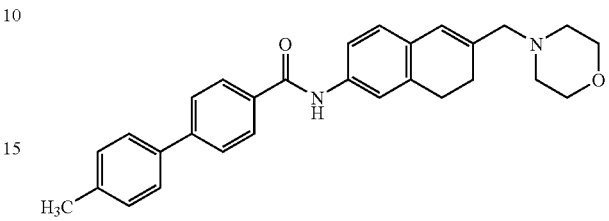

The titled compound was obtained as colorless powders by carrying out the same operation as in Example 1, using 6-(4-morpholinylmethyl)-7,8-dihydro-2-naphthalenamine obtained in Reference Example 109.

$^1$H-NMR (CDCl$_3$) δ: 2.33 (2H, t, J=8.1 Hz), 2.42–2.44 (7H, m), 2.84 (2H, t, J=8.1 Hz), 3.06 (2H, s), 3.72 (4H, t, J=4.2 Hz), 6.36 (1H, s), 7.01 (1H, d, J=8.1 Hz), 7.25–7.29 (–2H, m), 7.37 (1H, d, J=8.1 Hz), 7.51–7.54 (3H, m), 7.68 (2H, d, J=8.1 Hz), 7.85 (1H, s), 7.92 (2H, d, J=8.1 Hz).

Melting point: 196–197° C. (crystallization solvent: ethyl acetate-diisopropyl ether)

EXAMPLE 225

2'-Methyl-N-(6-(1-pyrrolidinylmethyl)-7,8-dihydro-2-naphthalenyl][1,1'-biphenyl]-4-carboxamide.

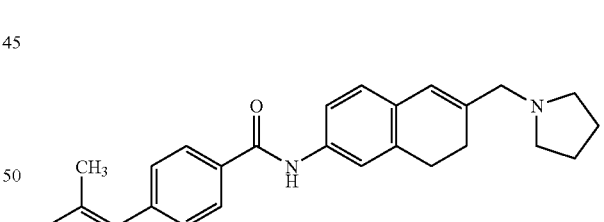

The titled compound was obtained as colorless powders by carrying out the same operation as in Example 1, using 6-(1-pyrrolidinylmethyl)-7,8-dihydro-2-naphthalenamine obtained in Reference Example 54.

Melting point: 177–178° C. (crystallization solvent: ethyl acetate-diisopropyl ether)

EXAMPLE 226

4'-Fluoro-N-methyl-N-[6-(1-pyrrolidinylmethyl)-7,8-dihydro-2-naphthalenyl][1,1'-biphenyl]-4-carboxamide Hydrochloride

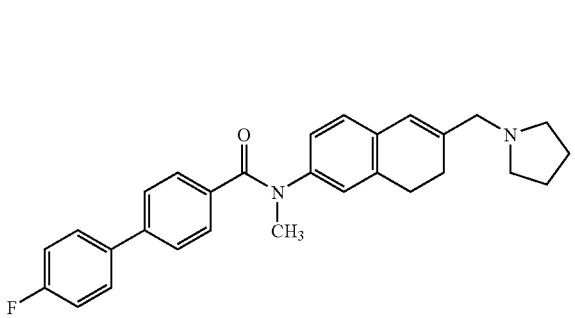

N-Methyl-6-(1-pyrrolidinylmethyl)-7.8-dihydro-2-naphthalenamine dihydrochloride (315 mg, 1.0 mmol) obtained in Reference Example 113 was dissolved in N,N-dimethylformamide (25 ml). 4-Bromobenzoic acid (402 mg, 2.0 mmol), WSC (383 mg, 2.0 mmol), HOBt (270 mg, 2.0 mmol) and DMAP (244 mg, 2.0 mmol) were added to the solution, which was stirred at room temperature for 16 hours. Ethyl acetate and water were added to the reaction mixture, and extraction was conducted. The ethyl acetate layer was concentrated under reduced pressure. The residue was purified by aluminum column chromatography (development solvent; ethyl acetate: n-hexane=33:67). The eluate was concentrated under reduced pressure, which was dissolved in dimethoxyethane-tetrahydrofuran (10:1, 5.5 ml) 4-Fluorophenylboric acid (73 mg, 0.52 mmol) tetrakis(triphenylphosphine)palladium complex (15 mg, 0.013 mmol) and 2N aqueous sodium carbonate solution (0.433 ml) were added to the solution, which was refluxed with heating under nitrogen atmosphere at 90 for 5.5 hours. The reaction mixture was poured into cold water, and extraction was conducted using ethyl acetate. The ethyl acetate layer was concentrated, and the residue was purified by aluminum column chromatography (development solvent; ethyl acetate). 4N Hydrogen chloride-ethyl acetate solution was added to the eluate, which was concentrated under reduced pressure. The resulting residue was recrystallized from methanol-ethyl acetate, to give the titled compound (108 mg).

$^1$H-NMR (DMSO-$d_6$) δ: 1.92–1.98 (4H, m), 2.39 (2H, t, J=8.1 Hz), 2.73 (2H, t, J=8.1 Hz), 3.00 (2H, m), 3.35 (3H, m), 3.44 (2H, m), 3.83 (2H, d, J=5.6 Hz), 6.62 (1H, s), 6.92–7.01 (2H, m), 7.11 (1H, s), 7.26 (2H, dd, J=8.9, 5.6 Hz), 7.38 (2H, d, J=8.1 Hz), 7.55 (2H, d, J=8.1 Hz), 7.69 (2H, dd, J=8.9, 5.6 Hz), 10.60 (1H, brs.).

Melting point: 201–203° C. (crystallization solvent: methanol-diisopropyl ether)

FAB(pos) 441.2 [M+H]+

EXAMPLE 227

(E)-3-(4-Chlorophenyl)-N-[6-[(dimethylamino)methyl]-5,6,7,8-tetrahydro-2-naphthalenyl]-2-propenamide Hydrochloride

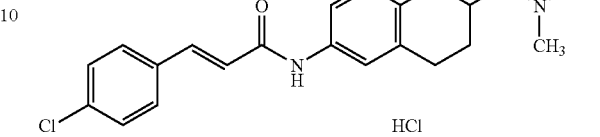

The titled compound was obtained as colorless powders by carrying out the same operation as in Example 4.

Melting point: 243–245° C. (crystallization solvent: ethanol-diisopropyl ether)

EXAMPLE 228

6-(4-Methylphenyl)-N-[5-methyl-6-(1-pyrrolidinylmethyl)-7,8-dihydro-2-naphthalenyl]nicotinamide

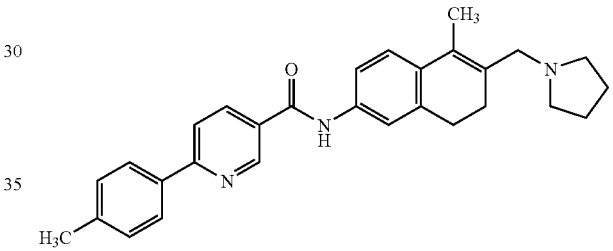

The titled compound was obtained as colorless powders by carrying out the same operation as in Example 1, using 5-methyl-6-(1-pyrrolidinylmethyl)-7,8-dihydro-2-naphthalenamine obtained in Reference Example 69.

Melting point: 175–176° C. (crystallization solvent: ethyl acetate-diisopropyl ether)

Elemental analysis for $C_{29}H_{30}N_3O$ Calcd. C, 79.78; H, 6.93; N, 9.63. Found: C, 79.66; H, 6.97; N, 9.68.

EXAMPLE 229

4'-Fluoro-N-[5-methyl-6-(1-pyrrolidinylmethyl)-7,8-dihydro-2-naphthalenyl][1,1'-biphenyl]-4-carboxamide The titled compound was obtained as colorless powders by carrying out the same operation as in Example 1, using 5-methyl-6-(1-pyrrolidinylmethyl)-7,8-dihydro-2-naphthalenamine obtained in Reference Example 69.

Melting point: 199–201° C. (crystallization solvent: ethyl acetate-diisopropyl ether)

Elemental analysis for $C_{29}H_{30}FN_2O$ Calcd.: C, 79.06; H, 6.63; N, 6.36. Found: C, 79.01; H, 6.81; N, 6.45.

EXAMPLE 230

6-(4-Fluorophenyl)-N-[5-methyl-6-(1-pyrrolidinylmethyl)-7,8-dihydro-2-naphthalenyl]nicotinamide

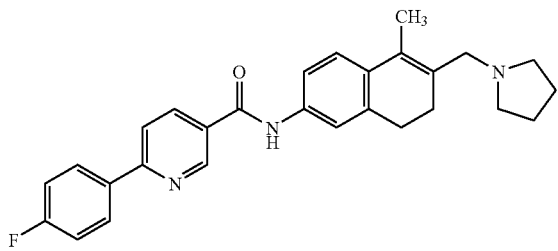

The titled compound was obtained as colorless powders by carrying out the same operation as in Example 1, using 5-methyl-6-(1-pyrrolidinylmethyl)-7,8-dihydro-2-naphthalenamine obtained in Reference Example 69.

Melting point: 204–205° C. (crystallization solvent: ethyl acetate-diisopropyl ether)

Elemental analysis for $C_2H_{28}FN_3O$ Calcd.: C, 76.17; H, 6.39; N, 9.52. Found: C, 76.03; H, 6.44; N, 9.62.

EXAMPLE 231

4-(4-Fluorophenyl)-N-[5-methyl-6-(1-pyrrolidinylmethyl)-7,8-dihydro-2-naphthalenyl]-1-piperidinecarboxamide

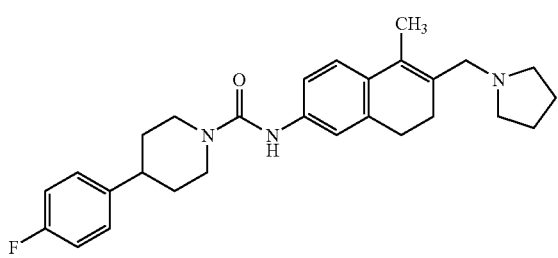

The titled compound was obtained as colorless powders by carrying out the same operation as in Example 99, using 5-methyl-6-(1-pyrrolidinylmethyl)-7,8-dihydro-2-naphthalenamine obtained in Reference Example 69.

Melting point: 172–173° C. (crystallization solvent: ethyl acetate-diisopropyl ether)

EXAMPLE 232

4'-Methyl-N-[6-(1-pyrrolidinylmethyl)-7,8-dihydro-2-naphthalenyl][1,1'-biphenyl]-4-carboxamide

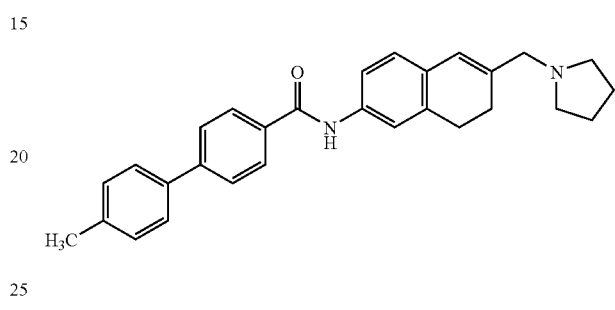

The titled compound was obtained as colorless powders by carrying out the same operation as in Example 1, using 6-(1-pyrrolidinylmethyl)-7,8-dihydro-2-naphthalenamine obtained in Reference Example 54.

Melting point: 176–177° C. (crystallization solvent: ethyl acetate-diisopropyl ether)

EXAMPLE 233

N-[5-Methyl-6-(1-pyrrolidinylmethyl)-7,8-dihydro-2-naphthalenyl]-6-phenylnicotinamide

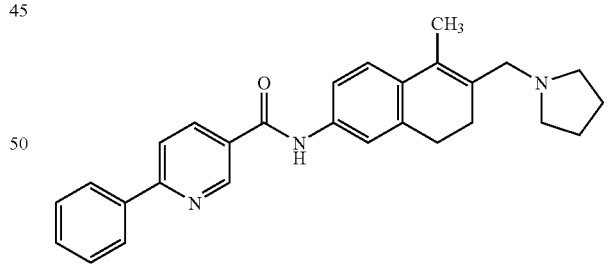

The titled compound was obtained as colorless powders by carrying out the same operation as in Example 1, using 5-methyl-6-(1-pyrrolidinylmethyl)-7,8-dihydro-2-naphthalenamine obtained in Reference Example 69.

Melting point: 178–179° C. (crystallization solvent: ethyl acetate-diisopropyl ether)

Elemental analysis for $C_{28}H_{29}N_3O$ Calcd.: C, 79.40; H, 6.90; N, 9.92. Found: C, 79.13; H, 6.82; N, 10.03.

EXAMPLE 234

4'-Methoxy-N-[5-methyl-6-(1-pyrrolidinylmethyl)-7,8-dihydro-2-naphthalenyl][1,1'-biphenyl]-4-carboxamide

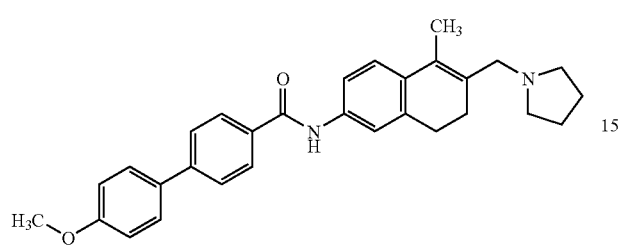

The titled compound was obtained as colorless powders by carrying out the same operation as in Example 1, using 5-methyl-6-(1-pyrrolidinylmethyl)-7,8-dihydro-2-naphthalenamine obtained in Reference Example 69.

$^1$H-NMR (CDCl$_3$) δ: 1.78 (4H, m), 2.10 (3H, s), 2.37 (2H, t, J=8.1 Hz), 2.53 (4H, m), 2.76 (2H, t, J=8.1 Hz), 3.28 (2H, s), 3.87 (3H, s), 7.01 (1H, d, J=8.6 Hz), 7.27 (2H, d, J=7.8 Hz), 7.46 (1H, d, J=7.8 Hz), 7.48 (1H, s), 7.57 (2H, d, J=8.6 Hz), 7.66 (2H, d, J=8.6 Hz), 7.81 (1H, s), 7.92 (2H, d, J=7.8 Hz).

Melting point: 179–180° C. (crystallization solvent: ethyl acetate-diisopropyl ether)

Elemental analysis for C$_{30}$H$_{32}$N$_2$O$_2$ Calcd.: C, 79.61; H, 7.13; N, 6.19. Found: C, 79.35; H, 7.28; N, 6.24.

EXAMPLE 235

4-(4-Methoxyphenyl)-N-[5-methyl-6-(1-pyrrolidinylmethyl)-7,8-dihydro-2-naphthalenyl]-1-piperidinecarboxamide

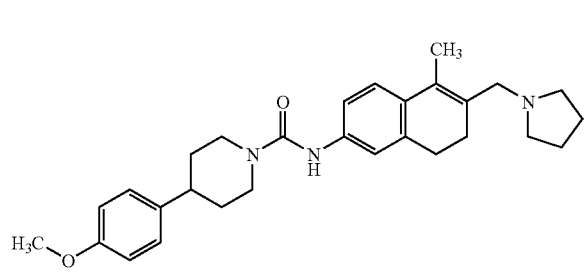

The titled compound was obtained as colorless powders by carrying out the same operation as in Example 99, using 5-methyl-6-(1-pyrrolidinylmethyl)-7,8-dihydro-2-naphthalenamine obtained in Reference Example 69.

$^1$H-NMR (CDCl$_3$) δ: 1.67 (2H, dd, J=13.4, 4.0 Hz), 1.78 (4H, m), 1.89 (2H, d, J=11.4 Hz), 2.07 (3H, s), 2.34 (2H, t, J=7.5 Hz), 2.52 (4H, m), 2.68–2.73 (3H, m), 2.98 (2H, t, J=7.5 Hz), 3.26 (2H, s), 3.80 (3H, s), 4.20 (2H, d, J=13.4 Hz), 6.36 (1H, s), 6.86 (2H, d, J=8.4 Hz), 7.12–7.20 (5H, m).

Melting point: 163–164° C. (crystallization solvent: ethyl acetate-diisopropyl ether)

Elemental analysis for C$_{28}$H$_{37}$N$_3$O$_2$ Calcd.: C, 75.13; H, 8.33; N, 9.39. Found: C, 74.96; H, 8.14; N, 9.10.

EXAMPLE 236

4-(4-Methoxyphenyl)-N-[6-(1-pyrrolidinylmethyl)-7,8-dihydro-2-naphthalenyl]-1-piperidinecarboxamide

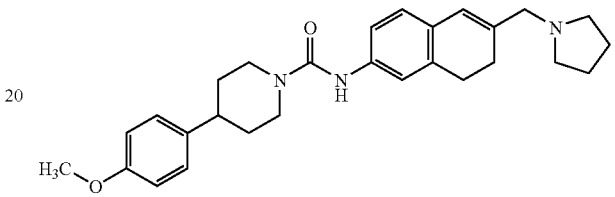

The titled compound was obtained as colorless powders by carrying out the same operation as in Example 1, using 6-(1-pyrrolidinylmethyl)-7,8-dihydro-2-naphthalenamine obtained in Reference Example 54.

$^1$H-NMR (CDCl$_3$) δ: 1.61–1.91 (8H, m) 2.31 (2H, t, J=8.1 Hz), 2.54 (4H, m), 2.73–2.81 (3H, m), 2.98 (2H, t, J=7.8 Hz), 3.16 (2H, s), 3.79 (3H, s), 4.20 (2H, d, J=13.1 Hz), 6.31 (1H, s), 6.36 (1H, s), 6.86 (2H, d, J=8.6 Hz), 7.06–7.20 (5H, m).

Melting point: 175–176° C. (crystallization solvent: ethyl acetate-diisopropyl ether)

EXAMPLE 237

4-(Benzyloxy)-N-[6-(1-pyrrolidinylmethyl)-7,8-dihydro-2-naphthalenyl]benzamide

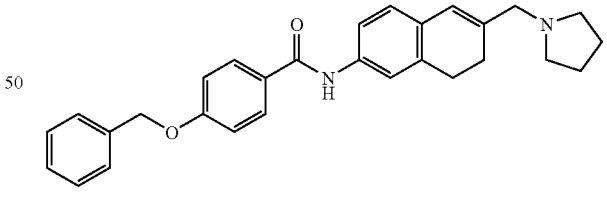

The titled compound was obtained as colorless powders by carrying out the same operation as in Example 1, using 6-(1-pyrrolidinylmethyl)-7,8-dihydro-2-naphthalenamine obtained in Reference Example 54.

Melting point: 174–1,75° C. (crystallization solvent: ethyl acetate-diisopropyl ether)

Elemental analysis for C$_{28}$H$_{30}$N$_2$O$_2$ Calcd.: C, 78.84; H, 7.09; N, 6.87. Found: C, 79.06; H, 6.99; N, 6.41.

EXAMPLE 238

4-(4-Methylphenyl)-N-[5-methyl-6-(1-pyrrolidinyl-methyl)-7,8-dihydro-2-naphthalenyl]-1-piperidinecarboxamide

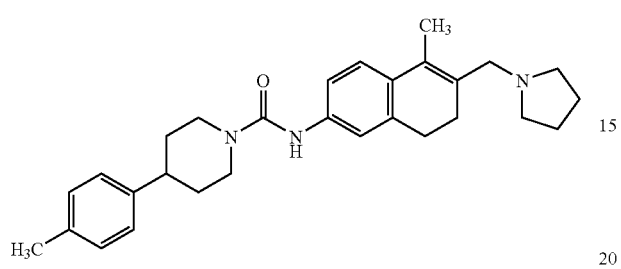

The titled compound was obtained by carrying out the same operation as in Example 99, using 5-methyl-6-(1-pyrrolidinylmethyl)-7,8-dihydro-2-naphthalenamine obtained in Reference Example 69.

$^1$H-NMR (CDCl$_3$) δ: 1.65–1.78 (6H, m), 1.90 (2H, d, J=12.9 Hz), 2.07 (3H, s), 2.33–2.37 (5H, m), 2.53 (4H, m), 2.68–2.74 (3H, m), 2.99 (2H, m), 3.27 (2H, s), 4.21 (2H, d, J=13.2 Hz), 6.37 (1H, s), 7.09–7.21 (7H, m).

Melting point: 159–160° C. (crystallization solvent: ethyl acetate-diisopropyl ether)

FAB(pos) 444.3 [M+H]+

EXAMPLE 239

4-(4-Fluorophenyl)-N-[6-(1-piperidinylmethyl)-7,8-dihydro-2-naphthalenyl]-1-piperidinecarboxamide

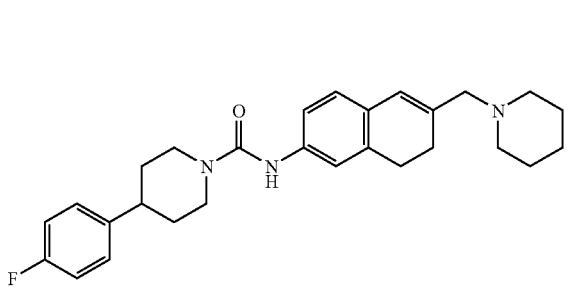

The titled compound was obtained by carrying out the same operation as in Example 99, using 6-(1-piperidinylmethyl)-7,8-dihydro-2-naphthalenamine dihydrochloride obtained in Reference Example 114.

$^1$H-NMR (CDCl$_3$) δ: 1.43 (2H, m), 1.56–1.75 (6H, m), 1.89 (2H, d, J=12.3 Hz), 2.27–2.36 (6H, m), 2.70 (1H, m), 2.78 (2H, t, J=7.5 Hz), 2.88–3.00 (4H, m), 4.20 (2H, d, J=13.2 Hz), 6.29 (1H, s), 6.38 (1H, s), 6.91–7.08 (4H, m), 7.14–7.20 (3H, m).

Melting point: 194–195° C. (crystallization solvent: ethyl acetate-diisopropyl ether)

EXAMPLE 240

4-(4-Methylphenyl)-N-[6-(1-piperidinylmethyl)-7,8-dihydro-2-naphthalenyl]-1-piperidinecarboxamide

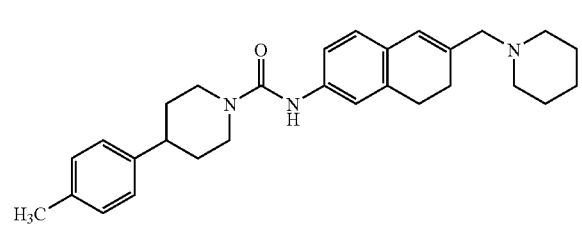

The titled compound was obtained by carrying out the same operation as in Example 99, using 6-(1-piperidinylmethyl)-7,8-dihydro-2-naphthalenamine dihydrochloride obtained in Reference Example 114.

$^1$H-NMR (CDCl$_3$) δ: 1.43 (2H, m), 1.56–1.74 (6H, m), 1.90 (2H, d, J=12.0 Hz), 2.27–2.36 (9H, m), 2.69 (1H, m), 2.79 (2H, t, J=8.1 Hz), 2.94–3.01 (4H, m), 4.19 (2H, d, J=13.2 Hz), 6.29 (1H, s), 6.35 (1H, s), 6.93 (2H, d, J=8.1 Hz), 7.05–7.26 (5H, m).

Melting point: 209–210° C. (crystallization solvent: ethyl acetate-diisopropyl ether)

EXAMPLE 241

4-(4-Methylphenyl)-N-[6-[(4-methyl-1-piperazinyl)methyl]-7,8-dihydro-2-naphthalenyl]-1-piperidinecarboxamide

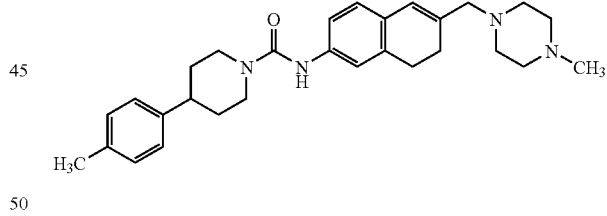

The titled compound was obtained by carrying out the same operation as in Example 99, using 6-[(4-methyl-1-piperazinyl)methyl]-7,8-dihydro-2-naphthalenamine obtained in Reference Example 106.

$^1$H NMR (CDCl$_3$) δ: 1.62–1.77 (2H, m), 1.90 (2H, d, J=12.0 Hz), 2.28 (2H, t, J=8.1 Hz), 2.29 (3H, s), 2.33 (3H, s), 2.46 (8H, bs), 2.64–2.73 (1H, m), 2.79 (2H, t, J=8.1 Hz), 2.96 (2H, d, J=10.5 Hz), 3.05 (2H, s), 4.19 (2H, d, J=13.5 Hz), 6.31 (1H, s), 6.34 (1H, s), 6.93 (1H, d, J=8.4 Hz), 7.04–7.16 (5H, m), 7.23 (1H, s).

Melting point: 214–216° C. (crystallization solvent: tetrahydrofuran-n-hexane)

Elemental analysis for C$_{29}$H$_{38}$N$_4$O Calcd.: C, 75.94; H, 8.35; N, 12.22. Found: C, 75.67; H, 8.47; N, 12.27.

EXAMPLE 242

4-(4-Methoxyphenyl)-N-[6-[(4-methyl-1-piperazinyl)methyl]-7,8-dihydro-2-naphthalenyl]-1-piperidinecarboxamide

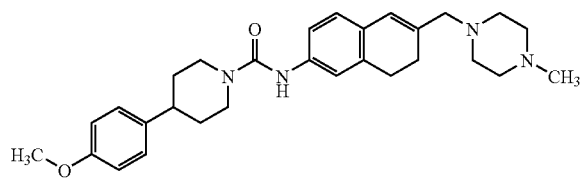

The titled compound was obtained by carrying out the same operation as in Example 99, using 6-[(4-methyl-1-piperazinyl)methyl]-7,8-dihydro-2-naphthalenamine obtained in Reference Example 106.

$^1$H NMR (CDCl$_3$) δ: 1.68–1.76 (2H, m), 1.89 (2H, d, J=11.1 Hz), 2.29 (2H, t, J=8.1 Hz), 2.29 (3H, s), 2.46 (8H, bs), 2.64–2.71 (1H, m), 2.79 (2H, t, J=8.1 Hz), 2.82–3.03 (2H, m), 3.05 (2H, s), 3.80 (3H, s), 4.19 (2H, d, J=12.6 Hz), 6.31 (1H, s), 6.34 (1H, s), 6.87 (2H, d, J=8.7 Hz), 6.93 (1H, d, J=8.4 Hz), 7.06 (1H, dd, J=8.1, 2.1 Hz), 7.14 (2H, d, J=8.7 Hz), 7.23 (1H, s).

Melting point: 198–200° C. (crystallization solvent: tetrahydrofuran-n-hexane)

Elemental analysis for C$_{29}$H$_{38}$N$_4$O$_2$ Calcd.: C, 73.38; H, 8.07; N, 11.80. Found: C, 73.04; H, 7.95; N, 11.67.

EXAMPLE 243

4-(4-Chlorophenyl)-N-[6-[(4-methyl-1-piperazinyl)methyl]-7,8-dihydro-2-naphthalenyl]-1-piperidinecarboxamide

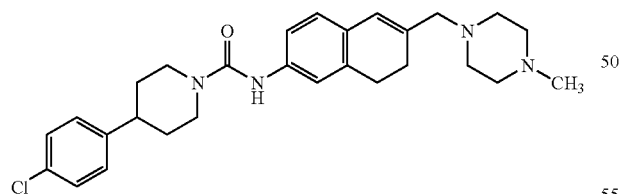

The titled compound was obtained by carrying out the same operation as in Example 99, using 6-[(4-methyl-1-piperazinyl)methyl]-7,8-dihydro-2-naphthalenamine obtained in Reference Example 106.

$^1$H NMR (CDCl$_3$) δ: 1.64–1.76 (2H, m), 1.90 (2H, d, J=11.1 Hz), 2.29 (2H, t, J=8.1 Hz), 2.29 (3H, s), 2.46 (8H, bs), 2.66–2.72 (1H, m), 2.79 (2H, t, J=8.1 Hz), 2.81–3.03 (2H, m), 3.05 (2H, s), 4.20 (2H, d, J=12.6 Hz), 6.31 (1H, s), 6.34 (1H, s), 6.93 (1H, d, J=7.8 Hz), 7.04–7.07 (1H, m), 7.14 (2H, d, J=8.4 Hz), 7.22 (1H, s), 7.28 (2H, d, J=8.4 Hz).

Melting point: 201–203° C. (crystallization solvent: tetrahydrofuran-n-hexane)

EXAMPLE 244

N-[2-[(Dimethylamino)methyl]-1H-inden-6-yl][1,1'-biphenyl]-4-carboxamide

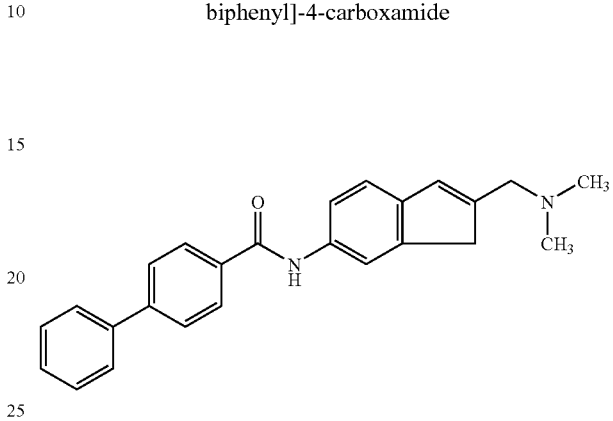

The titled compound was obtained by carrying out the same operation as in Example 1, using 2-[(dimethylamino)methyl]-1H-inden-6-amine obtained in Reference Example 116.

Elemental analysis for C$_{25}$H$_{24}$N$_2$O.0.5H$_2$O Calcd.: C, 79.55; H, 6.68; N, 7.42. Found: C, 79.38; H, 6.76; N, 7.34.

Melting point: 187–189° C. (crystallization solvent: ethyl acetate-diisopropyl ether)

FAB(pos) 369.2 [M+H]+

EXAMPLE 245

N-[2-[(Dimethylamino)methyl]-1H-inden-6-yl]-4'-fluoro[1,1'-biphenyl]-4-carboxamide

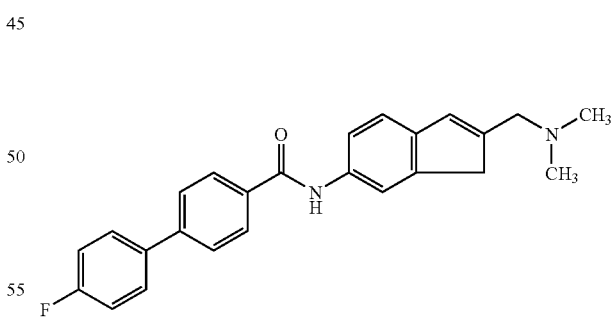

The titled compound was obtained by carrying out the same operation as in Example 1, using 2-[(dimethylamino)methyl]-1H-inden-6-amine obtained in Reference Example 116.

Melting point: 209–211° C. (crystallization solvent: ethyl acetate-diisopropyl ether)

FAB(pos) 387.2 [M+H]+

EXAMPLE 246

4'-Chloro-N-[2-[(dimethylamino)methyl]-1H-inden-6-yl][1,1'-biphenyl]-4-carboxamide

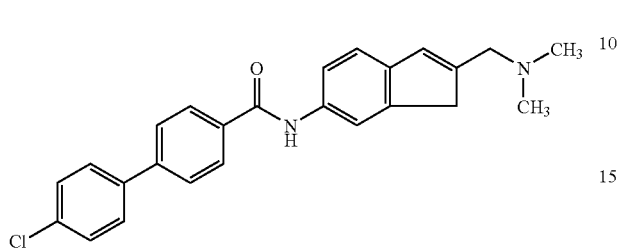

The titled compound was obtained by carrying out the same operation as in Example 1, using 2[(dimethylamino)methyl]-1H-inden-6-amine obtained in Reference Example 116.

Melting point: 218–220° C. (crystallization solvent: ethyl acetate-diisopropyl ether)

FAB(pos) 403.2 [M+H]+

EXAMPLE 247

4'-Chloro-N-[2-(1-pyrrolidinylmethyl)-3,4-dihydro-2H-1,4-benzoxazin-6-yl][1,1'-biphenyl]-4-carboxamide

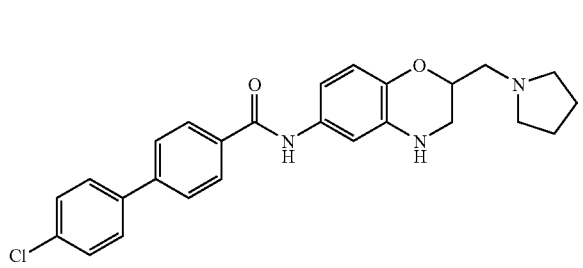

The titled compound was obtained by carrying out the same operation as in Example 1, using 6-amino-2-(1-pyrrolidinylmethyl)-3,4-dihydro-2H-1,4-benzoxazine obtained in Reference Example 117.

$^1$H-NMR (CDCl$_3$) δ: 1.70–1.90 (4H, m), 2.50–2.70 (4H, m), 2.73 (2H, d, J=6.0 Hz), 3.18–3.24 (1H, m), 3.45–3.49 (1H, m), 3.87 (1H, brs), 4.26–4.28 (1H, m), 6.61 (1H, dd, J=2.7, 8.4 Hz), 6.80 (1H, d, J=8.4 Hz), 7.26 (1H, d, J=2.7 Hz), 7.44 (2H, d, J=8.4 Hz), 7.55 (2H, d, J=8.4 Hz), 7.64 (2H, d, J=8.1 Hz), 7.71 (1H, s), 7.91 (2H, d, J=8.1 Hz).

Melting point: 221–222° C. (crystallization solvent: diisopropyl ether)

EXAMPLE 248

4'-Fluoro-N-[2-(1-pyrrolidinylmethyl)-3,4-dihydro-2H-1,4-benzoxazin-6-yl][1,1'-biphenyl]-4-carboxamide

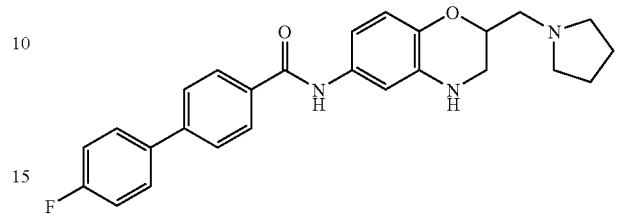

The titled compound was obtained by carrying out the same operation as in Reference Example 1, using 6-amino-2-(1-pyrrolidinylmethyl)-3,4-dihydro-2H-1,4-benzoxazine obtained in Reference Example 117.

$^1$H-NMR (CDCl$_3$) δ: 1.70–1.90 (4H, m), 2.50–2.70 (4H, m), 2.73 (2H, d, J=6.3 Hz), 3.18–3.24 (1H, m), 3.45–3.49 (1H, m), 3.88 (1H, brs), 4.24–4.30 (1H, m), 6.62 (1H, dd, J=2.7, 8.4 Hz), 6.80 (1H, d, J=8.4 Hz), 7.13–7.19 (2H, m), 7.26 (1H, d, J=2.7 Hz), 7.56–7.60 (2H, m), 7.63 (2H, d, J=8.4 Hz), 7.71 (1H, s), 7.90 (2H, d, J=8.4 Hz).

Melting point: 204–206° C. (crystallization solvent: diisopropyl ether)

EXAMPLE 249

6-(4-Methylphenyl)-N-[2-(1-pyrrolidinylmethyl)-3,4-dihydro-2H-1,4-benzoxazin-6-yl]nicotinamide

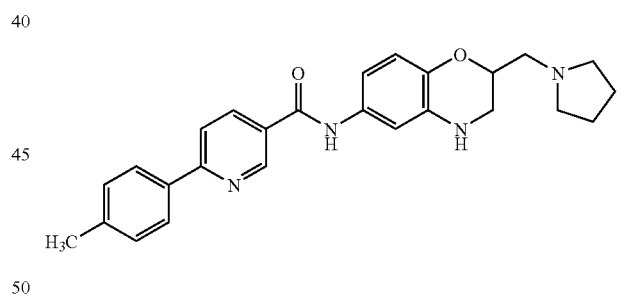

The titled compound was obtained by carrying out the same operation as in Reference Example 1, using 6-amino-2-(1-pyrrolidinylmethyl)-3,4-dihydro-2H-1,4-benzoxazine obtained in Reference Example 117.

$^1$H-NMR (CDCl$_3$) δ: 1.70–1.85 (4H, m), 2.43 (3H., s), 2.50–2.70 (4H, m), 2.74 (2H, d, J=6.3 Hz), 3.19–3.25 (1H, m), 3.45–3.49 (1H, m), 3.90 (1H, brs), 4.27–4.29 (1H, m), 6.63 (1H, dd, J=2.4, 8.7 Hz), 6.81 (1H, d, J=8.7 Hz), 7.26 (1H, d, J=2.7 Hz), 7.31 (2H, d, J=8.1 Hz), 7.67 (1H, s), 7.81 (1H, d, J=8.1 Hz), 7.93 (2H, d, J=7.8 Hz), 8.21 (1H, dd, J=2.4, 8.4 Hz), 9.09 (1H, d, J=2.4 Hz).

Melting point: 207–208° C. (crystallization solvent: diisopropyl ether)

EXAMPLE 250

4-(4-Fluorophenyl)-N-[2-(1-pyrrolidinylmethyl)-3,4-dihydro-2H-1,4-benzoxazin-6-yl]-1-piperidinecarboxamide

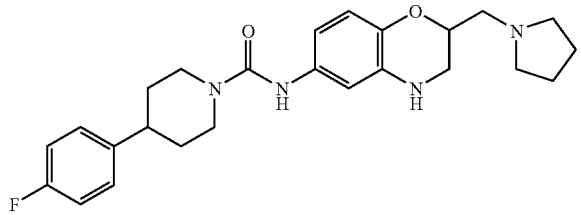

The titled compound was obtained by carrying out the same operation as in Reference Example 1, using 6-amino-2-(1-pyrrolidinylmethyl)-3,4-dihydro-2H-1,4-benzoxazine obtained in Reference Example 117.

$^1$H-NMR(CDCl$_3$) δ: 1.60–1.90 (8H, m), 2.50–2.70 (5H, m), 2.71 (2H, d, J=6.3 Hz), 2.91–3.00 (2H, m), 3.15–3.21 (1H, brs), 3.42–3.45 (1H, m), 3.77 (1H, brs), 4.15–4.25 (3H, m), 6.20 (1H, s), 6.38 (1H, dd, J=2.1, 8.4 Hz), 6.73 (1H, d, J=8.4 Hz), 6.91 (1H, d, J=2.1 Hz), 6.97–7.03 (2H, m), 7.14–7.19 (2H, m).

Melting point: 192–195° C. (crystallization solvent: diisopropyl ether)

EXAMPLE 251

4'-Chloro-N-[4-(methylsulfonyl)-2-(1-pyrrolidinylmethyl)-3,4-dihydro-2H-1,4-benzoxazin-6-yl][1,1'-biphenyl]-4-carboxamide

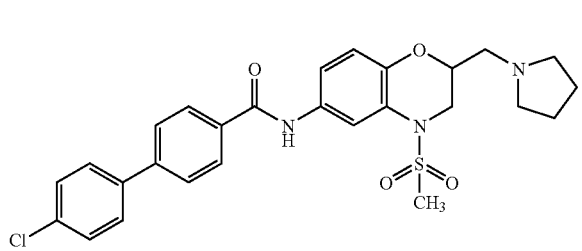

The titled compound was obtained by carrying out the same operation as in Reference Example 1, using 6-amino-4-(methylsulfonyl)-2-(1-pyrrolidinylmethyl)-3,4-dihydro-2H-1,4-benzoxazine obtained in Reference Example 118.

$^1$H-NMR (CDCl$_3$) δ: 1.75–1.85 (4H, m), 2.55–2.70 (4H, m), 2.78 (2H, d, J=6.0 Hz), 3.04 (3H, s), 3.27–3.34 (1H, m), 4.24–4.31 (1H, m), 4.31–4.35 (1H, m), 6.98 (1H, d, J=8.7 Hz), 7.45 (2H, d, J=9.0 Hz), 7.50–7.60 (1H, m), 7.53 (2H, d, J=9.0 Hz), 7.67 (2H, d, J=8.4 Hz), 7.84 (1H, s), 7.84 (1H, brs), 7.94 (2H, d, J=8.4 Hz).

Melting point: 203–204° C. (crystallization solvent: diisopropyl ether)

EXAMPLE 252

N-[6-[(4-Methyl-1-piperazinyl)methyl]-7,8-dihydro-2-naphthalenyl][1,1'-biphenyl]-4-carboxamide

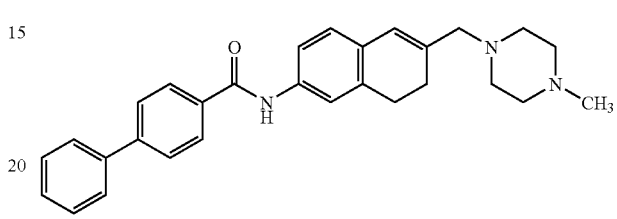

The titled compound was obtained by carrying out the same operation as in Reference Example 1, using 6-[(4-methyl-1-piperazinyl)methyl]-7,8-dihydro-2-naphthalenamine obtained in Reference Example 106.

$^1$H NMR (CDCl$_3$): 2.31 (3H, s), 2.33 (2H, t; J=8.1 Hz) 2.49 (8H, bs), 2.84 (2H, t, J=8.1 Hz), 3.07 (2H, s), 6.36 (1H, s), 7.02 (1H, d, J=8.1 Hz), 7.35–7.52 (5H, m), 7.63 (2H, d, J=8.1 Hz), 7.71 (2H, d, J=8.1 Hz), 7.80 (1H, s), 7.94, (2H, d, J=8.1 Hz).

Melting point: 196–198° C. (crystallization solvent: ethyl acetate)

EXAMPLE 253

4'-Methyl-N-[5-methyl-6-[(4-methyl-1-piperazinyl)methyl]-7,8-dihydro-2-naphthalenyl][1,1'-biphenyl]-4-carboxamide

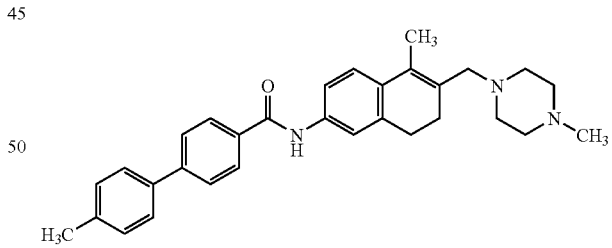

The titled compound was obtained by carrying out the same operation as in Reference Example 1, using 5-methyl-6-[(4-methyl-1-piperazinyl)methyl]-7,8-dihydro-2-naphthalenamine obtained in Reference Example 115.

$^1$H NMR (CDCl$_3$) δ: 2.08 (3H, s), 2.29 (3H, s), 2.34 (2H, t, J=7.8 Hz), 2.42 (3H, s), 2.45 (8H, bs), 2.75 (2H, t, J=7.8 Hz), 3.16 (2H, s), 7.26–7.30 (3H, m), 7.44 (1H, d, J=8.4 Hz), 7.53–7.55 (3H, m), 7.70 (2H, d, J=8.4 Hz), 8.00 (1H, s), 7.93 (2H, d, J=8.4 Hz).

Melting point: 212–214° C. (crystallization solvent: ethyl acetate)

EXAMPLE 254

4'-Methoxy-N-[5-methyl-6-[(4-methyl-1-piperazinyl)methyl]-7,8-dihydro-2-naphthalenyl][1,1'-biphenyl]-4-carboxamide

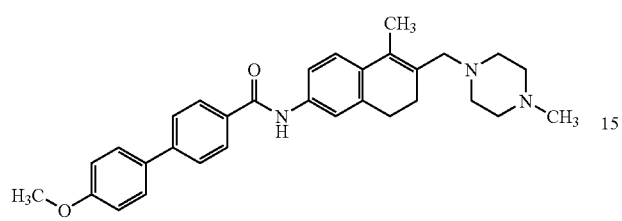

The titled compound was obtained by carrying out the same operation as in Reference Example 1, using 5-methyl-6-[(4-methyl-1-piperazinyl)methyl]-7,8-dihydro-2-naphthalenamine obtained in Reference Example 115.

$^1$H NMR (CDCl$_3$) δ: 2.08 (3H, s), 2.29 (3H, s), 2.34 (2H, t, J=7.8 Hz), 2.45 (8H, bs), 2.75 (2H, t, J=7.8 Hz), 3.16 (2H, s), 3.87 (3H, s), 7.01 (2H, d, J=8.1 Hz), 7.27 (1H, d, J=8.4 Hz), 7.44 (1H, d, J=8.4 Hz), 7.51 (1H, s), 7.58 (2H, d, J=8.4 Hz), 7.67 (2H, d, J=8.4 Hz), 7.81 (1H, s), 7.92 (2H, d, J=8.4 Hz).

Melting point: 215–217° C. (crystallization solvent: ethyl acetate)

EXAMPLE 255

4'-Fluoro-N-[5-methyl-6-[(4-methyl-1-piperazinyl)methyl]-7,8-dihydro-2-naphthalenyl][1,1'-biphenyl]-4-carboxamide

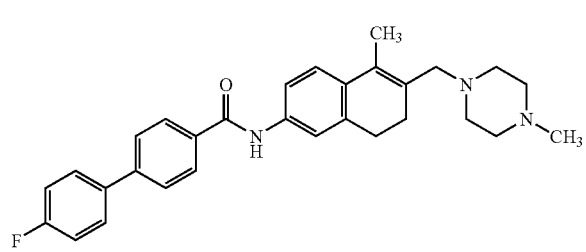

The titled compound was obtained by carrying out the same operation as in Reference Example 1, using 5-methyl-6-[(4-methyl-1-piperazinyl)methyl]-7,8-dihydro-2-naphthalenamine obtained in Reference Example 115.

$^1$H NMR (CDCl$_3$) δ: 2.08 (3H, s), 2.29 (3H, s), 2.34 (2H, t, J=7.8 Hz), 2.46 (8H, bs), 2.75 (2H, t, J=7.8 Hz), 3.16 (2H, s), 7.17 (2H, d, J=8.4 Hz). 7.28 (1H, d, J=8.4 Hz), 7.44 (1H, d, J=8.4 Hz), 7.51 (1H, s), 7.57–7.62 (2H, m), 7.66 (2H, d, J=8.4 Hz), 7.82 (1H, s), 7.94 (2H, d, J=8.4 Hz).

Melting point: 233–235° C. (crystallization solvent: ethyl acetate)

EXAMPLE 256

4'-Chloro-N-[5-methyl-6-[(4-methyl-1-piperazinyl)methyl]-7,8-dihydro-2-naphthalenyl][1,1'-biphenyl]-4-carboxamide

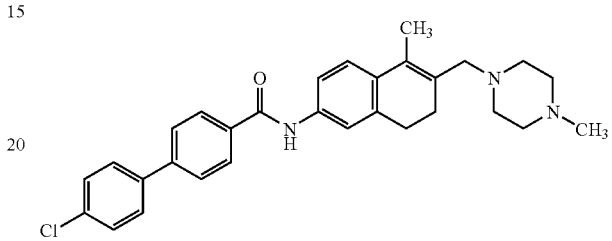

The titled compound was obtained by carrying out the same operation as in Reference Example 1, using 5-methyl-6-[(4-methyl-1-piperazinyl)methyl]-7,8-dihydro-2-naphthalenamine obtained in Reference Example 115.

$^1$H NMR (CDCl$_3$) δ: 2.08 (3H, s), 2.29 (3H, s), 2.34 (2H, t, J=7.8 Hz), 2.46 (8H, bs), 2.75 (2H, t, J=7.8 Hz), 3.16 (2H, s), 7.28 (1H, d, J=8.4 Hz), 7.43–7.47 (3H, m), 7.51 (1H, s), 7.56 (−2H, d, J=8.4 Hz), 7.67 (2H, d, J=8.4 Hz), 7.80 (1H, s), 7.94 (2H, d, J=8.4 Hz).

Melting point: 216–218° C. (crystallization solvent: ethyl acetate)

EXAMPLE 257

6-(4-Chlorophenyl)-N-[5-methyl-6-[(4-methyl-1-piperazinyl)methyl]-7,8-dihydro-2-naphthalenyl]nicotinamide

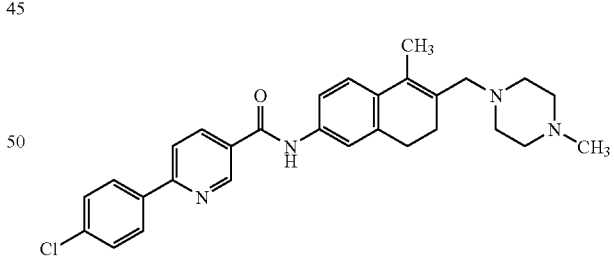

The titled compound was obtained by carrying out the same operation as in Reference Example 1, using 5-methyl-6-[(4-methyl-1-piperazinyl)methyl]-7,8-dihydro-2-naphthalenamine obtained in Reference Example 115.

$^1$H NMR (CDCl$_3$) δ: 2.09 (3H, s), 2.29 (3H, s), 2.35 (2H, t, J=8.1 Hz), 2.46 (8H, bs), 2.75 (2H, t, J=8.1 Hz), 3.16 (2H, s), 7.28 (1H, d, J=8.4 Hz), 7.43–7.50 (4H, m), 7.83 (2H, d, J=8.4 Hz), 8.01 (2H, d, J=8.4 Hz), 8.27 (1H, d, J=8.4 Hz), 9.13 (1H, s).

Melting point: 219–221° C. (crystallization solvent: ethyl acetate)

EXAMPLE 258

5-(4-Chlorophenyl)-N-[5-methyl-6-[(4-methyl-1-piperazinyl)methyl]-7,8-dihydro-2-naphthalenyl]-2-pyridinecarboxamide

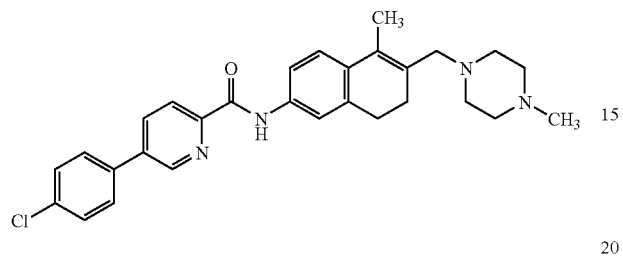

The titled compound was obtained by carrying out the same operation as in Reference Example 1, using 5-methyl-6-[(4-methyl-1-piperazinyl)methyl]-7,8-dihydro-2-naphthalenamine obtained in Reference Example 115.

$^1$H NMR (CDCl$_3$) δ: 2.09 (3H, s), 2.29 (3H, s), 2.35 (2H, t, 3=8.1 Hz), 2.45 (8H, bs), 2.77 (2H, t, J=8.1 Hz), 3.16 (2H, s), 7.30 (1H, d, J=8.1 Hz), 7.49–7.63 (6H, m), 8.05 (1H, dd, J=2.4 Hz, 8.4 Hz), 8.36 (1H, d, J=8.1 Hz), 8.79 (1H, d, J=1.2 Hz), 9.97 (1H, s).

Melting point: 177–179° C. (crystallization solvent: ethyl acetate)

EXAMPLE 259

N-[5-Methyl-6-[(4-methyl-1-piperazinyl)methyl]-7,8-dihydro-2-naphthalenyl]-4-(4-methylphenyl)-1-piperidinecarboxamide

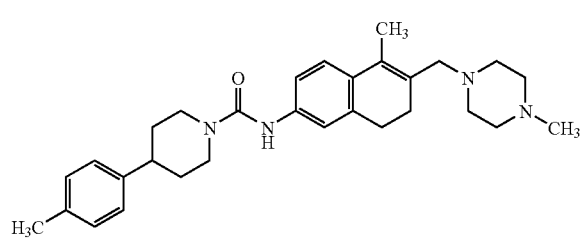

The titled compound was obtained by carrying out the same operation as in Reference Example 99, using 5-methyl-6-[(4-methyl-1-piperazinyl)methyl]-7,8-dihydro-2-naphthalenamine obtained in Reference Example 115.

$^1$H NMR (CDCl$_3$) δ: 1.60–1.78 (4H, m), 2.05 (3H, s), 2.28 (3H, s), 2.29 (2H, t, J=8.1 Hz), 2.33 (3H, s), 2.46 (8H, bs), 2.65–2.72 (3H, m), 2.93–3.03 (2H, m), 3.13 (2H, s), 4.18–4.23 (2H, m), 6.40 (1H, s), 7.09–7.24 (7H, m).

Melting point: 176–178° C. (crystallization solvent: ethyl acetate n-hexane)

EXAMPLE 260

4-(4-Methoxyphenyl)-N-[5-methyl-6-[(4-methyl-1-piperazinyl)methyl]-7,8-dihydro-2-naphthalenyl]-1-piperidinecarboxamide

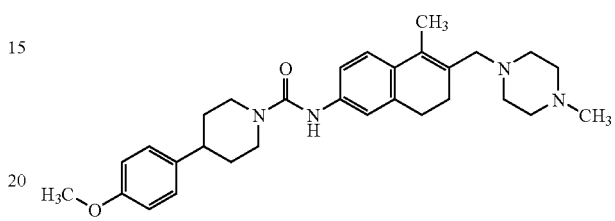

The titled compound was obtained by carrying out the same operation as in Reference Example 99, using 5-methyl-6-[(4-methyl-1-piperazinyl)methyl]-7,8-dihydro-2-naphthalenamine obtained in Reference Example 115.

$^1$H NMR (CDCl$_3$) δ: 1.68–1.92 (4H, m), 2.05 (3H, s), 2.28 (3H, s), 2.29 (2H, t, J=8.1 Hz), 2.45 (8H, bs), 2.67–2.72 (3H, m), 2.95–3.02 (0.2H, m), 3.14 (2H, s), 3.80 (3H, s), 4.18–4.22 (2H, m), 6.36 (1H, s), 6.87 (2H, d, J=8.4 Hz), 7.12–7.21 (5H, m).

Melting point: 175–177° C. (crystallization solvent: ethyl acetate)

EXAMPLE 261

4-(4-Chlorophenyl)-N-[5-methyl-6-[(4-methyl-1-piperazinyl)methyl]-7,8-dihydro-2-naphthalenyl]-1-piperidinecarboxamide

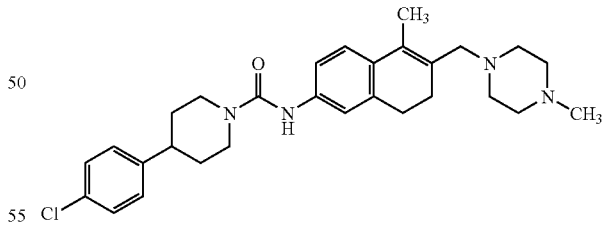

The titled compound was obtained by carrying out the same operation as in Reference Example 99, using 5-methyl-6-[(4-methyl-1-piperazinyl)methyl]-7,8-dihydro-2-naphthalenamine obtained in Reference Example 115.

$^1$H NMR (CDCl$_3$) δ: 1.67–1.92 (4H, m), 2.05 (3H, s), 2.28 (3H, s), 2.29 (2H, t, J=8.1 Hz). 2.45 (8H, bs), 2.67–2.72 (3H, m), 2.95–3.02 (2H, m), 3.14 (2H, s), 4.18–4.23 (2H, m), 6.36 (1H, s), 7.13–7.30 (7H, m).

EXAMPLE 262

4-[(4-Chlorophenyl)(phenyl)methyl]-N-[4-methyl-3-(1-pyrrolidinylmethyl)-2H-chromen-7-yl]-1-piperazinecarboxamide

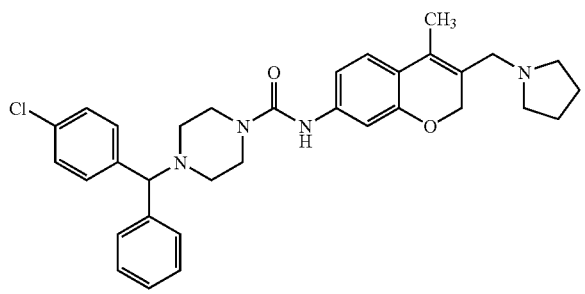

The titled compound was obtained by carrying out the same operation as in Reference Example 99, using 4-methyl-3-(1-pyrrolidinylmethyl)-2H-chromen-7-amine obtained in Reference Example 107.

$^1$H NMR (CDCl$_3$) δ: 1.76 (4H, s), 2.01 (3H, s), 2.42 (4H, t, J=5.1 Hz), 2.49 (4H, s), 3.22 (2H, s), 3.48 (4H, t, J=5.1 Hz), 4.24 (1H, s), 4.68 (2H, s), 6.23 (1H, s), 6.77 (1H, s), 6.96 (1H, d, J=8.7 Hz), 7.09 (1H, d, J=8.7 Hz), 7.19–7.61 (9H, m).

Melting point: 104–106° C. (crystallization solvent: ethyl acetate-n-hexane)

EXAMPLE 263

N-(2,2-Diphenylethyl)-N'-[4-methyl-3-(1-pyrrolidinylmethyl)-2H-chromen-7-yl]urea

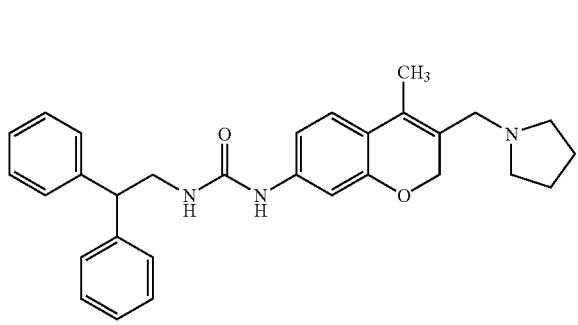

The titled compound was obtained by carrying out the same operation as in Reference Example 99, using 4-methyl-3-(1-pyrrolidinylmethyl)-2H-chromen-7-amine obtained in Reference Example 107.

$^1$H NMR (CDCl$_3$) δ: 1.76 (4H, s), 1.99 (3H, s), 2.49 (4H, s), 3.22 (2H, s), 3.83 (2H, t, J=7.8 Hz), 4.18 (1H, t, J=7.8 Hz), 4.66 (2H, s), 4.96 (1H, s), 6.48 (1H, s), 6.57 (1H, s), 6.69 (1H, d, J=8.1 Hz), 6.98 (1H, d, J=8.1 Hz), 7.20–7.30 (10H, m).

Melting point: 166–168° C. (crystallization solvent: ethyl acetate-n-hexane)

EXAMPLE 264

N-[4-Methyl-3-(1-pyrrolidinylmethyl)-2H-chromen-7-yl]-3,4-dihydro-2(1H)-isoquinolinecarboxamide

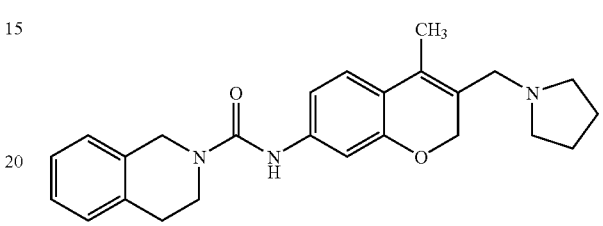

The titled compound was obtained by carrying out the same operation as in Reference Example 99, using 4-methyl-3-(1-pyrrolidinylmethyl)-2H-chromen-7-amine obtained in Reference Example 107.

$^1$H NMR (CDCl$_3$) δ: 1.76 (4H, s), 2.02. (3H, s), 2.49 (4H, s), 2.92 (2H, t, J=6.0 Hz), 3.23 (2H, s), 3.71 (2H, t, J=6.0 Hz), 4.65 (2H, s), 4.68 (2H, s), 6.43 (1H, s), 6.86 (1H, d, J=1.8 Hz), 7.02–7.22 (6H, m).

Melting point: 135–137° C. (crystallization solvent: ethyl acetate-n-hexane)

EXAMPLE 265

N-[4-Methyl-3-(1-pyrrolidinylmethyl)-2H-chromen-7-yl]-4-(1-piperidinyl)-1-piperidinecarboxamide

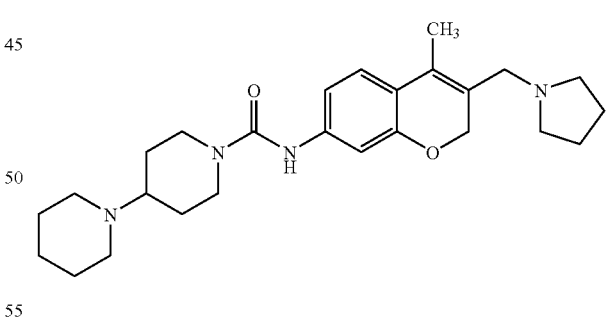

The titled compound was obtained by carrying out the same operation as in Reference Example 99, using 4-methyl-3-(1-pyrrolidinylmethyl)-2H-chromen-7-amine obtained in Reference Example 107.

$^1$H NMR (CDCl$_3$) δ: 1.27–1.89 (14H, m), 2.02 (3H, s), 2.49–2.51 (9H, m), 2.83–2.90 (2H, m), 3.23 (2H, s), 4.08–4.12 (2H, m), 4.68 (2H, s), 6.31 (1H, s), 6.80 (1H, d, J=2.4 Hz), 6.98 (1H, dd, J=2.4 Hz, 8.4 Hz), 7.09 (1H, d, J=8.4 Hz).

Melting point: 98–100° C. (crystallization solvent: ethyl acetate-n-hexane)

EXAMPLE 266

2-(4-Methyl-6-oxo-2-phenyl-1,6-dihydro-5-pyrimidinyl)-N-[4-methyl-3-(1-pyrrolidinylmethyl)-2H-chromen-7-yl]acetamide

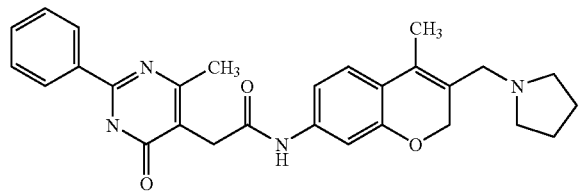

The titled compound was obtained by carrying out the same operation as in Reference Example 1, using 4-methyl-3-(1-pyrrolidinylmethyl)-2H-chromen-7-amine obtained in Reference Example 107.

$^1$H NMR (CDCl$_3$) δ: 1.76 (4H, s), 1.98 (3H, s), 2.49 (4H, s), 2.61 (3H, s), 3.22 (2H, s), 3.65 (2H, s), 4.65 (2H, s), 6.86–7.00 (4H, m), 7.54 (3H, s), 8.01 (2H, s), 8.87 (1H, s).

Melting point 255–257° C. (crystallization solvent: ethyl acetate-n-hexane)

EXAMPLE 267

Benzyl 2-[[4-methyl-3-(1-pyrrolidinylmethyl)-2H-chromen-7-yl]amino]-2-oxoethylcarbamate

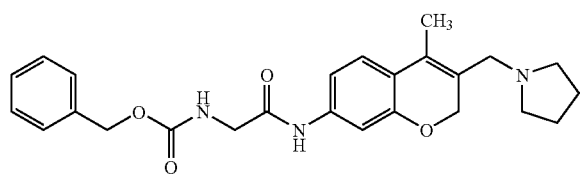

The titled compound was obtained by carrying out the same operation as in Reference Example 1, using 4-methyl-3-(1-pyrrolidinylmethyl)-2H-chromen-7-amine obtained in Reference Example 107.

$^1$H NMR (CDCl$_3$) δ: 1.78 (4H, s), 2.03 (3H, s), 2.53 (4H, s), 3.26 (2H, s), 3.99 (2H, d, J=4.8 Hz), 4.71 (2H, s), 5.17 (2H, s), 5.50 (1H, bs), 7.00–7.14 (4H, m), 7.36 (5H, s), 7.80 (1H, bs).

Melting point: 143–145° C. (crystallization solvent ethyl acetate-n-hexane)

| Preparation Example 1 | |
|---|---|
| (1) Compound obtained in Reference Example 25 | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Carboxymethylcellulose calcium | 20 mg |
| Total | 120 mg |

In accordance with a conventional manner, the above (1) to (6) are admixed and tableted using a tableting machine to give tablets.

| Preparation Example 2 | |
|---|---|
| (1) Compound obtained in Example 1 | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Carboxymethylcellulose calcium | 20 mg |
| Total | 120 mg |

In accordance with a conventional manner, the above (1) to (6) are admixed and tableted using a tableting machine to give tablets.

REFERENCE EXAMPLE 1-1

Amplification of Rat SLC-1 Receptor cDNA by PCR Method Using Rat-Brain-Originated cDNA Reverse transcription reaction was done using random primer, with rat-brain-originated poly (A)$^+$RNA (Clone Tech Co.) used as a template. Reagent from the TaKaRa RNA PCR ver. 2 kit was used for the reverse transcription reaction. Next, using this reverse transcription product as a template, amplification was done by a PCR method using synthetic DNA primers with sequence numbers 1 and 2. Synthetic DNA primer was constructed to amplify genes in the domain where genes are translated by receptor protein. At that time, individual restriction enzyme recognition sequences were also added on the 5' side and 3' side of the gene, to add a nucleotide sequence on the 5' side of gene which recognized restriction enzyme Sal I, and to add a nucleotide sequence on the 3' side of the gene which recognized the restriction enzyme Spe I. The reactant was constituted of 5 μl of cDNA template, 0.4 μM of synthetic DNA primer, 0.25 mM of dNTPs, 0.5 μl of Pfu (StrataGene Co.) DNA polymerase, and buffers attached to enzymes, with total reaction quantity set at 50 μl.

A thermal cycler (Parkin Elmer Co.) was used to produce cycles for amplification. After heating at 94° C. for 60 seconds, the cycle consisting of 94° C. for 60 seconds, 60° C. for 30 seconds, and 72° C. for 150 seconds, was repeated 35 times, and finally reaction was conducted at 72° C. for 10 minutes. After 0.8% agarose gel electrophoresis, the amplified products were confirmed by ethidium bromide dying.

REFERENCE EXAMPLE 1-2

Subcloning of PCR Products into Plasmid Vector, and Confirmation of an Amplified cDNA Sequence by Decoding of a Nucleotide Sequence in an Inserted cDNA Portion The reaction product after PCR conducted in Reference Example 1-1 was separated using 0.8% low-melting point agarose gel. After the band section was cut out using a razor, DNA was recovered by conducting fragmentation, phenol extraction, phenol-chloroform extraction and ethanol precipitation. The recovered DNA was subcloned on plasmid vector PCR-Script Amp SK($^+$) in accordance with prescription of the PCR-Script™ Amp SK(+) cloning kit (Stratagene Co.). After this was introduced into *Escherichia coli*XL-1 Blue (Stratagene Co.) by transformation, the clones with fragments of inserted cDNA were selected in LB agar culture medium containing ampicillin and X-gal. Only clones showing white color were separated using a sterilized toothpick, and transformant E. coli XL-1 Blue/rat SLC-1 was obtained.

Each clone was cultured overnight in LB culture medium containing ampicillin, and plasmid DNA was prepared using QIA prep8 mini prep (Qiagen). A portion of the prepared DNA was digested with Sal I and Spe I, and the size of the inserted receptor cDNA fragment was confirmed. Reactions to determine nucleotide sequences were carried out using a DyeDeoxy Terminator Cycle Sequence Kit (Parkin Elmer Co.), and decoded using a fluorescent light automatic sequencer. The sequences of the 3 clones obtained were analyzed, and it was confirmed that all of them match the reported gene sequence (Sequence number: 4) in which the Sal I recognition sequence is added on the 5' side and the Spe I recognition sequence is added on the 3' side of the cDNA sequence (Lakaye, B., et al., Biochim. Biophys. Acta, Vol. 1401, pp. 216–220 (1998), accession No. AF08650) coding rat SLC-1 protein (Sequence number: 3).

REFERENCE EXAMPLE 1-3

Preparation of CHO Cells for Rat SLC-1 Expression

The full-length amino acid sequence of rat brain originated SLC-1, which was confirmed in Reference Example 1-2, was coded, and plasmid was prepared using a plasmid Midi Kit (Qiagen) from the E. coli transformed by the plasmid, to which the gene with Sal I recognition sequence added to the 5' side and Spe I recognition sequence added to the 3' side, had been introduced. Then, the insert section was cut out by digesting with Sal I and Spe I. The insert DNA was cut out with a razor from the agarose gel after electrophoresis.

Next, fragmentation, phenol extraction, phenol-chloroform extraction, and ethanol precipitation, were conducted and the DNA was recovered. This insert DNA was added to vector plasmid pAKKO-111H (the same vector plasmid as pAKKO1.11H described in Hinuma, S., et al., Biochim. Biophys. Acta, Vol. 1219, pp. 251–259 (1994)) for animal cell expression which was digested with Sal I and Spe I, and ligation was conducted using T4 ligase (TaKaRa Shuzo), to construct pAKKO-SLC-1 plasmid for protein expression.

After E. coli DH5 transformed by pAKKO-SLC-1 was cultured, pAKKO-SLC-1 plasmid DNA was prepared using a Plasmid Midi Kit (Qiagen). This was introduced into CHO dhfr⁻ cells in accordance with the attached protocol, using a CellPhect Transfection Kit (Amersham Pharmacia Biotech Co.). A coprecipitating suspension of 10 μg of DNA and calcium phosphate was prepared, and this suspension was added to 10 cm Petri dishes in which $5\times10^5$ or $1\times10^6$ of CHO dhfr⁻ cells had been seeded 24 hours previously. After these cells were cultured for 1 day in MEMα culture medium containing 10% fetal bovine serum, subculture was conducted, and cultivation was conducted in selective culture medium, MEMα culture medium containing no nucleic acid but containing 10% dialyzed fetal bovine serum. 56 clones of colonies of the transformed CHO cells expressing SLC-1, proliferated in the selective culture medium, were selected.

REFERENCE EXAMPLE 1-4

Selection of CHO/SLC-1 cell Strain Expressing a Large Quantity of Full-Length Rat SLC-1 Receptor Protein mRNA The quantity of-expressed full-length rat SLC-1 receptor protein mRNA of 56 clones of the CHO/SLC-1 strains established in Reference Example 1-3, was measured using a Cytostar T Plate (Amersham Pharmacia Biotech Co.) as shown below according to the attached protocol. Each well of the Cytostar T Plate was seeded with each clone of the CHO/SLC-1 strain by $2.5\times10^4$, and cultured for 24 hours, then the cells were fixed using 10% formalin. After 0.25% Triton X-100 was added to each well to increase cell permeability, $^{35}$S-labeled riboprobes with sequence number: 5 were added and hybridized. 20 mg/ml of RNaseA was added to each well to digest free riboprobes. After the plate was thoroughly washed, the radioactivity of the hybridized riboprobes was determined using a Topcounter. Strains with high radioactivity showed large amounts of mRNA expression. In particular, mainly used was Clone number 44 among 3 clones which showed large amounts of mRNA expression.

REFERENCE EXAMPLE 1-5

Isolation of Plasmid Containing Human SLC-1 cDNA

After nicks were inserted into the DNA of Human fetal brain originated cDNA library (SUPERSCRIPT™ cDNA Library; GIBCOBRL Co.) according to the manual of the Genetrapper cDNA positive selection system (GIBCOBRL Co.), using pharge F1 endonuclease, single stranded human fetal brain originated cDNA library was prepared by digesting the above-mentioned library with Escherichia coli exonuclease III.

Biotin-14-dCTP was added to the 3' end of synthetic oligonucleotide (equivalent to 1434–1451 of accession No. U71092), sequence number: 6 which was prepared according to the report by Kolakowski Jr., et al. (Kolakowski Jr., et al. (1996) FEBS Lett. Vol. 398, pp. 253–258) using Terminal Deoxynucleotidyl Transferase, and biotinated oligonucleotide was prepared. The above manual was followed regarding composition of a reaction mixture and reaction time.

After 4 μg of single stranded human fetal brain originated cDNA library was kept at 95° C. for 1 minute, the library was rapidly cooled on ice. 20 ng of biotinated oligonucleotide was added, which was hybridized using the attached hybridization buffer at 37° C. for 1 hour. Streptoavidin beads were added to the mixture, then single stranded human fetal brain originated cDNA hybridized by biotinated oligonucleotide, was isolated using a MAGNA-SEP Magnetic Particle Separator (GIBCOBRL Co.). The complementary strand was synthesized according to the manual, using as primer 50 ng of synthetic oligonucleotide (equivalent to 1011–1028 of accession No. U71092) of sequence number: 7, prepared based on the report by Kolakowski Jr., et al (Kolakowski Jr., et al. (1996) FEBS Lett. Vol. 398, pp. 253–258), to give the double stranded plasmid.

REFERENCE EXAMPLE 1-6

Determination of nucleotide sequence of plasmid containing isolated human SLC-1 cDNA After the plasmid obtained in Reference Example 1-5 was introduced into ELECTROMAX™DH10B™ Cells by the electroporation method, clones with cDNA inserted fragments were selected in LB agar culture medium containing ampicillin and X-gal. Using a sterilized toothpick, only the clones showing white color were separated to give transformant E. coli DH10B/hSLC-1. Individual clones were cultured overnight in LB culture medium containing ampicillin, and the plasmid DNA was refined using QIA prep8 mini prep (Qiagen). The reactions to determine nucleotide sequence were conducted using a DyeDeoxy Terminator Cycle Sequence Kit (Parkin Elmer Co.), and the nucleotide sequence was decoded using a fluorescent light automatic sequencer.

As the results, obtained was the sequence shown in Sequence number: 8. The amino acid sequence (Sequence number: 9) coded by the nucleotide sequence obtained here, differs from the human SLC-1 amino acid sequence predicted as the sequence analogized from rat SLC-1 based on human chromosome DNA sequence (accession number: Z86090) containing human SLC-1 sequence, in the report by Lakaye, et al. (Lakaye, B., et al. (1998) Biochim. Biophys. Acta. Vol. 1401, pp. 216–220). This shows the presence of ATG, the initiation codon, on mRNA, in the 69 and 64 amino acids upstream from the estimated sequence. *Escherichia coli* DH10B/phSLC1L8, the transformant produced by the plasmid containing DNA coding this sequence was deposited at IFO and NIBH.

REFERENCE EXAMPLE 1-7

Amplification of Human SLC-1cDNA by PCR Method Using Human Fetal Brain Originated cDNA Amplification by the PCR method was conducted using as the template plasmid containing human SLC-1 DNA sequence cloned by the gene trap method, and using synthetic DNA primers of sequence number: 10 and sequence number: 11, and synthetic DNA primers of sequence number: 12 and sequence number: 13, respectively. The former amplified DNA and the latter amplified DNA were named as "human SLC-1(S)" and "human SLC-1(L)", respectively. The synthetic DNA primer was constructed so that the genes in the domain translated to the receptor protein were amplified. At that time, a recognition sequence for each restriction enzyme was added on the 5' side and 3' side, so that the nucleotide sequence recognized by restriction enzyme Sal I would be added on the 5' side of the gene, and the nucleotide sequence recognized by restriction enzyme Spe I would be added on the 3' side. The composition of the reaction mixture for human SLC-1(S) amplification was: 5 µl of plasmid template containing human SLC-1 DNA sequence, 0.4 µM of respective synthetic DNA primers, 0.2 mM of dNTPs and 0.5 µl of Pfu DNA polymerase and buffers attached to the enzyme, with total quantity for reaction set at 50 µl. A thermal cycler (Parkin Elmer Co.) was used for the cycles for amplification. After heating at 94° C. for 60 seconds, the cycle consisting of 94° C. for 60 seconds, 57° C. for 60 seconds, and 72° C. for 150 seconds, was repeated 25 times, and finally the temperature of the reactant was maintained at 72° C. for 10 minutes. The composition of the reaction mixture for human SLC-1(L) amplification was 5 µl of plasmid template containing human SLC-1 DNA sequence, 0.4 µM of respective synthetic DNA primers, 0.2 mM of dNTPs, 0.5 µl of Pfu DNA polymerase and buffers attached to the enzymes, with total quantity for reaction set at 50 µl. A thermal cycler (Parkin Elmer Co.) was used for the cycles for amplification. After heating at 94° C. for 60 seconds, the cycle consisting of 94° C. for 60 seconds, 60° C. for 60 seconds, and 72° C. for 3 minutes, was repeated 25 times, and finally the temperature of the reactant was maintained at 72° C. for 10 minutes. After 0.8% agarose gel electrophoresis, confirmation of amplified products was conducted by ethidium bromide dying.

REFERENCE EXAMPLE 1-8

Subcloning of PCR product into plasmid vector and confirmation of amplified cDNA sequence by decoding of nucleotide sequence of inserted cDNA section The reaction product after PCR in Reference Example 1-7 was separated using 0.8% low-melting point agarose gel, and the band section was cut out using a razor. After that, fragmentation, phenol extraction, phenol-chloroform extraction, and ethanol precipitation were conducted, and the DNA was recovered. The recovered DNA was subcloned into pCR-Script Amp SK($^+$) plasmid vector, as prescribed by the PCR-Script™ Amp SK($^+$) cloning kit (Stratagene Co.). After this was introduced into *Escherichia coli* DH5a competent cells (TOYOBO) and transformed, the clones with cDNA inserted fragments were selected in LB agar culture medium containing ampicillin and X-gal. Using a sterilized toothpick, only clones showing white color were separated to give E. coli DH5a/hSLC-1(S), which is a transformant of human SLC-1 (S), and E. coli DH5α/hSLC-1(L), which is a transformant of human SLC-1 (L). Each clone was cultured overnight in LB culture medium containing ampicillin, and plasmid DNA was prepared using QIA prep8 mini prep (Qiagen). Some of the prepared DNA was digested with Sal I and Spe I restriction enzymes, and the size of the receptor cDNA fragments inserted was confirmed. The reactions to determine nucleotide sequence were conducted using a DyeDeoxy Terminator Cycle Sequence Kit (Parkin Elmer Co.) and the nucleotide sequence was decoded using a fluorescent light automatic sequencer. The sequence of the obtained clones respectively matched the DNA sequence (sequence number: 14) which should be amplified by synthetic DNA primers of sequence number: 10 and sequence number: 11 using human SLC-1 gene as a template, and the DNA sequence (sequence number: 15) which should be amplified by synthetic DNA primers of sequence number: 12 and sequence number: 13 using human SLC-1 gene as a template.

REFERENCE EXAMPLE 1–9

Preparation of CHO CELLS for Expression of Human SLC-1(S), and CHO Cells for Expression of Human SLC-1(L)

Plasmid was prepared from the *E. coli* clones transformed by the plasmid wherein inserted were human SLC-1(S) and human SLC-1(L) whose sequences were confirmed in Reference Example 1-8, using a Plasmid Midi Kit (Qiagen), and the insert section was cut out using Sal I and Spe I restriction enzymes. After electrophoresis was conducted, the insert DNA was cut out from agarose gel using a razor. Next, fragmentation, phenol extraction, phenol-chloroform extraction, and ethanol precipitation were conducted, and the insert DNA was recovered.

This insert DNA was added to pAKKO-111H vector plasmid for animal cell expression, digested with Sal I and Spe I (the same vector plasmid as the pAKKO1.11H described in Hinuma, S., et al., Biochim. Biophys. Acta, Vol. 1219, pp. 251–259 (1994)), and ligation was conducted by adding T4 ligase (TaKaRa Shuzo), to construct pAKKO-hSLC-1(S) and pAKKO-hSLC-1(L) plasmids for protein expression.

After *E. coli* DH5α (TOYOBO) transformed by pAKKO-hSLC-1(S) and pAKKO-hSLC-1(L) was cultured, pAKKO-hSLC-1(S) and pAKKO-hSLC-1(L) plasmid DNAs were prepared using a Plasmid Midi Kit (Qiagen). These were introduced into CHO dhfr⁻ cells in accordance with the attached protocol, using a CellPhect Transfection Kit (Amersham Pharmacia Biotech Co.). A coprecipitative suspension of 10 µg of DNA with calcium phosphate was made, which was added to 10 cm Petri dishes seeded 24 hours in advance with $5\times10^5$ or $1\times10^6$ CHO dhfr⁻ cells. After the above was cultured for 1 day in MEMα culture medium containing 10% fetal bovine serum, subculture was conducted, and then cultivation was conducted in MEMα culture medium containing no nucleic acid but containing 10% dialyzed fetal bovine serum, which is a selective culture medium. 56 clones of colonies of transformed cells which are human SLC-1(S) gene introduced CHO cells, and 61 clones of colonies of transformed cells which are human SLC-1(L) gene introduced CHO cells, both of which proliferated in the selective culture medium, were selected.

REFERENCE EXAMPLE 1-10

Selection of Cell Colonies into which Genes with Large Quantities of Human SLC-1(S) and Human SLC-1 (L) mRNA expression have been introduced The quantities of expressed mRNA of 56 clones of CHO/hSLC-1(S) colonies and 61 clones of CHO/hSLC-1(L) colonies, both of which were established in Reference Example 1-9, were measured in accordance with the attached protocol using a Cytostar T Plate (Amersham Pharmacia Biotech Co.) as shown below.

After each well of the Cytostar T Plate was seeded with each clone of CHO/hSLC-1(S) colonies and CHO/hSLC-1 (L) colonies by $2.5\times10^4$, and cultured for 24 hours, the cells were fixed using 10% formalin.

After 0.25% Triton X-100 was added to each well to increase cell permeability, $^{35}$S-labeled riboprobe of sequence number: 16 was added and hybridization was conducted.

20 mg/ml of RNaseA was added to each well to digest free riboprobe. After the plate was washed well, the radioactivity of the hybridized riboprobe was determined. Colonies showing high radioactivity expressed large quantities of mRNA. Of the 7 clones which expressed large quantities of mRNA, mainly used was Clone number 57.

EXPERIMENTAL EXAMPLE 1

Determination of Antagonist Activity using GTPgS Binding Assay of Test Compound

Membrane fraction was prepared by the following method, using the human SLC-1 expressing CHO cell clone 57 obtained in Reference Example 1-10, and the rat SLC-1 expressing CHO cell clone 44 obtained in Reference Example 1-4.

The human and rat SLC-1 expressing CHO cells ($1\times10^8$) were scraped in buffer saline phosphate (pH 7.4) to which 5 mM EDTA (ethylenediaminetetraacetic acid) had been added, and centrifuged. 10 ml of homogenized buffer (10 mM NaHCO$_3$, 5 mM EDTA, pH 7.5) was added to the cell pellets, and they were homogenized using a Polytron homogenizer. The supernatant obtained by centrifugation at 400×g for 15 minutes was further centrifuged at 100,000×g for 1 hour, to obtain the membrane fraction precipitate. This precipitate was suspended in 2 ml of assay buffer [50 mM Tris-HCl(pH 7.5), 1 mM EDTA, 0.1% BSA (bovine serum albumin), 10 mM MgCl$_2$, 100 mM NaCl, 1 µM GDP (guanosine 5'-diphosphate), 0.25 mM PMSF (phenylmethylsulfonyl fluoride), 1 mg/ml pepstatin, 20 mg/ml leupeptin, 10 mg/ml phosphoramidon], which was centrifuged at 100,000×g for 1 hour. The membrane fraction recovered as precipitate was suspended again in 2 ml of assay buffer, and after the suspension was divided, individual portions were preserved at −80° C. and thawed before every use.

Determination of antagonist activity of the test compound was conducted as shown below. After 171 µl of SLC-1 expressing CHO cell membrane-fractions diluted with assay buffer was poured into each well of a 96-well polypropylene plate, 2 µl of $3\times10^{-10}$M MCH diluted with DMSO solution, 2 µl of test compound solution diluted to various concentrations, and 25 µl of [$^{35}$S]-Guanosine 5'-(γ-thio) triphosphate (produced by Daiichi Kagaku Yakuhin) were added respectively. (Final concentration of cell membrane: 20 µg/ml, final concentration of [$^{35}$S]-Guanosine 5'-(γ-thio) triphosphate: 0.33 nM).

After this reaction mixture was allowed to react for 1 hour under stirring, it was filtered under vacuum using a glass filter (GF-C), then the filter was washed 3 times with 300 µl of washing solution (50 mM Tris-HCl buffer solution pH 7.5). 50 ml of liquid scintillator was added to the glass filter, and residual radioactivity was determined using a liquid scintillation counter.

The IC$_{50}$ value of the compound was calculated from the binding inhibition rate (%), based on the definition that the binding inhibition rate (%)=(radioactivity when compound and MCH were added−radioactivity when DMSO solution was added)/(radioactivity when MCH was added−radioactivity when DMSO solution was added)×100.

The results were shown below.

| Compound Number | Inhibition Activity (IC$_{50}$ value: nM) |
| --- | --- |
| Reference Example 25 | 90 |
| Example 1 | 40 |

INDUSTRIAL APPLICABILITY

Compounds (I), (I') and salts thereof possess excellent MCH receptor antagonistic activities, and are useful as an agent for preventing or treating obesity, etc.

The invention claimed is:

1. A compound of the formula:

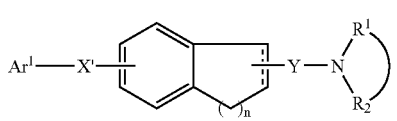

(I'-1)

wherein $Ar^1$ is a cyclic group which may have 1 to 5 substituents selected from the group consisting of:
(1) oxo,
(2) halogen atoms,
(3) $C_{1-3}$ alkylenedioxy,
(4) nitro,
(5) cyano,
(6) optionally halogenated $C_{1-6}$ alkyl,
(7) hydroxy-$C_{1-6}$ alkyl,
(8) carboxy-$C_{1-6}$ alkyl,
(9) $C_{1-6}$ alkoxy-carbonyl-$C_{1-6}$ alkyl,
(10) $C_{6-14}$ aryloxy-$C_{6-14}$ alkyl
(11) $C_{1-6}$ alkyl-$C_{6-14}$ aryl-$C_{2-6}$ alkenyl,
(12) optionally halogenated $C_{3-6}$ cycloalkyl,
(13) optionally halogenated $C_{1-6}$ alkoxy,
(14) optionally halogenated $C_{1-6}$ alkylthio,
(15) $C_{7-19}$ aralkyl,
(16) hydroxy,
(17) $C_{6-14}$ aryloxy,
(18) $C_{7-19}$ aralkyloxy,
(19) $C_{6-14}$ aryl-carbamoyl,
(20) amino,
(21) amino-$C_{1-6}$ alkyl,
(22) mono-$C_{1-6}$ alkylamino,
(23) di-$C_{1-6}$ alkylamino,
(24) mono-$C_{1-6}$ alkylamino-$C_{1-6}$ alkyl,
(25) di-$C_{1-6}$ alkylamino-$C_{1-6}$ alkyl,
(26) 5 to 7 membered saturated cyclic amino,
(27) 5 to 7 membered non-aromatic heterocyclic groups,
(28) acyl,
(29) acylamino,
(30) acyloxy, and
(31) aromatic hetero ring $C_{1-6}$ alkoxy,
wherein the above (15), (17), (18) and (19) may have 1 to 5 substituents selected from the group consisting of halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkyl-carbonyl, $C_{1-6}$ alkoxy-carbonyl, mono-$C_{1-6}$alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$, alkoxy-carboxamide, $C_1$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, the above (26) and (27) may have 1 to 5 substituents selected from the group consisting of
1) oxo,
2) optionally halogenated $C_{1-6}$, alkyl,
3) optionally halogenated $C_{1-6}$, alkyl-carbonyl,
4) optionally halogenated $C_{1-6}$ alkylsulfonyl,
5) $C_{6-14}$ aryl,
6) $C_{7-19}$ aralkyl,
7) $C_{6-14}$ aryl-carbonyl,
8) 5 to 10 membered aromatic heterocyclic group which may have 1 to 5 substituents selected from the group consisting of
8a) halogen atom,
8b) $C_{1-3}$ alkylenedioxy,
8c) nitro,
8d) cyano,
8e) optionally halogenated $C_{1-6}$ alkyl
8f) $C_{6-14}$ aryloxy-$C_{1-6}$ alkyl,
8g) $C_{1-6}$ alkyl-$C_{6-14}$ aryl-$C_{2-6}$, alkenyl,
8h) optionally halogenated $C_{3-6}$ cycloalkyl,
8i) optionally halogenated $C_{1-6}$ alkoxy,
8j) optionally halogenated $C_{1-6}$ alkylthio,
8k) $C_{7-19}$ aralkyl,
8l) hydroxy,
8m) $C_{6-14}$ aryloxy, 8n) C_{7-19} aralkyloxy,
8o) amino,
8p) amino-C_{1-6} alkyl,
8q) mono-C_{1-6} alkylamino,
8r) di-C_{1-6} alkylamino,
8s) mono-C_{1-6} alkylamino-C_{1-6} alkyl,
8t) di-C_{1-6} alkylamino-C_{1-6} alkyl,
8u) 5 to 7 membered saturated cyclic amino,
8v) acyl,
8w) acylamino and
8x) acyloxy, and
9) 5 to 8 membered monocyclic non-aromatic heterocyclic group,
   wherein the above 5), 6), 7), 8k), 8m) and 8n) may have 1 to 5 substituents selected from the group consisting of halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy,
   provided that when the cyclic group is a non-aromatic cyclic hydrocarbon group or a non-aromatic heterocyclic group, the cyclic group may have 1 to 3 substituents selected from the group consisting of
the "$C_{6-14}$ aryl which may have substituents" as defined in the above 5), and the "5 to 10 membered aromatic heterocyclic groups which may have substituents" as defined in the above 8);
==== is a single bond or double bond;
n is an integer of 2 to 4;
X' is —CONR$^{8c}$—, where R$^{8c}$ is hydrogen atom or $C_{1-6}$ alkyl;
Y is a $C_{1-3}$ alkylene;
R$^1$ and R$^2$ are independently hydrogen atom or a $C_{1-6}$ alkyl group;
R$^1$ and R$^2$, together with the adjacent nitrogen atom, may form a 3 to 8 membered nitrogen-containing hetero ring which contains at least one nitrogen atom in addition to carbon atoms, and which may further contain 1 to 3 heteroatoms selected from nitrogen, sulfur and oxygen atom, wherein the nitrogen-containing hetero rings may have 1 to 5 substituents as defined for the above (26) "5 to 7 membered saturated cyclic amino" in the definition of Ar$^1$;
a ring of the formula:

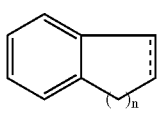

may have further 1 to 3 substituents selected from the group consisting of formyl, optionally halogenated $C_{1-6}$ alkyl-carbonyl, optionally halogenated $C_{1-6}$ alkylsulfonyl, optionally halogenated $C_{1-6}$ alkyl, cyano and hydroxy;
provided that N-[2-(N,N-dimethylamino)methyl-6-tetralinyl]-4-biphenylylcarboxamide is excluded; or a salt thereof.

2. A compound according to claim 1, which is of the formula:

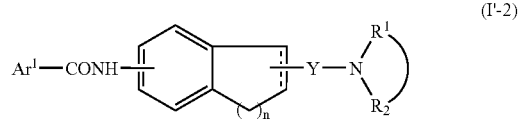
(I'-2)

3. A compound of the formula:

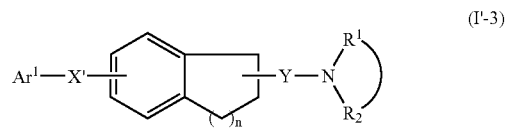
(I'-3)

wherein Ar$^1$ is a cyclic group which may have 1 to 5 substituents selected from the group consisting of
(1) oxo,
(2) halogen atoms,
(3) $C_{1-3}$ alkylenedioxy,
(4) nitro,
(5) cyano,
(6) optionally halogenated $C_{1-6}$alkyl,
(7) hydroxy-$C_{1-6}$alkyl,
(8) carboxy-$C_{1-6}$alkyl,
(9) $C_{1-6}$alkoxy-carbonyl-$C_{1-6}$alkyl,
(10) $C_{6-14}$ aryloxy-$C_{1-6}$alkyl,
(11) $C_{1-6}$ alkyl-$C_{6-14}$ aryl-$C_{2-6}$ alkenyl,
(12) optionally halogenated $C_{3-6}$cycloalkyl,
(13) optionally halogenated $C_{1-6}$ alkoxy,
(14) optionally halogenated $C_{1-6}$ alkylthio,
(15) $C_{7-19}$ aralkyl,
(16) hydroxy,
(17) $C_{6-14}$ aryloxy,
(18) $C_{7-19}$ aralkyloxy,
(19) $C_{6-14}$ aryl-carbamoyl,
(20) amino,
(21) amino-$C_{1-6}$alkyl,
(22) mono-$C_{1-6}$alkylamino,
(23) di-$C_{1-6}$ alkylamino,
(24) mono-$C_{1-6}$alkylamino-$C_{1-6}$alkyl,
(25) di-$C_{1-6}$alkylamino-$C_{1-6}$ alkyl,
(26) 5 to 7 membered saturated cyclic amino,
(27) 5 to 7 membered non-aromatic heterocyclic groups,
(28) acyl,
(29) acylamino,
(30) acyloxy, and
(31) aromatic hetero ring-$C_{1-6}$alkoxy,
    wherein the above (15), (17), (18) and (19) may have 1 to 5 substituents selected from the group consisting of halogen atom, $C_{1-3}$ alkylenedioxy, nitro, cyano, optionally halogenated $C_{1-6}$alkyl, optionally halogenated $C_{3-6}$ cycloalkyl, optionally halogenated $C_{1-6}$alkoxy, optionally halogenated $C_{1-6}$alkylthio, hydroxy, amino, mono-$C_{1-6}$ alkylamino, di-$C_{1-6}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkylcarbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$alkyl-carboxamide, $C_{1-6}$ alkoxy-carboxamide, $C_{1-6}$alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy, the above (26) and (27) may have 1 to 5 substituents selected from the group consisting of
1) oxo,
2) optionally halogenated $C_{1-6}$ alkyl,
3) optionally halogenated $C_{1-6}$ alkyl-carbonyl,
4) optionally halogenated $C_{1-6}$ alkylsulfonyl,
5) $C_{6-14}$ aryl,
6) $C_{7-19}$ aralkyl,
7) $C_{6-14}$ aryl-carbonyl,
8) 5 to 10 membered aromatic heterocyclic group which may have 1 to 5 substituents selected from the group consisting of
   8a) halogen atom,
   8b) $C_{1-3}$ alkylenedioxy,
   8c) nitro,
   8d) cyano,
   8e) optionally halogenated $C_{1-6}$ alkyl,
   8f) $C_{6-14}$ aryloxy-$C_{1-6}$ alkyl,
   8g) $C_{1-6}$ alkyl-$C_{6-14}$ aryl-$C_{2-6}$ alkenyl,
   8h) optionally halogenated $C_{3-6}$ cycloalkyl,
   8i) optionally halogenated $C_{1-6}$ alkoxy,
   8j) optionally halogenated $C_{1-6}$ alkylthio,
   8k) $C_{7-19}$ aralkyl,
   8l) hydroxy,
   8m) $C_{6-14}$ aryloxy,
   8n) $C_{7-19}$ aralkyloxy,
   8o) amino,
   8p) amino-$C_{1-6}$ alkyl,
   8q) mono-$C_{1-6}$ alkylamino,
   8r) di-$C_{1-6}$ alkylamino,
   8s) mono-$C_{1-6}$alkylamino-$C_{1-6}$ alkyl,
   8t) di-$C_{1-6}$ alkylamino-$C_{1-6}$ alkyl,
   8u) 5 to 7 membered saturated cyclic amino,
   8v) acyl,
   8w) acylamino and
   8x) acyloxy, and
9) 5 to 8 membered monocyclic non-aromatic heterocyclic group,
   wherein the above 5), 6), 7), 8k), 8m) and 8n) may have 1 to 5 substituents selected from the group consisting of halogen atom, $C_{1-3}$ alkylenedioxy, nitro, cyano, optionally halogenated C-6 alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkyl carbonyl, $C_{1-6}$ alkoxy-carbonyl, mono-$C_{1-6}$alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide $C_{1-6}$alkoxy-carboxamide, $C_{1-6}$alkylsulfonylamino, $C_{1-6}$alkyl-carbonyloxy, $C_{1-6}$ alkoxy-carbonyloxy, mono-$C_{1-6}$ alkyl-carbamoyloxy and di-$C_{1-6}$alkyl-carbamoyloxy, provided that when the cyclic group is a non-aromatic cyclic hydrocarbon group or a non-aromatic heterocyclic group, the cyclic group may have 1 to 3 substituents selected from the group consisting of the "$C_{6-14}$ aryl which may have substituents" as defined in the above 5), and the "5 to 10 membered aromatic heterocyclic groups which may have substituents" as defined in the above 8);

n is an integer of 2 to 4;

X' is —$CONR^{8c}$— where $R^{8c}$ is hydrogen atom or $C_{1-6}$ alkyl;

Y is a $C_{1-3}$ alkylene;

$R^1$ and $R^2$ are independently hydrogen atom or a $C_{1-6}$ alkyl group;

$R^1$ and $R^2$, together with the adjacent nitrogen atom, may form a 3 to 8 membered nitrogen-containing hetero ring which contains at least one nitrogen atom in addition to carbon atoms, and which may further contain 1 to 3 hetero atoms selected from nitrogen, sulfur and oxygen atom, wherein the nitrogen-containing hetero ring may have 1 to 5 substituents as defined for the above (26) "5 to 7 membered saturated cyclic amino" in the definition of $Ar^1$;

a ring of the formula:

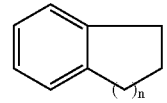

may have further 1 to 3 substituents selected from the group consisting of formyl, optionally halogenated $C_{1-6}$alkyl-carbonyl, optionally halogenated $C_{1-6}$ alkylsulfonyl, optionally halogenated $C_{1-6}$alkyl, cyano and hydroxy;

provided that N-[2-(N,N-dimethylamino)methyl-6-tetralinyl]-4-biphenylylcarboxamide is excluded; or a salt thereof.

4. A compound according to claim 3, which is of the formula:

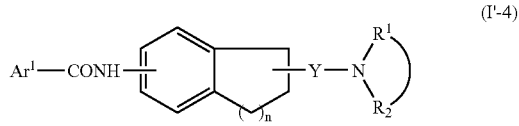

(I'-4)

5. A compound of the formula:

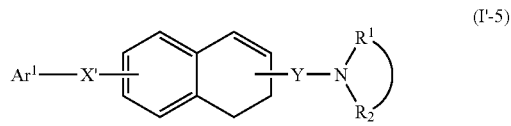

(I'-5)

wherein $Ar^1$ is a cyclic group which may have 1 to 5 substituents selected from the group consisting of
(1) oxo,
(2) halogen atoms,
(3) $C_{1-3}$ alkylenedioxy,
(4) nitro,
(5) cyano,
(6) optionally halogenated $C_{1-6}$alkyl,
(7) hydroxy-$C_{1-6}$ alkyl, (8) carboxy-$C_{1-6}$ alkyl,
(9) $C_{1-6}$alkoxy-carbonyl-$C_{1-6}$ alkyl,
(10) $C_{6-14}$ aryloxy-$C_{1-6}$ alkyl,
(11) $C_{1-6}$alkyl-$C_{6-14}$ aryl-$C_{2-6}$ alkenyl,
(12) optionally halogenated $C_{3-6}$ cycloalkyl.
(13) optionally halogenated $C_{1-6}$ alkoxy,
(14) optionally halogenated $C_{1-6}$ alkylthio,
(15) $C_{7-19}$ aralkyl,
(16) hydroxy,
(17) $C_{6-14}$ aryloxy,
(18) $C_{7-19}$ aralkyloxy,
(19) $C_{6-14}$ aryl-carbamoyl,
(20) amino,
(21) amino-$C_{1-6}$ alkyl,
(22) mono-$C_{1-6}$ alkylamino,
(23) di-$C_{1-6}$ alkylamino,
(24) mono-$C_{1-6}$ alkylamino-$C_{1-6}$ alkyl,
(25) di-$C_{1-6}$ alkylamino-$C_{1-6}$ alkyl,
(26) 5 to 7 membered saturated cyclic amino,
(27) 5 to 7 membered non-aromatic heterocyclic groups,
(28) acyl,
(29) acylamino,
(30) acyloxy, and
(31) aromatic hetero ring-$C_{1-6}$ alkoxy,
  wherein the above (15), (17), (18) and (19) may have 1 to 5 substituents selected from the group consisting of halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-C 6 alkylamino, di-$C_{1-6}$ alkylamino, amino-$C_{1-6}$ alkyl, mono-$C_{1-6}$ alkylamino-$C_{1-6}$ alkyl, di-$C_{1-6}$ alkylamino-$C_{1-6}$alkyl, formyl, carboxy, carbamoyl, thiocarbamoyl, optionally halogenated $C_{1-6}$alkylcarbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$ alkyl-carbamoyloxy,
  the above (26) and (27) may have 1 to 5 substituents selected from the group consisting of
1) oxo,
2) optionally halogenated $C_{1-6}$ alkyl,
3) optionally halogenated $C_{1-6}$ alkyl-carbonyl,
4) optionally halogenated $C_{1-6}$ alkylsulfonyl,
5) $C_{6-14}$ alkyl,
6) $C_{7-19}$ aralkyl,
7) $C_{6-14}$ aryl-carbonyl,
8) 5 to 10 membered aromatic heterocyclic group which may have 1 to 5 substituents selected from the group consisting of
  8a) halogen atom,
  8b) $C_{1-3}$ alkylenedioxy,
  8c) nitro,
  8d) cyano,
  8e) optionally halogenated $C_{1-4}$ alkyl,
  8f) $C_{6-14}$ aryloxy-$C_{16}$ alkyl,
  8g) $C_{1-6}$ alkyl-$C_{6-14}$ aryl-$C_{2-6}$ alkenyl,
  8h) optionally halogenated $C_{3-6}$ cycloalkyl,
  8i) optionally halogenated $C_{1-6}$ alkoxy,
  8j) optionally halogenated $C_{1-6}$ alkylthio
  8k) $C_{7-19}$ aralkyl,
  8l) hydroxy,
  8m) $C_{6-14}$ aryloxy,
  8n) $C_{7-19}$ aralkyloxy,
  8o) amino,
  8p) amino-$C_{1-6}$ alkyl,
  8q) mono-$C_{1-6}$ alkylamino,
  8r) di-$C_{1-6}$ alkylamino,
  8s) mono-$C_{1-6}$ alkylamino-$C_{1-6}$ alkyl,
  8t) di-$C_{1-6}$ alkylamino-$C_{1-6}$ alkyl,
  8u) 5 to 7 membered saturated cyclic amino,
  8v) acyl,
  8w) acylamino and
  8x) acyloxy, and
9) 5 to 8 membered monocyclic non-aromatic heterocyclic group,
  wherein the above 5), 6), 7), 8k), 8m) and 8n) may have 1 to 5 substituents selected from the group consisting of halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-C 6 alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkylcarbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy and di-$C_{1-6}$alkyl-carbamoyloxy,
  provided that when the cyclic group is a non-aromatic cyclic hydrocarbon group or a non-aromatic heterocyclic group, the cyclic group may have 1 to 3 substituents selected from the group consisting of the "$C_{6-14}$ aryl which may have substituents" as defined in the above 5), and the "5 to 10 membered aromatic heterocyclic groups which may have substituents" as defined in the above 8);

X' is —$CONR^{8c}$— where $R^{8c}$ is hydrogen atom or $C_{1-6}$ alkyl;

Y is a $C_{1-3}$ alkylene;

$R^1$ and $R^2$ are independently hydrogen atom or a $C_{1-6}$ alkyl group;

$R^1$ and $R^2$, together with the adjacent nitrogen atom, may form a 3 to 8 membered nitrogen-containing hetero ring which contain at least one nitrogen atom in addition to carbon atoms, and which may further contain 1 to 3 hetero atoms selected from nitrogen, sulfur and oxygen atom, wherein the nitrogen-containing hetero ring may have 1 to 5 substituents as defined for the above (26) "5 to 7 membered saturated cyclic amino" in the definition of $Ar^1$;

a ring of the formula:

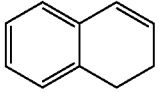

may have further 1 to 3 substituents selected from the group consisting of formyl, optionally halogenated $C_{1-6}$alkyl-carbonyl, optionally halogenated $C_{1-6}$alkylsulfonyl, optionally halogenated $C_{1-6}$ alkyl, cyano and hydroxy; or a salt thereof.

6. A compound according to claim 5, which is of the formula:

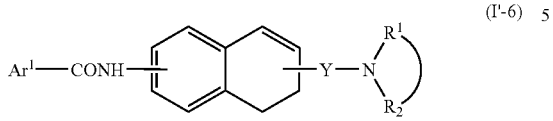

(I'-6)

7. A compound according to claim 1, which is N-[2-(N,N-dimethylamino)methyl-6-tetralinyl]-(4'-methoxybiphenyl-4-yl)carboxamide;
- 4'-fluoro-N-[6-[(N,N-dimethylamino)methyl]-7,8-dihydro-2-naphthalenyl][1,1'-biphenyl]-4-carboxamide;
- 4'-fluoro-N-[6-(1-piperidinylmethyl)-7,8-dihydro-2-naphthalenyl][1,1'-biphenyl]4-carboxamide;
- 4'-fluoro-N-[6-[(N,N-dimethylamino)methyl]-5,6,7,8-tetrahydro-2-naphthalenyl][1,1'-biphenyl]-4-carboxamide;
- (+)-4'-fluoro-N-[6-[(N,N-dimethylamino)methyl]-5,6,7,8-tetrahydro-2-naphthalenyl][1,1'-biphenyl]-4-carboxamide;
- (−)-4'-fluoro-N-[6-[(N,N-dimethylamino)methyl]-5,6,7,8-tetrahydro-2-naphthalenyl][1,1'-biphenyl]-4-carboxamide;
- 4'-fluoro-N-[6-(1-pyrrolidinylmethyl)-7,8-dihydro-2-naphthalenyl][1,1'-biphenyl]-4-carboxamide;
- 4'-chloro-N-[6-[(dimethylamino)methyl]-5-methyl-7,8-dihydro-2-naphthalenyl][1,1'-biphenyl]-4-carboxamide;
- 6-(4-methoxyphenyl)-N-[5-methyl-6-(1-pyrrolidinylmethyl)-7,8-dihydro-2-naphthalenyl]nicotinamide;
- 4-(4-chlorophenyl)-N-[6-(1-pyrrolidinylmethyl)-7,8-dihydro-2-naphthalenyl]-3,6-dihydro-1(2H)-pyridinecarboxamide;
- N-[6-[(dimethylamino)methyl]-7,8-dihydro-2-naphthalenyl]-4-(4-fluorophenyl)-1-piperidinecarboxamide;
- 4-(4-methoxyphenyl)-N-[6-(1-pyrrolidinylmethyl)-5-methyl-7,8-dihydro-2-naphthalenyl]-1-piperidinecarboxamide;
- 4'-fluoro-N-[6-[2-(1-pyrrolidinyl)ethyl]-7,8-dihydro-2-naphthalenyl][1,1'-biphenyl]-4-carboxamide;
- 4'-chloro-N-[6-[2-(1-pyrrolidinyl)ethyl]-7,8-dihydro-2-naphthalenyl][1,1'-biphenyl]-4-carboxamide;
- 4-(4-methoxyphenyl)-N-[5-methyl-6-(1-pyrrolidinylmethyl)-7,8-dihydro-2-naphthalenyl]-1-piperidinecarboxamide;
- 4-(4-chlorophenyl)-N-[6-[(4-methyl-1-piperazinyl)methyl]-7,8-dihydro-2-naphthalenyl]-1-piperidinecarboxamide;
- 4'-fluoro-N-[5-methyl-6-[(4-methyl-1-piperazinyl)methyl]-7,8-dihydro-2-naphthalenyl][1,1'-biphenyl]-4-carboxamide;
- 4'-chloro-N-[5-methyl-6-[(4-methyl-1-piperazinyl)methyl]-7,8-dihydro-2-naphthalenyl][1,1'-biphenyl]-4-carboxamide; or
- 4-(4-chlorophenyl)-N-[5-methyl-6-[(4-methyl-1-piperazinyl)methyl]-7,8-dihydro-2-naphthalenyl]-1-piperidinecarboxamide.

8. A method for preventing or treating diseases caused by a melanin-concentrating hormone in a mammal in need thereof, which comprises administering to said mammal an effective amount of a compound of claim 1.

9. A method for preventing or treating obesity in a mammal in need thereof, which comprises administering to said mammal an effective amount of a compound of claim 1.

10. A method for antagonizing melanin-concentrating hormone in a mammal in need thereof, comprising administering a compound of claim 1.

11. A pharmaceutical composition which comprises a compound as defined in claim 1, and a pharmaceutically acceptable carrier, diluent or excipient.

12. A pharmaceutical composition which comprises a compound as defined in claim 3 and a pharmaceutically acceptable carrier, diluent or excipient.

13. A pharmaceutical composition which comprises a compound as defined in claim 5 and a pharmaceutically acceptable carrier, diluent or excipient.

14. A pharmaceutical composition which comprises a compound as defined in claim 6 and a pharmaceutically acceptable carrier, diluent or excipient.

* * * * *

UNITED STATES PATENT AND TRADEMARK OFFICE
CERTIFICATE OF CORRECTION

PATENT NO.        : 7,115,750 B1
APPLICATION NO. : 10/088771
DATED              : October 3, 2006
INVENTOR(S)       : Kaneyoshi Kato et al.

It is certified that error appears in the above-identified patent and that said Letters Patent is hereby corrected as shown below:

In column 267, claim 1, the drawing in line 26-34, please delete the solid line between $R^1$ and $R^2$ and replace it with a dotted line.

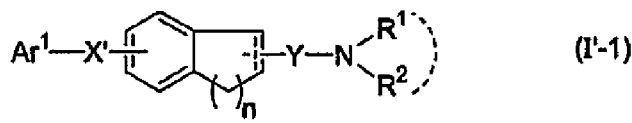

In column 268, claim 1, line 25, please place a dash line, -- - -- between "ring" and "$C_{1-6}$"

In column 268, claim 1, lines 39, 45, 46, and 61, please delete the comma after "$C_{1-6}$".

In column 270, claim 2, the drawing in line 10-15, please delete the solid line between $R^1$ and $R^2$ and replace it with a dotted line.

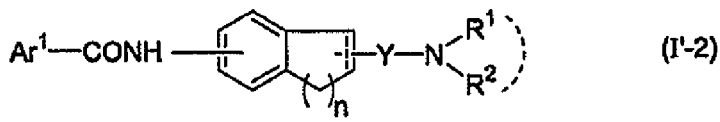

In column 270, claim 3, the drawing in line 20-25, please delete the solid line between $R^1$ and $R^2$ and replace it with a dotted line.

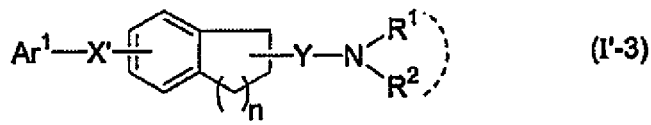

In column 271, claim 3, line 3, please replace the word "alkylcarbonyl" with --alkyl-carbonyl--.

In column 271 claim 3, line 60, please replace the word "alkylcarbonyl" with --alkyl-carbonyl--.

In column 272, claim 4, the drawing in line 44-47, please delete the solid line between $R^1$ and $R^2$ and replace it with a dotted line.

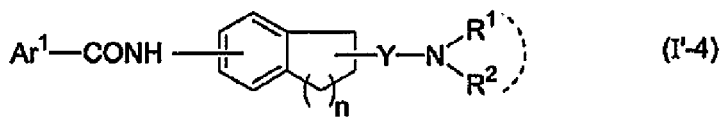

In column 272, claim 5, the drawing in line 53-57, please delete the solid line between $R^1$ and $R^2$ and replace it with dotted line.

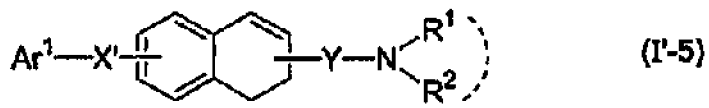

UNITED STATES PATENT AND TRADEMARK OFFICE
CERTIFICATE OF CORRECTION

PATENT NO.       : 7,115,750 B1
APPLICATION NO. : 10/088771
DATED            : October 3, 2006
INVENTOR(S)      : Kaneyoshi Kato et al.

It is certified that error appears in the above-identified patent and that said Letters Patent is hereby corrected as shown below:

In column 273, claim 5, line 31, please replace "mono-C 6," with --mono-$C_{1-6}$,--.

In column 273, claim 5, line 35, please replace "alkylcarbonyl" with --alkyl-carbonyl--.

In column 273, claim 5, line 59, please replace "$C_{1-4}$" with --$C_{1-6}$--.

In column 273, claim 5, line 60, please replace "$C_{16}$" with --$C_{1-6}$--.

In column 274, claim 5, line 21, please replace "di-6" with --di-$C_{1-6}$--.

In column 274, claim 5, line 25, please replace "alkylcarbonyl" with --alkyl-carbonyl--.

In column 275, claim 6, the drawing in line 5-9, please delete the solid line between $R^1$ and $R^2$ and replace it with a dotted line.

Signed and Sealed this

Eighth Day of May, 2007

JON W. DUDAS
*Director of the United States Patent and Trademark Office*

SEQUENCE LISTING

<160> NUMBER OF SEQ ID NOS: 16

<210> SEQ ID NO 1
<211> LENGTH: 32
<212> TYPE: DNA
<213> ORGANISM: Artificial Sequence
<220> FEATURE:
<223> OTHER INFORMATION: primer

<400> SEQUENCE: 1
gtcgacatgg atctgcaaac ctcgttgctg tg                                    32

<210> SEQ ID NO 2
<211> LENGTH: 32
<212> TYPE: DNA
<213> ORGANISM: Artificial Sequence
<220> FEATURE:
<223> OTHER INFORMATION: primer

<400> SEQUENCE: 2
actagttcag gtgcctttgc tttctgtcct ct                                    32

<210> SEQ ID NO 3
<211> LENGTH: 353
<212> TYPE: PRT
<213> ORGANISM: Rat

<400> SEQUENCE: 3

Met Asp Leu Gln Thr Ser Leu Leu Ser Thr Gly Pro Asn Ala Ser Asn
1               5                   10                  15

Ile Ser Asp Gly Gln Asp Asn Leu Thr Leu Pro Gly Ser Pro Pro Arg
            20                  25                  30

Thr Gly Ser Val Ser Tyr Ile Asn Ile Ile Met Pro Ser Val Phe Gly
        35                  40                  45

Thr Ile Cys Leu Leu Gly Ile Val Gly Asn Ser Thr Val Ile Phe Ala
    50                  55                  60

Val Val Lys Lys Ser Lys Leu His Trp Cys Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Thr Ile Asp Arg Tyr Leu Ala
    130                 135                 140

Thr Val His Pro Ile Ser Ser Thr Lys Phe Arg Lys Pro Ser Met Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Lys Ile Leu Gln Arg Met Thr Ser Ser Val Ala

```
                225                 230                 235                 240
Pro Ala Ser Gln Arg Ser Ile Arg Leu Arg Thr Lys Arg Val Thr Arg
                    245                 250                 255
Thr Ala Ile Ala Ile Cys Leu Val Phe Phe Val Cys Trp Ala Pro Tyr
                260                 265                 270
Tyr Val Leu Gln Leu Thr Gln Leu Ser Ile Ser Arg Pro Thr Leu Thr
            275                 280                 285
Phe Val Tyr Leu Tyr Asn Ala Ala Ile Ser Leu Gly Tyr Ala Asn Ser
        290                 295                 300
Cys Leu Asn Pro Phe Val Tyr Ile Val Leu Cys Glu Thr Phe Arg Lys
305                 310                 315                 320
Arg Leu Val Leu Ser Val Lys Pro Ala Ala Gln Gly Gln Leu Arg Thr
                325                 330                 335
Val Ser Asn Ala Gln Thr Ala Asp Glu Glu Arg Thr Glu Ser Lys Gly
            340                 345                 350
Thr
353

<210> SEQ ID NO 4
<211> LENGTH: 1074
<212> TYPE: DNA
<213> ORGANISM: Rat

<400> SEQUENCE: 4
gtcgacatgg atctgcaaac ctcgttgctg tccactggcc ccaatgccag caacatctcc          60
gatggccagg ataatctcac attgccgggg tcacctcctc gcacagggag tgtctcctac         120
atcaacatca ttatgccttc cgtgtttggt accatctgtc tcctgggcat cgtgggaaac         180
tccacggtca tctttgctgt ggtgaagaag tccaagctac actggtgcag caacgtcccc         240
gacatcttca tcatcaacct ctctgtggtg gatctgctct tcctgctggg catgccttc          300
atgatccacc agctcatggg gaacggcgtc tggcactttg gggaaaccat gtgcaccctc         360
atcacagcca tggacgccaa cagtcagttc actagcacct acatcctgac tgccatgacc         420
attgaccgct acttggccac cgtccacccc atctcctcca ccaagttccg gaagccctcc         480
atggccaccc tggtgatctg cctcctgtgg gcgctctcct tcatcagtat caccccctgtg        540
tggctctacg ccaggctcat tcccttccca gggggtgctg tgggctgtgg catccgcctg         600
ccaaacccgg acactgacct ctactggttc actctgtacc agttttttcct ggcctttgcc        660
cttccgtttg tggtcattac cgccgcatac gtgaaaatac tacagcgcat gacgtcttcg         720
gtggccccag cctcccaacg cagcatccgg cttcggacaa agagggtgac ccgcacggcc         780
attgccatct gtctggtctt ctttgtgtgc tgggcaccct actatgtgct gcagctgacc         840
cagctgtcca tcagccgccc gaccctcacg tttgtctact gtacaacgc ggccatcagc          900
ttgggctatg ctaacagctg cctgaacccc tttgtgtaca tagtgctctg tgagacttt          960
cgaaaacgct tggtgttgtc agtgaagcct gcagcccagg ggcagctccg cacggtcagc        1020
aacgctcaga cagctgatga ggagaggaca gaaagcaaag gcacctgaac tagt              1074

<210> SEQ ID NO 5
<211> LENGTH: 262
<212> TYPE: RNA
<213> ORGANISM: Rat

<400> SEQUENCE: 5
gcgaauuggg uaccgggccc ccccucgagg ucgacgguau cgauaagcuu gauaucgaau          60
```

| | |
|---|---|
| uccugcagcc cggggggaucc gcccacuagu ucaggugccu uugcuuucug uccucuccuc | 120 |
| aucagcuguc ugagcguugc ugaccgugcg gagcugcccc ugggcugcag gcuucacuga | 180 |
| caacaccaag cguuuucgaa aggucucaca gagcacuaug uacacaaagg gguucaggca | 240 |
| gcuguuagca uagcccaagc ug | 262 |

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6

| | |
|---|---|
| caacagctgc ctcaaccc | 18 |

<210> SEQ ID NO 7
<211> LENGTH: 18
<212> TYPE: DNA
<213> ORGANISM: Artificial Sequence
<220> FEATURE:
<223> OTHER INFORMATION: primer

<400> SEQUENCE: 7

| | |
|---|---|
| cctggtgatc tgcctcct | 18 |

<210> SEQ ID NO 8
<211> LENGTH: 1275
<212> TYPE: DNA
<213> ORGANISM: Human

<400> SEQUENCE: 8

| | |
|---|---|
| taggtgatgt cagtgggagc catgaagaag ggagtgggga gggcagttgg gcttggaggc | 60 |
| ggcagcggct gccaggctac ggaggaagac ccccttccca actgcgggc ttgcgctccg | 120 |
| ggacaaggtg gcaggcgctg gaggctgccg cagcctgcgt gggtggaggg gagctcagct | 180 |
| cggttgtggg agcaggcgac cggcactggc tggatggacc tggaagcctc gctgctgccc | 240 |
| actggtccca acgccagcaa cacctctgat ggccccgata acctcacttc ggcaggatca | 300 |
| cctcctcgca cggggagcat ctcctacatc aacatcatca tgccttcggt gttcggcacc | 360 |
| atctgcctcc tgggcatcat cgggaactcc acggtcatct tcgcggtcgt gaagaagtcc | 420 |
| aagctgcact ggtgcaacaa cgtccccgac atcttcatca tcaacctctc ggtagtagat | 480 |
| ctcctctttc tcctgggcat gccccttcatg atccaccagc tcatgggcaa tgggggtgtgg | 540 |
| cactttgggg agaccatgtg cacccctcatc acggccatgg atgccaatag tcagttcacc | 600 |
| agcacctaca tcctgaccgc catggccatt gaccgctacc tggccactgt ccaccccatc | 660 |
| tcttccacga agttccggaa gccctctgtg ccaccctgg tgatctgcct cctgtgggcc | 720 |
| ctctccttca tcagcatcac ccctgtgtgg ctgtatgcca gactcatccc cttcccagga | 780 |
| ggtgcagtgg gctgcggcat acgcctgccc aacccagaca ctgacctcta ctggttcacc | 840 |
| ctgtaccagt ttttcctggc ctttgccctg ccttttgtgg tcatcacagc cgcatacgtg | 900 |
| aggatcctgc agcgcatgac gtcctcagtg gccccggcct cccagcgcag catccggctg | 960 |
| cggacaaaga gggtgaccg cacagccatc gccatctgtc tggtcttctt tgtgtgctgg | 1020 |
| gcaccctact atgtgctaca gctgaccag ttgtccatca gccgcccgac cctcaccttt | 1080 |
| gtctacttat acaatgcggc catcagcttg ggctatgcca acagctgcct caaccccttt | 1140 |

```
gtgtacatcg tgctctgtga gacgttccgc aaacgcttgg tcctgtcggt gaagcctgca    1200
gcccaggggc agcttcgcgc tgtcagcaac gctcagacgg ctgacgagga gaggacagaa    1260
agcaaaggca cctga                                                    1275
```

<210> SEQ ID NO 9
<211> LENGTH: 422
<212> TYPE: PRT
<213> ORGANISM: Human

<400> SEQUENCE: 9

```
MeT Ser Val Gly Ala MeT Lys Lys Gly Val Gly Arg Ala Val Gly Leu
  1               5                  10                  15

Gly Gly Gly Ser Gly Cys Gln Ala Thr Glu Glu Asp Pro Leu Pro Asn
             20                  25                  30

Cys Gly Ala Cys Ala Pro Gly Gln Gly Gly Arg Arg Trp Arg Leu Pro
         35                  40                  45

Gln Pro Ala Trp Val Glu Gly Ser Ser Ala Arg Leu Trp Glu Gln Ala
     50                  55                  60

Thr Gly Thr Gly Trp MeT Asp Leu Glu Ala Ser Leu Leu Pro Thr Gly
 65                  70                  75                  80

Pro Asn Ala Ser Asn Thr Ser Asp Gly Pro Asp Asn Leu Thr Ser Ala
                 85                  90                  95

Gly Ser Pro Pro Arg Thr Gly Ser Ile Ser Tyr Ile Asn Ile Ile MeT
            100                 105                 110

Pro Ser Val Phe Gly Thr Ile Cys Leu Leu Gly Ile Ile Gly Asn Ser
        115                 120                 125

Thr Val Ile Phe Ala Val Val Lys Lys Ser Lys Leu His Trp Cys Asn
130                 135                 140

Asn Val Pro Asp Ile Phe Ile Ile Asn Leu Ser Val Val Asp Leu Leu
145                 150                 155                 160

Phe Leu Leu Gly MeT Pro Phe MeT Ile His Gln Leu MeT Gly Asn Gly
                165                 170                 175

Val Trp His Phe Gly Glu Thr MeT Cys Thr Leu Ile Thr Ala MeT Asp
            180                 185                 190

Ala Asn Ser Gln Phe Thr Ser Thr Tyr Ile Leu Thr Ala MeT Ala Ile
        195                 200                 205

Asp Arg Tyr Leu Ala Thr Val His Pro Ile Ser Ser Thr Lys Phe Arg
    210                 215                 220

Lys Pro Ser Val Ala Thr Leu Val Ile Cys Leu Leu Trp Ala Leu Ser
225                 230                 235                 240

Phe Ile Ser Ile Thr Pro Val Trp Leu Tyr Ala Arg Leu Ile Pro Phe
                245                 250                 255

Pro Gly Gly Ala Val Gly Cys Gly Ile Arg Leu Pro Asn Pro Asp Thr
            260                 265                 270

Asp Leu Tyr Trp Phe Thr Leu Tyr Gln Phe Leu Ala Phe Ala Leu
        275                 280                 285

Pro Phe Val Val Ile Thr Ala Ala Tyr Val Arg Ile Leu Gln Arg MeT
    290                 295                 300

Thr Ser Ser Val Ala Pro Ala Ser Gln Arg Ser Ile Arg Leu Arg Thr
305                 310                 315                 320

Lys Arg Val Thr Arg Thr Ala Ile Ala Ile Cys Leu Val Phe Phe Val
                325                 330                 335

Cys Trp Ala Pro Tyr Tyr Val Leu Gln Leu Thr Gln Leu Ser Ile Ser
            340                 345                 350
```

```
Arg Pro Thr Leu Thr Phe Val Tyr Leu Tyr Asn Ala Ala Ile Ser Leu
            355                 360                 365

Gly Tyr Ala Asn Ser Cys Leu Asn Pro Phe Val Tyr Ile Val Leu Cys
        370                 375                 380

Glu Thr Phe Arg Lys Arg Leu Val Leu Ser Val Lys Pro Ala Ala Gln
385                 390                 395                 400

Gly Gln Leu Arg Ala Val Ser Asn Ala Gln Thr Ala Asp Glu Glu Arg
                405                 410                 415

Thr Glu Ser Lys Gly Thr
            420
```

<210> SEQ ID NO 10
<211> LENGTH: 31
<212> TYPE: DNA
<213> ORGANISM: Artificial Sequence
<220> FEATURE:
<223> OTHER INFORMATION: primer

<400> SEQUENCE: 10
gtcgacatgg acctggaagc ctcgctgctg c                               31

<210> SEQ ID NO 11
<211> LENGTH: 31
<212> TYPE: DNA
<213> ORGANISM: Artificial Sequence
<220> FEATURE:
<223> OTHER INFORMATION: primer

<400> SEQUENCE: 11
actagttcag gtgcctttgc tttctgtcct c                               31

<210> SEQ ID NO 12
<211> LENGTH: 33
<212> TYPE: DNA
<213> ORGANISM: Artificial Sequence
<220> FEATURE:
<223> OTHER INFORMATION: primer

<400> SEQUENCE: 12
agtcgacatg tcagtgggag ccatgaagaa ggg                             33

<210> SEQ ID NO 13
<211> LENGTH: 33
<212> TYPE: DNA
<213> ORGANISM: Artificial Sequence
<220> FEATURE:
<223> OTHER INFORMATION: primer

<400> SEQUENCE: 13
aactagttca ggtgcctttg ctttctgtcc tct                             33

<210> SEQ ID NO 14
<211> LENGTH: 1074
<212> TYPE: DNA
<213> ORGANISM: Human

<400> SEQUENCE: 14
gtcgacatgg acctggaagc ctcgctgctg cccactggtc ccaacgccag caacacctct    60
gatggccccg ataacctcac ttcggcagga tcacctcctc gcacgggag catctcctac   120 atcaacatca tcatgccttc ggtgttcggc accatctgcc tcctgggcat catcgggaac   180
tccacggtca tcttcgcggt cgtgaagaag tccaagctgc actggtgcaa caacgtcccc   240

-continued

| | |
|---|---|
| gacatcttca tcatcaacct ctcggtagta gatctcctct ttctcctggg catgcccttc | 300 |
| atgatccacc agctcatggg caatggggtg tggcactttg gggagaccat gtgcaccctc | 360 |
| atcacggcca tggatgccaa tagtcagttc accagcacct acatcctgac cgccatggcc | 420 |
| attgaccgct acctggccac tgtccacccc atctcttcca cgaagttccg gaagccctct | 480 |
| gtggccaccc tggtgatctg cctcctgtgg gccctctcct tcatcagcat cacccctgtg | 540 |
| tggctgtatg ccagactcat ccccttccca ggaggtgcag tgggctgcgg catacgcctg | 600 |
| cccaacccag acactgacct ctactggttc accctgtacc agttttttcct ggcctttgcc | 660 |
| ctgccttttg tggtcatcac agccgcatac gtgaggatcc tgcagcgcat gacgtcctca | 720 |
| gtggcccccg cctcccagcg cagcatccgg ctgcggacaa agagggtgac ccgcacagcc | 780 |
| atcgccatct gtctggtctt cttttgtgtgc tgggcaccct actatgtgct acagctgacc | 840 |
| cagttgtcca tcagccgccc gacccctcacc tttgtctact tatacaatgc ggccatcagc | 900 |
| ttgggctatg ccaacagctg cctcaacccc tttgtgtaca tcgtgctctg tgagacgttc | 960 |
| cgcaaacgct tggtcctgtc ggtgaagcct gcagcccagg ggcagcttcg cgctgtcagc | 1020 |
| aacgctcaga cggctgacga ggagaggaca gaaagcaaag gcacctgaac tagt | 1074 |

<210> SEQ ID NO 15
<211> LENGTH: 1283
<212> TYPE: DNA
<213> ORGANISM: Human

<400> SEQUENCE: 15

| | |
|---|---|
| agtcgacatg tcagtgggag ccatgaagaa gggagtgggg agggcagttg ggcttggagg | 60 |
| cggcagcggc tgccaggcta cggaggaaga ccccttccc aactgcgggg cttgcgctcc | 120 |
| gggacaaggt ggcaggcgct ggaggctgcc gcagcctgcg tgggtggagg ggagctcagc | 180 |
| tcggttgtgg gagcaggcga ccggcactgg ctggatggac ctggaagcct cgctgctgcc | 240 |
| cactggtccc aacgccagca acacctctga tggccccgat aacctcactt cggcaggatc | 300 |
| acctcctcgc acggggagca tctcctacat caacatcatc atgccttcgg tgttcggcac | 360 |
| catctgcctc ctgggcatca tcgggaactc cacggtcatc ttcgcggtcg tgaagaagtc | 420 |
| caagctgcac tggtgcaaca acgtccccga catcttcatc atcaacctct cggtagtaga | 480 |
| tctcctcttt ctcctgggca tgcccttcat gatccaccag ctcatgggca atggggtgtg | 540 |
| gcactttggg gagaccatgt gcaccctcat cacggccatg gatgccaata gtcagttcac | 600 |
| cagcacctac atcctgaccg ccatggccat tgaccgctac ctggccactg tccacccat | 660 |
| ctcttccacg aagttccgga agccctctgt ggccaccctg tgatctgcc tcctgtgggc | 720 |
| cctctccttc atcagcatca cccctgtgtg gctgtatgcc agactcatcc ccttcccagg | 780 |
| aggtgcagtg ggctgcggca tacgcctgcc caacccagac actgacctct actggttcac | 840 |
| cctgtaccag ttttttcctgg cctttgccct gccttttgtg gtcatcacag ccgcatacgt | 900 |
| gaggatcctg cagcgcatga cgtcctcagt ggccccgcc tcccagcgca gcatccggct | 960 |
| gcggacaaag agggtgaccc gcacagccat cgccatctgt ctggtcttct tgtgtgctg | 1020 |
| ggcaccctac tatgtgctac agctgaccca gttgtccatc agccgcccga ccctcacctt | 1080 |
| tgtctactta tacaatgcgg ccatcagctt gggctatgcc aacagctgcc tcaaccccctt | 1140 |
| tgtgtacatc gtgctctgtg agacgttccg caaacgcttg gtcctgtcgg tgaagcctgc | 1200 |
| agcccagggg cagcttcgcg ctgtcagcaa cgctcagacg gctgacgagg agaggacaga | 1260 |

```
-continued
aagcaaaggc acctgaacta gtt                                              1283

<210> SEQ ID NO 16
<211> LENGTH: 420
<212> TYPE: RNA
<213> ORGANISM: Human

<400> SEQUENCE: 16
caaaagcugg agcuccaccg cgguggcggc cgcucuagcc cacuaguuca ggugccuuug          60
cuuucugucc ucuccucguc agccgucuga gcguugcuga cagcgcgaag cugccccugg         120
gcugcaggcu ucaccgacag gaccaagcgu uugcggaacg ucucacagag cacgauguac         180 acaaggggu ugaggcagcu guuggcauag cccaagcuga uggccgcauu guauaaguag          240 acaagguga gggucgggcg gcugauggac aacugguca gcuguagcac auaguagggu           300
gcccagcaca caaagaagac cagacagaug gcgauggcug ugcggucac ccucuuuguc          360 cgcagccgga ugcugcgcug ggaggcgggg gccacugagg acgucaugcg cugcaggauc         420
```